United States Patent
Hikida et al.

(10) Patent No.: US 10,023,540 B2
(45) Date of Patent: Jul. 17, 2018

(54) HYDROGEN BARRIER AGENT, HYDROGEN BARRIER FILM FORMING COMPOSITION, HYDROGEN BARRIER FILM, METHOD FOR PRODUCING HYDROGEN BARRIER FILM, AND ELECTRONIC ELEMENT

(71) Applicant: TOKYO OHKA KOGYO CO., LTD., Kawasaki-shi (JP)

(72) Inventors: Jiro Hikida, Kawasaki (JP); Kazuya Someya, Kawasaki (JP); Koichi Misumi, Kawasaki (JP); Dai Shiota, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/720,150

(22) Filed: Sep. 29, 2017

(65) Prior Publication Data
US 2018/0086717 A1   Mar. 29, 2018

(30) Foreign Application Priority Data

Sep. 29, 2016 (JP) ................................. 2016-192368
Sep. 28, 2017 (JP) ................................. 2017-189228

(51) Int. Cl.

| | | |
|---|---|---|
| *C07D 233/56* | (2006.01) | |
| *C07D 233/60* | (2006.01) | |
| *B01J 20/22* | (2006.01) | |
| *B01J 20/26* | (2006.01) | |
| *B01J 20/32* | (2006.01) | |
| *H01L 29/786* | (2006.01) | |
| *C09D 133/14* | (2006.01) | |
| *G02F 1/1335* | (2006.01) | |
| *H01L 27/32* | (2006.01) | |
| *G02F 1/1368* | (2006.01) | |
| *H01L 51/52* | (2006.01) | |

(52) U.S. Cl.
CPC ............ *C07D 233/60* (2013.01); *B01J 20/22* (2013.01); *B01J 20/261* (2013.01); *B01J 20/262* (2013.01); *B01J 20/3225* (2013.01); *C09D 133/14* (2013.01); *H01L 29/78606* (2013.01); *G02F 1/1368* (2013.01); *G02F 1/133512* (2013.01); *G02F 1/133514* (2013.01); *H01L 27/3262* (2013.01); *H01L 51/5237* (2013.01); *H01L 51/5253* (2013.01)

(58) Field of Classification Search
CPC ... C07D 233/00; C07D 233/56–233/59; C07D 235/00–235/32; C07D 239/00–239/96; H01L 29/78606; H01L 51/5237; H01L 51/5253
See application file for complete search history.

(56) References Cited

U.S. PATENT DOCUMENTS

| | | | |
|---|---|---|---|
| 7,968,150 B2 * | 6/2011 | Imori | .................. C07D 231/12 427/384 |
| 9,583,546 B2 | 2/2017 | Shin et al. | |
| 2015/0102332 A1 | 4/2015 | Shin et al. | |
| 2017/0247334 A1 | 8/2017 | Ishikawa et al. | |

FOREIGN PATENT DOCUMENTS

| | | |
|---|---|---|
| JP | 2015-079755 A | 4/2015 |
| TW | 201623248 A | 7/2016 |

OTHER PUBLICATIONS

Office Action dated May 8, 2018 in Taiwanese counterpart to present application, TW Patent Application No. 106133774.

* cited by examiner

*Primary Examiner* — Jose R Diaz
(74) *Attorney, Agent, or Firm* — Knobbe Martens Olson & Bear LLP

(57) ABSTRACT

To provide a hydrogen barrier agent capable of imparting hydrogen barrier performance to various materials; a hydrogen barrier film forming composition including the hydrogen barrier agent; a hydrogen barrier film including the hydrogen barrier agent; a method for producing a hydrogen barrier film, which uses the hydrogen barrier film forming composition; and an electronic element provided with the hydrogen barrier film. A compound having a specific structure including an imidazolyl group is used as the hydrogen barrier agent. Furthermore, the hydrogen barrier film forming composition is prepared by blending the above-mentioned hydrogen barrier agent into the base material component. In addition, the hydrogen barrier film is formed using the hydrogen barrier film forming composition.

8 Claims, No Drawings

HYDROGEN BARRIER AGENT, HYDROGEN BARRIER FILM FORMING COMPOSITION, HYDROGEN BARRIER FILM, METHOD FOR PRODUCING HYDROGEN BARRIER FILM, AND ELECTRONIC ELEMENT

This application is based on and claims the benefit of priority from Japanese Patent Application Nos. 2016-192368 and 2017-189228, respectively filed on 29 Sep. 2016 and 28 Sep. 2017, the content of which is incorporated herein by reference.

BACKGROUND OF THE INVENTION

Field of the Invention

The present invention relates to a hydrogen barrier agent, a hydrogen barrier film forming composition, a hydrogen barrier film, a method for producing a hydrogen barrier film, and an electronic element.

Related Art

Conventionally, a variety of functional films have been formed in various electronic elements. In electronic elements, development of an organic electronic element has been advanced with progress of development of a conductive organic material and an organic semiconductor. Typical examples of such organic electronic elements include an organic EL element. When the electronic element is an organic EL element, examples of the functional film include a passivation film, a transparent electrode film, a transparent insulating layer, a flattened film, an organic light-emitting film, a protective film, and the like.

Electronic elements, like an organic EL element, often include a thin film transistor (TFT) for driving an element. Furthermore, electronic elements often include wiring made of metal such as copper. Herein, in the TFT, the function may be damaged by reductive reaction by contact with hydrogen gas; and also in the metal wiring, the electric characteristics may be changed by reduction with hydrogen gas.

On the other hand, some materials of the functional film of the electronic element may emit hydrogen gas due to a method for a producing material. For example, SiN or the like used for a material of a passivation film may include ammonium gas due to its producing method. Consequently, hydrogen gas may be generated from SiN due to the decomposition of ammonium. In this way, in electronic elements such as an organic EL element, members such as TFT and metal wiring may be adversely affected by generation of hydrogen inside.

From such problems, for example, a method of allowing a metal thin film as a hydrogen absorbing material to be included in an organic electric field light-emitting element (organic EL element) has been proposed (see Patent Document 1).

Patent Document 1: Japanese Unexamined Patent Application, Publication No. 2015-79755

SUMMARY OF THE INVENTION

However, it is difficult to apply the method described in Patent Document 1 to a portion that requires transparency, and a step of causing a hydrogen absorbing material to be contained is added to a method for producing an electronic element, thus making the producing step of the electronic element complicated and causing the producing cost of the electronic element to increase. Therefore, a hydrogen barrier agent that is blended into a functional layer originally provided to the electronic element, so that hydrogen barrier property can be imparted to the functional layer, and a hydrogen barrier film formed by using the hydrogen barrier agent are demanded.

The present invention has been made in light of the above-mentioned problems, and an object of the present invention is to provide a hydrogen barrier agent capable of imparting hydrogen barrier performance to various materials; a hydrogen barrier film forming composition including the hydrogen barrier agent; a hydrogen barrier film including the hydrogen barrier agent; a method for producing a hydrogen barrier film, which uses the hydrogen barrier film forming composition; and an electronic element provided with the hydrogen barrier film.

The present inventors found that the above-mentioned problems can be solved by using a compound having a specific structure including an imidazolyl group, as a hydrogen barrier agent; preparing a hydrogen barrier film forming composition by blending the hydrogen barrier agent into the base material component; and forming a hydrogen barrier film using the hydrogen barrier film forming composition, and have reached completion of the present invention. Specifically, the present invention provides the following. Note here that "hydrogen" in the "hydrogen barrier" performance of the present invention means both various components of $H_2$ molecule, H radical, and $H^+$ (proton) and an entire mixed component including a combination of various components.

A first aspect of the present invention is a hydrogen barrier agent including a compound represented by the following formula (0):

wherein, in the formula (0), $R^2$ is an optionally substituted aromatic group, $R^{30}$ is a hydrogen atom or a monovalent substituent having 1 or more and 40 or less carbon atoms; $R^4$ represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 or more and 3 or less.

A second aspect of the present invention is a hydrogen barrier film forming composition including a base material component (A), and the hydrogen barrier agent (B) according to the first aspect.

A third aspect of the present invention is a hydrogen barrier film including the hydrogen barrier agent according to the first aspect.

A fourth aspect of the present invention is a hydrogen barrier film made of a cured product of the hydrogen barrier film forming composition according to the second aspect in which the base material component (A) includes the alkali-soluble resin (A1) and the photopolymerizable compound (A2), and which further includes a photopolymerization initiator (C).

A fifth aspect of the present invention is a method for producing a hydrogen barrier film, the method including forming a coating film by applying the hydrogen barrier film forming composition according to the second aspect on a substrate, in which the base material component (A) includes the alkali-soluble resin (A1) and the photopolymerizable compound (A2) and which further includes the photopolymerization initiator (C); and exposing the coating film.

A sixth aspect of the present invention is an electronic element including a passivation film, and the hydrogen barrier film according to the third aspect or the fourth aspect.

The present invention can provide a hydrogen barrier agent capable of imparting hydrogen barrier performance to various materials; a hydrogen barrier film forming composition including the hydrogen barrier agent; a hydrogen barrier film including the hydrogen barrier agent; a method for producing a hydrogen barrier film, which uses the hydrogen barrier film forming composition; and an electronic element provided with the hydrogen barrier film.

DETAILED DESCRIPTION OF THE INVENTION

<<Hydrogen Barrier Agent>>

A hydrogen barrier agent includes a compound represented by the following formula (0). The hydrogen barrier agent is blended with various materials, thereby imparting hydrogen barrier property to various articles.

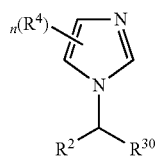
(0)

In the formula (0), $R^2$ is an optionally substituted aromatic group, $R^{30}$ is a hydrogen atom or a monovalent substituent having 1 or more and 40 or less carbon atoms. $R^4$ represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 or more and 3 or less.

In the formula (0), $R^2$ is an optionally substituted aromatic group. The optionally substituted aromatic group may be either an optionally substituted aromatic hydrocarbon group or an optionally substituted aromatic heterocyclic group.

The type of the aromatic hydrocarbon group is not particularly limited without interfering with the object of the present invention. The aromatic hydrocarbon group may be a monocyclic aromatic group, may be formed by fusion of two or more aromatic hydrocarbon groups, or may be formed by bonding of two or more aromatic hydrocarbon groups through a single bond. The aromatic hydrocarbon group is preferably a phenyl group, a naphthyl group, a biphenylyl group, an anthryl group, or a phenanthrenyl group.

The type of the aromatic heterocyclic group is not particularly limited without interfering with the object of the present invention. The aromatic heterocyclic group may be either a monocyclic group or a polycyclic group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzimidazolyl group.

Examples of the substituent, which a phenyl group, a polycyclic aromatic hydrocarbon group, or an aromatic heterocyclic group may have, include a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, and an organic group. When the phenyl group, the polycyclic aromatic hydrocarbon group, or the aromatic heterocyclic group have plural substituents, the plural substituents may be the same or different.

When the substituent, which the aromatic group has, is an organic group, examples of the organic group include an alkyl group, an alkenyl group, a cycloalkyl group, a cycloalkenyl group, an aryl group, an aralkyl group, or the like. This organic group may have a bond or a substituent, other than a hydrocarbon group such as a heteroatom, in the organic group. This organic group may be either linear, branched, or cyclic. This organic group is usually monovalent, but can be a divalent or higher polyvalent organic group when forming a cyclic structure.

When the aromatic group has a substituent on neighboring carbon atoms, two substituents bonded on neighboring carbon atoms may be bonded to form a cyclic structure. Examples of the cyclic structure include an aliphatic hydrocarbon ring, and an aliphatic ring having a heteroatom.

When the substituent, which the aromatic group has, is an organic group, the bond included in the organic group is not particularly limited, without impairing the effect of the present invention; and the organic group may include a bond having a heteroatom such as an oxygen atom, a nitrogen atom, or a silicon atom. Specific examples of the bonded containing a heteroatom include, an ether bond, a thioether bond, a carbonyl bond, a thiocarbonyl bond, a ester bond, a amide bond, a urethane bond, an imino bond (—N═C(—R)—, —C(═NR)—: R represents a hydrogen atom or a monovalent organic group), a carbonate bond, a sulfonyl bond, a sulfinyl bond, an azo bond, and the like.

From the viewpoint of heat resistance of the compound represented by the formula (0), the bond containing a heteroatom, which an organic group may have, is preferably an ether bond, a thioether bond, a carbonyl bond, a thiocarbonyl bond, an ester bond, an amide bond, an amino bond (—NR—: R represents a hydrogen atom or a monovalent organic group), an urethane bond, an imino bond (—N═C(—R)—, —C(═NR)—: R represents a hydrogen atom or a monovalent organic group), a carbonate bond, a sulfonyl bond, or a sulfinyl bond.

When the organic group is a substituent other than the hydrocarbon group, the type of the substituent other than the hydrocarbon group is not particularly limited without interfering with the object of the present invention. Specific examples of the substituent other than the hydrocarbon group include a halogen atom, a hydroxy group, a mercapto group, a sulfide group, a cyano group, an isocyano group, a cyanato group, an isocyanato group, a thiocyanato group, an isothiocyanato group, an silyl group, an silanol group, an alkoxy group, an alkoxycarbonyl group, an amino group, a monoalkylamino group, a dialkylamino group, a monoarylamino group, a diarylamino group, a carbamoyl group, a thiocarbamoyl group, a nitro group, a nitroso group, a carboxylate group, an acyl group, an acyloxy group, a sulfino group, a sulfonato group, a phosphino group, a phosphinyl group, a phosphonato group, an alkyl ether group, an alkenyl ether group, an alkyl thioether group, an alkenyl thioether group, an aryl ether group, an aryl thioether group, and the like. The hydrogen atom included in the substituent mentioned above may be substituted with a hydrocarbon group. The hydrocarbon group included in the substituent mentioned above may be either linear, branched, or cyclic.

The substituent, which a phenyl group, a polycyclic aromatic hydrocarbon group, or an aromatic heterocyclic group has, is preferably an alkyl group having 1 or more and 12 or less carbon atoms, an aryl group having 1 or more and 12 or less carbon atoms, an alkoxy group having 1 or more and 12 or less carbon atoms, an aryloxy group having 1 or more and 12 or less carbon atoms, an arylamino group having 1 or more and 12 or less carbon atoms, and a halogen atom.

In view of the effect of the present invention, examples of $R^2$ preferably include a phenyl group, a furyl group, and a thienyl group, each of which is optionally substituted.

In the formula (0), $R^{30}$ is a hydrogen atom or a monovalent substituent having 1 or more and 40 or less carbon atoms. When $R^{30}$ is a monovalent substituent having 1 or more and 40 or less carbon atoms, the monovalent substituent of $R^{30}$ is not particularly limited, but examples thereof include an optionally substituted alkyl group having 1 or more and 40 or less carbon atoms, or an optionally substituted n conjugated group having 4 or more and 40 or less carbon atoms. Examples of the substituents which these alkyl group or n conjugated group may have include a carboxy group, an alkyloxycarbonyl group, an alkyl group, an aryl group, a halogen atom, a hydroxy group, a mercapto group, a sulfide group, a silyl group, a silanol group, a nitro group, a nitroso group, a sulfonato group, a phosphino group, a phosphinyl group, a phosphonato group, or the like. $R^{30}$ is preferably an alkyl group which may have a substituent, and preferably a monovalent group represented by the following formula (0-1).

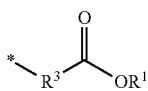
(0-1)

In the formula (0-1), $R^1$ is a hydrogen atom or an alkyl group; $R^3$ is an optionally substituted alkylene group; and * represents a bond.

In the formula (0-1), $R^1$ is a hydrogen atom or an alkyl group. When $R^1$ is an alkyl group, the alkyl group may be a linear alkyl group or a branched alkyl group. The number of carbon atoms of the alkyl group is not particularly limited, but it is preferably 1 or more and 20 or less, preferably 1 or more and 10 or less, and more preferably 1 or more and 5 or less.

Specific examples of the alkyl group suitable as $R^1$ include a methyl group, an ethyl group, an n-propyl group, an isopropyl group, an n-butyl group, an isobutyl group, an sec-butyl group, a tert-butyl group, an n-pentyl group, an isopentyl group, a tert-pentyl group, an n-hexyl group, an n-heptyl group, an n-octyl group, a 2-ethyl-n-hexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group.

In the formula (0-1), $R^3$ is an optionally substituted alkylene group. The substituent, which an alkylene group may have, is not particularly limited, without interfering with the object of the present invention. Specific examples of the substituent, which an alkylene group may have, include a hydroxy group, an alkoxy group, an amino group, a cyano group, a halogen atom, and the like. The alkylene group may be either a linear alkylene group or a branched alkylene group, and is preferably a linear alkylene group. The number of carbon atoms of the alkylene group is not particularly limited, but is preferably 1 or more and 20 or less, more preferably 1 or more and 10 or less, and still more preferably 1 or more and 5 or less, and a methylene group is particularly preferable. In the formula (0-1), $R^3$ is an optionally substituted alkylene group.

The alkoxy group as the substituent bonded to the alkylene group may be either a linear alkoxy group or a branched alkoxy group. The number of carbon atoms of the alkoxy group as the substituent is not particularly limited, but is preferably 1 or more and 10 or less, more preferably 1 or more and 6 or less, and particularly preferably 1 or more and 3 or less.

The amino group as the substituent bonded to the alkylene group may be a monoalkylamino group or a dialkylamino group. The alkyl group included in the monoalkylamino group or dialkylamino group may be either a linear alkyl group or a branched alkyl group. The number of carbon atoms of the alkyl group included in the monoalkylamino group or dialkylamino group is not particularly limited, but is preferably 1 or more and 10 or less, more preferably 1 or more and 6 or less, and particularly preferably 1 or more and 3 or less.

Specific examples of the alkylene group suitable as $R^3$ include a methylene group, an ethane-1,2-diyl group, an n-propane-1,3-diyl group, an n-propane-2,2-diyl group, an n-butane-1,4-diyl group, an n-pentane-1,5-diyl group, an n-hexane-1,6-diyl group, an n-heptane-1,7-diyl group, an n-octane-1,8-diyl group, an n-nonane-1,9-diyl group, an n-decane-1,10-diyl group, an n-undecane-1,11-diyl group, an n-dodecane-1,12-diyl group, an n-tridecane-1,13-diyl group, an n-tetradecane-1,14-diyl group, an n-pentadecane-1,15-diyl group, an n-hexadecane-1,16-diyl group, an n-heptadecane-1,17-diyl group, an n-octadecane-1,18-diyl group, an n-nonadecane-1,19-diyl group, and an n-icosane-1,20-diyl group.

In the formula (0), $R^4$ is a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group, and n is an integer of 0 or more and 3 or less. When n is an integer of 2 to 3, plural $R^4$(s) may be the same or different.

When $R^4$ is an organic group, the organic group is the same as an organic group, which an aromatic group may have as a substituent, as for $R^2$.

When $R^4$ is an organic group, the organic group is preferably an alkyl group, an aromatic hydrocarbon group, and an aromatic heterocyclic group. The alkyl group is preferably a linear or branched alkyl group having 1 or more and 8 or less carbon atoms, and more preferably a methyl group, an ethyl group, an n-propyl group, and an isopropyl group. The aromatic hydrocarbon group is preferably a phenyl group, a naphthyl group, a biphenylyl group, an anthryl group, and a phenanthrenyl group, more preferably a phenyl group and a naphthyl group, and particularly preferably a phenyl group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzimidazolyl group, and more preferably a furyl group and a thienyl group.

When $R^4$ is an alkyl group, the position of the alkyl group bonding on an imidazole ring is preferably any one of 2-, 4-, and 5-positions, and more preferably 2-position. When $R^4$ is an aromatic hydrocarbon group and an aromatic heterocyclic group, the position of these groups bonding on imidazole is preferably 2-position.

Among the compounds represented by the above-mentioned formula (0), in view of the excellent effect of the present invention, the compound is preferably a compound represented by the following formula (0-1-1), and more preferably a compound represented by the formula (0-1-1) wherein $R^{30}$ is the above-mentioned formula (0-1).

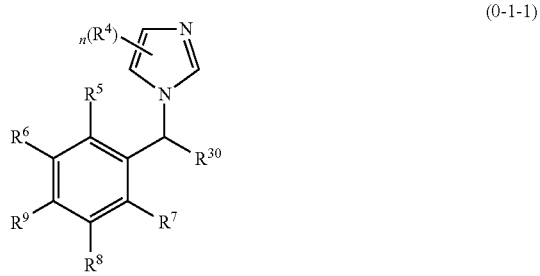

(0-1-1)

In the formula (0-1-1), $R^{30}$, $R^4$, and n are the same as those defined in the formula (0); and $R^5$, $R^6$, $R^7$, $R^8$, and $R^9$ are each independently a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group.

In the formula (0-1-1), at least one of $R^5$, $R^6$, $R^7$, $R^8$, and $R^9$ is preferably a group other than a hydrogen atom in view of the solvent solubility and the like. When $R^5$, $R^6$, $R^7$, $R^8$, and $R^9$ are organic groups, the organic group is the same as an organic group, which $R^2$ in the formula (0) has as a substituent. $R^5$, $R^6$, $R^7$, and $R^8$ are preferably hydrogen atoms in view of solubility of an imidazole compound in solvent.

Among these, at least one of $R^5$, $R^6$, $R^7$, $R^8$, and $R^9$ is preferably the following substituent; and $R^9$ is particularly preferably the following substituent. When $R^9$ is the following substituent, $R^5$, $R^6$, $R^7$, and $R^8$ are preferably hydrogen atom.

($R^{10}$ is a hydrogen atom or an organic group.)

When $R^{10}$ is an organic group, the organic group is the same as an organic group, which $R^2$ in the formula (0) has as a substituent. $R^{10}$ is preferably an alkyl group, more preferably, an alkyl group having 1 or more and 8 or less carbon atoms, particularly preferably an alkyl group having 1 or more and 3 or less carbon atoms, and most preferably a methyl group.

Among the compounds represented by the formula (0-1-1) mentioned above, a compound represented by the following formula (0-1-1-1) is preferable.

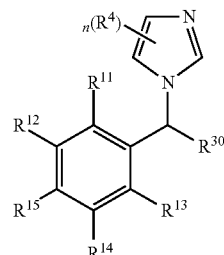

(0-1-1-1)

In the formula (0-1-1-1), $R^{30}$, $R^4$, and n are the same as those defined in the formula (0); and $R^{11}$, $R^{12}$, $R^{13}$, $R^{14}$, and $R^{15}$ are each independently a hydrogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group.

In the formula (0-1-1-1), at least one of $R^{11}$, $R^{12}$, $R^{13}$, $R^{14}$, and $R^{15}$ is preferably a group other than a hydrogen atom. Among the compounds represented by the formula (0-1-1-1), at least one of $R^{11}$, $R^{12}$, $R^{13}$, $R^{14}$, and $R^{15}$ is preferably represented by the above-mentioned —O—$R^{10}$; and $R^{15}$ is particularly preferably a group represented by —O—$R^{10}$. When $R^{15}$ is a group represented by —O—$R^{10}$, $R^{11}$, $R^{12}$, $R^{13}$, and $R^{14}$ are preferably hydrogen atoms.

The method for synthesizing the above-mentioned compound represented by the formula (0) is not particularly limited. For example, imidazolylation is performed by reacting a halogen-containing carboxylic acid derivative represented by the following formula (I) with an imidazole compound represented by the following formula (II) in accordance with a conventional method, thereby making it possible to synthesize the above-mentioned compound represented by the formula (0).

(I)

(II)

In the formulas (I) and (II), $R^2$, $R^{30}$, $R^4$, and n are the same as those defined in the formula (0). In the formula (I), Hal is a halogen atom.

Suitable specific examples of the compound represented by the formula (0) include the following.

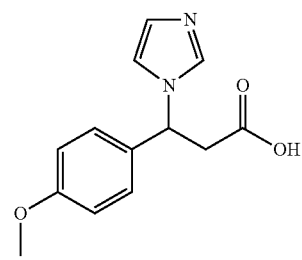

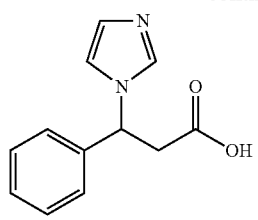
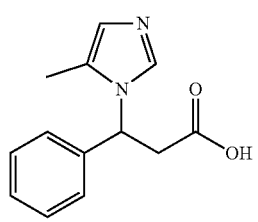
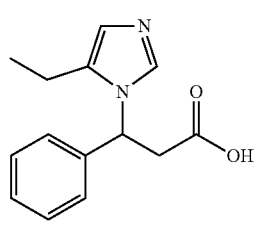
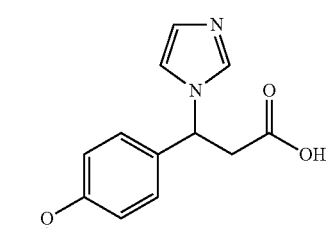
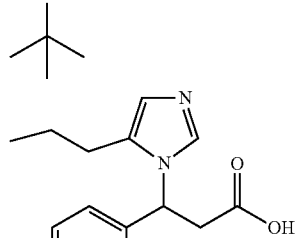
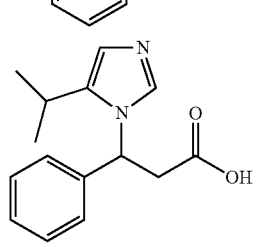
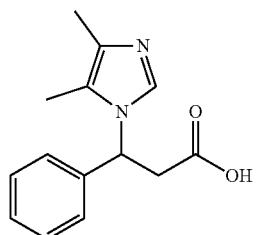
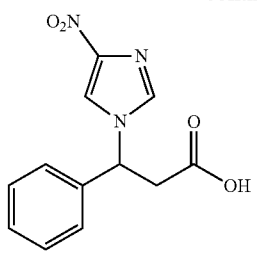
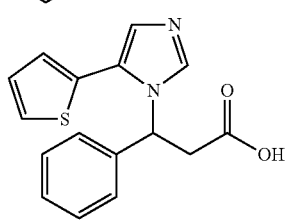
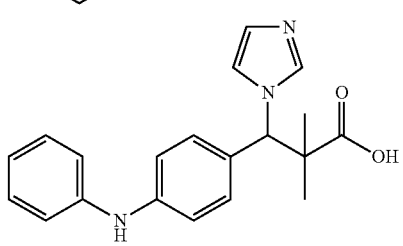
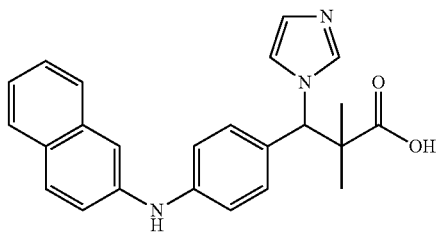
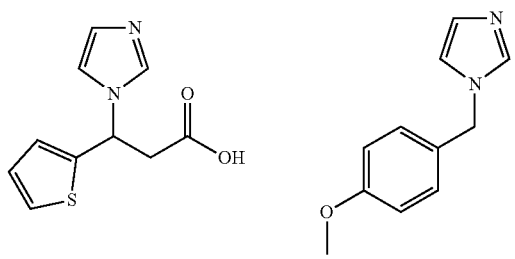
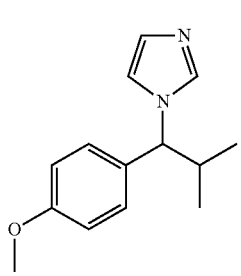
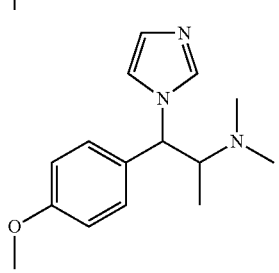

-continued

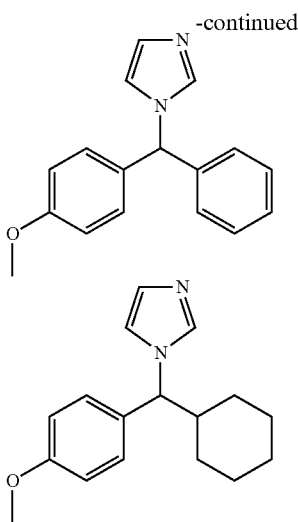

<<Hydrogen Barrier Film Forming Composition>>

A hydrogen barrier film forming composition includes a base material component (A) and the hydrogen barrier agent (B) mentioned above. Hereinafter, components that can be contained in the hydrogen barrier film forming composition, and suitable compositions as the hydrogen barrier film forming composition are described.

<Base Material Component (A)>

A base material component (A) is a component that imparts, to a hydrogen barrier film forming composition, film-forming property capable of forming a film having a desired shape as it is by a well-known method such as a melt process method, or film-forming property capable of forming a film having a desired shape by treatment such as exposure, heating, and reaction with water. The base material component (A) is not particularly limited as long as it is a material capable of giving desired film-forming property to the hydrogen barrier film forming composition. As the base material component (A), typically, a resin material including a high molecular compound, a thermosetting material hardened when a high molecular compound is generated by cross-linking by heating, or chemical modification such as intramolecular cyclization is generated by heating, a photo-polymerizable compound capable of being hardened by exposure, and a hydrolytic condensable silane compound in which hydrolytic condensation occurs by water content in the composition or in the atmosphere are used. Examples of the hydrolytic condensable silane compound include an alkoxysilane compound such as tetramethoxy silane, tetraethoxy silane, methyl trimethoxy silane, ethyl trimethoxy silane, methyl triethoxy silane, ethyl triethoxy silane, phenyl trimethoxy silane, phenyl triethoxy silane, dimethyl dimethoxy silane, diethyl dimethoxy silane, dimethyl diethoxy silane, diethyl diethoxy silane, diphenyl dimethoxy silane, and diphenyl diethoxy silane. The hydrolytic condensable silane compound may be a hydrolytic condensate of these silane compounds.

[Resin Material]

Examples of resin material as base material component (A) include polyacetal resin, polyamide resin, polycarbonate resin, polyester resin (polybutylene terephthalate, polyethylene terephthalate, polyethylene naphthalate, polyarylate, etc.), FR-AS resin, FR-ABS resin, AS resin, ABS resin, polyphenylene oxide resin, polyphenylene sulfide resin, polysulfone resin, polyether sulfone resin, polyetherether ketone resin, fluorinated resins, polyimide resin, polyamideimide resin, polyamidebismaleimide resin, polyetherimide resin, polybenzoxazole resin, polybenzothiazole resin, polybenzimidazole resin, silicone resin, BT resin, polymethylpentene, ultra high molecular weight polyethylene, FR-polypropylene, (meth)acrylic resin (for example, polymethylmethacrylate), polystyrene, and the like.

When a resin material is used as the base material component (A), a hydrogen barrier film is produced by forming a film from a resin material in which a predetermined amount of the above-mentioned hydrogen barrier agent (B) is blended with the resin material, by employing a desired method among conventionally known film formation methods. Examples of the film formation methods include melting processing methods such as a T-die method (a casting method), an inflation method, and a pressing method, a casting method using a solution, and the like. In the casting method, a solution including a resin material and the hydrogen barrier agent (B) are applied or cast on the substrate to form a film including a solution, followed by removing the solvent from the film by heating or the like. Thus, a hydrogen barrier film is formed. The hydrogen barrier film obtained by using a resin material may be subjected to drawing treatment such as uniaxial drawing and biaxial drawing, if necessary.

When the above-mentioned resin material is used as the base material component (A), the hydrogen barrier film forming composition may include additives and reforming agents, such as an antioxidant, an ultraviolet absorber, a flame retardant, a mold release agent, a plasticizer, a filler, and a reinforcement material, if necessary. Furthermore, when the hydrogen barrier film forming composition is a composition for casting, the hydrogen barrier film forming composition may include a solvent. Types of the solvent are appropriately selected depending on the types of resin materials.

When the hydrogen barrier film forming composition includes the above-mentioned resin material and the hydrogen barrier agent (B), the content of the hydrogen barrier agent is 0.01 mass % or more and 30 mass % or less, more preferably 0.05 mass % or more and 20 mass % or less, and particularly preferably 0.1 mass % or more 10 mass % or less with respect to the mass of the resin material of the hydrogen barrier film forming composition.

[Thermosetting Material]

As the thermosetting material, precursor materials of conventionally widely used various thermosetting resins are used. Specific examples of the thermosetting resin include a phenol resin, an epoxy resin, an oxetane resin, a melamine resin, a urea resin, an unsaturated polyester resin, an alkyd resin, a polyurethane resin, a polyimide resin, a polybenzoxazole resin, a polybenzimidazole resin, or the like.

Furthermore, resins which cause an aromatic ring formation reaction in molecules and/or a cross-linking reaction between molecules are also suitably used as the thermosetting material. Hereinafter, resins which cause an aromatic ring formation reaction in molecules and/or a cross-linking reaction between molecules by heating may also be called a precursor resin.

Among them, because a hydrogen barrier film having excellent heat resistance, chemical resistance, mechanical property, and the like, can be easily formed, an epoxy resin precursor and a precursor resin are particularly preferable. Hereinafter, as to the thermosetting material, a particularly suitable precursor material as the base material component (A) will be described.

(Epoxy Resin Precursor)

As an epoxy resin precursor, conventionally widely known various epoxy compounds can be used. The molecular weight of such epoxy compounds is not particularly limited. Among the epoxy compounds, because a hydrogen barrier film having excellent heat resistance, chemical resistance, mechanical property, and the like, can be easily formed, a polyfunctional epoxy compound having two or more epoxy groups in a molecule is preferable.

The polyfunctional epoxy compound is not particularly limited as long as it is a di- or more functional epoxy compound. Examples of polyfunctional epoxy compound include difunctional epoxy resin such as bisphenol A type epoxy resin, bisphenol S type epoxy resin, bisphenol AD type epoxy resin, naphthalene type epoxy resin, and biphenyl type epoxy resin; glycidyl ester type epoxy resin such as dimer acid glycidyl ester and triglycidyl ester; glycidyl amine type epoxy resin such as tetraglycidyl aminodiphenylmethane, triglycidyl-p-aminophenol, tetraglycidyl metaxylylenediamine, and tetraglycidyl bisaminomethylcyclohexane; heterocyclic epoxy resin such as triglycidyl isocyanurate; trifunctional epoxy resin such as phloroglucinol triglycidylether, trihydroxybiphenyl triglycidylether, trihydroxyphenylmethane triglycidylether, glycerin triglycidylether, 2-[4-(2,3-epoxypropoxy)phenyl-2-[4-[1,1-bis[4-(2,3-epoxypropxy)phenyl]ethyl]phenyl]propane, and 1,3-bis[4-[1-[4-(2,3-epoxypropoxy)phenyl]-1-[4-[1-[4-(2,3-epoxypropoxy)phenyl]-1-methylethyl]phenyl]ethyl]phenoxy]-2-propanol; and tetrafunctional epoxy resin such as tetrahydroxyphenylethane tetraglycidylether, tetraglycidyl benzophenone, bisresorcinol tetraglycidylether, and tetraglycidoxybiphenyl.

Furthermore, an alicyclic epoxy compound is also preferable as the polyfunctional epoxy compound from the viewpoint of providing a cured product having high hardness. Specific examples of the aliphatic epoxy compound having an alicyclic epoxy group include 2-(3,4-epoxycyclohexyl-5,5-spiro-3,4-epoxy)cyclohexane-meta-dioxane, bis(3,4-epoxycyclohexylmethyl)adipate, bis(3,4-epoxy-6-methylcyclohexylmethyl)adipate, 3,4-epoxy-6-methylcyclohexyl-3',4'-epoxy-6'-methylcyclohexane carboxylate, ε-caprolactone-modified 3,4-epoxycyclohexylmethyl-3',4'-epoxycyclohexane carboxylate, trimethylcaprolactone-modified 3,4-epoxycyclohexylmethyl-3',4'-epoxycyclohexane carboxylate, β-methyl-δ-valerolactone-modified 3,4-epoxycyclohexylmethyl-3',4'-epoxycyclohexane carboxylate, methylenebis(3,4-epoxycyclohexane), di(3,4-epoxycyclohexylmethyl)ether of ethylene glycol, ethylenebis(3,4-epoxycyclohexane carboxylate), dioctyl epoxycyclohexahydrophthalate, di-2-ethylhexyl epoxycyclohexahydrophthalate, an epoxy resin having a tricyclodecene oxide group, and a compound represented by the following formulae (a01-1) to (a01-5).

Among these specific examples of the alicyclic epoxy compound, an alicyclic epoxy compound represented by any one of the following formulae (a01-1) to (a01-5) is preferable, since it gives a cured article which is excellent in transparency and also has high hardness.

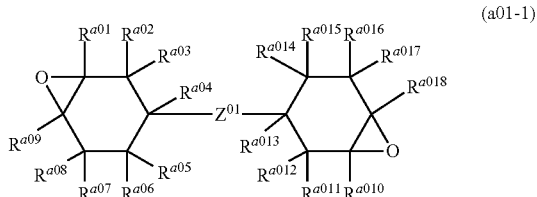

(a01-1)

In the formula (a01-1), $Z^{01}$ is a single bond or a bridging group (divalent group having one or more atoms). $R^{a01}$ to $R^{a018}$ are each independently a group selected from the group consisting of a hydrogen atom, a halogen atom and an organic group.

Example of bridging group $Z^{01}$ includes a divalent group selected form the group consisting of a divalent hydrocarbon group, —O—, —O—CO—, —S—, —SO—, —SO$_2$—, —CBr$_2$—, —C(CBr$_3$)$_2$—, —C(CF$_3$)$_2$—, and —R$^{a019}$—O—CO— or a group formed by bonding plural of these divalent groups.

When the bridging group $Z^{01}$ is a divalent hydrocarbon group, example of the hydrocarbon group includes a linear or branched alkylene group having 1 or more and 18 or less carbon atoms, a divalent alicyclic hydrocarbon group and the like. The linear or branched alkylene group having 1 or more and 18 or less carbon atoms includes, for example, a methylene group, a methylmethylene group, a dimethylmethylene group, a dimethylene group, a trimethylene group, and the like. Above described divalent alicyclic hydrocarbon group includes, for example, a cycloalkylene group (including a cydlohexylidene group) such as a 1,2-cyclopentylene group, a 1,3-cyclopentylene group, a cyclopentylidene group, a 1,2-cyclohexylene group, 1,3-cyclohexylene group, 1,4-cyclohexylene group, and a cyclohexylidene group.

$R^{a019}$ is an alkylene group having 1 or more and 8 or less carbon atoms and preferably a methylene group of an ethylene group.

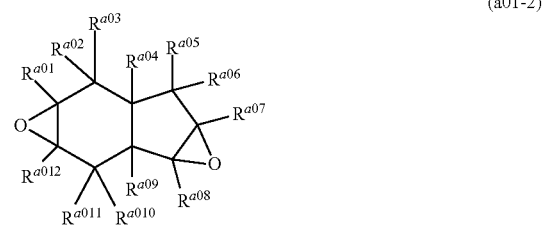

(a01-2)

In the formula (a01-2), $R^{a01}$ to $R^{a012}$ each independently represent a group selected from the group consisting of a hydrogen atom, a halogen atom, and an organic group.

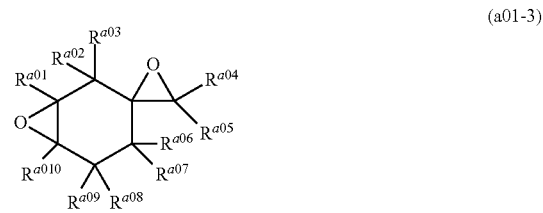

(a01-3)

In the formula (a01-3), $R^{a01}$ to $R^{a010}$ each independently represent a group selected from the group consisting of a hydrogen atom, a halogen atom, and an organic group. $R^{a02}$ and $R^{a08}$ may be combined to each other.

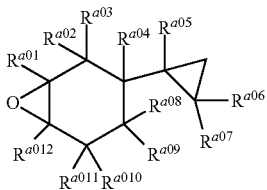

(a01-4)

In the formula (a01-4), $R^{a01}$ to $R^{a012}$ each independently represent a group selected from the group consisting of a hydrogen atom, a halogen atom, and an organic group. $R^{a02}$ and $R^{a010}$ may be combined to each other.

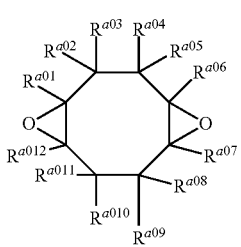

(a01-5)

In the formula (a01-5), $R^{a01}$ to $R^{a012}$ each independently represent a group selected from the group consisting of a hydrogen atom, a halogen atom, and an organic group.

In the formulae (a01-1) to (a01-5), when $R^{a01}$ to $R^{a018}$ are organic groups, the organic group is not particularly limited as long as the object of the present invention is not impaired, and may be a hydrocarbon group, or a group consisting of a carbon atom and a halogen atom, or a group having heteroatoms such as a halogen atom, an oxygen atom, a sulfur atom, a nitrogen atom, and a silicon atom, together with a carbon atom and a hydrogen atom. Examples of the halogen atom include a chlorine atom, a bromine atom, an iodine atom, and a fluorine atom.

The organic group is preferably a group consisting of a hydrocarbon group, a group consisting of a carbon atom, a hydrogen atom, and an oxygen atom; a halogenated hydrocarbon group, a group consisting of a carbon atom, an oxygen atom, and a halogen atom; and a group consisting of a carbon atom, a hydrogen atom, an oxygen atom, and a halogen atom. When the organic group is a hydrocarbon group, the hydrocarbon group may be an aromatic hydrocarbon group, or an aliphatic hydrocarbon group, or a group including an aromatic skeleton and an aliphatic skeleton. The number of carbon atoms of the organic group is preferably 1 or more and 20 or less, more preferably 1 or more and 10 or less, and particularly preferably 1 or more and 5 or less.

Specific examples of the hydrocarbon group include chain alkyl groups such as a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethylhexyl group, an n-nonyl group, an n-decyl group, an n-undecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; chain alkenyl groups such as a vinyl group, a 1-propenyl group, a 2-n-propenyl group(allyl group), a 1-n-butenyl group, a 2-n-butenyl group, and a 3-n-butenyl group; cycloalkyl groups such as a cyclopropyl group, a cyclobutyl group, a cyclopentyl group, a cyclohexyl group, and a cycloheptyl group; aryl groups such as a phenyl group, an o-tolyl group, an m-tolyl group, a p-tolyl group, an α-naphthyl group, a β-naphthyl group, a biphenyl-4-yl group, a biphenyl-3-yl group, a biphenyl-2-yl group, an anthryl group, and a phenanthryl group; and aralkyl groups such as a benzyl group, a phenethyl group, an α-naphthylmethyl group, a β-naphthylmethyl group, an α-naphthylethyl group, and a β-naphthylethyl group.

Specific examples of the halogenated hydrocarbon group include halogenated chain alkyl groups such as a chloromethyl group, a dichloromethyl group, a trichloromethyl group, a bromomethyl group, a dibromomethyl group, a tribromomethyl group, a fluoromethyl group, a difluoromethyl group, a trifluoromethyl group, a 2,2,2-trifluoroethyl group, a pentafluoroethyl group, a heptafluoropropyl group, a perfluorobutyl group, and a perfluoropentyl group, a perfluorohexyl group, a perfluoroheptyl group, a perfluorooctyl group, a perfluorononyl group, and a perfluorodecyl group; halogenated cycloalkyl groups such as a 2-chlorocyclohexyl group, a 3-chlorocyclohexyl group, a 4-chlorocyclohexyl group, a 2,4-dichlorocyclohexyl group, a 2-bromocyclohexyl group, a 3-bromocyclohexyl group, and a 4-bromocyclohexyl group; halogenated aryl groups such as a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-bromophenyl group, a 3-bromophenyl group, a 4-bromophenyl group, a 2-fluorophenyl group, a 3-fluorophenyl group, and a 4-fluorophenyl group; and halogenated aralkyl groups such as a 2-chlorophenylmethyl group, a 3-chlorophenylmethyl group, a 4-chlorophenylmethyl group, a 2-bromophenylmethyl group, a 3-bromophenylmethyl group, a 4-bromophenylmethyl group, a 2-fluorophenylmethyl group, a 3-fluorophenylmethyl group, and a 4-fluorophenylmethyl group.

Specific examples of the group consisting of a carbon atom, a hydrogen atom, and an oxygen atom include hydroxy chain alkyl groups such as a hydroxymethyl group, a 2-hydroxyethyl group, a 3-hydroxy-n-propyl group, and a 4-hydroxy-n-butyl group; halogenated cycloalkyl groups such as a 2-hydroxycyclohexyl group, a 3-hydroxycyclohexyl group, and a 4-hydroxycyclohexyl group; hydroxyaryl groups such as a 2-hydroxyphenyl group, a 3-hydroxyphenyl group, a 4-hydroxyphenyl group, a 2,3-dihydroxyphenyl group, a 2,4-dihydroxyphenyl group, a 2,5-dihydroxyphenyl group, a 2,6-dihydroxyphenyl group, a 3,4-dihydroxyphenyl group, and a 3,5-dihydroxyphenyl group; hydroxyaralkyl groups such as a 2-hydroxyphenylmethyl group, a 3-hydroxyphenylmethyl group, and a 4-hydroxyphenylmethyl group; chain alkoxy groups such as a methoxy group, an ethoxy group, an n-propoxy group, an isopropoxy group, an n-butyloxy group, an isobutyloxy group, a sec-butyloxy group, a tert-butyloxy group, an n-pentyloxy group, an n-hexyloxy group, an n-heptyloxy group, an n-octyloxy group, a 2-ethylhexyloxy group, an n-nonyloxy group, an n-decyloxy group, an n-undecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, and an n-icosyloxy group; chain alkenyloxy groups such as a vinyloxy group, a 1-propenyloxy group, a 2-n-propenyloxy group (allyloxy group), a 1-n-butenyloxy group, a 2-n-butenyloxy group, and a 3-n-butenyloxy group; aryloxy groups such as a phenoxy group, an o-tolyloxy group, an m-tolyloxy group, a p-tolyloxy group, an α-naphthyloxy group, a β-naphthyloxy group, a biphenyl-4-yloxy group, a biphenyl-3-yloxy group, a biphenyl-2-yloxy group, an anthryloxy group, and a phenanthryloxy group; aralkyloxy groups such as a benzyloxy group, a phenethyloxy group, an α-naphthylmethyloxy group, a β-naphthylmethyloxy group, an α-naphthylethyloxy group, and a β-naphthylethyloxy group; alkoxyalkyl groups such as a methoxymethyl group, an ethoxymethyl group, an n-propoxymethyl group, a 2-methoxyethyl group, a 2-ethoxyethyl group, a 2-n-propoxyethyl group, a 3-methoxy-n-propyl group, a 3-ethoxy-n-propyl group, a 3-n-propoxy-n-propyl group, a 4-methoxy-n-butyl group, a 4-ethoxy-n-butyl group, and a 4-n-propoxy-n-butyl group; alkoxyalkoxy groups such as a methoxymethoxy group, an ethoxymethoxy group, an n-propoxymethoxy group, a 2-methoxyethoxy group, a 2-ethoxyethoxy group, a 2-n-propoxyethoxy group, a 3-methoxy-n-propoxy group, a 3-ethoxy-n-propoxy group, a 3-n-propoxy-n-propoxy group, a 4-methoxy-n-butyloxy group, a 4-ethoxy-n-butyloxy group, and a 4-n-propoxy-n-butyloxy group; alkoxyaryl groups such as a 2-methoxyphenyl group, a 3-methoxyphenyl group, and a 4-methoxyphenyl group; alkoxyaryloxy groups such as a 2-methoxyphenoxy group, a 3-methoxyphenoxy group, and a 4-methoxyphenoxy group; aliphatic acyl groups such as a formyl group, an acetyl group, a propionyl group, a butanoyl group, a pentanoyl group, a hexanoyl group, a heptanoyl group, an octanoyl group, a nonanoyl group, and a decanoyl group; aromatic acyl groups such as a benzoyl group, an α-naphthoyl group, and a β-naphthoyl group; chain alkyloxycarbonyl groups such as a methoxycarbonyl group, an ethoxycarbonyl group, an n-propoxycarbonyl group, an n-butyloxycarbonyl group, an n-pentyloxycarbonyl group, an n-hexylcarbonyl group, an n-heptyloxycarbonyl group, an n-octyloxycarbonyl group, an n-nonyloxycarbonyl group, and an n-decyloxycarbonyl group; aryloxycarbonyl groups such as a phenoxycarbonyl group, an α-naphthoxycarbonyl group, and a β-naphthoxycarbonyl group; aliphatic acyloxy groups such as a formyloxy group, an acetyloxy group, a propionyloxy group, a butanoyloxy group, a pentanoyloxy group, a hexanoyloxy group, a heptanoyloxy group, an octanoyloxy group, a nonanoyloxy group, and a decanoyloxy group; and aromatic acyloxy groups such as a benzoyloxy group, an α-naphthoyloxy group, and a β-naphthoyloxy group.

$R^{a01}$ to $R^{a018}$ are preferably each independently a group selected from the group consisting of a hydrogen atom, a halogen atom, an alkyl group having 1 or more and 5 or less carbon atoms, and an alkoxy group having 1 or more and 5 or less carbon atoms and, particularly, all $R^{a01}$ to $R^{a018}$ are more preferably hydrogen atoms in view of the fact that a cured article obtained by using a curable composition has excellent mechanical properties.

In the formulae (a01-2) to (a01-5), $R^{a01}$ to $R^{a012}$ are the same as $R^{a01}$ to $R^{a012}$ in the formula (a01-1). In the formula (a01-2) and the formula (a01-4), the divalent group formed when $R^{a02}$ and $R^{a010}$ are combined to each other includes, for example, —CH$_2$— and —C(CH$_3$)$_2$—. In the formula (a01-3), the divalent group formed when $R^{a02}$ and $R^{a08}$ are combined to each other includes, for example, —CH$_2$— and —C(CH$_3$)$_2$—.

Specific examples of a suitable compound for the alicyclic epoxy compounds represented by the formula (a01-1) include alicyclic epoxy compounds represented by the following formulae (a01-1a), (a01-1b) and (a01-1c), 2,2-bis(3, 4-epoxycyclohexane-1-yl)propane [=2,2-bis(3,4-epoxy-epoxycyclohexyl)propane], and the like.

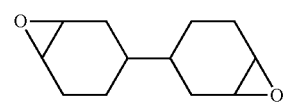

(a01-1a)

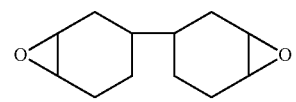

(a01-1b)

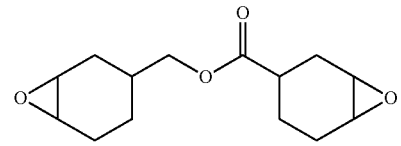

(a01-1c)

Specific examples of suitable compound for the alicyclic epoxy compounds represented by the formula (a01-2) include bicyclononadiene diepoxide represented by the following formula (a01-2a), or dicyclononadiene diepoxide, and the like.

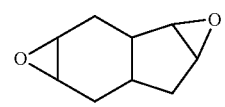

(a01-2a)

Specific examples of suitable compound for the alicyclic epoxy compounds represented by the formula (a01-3) include S-spiro[3-oxatricyclo[3.2.1.0$^{2,4}$]octane-6,2'-oxirane], and the like.

Specific examples of suitable compound for the alicyclic epoxy compounds represented by the formula (a1-04) include 4-vinylcyclohexene dioxide, dipentene dioxide, limonene dioxide, 1-methyl-4-(3-methyloxirane-2-yl)-7-oxabicyclo[4.1.0]heptane, and the like.

Specific examples of suitable compound for the alicyclic epoxy compounds represented by the formula (a01-5) include 1,2,5,6-diepoxycyclooctane, and the like.

[Precursor Resin]

The base material component (A) is preferably a precursor resin which causes an aromatic ring formation reaction in molecules, and/or a cross-linking reaction between molecules by heating.

With the aromatic ring formation reaction in a molecule, a structure of a molecular chain constituting resin becomes rigid, so that a hydrogen barrier film having excellent heat resistance and mechanical property can be formed. Examples of the preferable reactions among the aromatic ring formation reactions in a molecule include reactions shown by the following formulae (I) to (VI). Note here that the reactions in the following formulae are only examples of the aromatic ring formation reaction, and structures of the resin used as the base material component (A) and causing the aromatic ring formation reaction in molecules by heating are not limited to the structures of the precursor polymers shown in the following formulae.

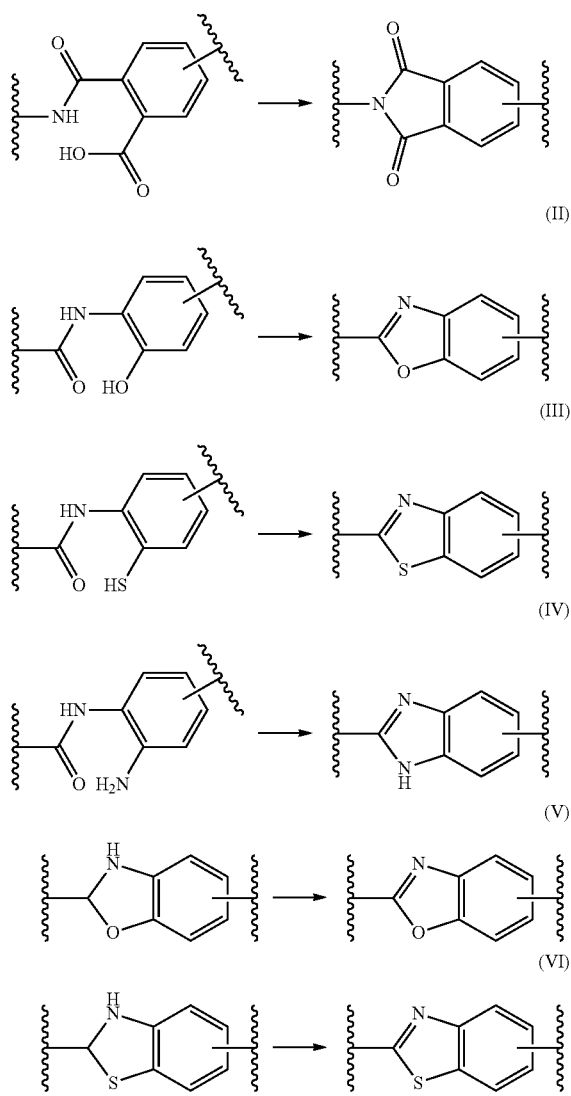

(Resin Including Group Selected from Hydroxy Group, Carboxylic Acid Anhydride Group, Carboxy Group, and Epoxy Group)

With the crosslinking reaction between molecules, molecular chains constituting resin are crosslinked to each other, and a three-dimensional crosslinked structure is formed. Therefore, when resin which causes crosslinking reaction by heating and which includes a group selected from a hydroxy group, a carboxylic acid anhydride group, a carboxy group, and an epoxy group in a molecule is used as the base material component (A), a hydrogen barrier film having excellent heat resistance and mechanical property can be obtained.

When a resin having a hydroxy group is used, with the action of a dehydration-condensation agent, crosslink is generated between molecules contained in the resin by dehydration condensation between hydroxy groups. Furthermore, since the hydroxy group includes an active hydrogen atom and is highly reactive, it is reacted with various crosslinking agents, thereby providing a cured product including a crosslinked resin.

When resin including a carboxylic acid anhydride group, carboxy groups generated by hydrolysis of acid anhydride groups are crosslinked by dehydration condensation by the action of the dehydration-condensation agent. Furthermore, since the acid anhydride group itself is also highly reactive, for example, a cured product including crosslinked resin is provided by using crosslinking agents such as polyol having two or more hydroxy groups and polyamine having two or more amino groups, and the like.

When a resin having a carboxy group is used, with the action of a dehydration-condensation agent, molecules contained in the resin are cross-linked by dehydration condensation between carboxy groups. Furthermore, crosslink can be carried out by using a crosslinking agent having a functional group capable of being reacted with a carboxy group, for example, an isocyanate group.

When a resin having an epoxy group is used, by using a well-known curing accelerator and the like, if necessary, molecules included in the resin are cross-linked by the polyaddition reaction between the epoxy groups.

Examples of the resin having a hydroxy group in a molecule include a novolak resin. The novolak resin is not particularly limited, but it is preferably a resin obtained by condensation-reacting 0.5 mol or more and 1.0 mol or less of condensation agent such as formaldehyde or paraformaldehyde relative to 1 mol of phenols in the presence of an acidic catalyst.

Examples of the phenols include phenol; cresols such as o-cresol, m-cresol, and p-cresol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; alkylphenols such as 2-isopropylphenol, 3-isopropylphenol, 4-isopropylphenol, o-butylphenol, m-butylphenol, p-butylphenol, and p-tert-butylphenol; trialkylphenols such as 2,3,5-trimethylphenol, and 3,4,5-trimethylphenol; polyhydric phenol such as resorcinol, catechol, hydroquinone, hydroquinone monomethylether, pyrogallol, and phloroglucinol; alkyl polyhydric phenols such as alkylresorcinol, alkylcatechol, and alkylhydroquinone (number of carbon atoms of alkyl group included in the alkyl polyhydric phenols is 1 or more and 4 or less); α-naphthol; β-naphthol; hydroxydiphenyl; and bisphenol A. These phenols can be used alone or in combination of two or more types thereof.

Among phenols, m-cresol and p-cresol are preferable, and a combination of m-cresol and p-cresol is more preferable. By adjusting the blending ratio of both m-cresol and p-cresol, various properties such as sensitivity of photoresist and heat resistance can be adjusted. The blending ratio of m-cresol and p-cresol is not particularly limited, but the blending ratio of m-cresol/p-cresol is preferably 3/7 or more and 8/2 or less (mass ratio). When the ratio of m-cresol is less than the above-mentioned lower limit value, the sensitivity may be deteriorated, and when the ratio is beyond the above-mentioned upper limit value, the heat resistance may be deteriorated.

Examples of the acid catalyst to be used for producing a novolak resin include inorganic acids such as hydrochloric acid, sulfuric acid, nitric acid, phosphoric acid, and phosphorous acid; organic acids such as formic acid, oxalic acid, acetic acid, diethyl sulfuric acid, and paratoluene sulfonic acid; metal salts such as zinc acetate, and the like. These acid catalysts can be used alone or in combination of two or more types thereof.

The mass average molecular weight of the novolak resin based on polystyrene by gel permeation chromatography (GPC) measurement is preferably 1000 or more and 50000 or less.

Preferable resin including a carboxylic acid anhydride group in a molecule is a copolymer obtained by polymerizing a mixture of a monomer including an unsaturated double bond, monomers including at least one monomer selected from maleic anhydride, citraconic anhydride, and itaconic anhydride. As such a polymer, a styrene-maleic acid copolymer is preferable.

Preferable resin having a carboxy group in a molecule includes resin obtained by hydrolyzing an acid anhydride group in the resin having a carboxylic acid anhydride group in the above-mentioned molecule, or a copolymer obtained by polymerizing a mixture of monomers including one or more monomers selected from (meth)acrylic acid, crotonic acid, maleic acid, fumaric acid, citraconic acid, mesaconic acid, and itaconic acid, and having an unsaturated double bond.

An epoxy group-containing resin having an epoxy group in a molecule will be described later in detail.

Among such compounds which cause an aromatic ring formation reaction in molecules, or crosslinking reaction between molecules, because a hydrogen barrier film having excellent heat resistance can be easily formed, polyamic acid, a polybenzoxazole precursor, a polybenzothiazole precursor, a polybenzimidazole precursor, a styrene-maleic acid copolymer, and an epoxy group-containing resin are preferable. These resins are described below.

[Polyimide Resin Precursor]

Examples of the polyimide resin precursor include polyamic acid. As the base material component (A), a hydrogen barrier film forming composition containing polyamic acid is formed as a film, and then, the formed film is heated in the presence of an imidization agent if necessary. Thus, a hydrogen barrier film including a polyimide resin and having excellent heat resistance is formed.

Molecular weight (mass average molecular weight) of the polyamic acid is preferably 5,000 or more and 30,000 or less, and more preferably 10,000 or more and 20,000 or less. Use of polyamic acid having a mass average molecular weight in such a range makes it easy to form a hydrogen barrier film having excellent heat resistance. As a preferred polyamic acid, polyamic acid consisting of a constituent unit represented by the following formula (A1) can be exemplified.

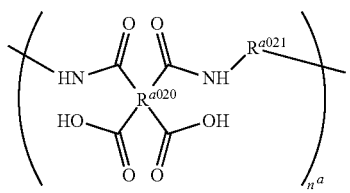

(A1)

In the formula (A1), $R^{a020}$ is a tetravalent organic group; $R^{a021}$ is a divalent organic group; and $n^a$ is the number of repetitions of the constituent unit represented by the formula (A1).

In the formula (A1), the number of carbon atoms of $R^{a020}$ and $R^{a021}$ is preferably 2 or more and 50 or less, and more preferably 2 or more and 30 or less. Each of $R^{a020}$ and $R^{a021}$ can be either an aliphatic group, an aromatic group, or a group with a combination of these structures. The tetravalent aromatic group is same as below-mentioned $R^{a022}$. $R^{a020}$ and $R^{a021}$ can include, in addition to a carbon atom and a hydrogen atom, a halogen atom, an oxygen atom, and a sulfur atom. In a case in which $R^{a020}$ and $R^{a021}$ include an oxygen atom, a nitrogen atom or a sulfur atom, the oxygen atom, the nitrogen atom or the sulfur atom can be included in $R^{a020}$ and $R^{a021}$ as a group selected from: a nitrogen-containing heterocyclic group; —CONH—; —NH—; —N=N—; —CH=N—; —COO—; —O—; —CO—; —SO—; —SO$_2$—; —S—; and —S—S—, and more preferably included in $R^{a020}$ and $R^{a021}$ as a group selected from: —O—; —CO—; —SO—; —SO$_2$—; —S—; and —S—S—.

Polyamic acid is generally prepared by reacting a tetracarboxylic dianhydride component with a diamine component. Hereinafter, the tetracarboxylic dianhydride component and the diamine component used for preparation of the polyamic acid, and a manufacturing method of the polyamic acid are described.

(Tetracarboxylic Dianhydride Component)

The tetracarboxylic dianhydride component, which is a synthesis material for the polyamic acid, is not particularly limited as long as it can generate the polyamic acid by reacting with the diamine component. The tetracarboxylic dianhydride component can be appropriately selected from tetracarboxylic dianhydrides which are conventionally used as a synthesis material for the polyamic acid. The tetracarboxylic dianhydride component can be either an aromatic tetracarboxylic dianhydride or an aliphatic tetracarboxylic dianhydride. For example, The tetracarboxylic dianhydride component is an tetracarboxylic dianhydride represented by the following formula (a1-1). An aromatic tetracarboxylic dianhydride is preferable. The tetracarboxylic dianhydride component can be used either singly or in combination of two or more.

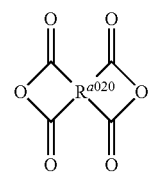

(a1-1)

In the formula (a1-1), $R^{a020}$ is the same as $R^{a020}$ in the formula (A1).

Specific examples of preferred aromatic tetracarboxylic dianhydride include: pyromellitic dianhydride; 3,3',4,4'-biphenyl tetra carboxylic dianhydride; 2,3,3',4'-biphenyl tetra carboxylic dianhydride; 3,3',4,4'-benzophenone tetra carboxylic dianhydride; 4,4'-oxydiphthalic anhydride; 3,3',4,4'-diphenyl sulfone tetra carboxylic dianhydride; and the like. Among these, 3,3',4,4'-biphenyl tetra carboxylic dianhydride is preferable from the viewpoint of price, availability, and the like. In addition, the photosensitive composition described in the fifth aspect may be selected.

(Diamine Component)

The diamine component, which is a synthesis material for the polyamic acid, is not particularly limited as long as it can generate the polyamic acid by reacting with the tetracarboxylic dianhydride component. The diamine component can be appropriately selected from diamines which are conventionally used as a synthesis material for the polyamic acid. For example, the diamine component is a diamine component represented by the following formula (a1-2) or a diamine capable of providing a below-mentioned $Y^d$. The diamine component can be either an aromatic diamine or an aliphatic diamine; however, an aromatic diamine is preferable. The diamine component can be used either singly or in combination of two or more.

$$H_2N—R^{a021}—NH_2 \quad\quad (a1-2)$$

In the formula (a1-2), $R^{a021}$ is the same as $R^{a021}$ in the formula (A1).

Specific examples of preferred aromatic diamine include: p-phenylenediamine; m-phenylenediamine; 2,4-diamino toluene; 4,4'-diamino biphenyl; 4,4'-diamino-2,2'-bis (trifluoromethyl) biphenyl; 3,3'-diaminodiphenyl sulfone; 4,4'-diaminodiphenyl sulfone; 4,4'-diaminodiphenyl sulfide; 4,4'-diaminodiphenylmethane; 4,4'-diamino diphenyl ether; 3,4'-diamino diphenyl ether; 3,3'-diamino diphenyl ether; 1,4-bis (4-aminophenoxy) benzene; 1,3-bis (4-aminophenoxy) benzene; 1,3-bis (3-aminophenoxy) benzene; 4,4'-bis (4-aminophenoxy) biphenyl; bis[4-(4-aminophenoxy) phenyl] sulfone; bis[4-(3-aminophenoxy) phenyl] sulfone; 2,2-bis[4-(4-aminophenoxy) phenyl] propane; and 2,2-bis[4-(4-aminophenoxy) phenyl] hexafluoropropane; 9,9-bis(4-aminophenyl)-9H-fluorene; 9,9-bis(4-amino-3-methylphenyl)-9H-fluorene; 4,4'-[1,4-phenylenebis(1-methylethane-1,1-diyl)]dianiline; and the like. Among these, p-phenylenediamine, m-phenylenediamine, 2,4-diamino toluene, and 4,4'-diamino diphenyl ether are preferable from the viewpoint of price, availability, and the like. In addition, the photosensitive composition described in the fifth aspect may be selected.

(Manufacturing Method of Polyamic Acid)

The polyamic acid can be obtained by reacting the above described tetracarboxylic dianhydride component with the diamine component in solvent in which both of the components are soluble. Amounts of the tetracarboxylic dianhydride component and the diamine component to be used upon synthesis of the polyamic acid are not particularly limited. It is preferable to use 0.50 mole or more and 1.50 moles or less, and more preferable to use 0.60 moles or more and 1.30 moles or less, and particularly preferable to use 0.70 moles or more and 1.20 moles or less of the diamine component with respect to 1 mole of the tetracarboxylic dianhydride component.

Solvents which can be used for synthesis of the polyamic acid include, for example: aprotic polar organic solvents such as N,N,N',N'-tetramethyl urea, N-methyl-2-pyrrolidone, N,N-dimethylformamide, N,N-dimethylacetamide, hexamethylphosphoramide, 1,3-dimethyl-2-imidazolidinone and the γ-butyrolactone; and glycol ethers such as diethyleneglycol dialkyl ether, ethyleneglycol monoalkyl ether acetate, diethyleneglycol monoalkyl ether acetate, propylene glycol monoalkyl ether acetate and propylene glycol monoalkyl ether propionate. These solvents can be used independently, or by combining two or more types. Among these, it is preferable to use N,N,N',N'-tetramethyl urea.

An amount of the solvent to be used upon synthesis of the polyamic acid is not particularly limited as long as the polyamic acid of a desired molecular weight can be synthesized. Typically, the amount of the solvent to be used is preferably 100 parts by mass or more and 4000 parts by mass or less and more preferably 150 parts by mass or more and 2000 parts by mass or less with respect to 100 parts by mass of a combination of the tetracarboxylic dianhydride component and the diamine component.

The temperature at which the reaction between the tetracarboxylic dianhydride component and the diamine component is carried out is not particularly limited as long as the reaction proceeds preferably. Typically, the temperature at which the reaction between the tetracarboxylic dianhydride component and the diamine component is carried out is preferably −5° C. or higher and 150° C. or lower, more preferably 0° C. or higher and 120° C. or lower, and particularly preferably 0° C. or higher and 70° C. or lower. The duration of the reaction between the tetracarboxylic dianhydride component and the diamine component depends on the reaction temperature; however, the duration is preferably 1 hour or longer and 50 hours or shorter, more preferably 2 hours or longer and 40 hours or shorter, and particularly preferably 5 hours or longer and 30 hours or shorter.

With the above-mentioned method, a solution or paste of polyamic acid is obtained. Such a solution or paste may be used as it is for preparation of a hydrogen barrier film forming composition. Furthermore, a solid polyamic acid obtained by removing a solvent from the solution or paste of polyamic acid may be used for preparation of a hydrogen barrier film forming composition.

[Polybenzoxazole Precursor]

A polybenzoxazole precursor is produced typically by reacting aromatic diamine diol and a dicarbonyl compound having a specific structure with each other. Hereinafter, the aromatic diamine diol, the dicarbonyl compound, a solvent to be used for synthesis of the polybenzoxazole precursor, and a method for producing the polybenzoxazole precursor are described.

(Aromatic Diamine Diol)

As an aromatic diamine diol, ones that have been conventionally used for synthesis of polybenzoxazole can be used without particular limitation. As the aromatic diamine diol, a compound represented by the following formula (a02) is preferably used. One type of the aromatic diamine diol may be used alone or may be used in combination of two or more types thereof.

(a02)

In the formula (a02), $R^{a022}$ is a tetravalent organic group including one or more aromatic rings. Regarding the combination of two pairs of the amino group and the hydroxy group included in aromatic diamine diol represented by the formula (a02), in each combination, the amino group and the hydroxy group are bonded to two adjacent carbon atoms on the aromatic ring included in $R^{a022}$.

In the formula (a02), $R^{a022}$ is a tetravalent organic group including one or more aromatic rings, and the number of carbon atoms thereof is preferably 6 or more and 50 or less, and more preferably 6 or more and 30 or less. $R^{a02}2$ may be either an aromatic group or a group where 2 or more aromatic groups are bonded via an aliphatic hydrocarbon group, a halogenated aliphatic hydrocarbon group, or a bond containing heteroatoms such as oxygen atom, sulfur atom and nitrogen atom. The bond containing heteroatoms such as oxygen atom, sulfur atom and nitrogen atom included in $R^{a022}$ is preferably —CONH—; —NH—; —N=N—; —CH=N—; —COO—; —O—; —CO—; —SO—; —SO$_2$—; —S—; and —S—S—, and more preferably —O—; —CO—; —SO—; —SO$_2$—; —S—; and —S—S—.

An aromatic ring included in $R^{a022}$ may be an aromatic heterocycle. In $R^{a022}$, aromatic ring(s) bonding with amino group(s) and hydroxy group(s) is preferably benzene ring. In $R^{a022}$, when a ring bonding with amino group(s) and hydroxy group(s) is fused ring including two or more rings, ring bonding with amino group(s) and hydroxy group(s) in the fused ring is preferably benzene ring.

Specific examples of $R^{a022}$ include groups represented by the following formulae (a02-1) to (a02-9).

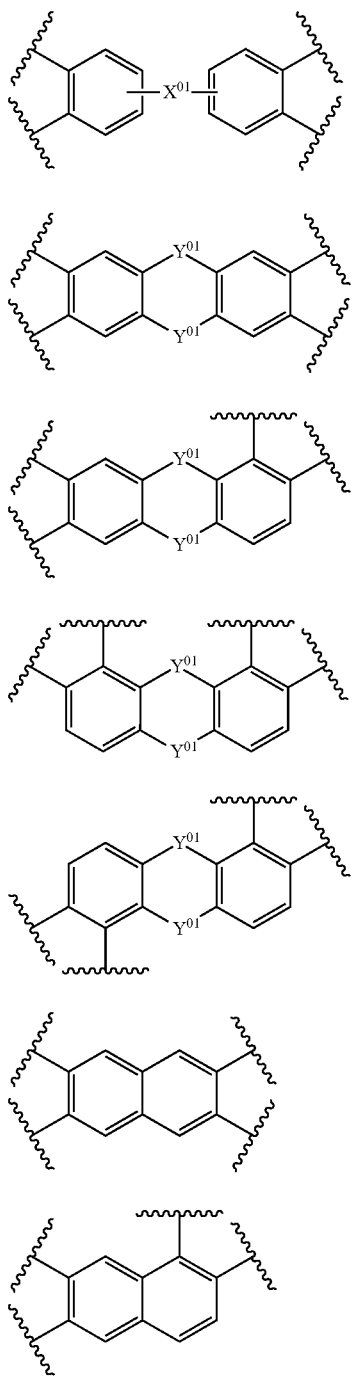

(a02-1)

(a02-2)

(a02-3)

(a02-4)

(a02-5)

(a02-6)

(a02-7)

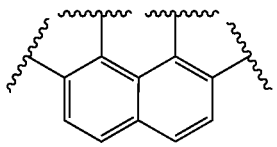

(a02-8)

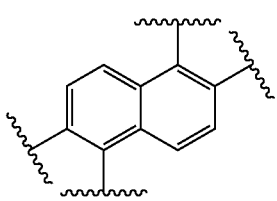

(a02-9)

In the formula (a02-1), $X^{01}$ is one selected from the group consisting of a alkylene group having 1 or more and 10 or less carbon atoms, a fluorinated alkylene group having 1 or more and 10 or less carbon atoms, —O—, —S—, —SO—, —SO$_2$—, —CO—, —COO—, —CONH—, and single bond. In the formulae (a02-2) to (a02-5), $Y^{01}$ may be the same as or different from each other, and is one selected from the group consisting of —CH$_2$—, —O—, —S—, —SO—, —SO$_2$—, —CO— and single bond.

Groups represented by above-mentioned formulae (a02-1) to (a02-9) may have one or more substituent on an aromatic ring.

Suitable examples of substituent include a fluorine atom, an alkyl group having 1 or more and 6 or less carbon atoms, an alkoxy group having 1 or more and 6 or less carbon atoms, a fluorinated alkyl group having 1 or more and 6 or less carbon atom, and a fluorinated alkoxy group having 1 or more and 6 or less carbon atoms. When substituent is a fluorinated alkyl group or a fluorinated alkoxy group, a perfluoroalkyl group or a perfluoroalkoxy group is preferable.

Specific examples of the compound represented by the above-mentioned formula (a02) include 2,4-diamino-1,5-benzenediol, 2,5-diamono-1,4-benzenediol, 2,5-diamono-3-fluoro-1,4-benzenediol, 2,5-diamino-3,6-difluoro-1,4-benzenediol, 2,6-diamino-1,5-dihydroxynaphthalene, 1,5-diamino-2,6-dihydroxynaphthalene, 2,6-diamino-3,7-dihydroxynaphthalene, 1,6-diamino-2,5-dihydroxynaphthalene, 4,4'-diamino-3,3'-dihydroxybiphenyl, 3,3'-diamino-4,4'-dihydroxybiphenyl, 2,3'-diamino-3,2'-dihydroxybiphenyl, 3,4'-diamino-4,3'-dihydroxybiphenyl, 4,4'-diamino-3,3'-dihydroxy-6,6'-ditrifluoromethylbiphenyl, 3,3'-diamino-4,4'-dihydroxy-6,6'-ditrifluoromethylbiphenyl, 2,3'-diamino-3,2'-dihydroxy-6,6'-ditrifluoromethylbiphenyl, 3,4'-diamino-4,3'-dihydroxy-6,6'-ditrifluoromethylbiphenyl, 4,4'-diamino-3,3'-dihydroxy-5,5'-ditrifluoromethylbiphenyl, 3,3'-diamino-4,4'-dihydroxy-5,5'-ditrifluoromethylbiphenyl, 2,3'-diamino-3,2'-dihydroxy-5,5'-ditrifluoromethylbiphenyl, 3,4'-diamino-4,3'-dihydroxy-5,5'-ditrifluoromethylbiphenyl, bis(4-amino-3-hydroxyphenyl)methane, bis(3-amino-4-hydroxyphenyl)methane, 3,4'-diamino-4,3'-dihydroxydiphenylmethane, bis(4-amino-3-hydroxy-6-trifluoromethylphenyl)methane, bis(3-amino-4-hydroxy-6-trifluoromethylphenyl)methane, 3,4'-diamino-4,3'-dihydroxy-6,6'-ditrifluoromethyldiphenylmethane, bis(4-amino-3-hydroxyphenyl)difluoromethane, bis(3-amino-4-hydroxyphenyl)difluoromethane, 3,4'-diamino-4,3'-dihydroxydiphenyldifluoromethane, bis(4-amino-3-hydroxy-6-trifluoromethylphenyl)difluoromethane, bis(3- amino-4-hydroxy-6-trifluoromethylphenyl)difluoromethane, 3,4'-diamino-4,3'-dihydroxy-6,6'-ditrifluoromethyldiphenyldifluoromethane, bis(4-amino-3-hydroxyphenyl)ether, bis(3-amino-4-hydroxyphenyl)ether, 3,4'-diamino-4,3'-dihyroxydiphenylether, bis(4-amino-3-hydroxy-6-trifluoromethylphenyl)ether, bis(3-amino-4-hydroxy-6-trifluoromethylphenyl) ether, 3,4'-diamino-4,3'-dihydroxy-6,6'-ditrifluoromethyldiphenylether, bis(4-amino-3-hydroxyphenyl)ketone, bis(3-amino-4-hydroxyphenyl)ketone, 3,4'-diamino-4,3'-dihydroxydiphenylketone, bis(4-amino-3-hydroxy-6-trifluoromethylphenyl)ketone, bis(3-amino-4-hydroxy-6-trifluoromethylphenyl)ketone, 3,4'-diamino-4,3'-dihydroxy-6,6'-ditrifluoromethyldiphenylketone, 2,2-bis(4-amino-3-hydroxyphenyl)propane, 2,2-bis(3-amino-4-hydroxyphenyl)propane, 2-(3-amino-4-hydroxyphenyl)-2-(4'-amino-3'-hydroxyphenyl)propane, 2,2-bis(4-amino-3-hydroxy-6-trifluoromethylphenyl)propane, 2,2-bis(3-amino-4-hydroxy-6-trifluoromethylphenyl)propane, 2-(3-amino-4-hydroxy-6-trifluoromethylphenyl)-2-(4'-amino-3'-hydroxy-6'-trifluoromethylphenyl)propane, 2,2-bis(3-amino-4-hydroxy-5-trifluoromethylphenyl)propane, 2,2-bis(4-amino-3-hydroxyphenyl)hexafluoropropane, 2,2-bis(3-amino-4-hydroxyphenyl)hexafluoropropane, 2-(3-amino-4-hydroxyphenyl)-2-(4'-amino-3'-hydroxyphenyl)hexafluoropropane, 2,2-bis(4-amino-3-hydroxy-6-trifluoromethylphenyl)hexafluoropropane, 2,2-bis(3-amino-4-hydroxy-6-trifluoromethylphenyl)hexafluoropropane, 2-(3-amino-4-hydroxy-6-trifluoromethylphenyl)-2-(4'-amino-3'-hydroxy-6'-trifluoromethylphenyl)hexafluoropropane, 2,2-bis(3-amino-4-hydroxy-5-trifluoromethylphenyl)hexafluoropropane, bis(4-amino-3-hydroxyphenyl)sulfone, bis(3-amino-4-hydroxyphenyl)sulfone, 3,4'-diamino-4,3'-dihydroxydiphenylsulfone, bis(4-amino-3-hydroxy-6-trifluoromethylphenyl)sulfone, bis(3-amino-4-hydroxy-6-trifluoromethylphenyl)sulfone, 3,4'-diamino-4,3'-dihydroxy-6,6'-ditrifluoromethyldiphenylsulfone, bis(4-amino-3-hydroxyphenyl)sulfide, bis(3-amino-4-hydroxyphenyl)sulfide, 3,4'-diamino-4,3'-dihydroxydipehylsulfide, bis(4-amino-3-hydroxy-6-trifluoromethylphenyl)sulfide, bis(3-amino-4-hydroxy-6-trifluoromethylphenyl)sulfide, 3,4'-diamino-4,3'-dihydroxy-6,6'-ditrifluoromethyldiphenylsulfide, (4-amino-3-hydroxyphenyl) 4-amino-3-hydroxyphenylbenzoate, (3-amino-4-hydroxyphenyl) 3-amino-4-hydroxyphenylbenzoate, (3-amino-4-hydroxyphenyl) 4-amino-3-hydroxyphenylbenzoate, (4-amino-3-hydroxyphenyl) 3-amino-4-hydroxyphenylbenzoate, N-(4-amino-3-hydroxyphenyl)4-amino-3-hydroxybenzamide, N-(3-amino-4-hydroxyphenyl)3-amino-4-hydroxyphenylbenzamide, N-(3-amino-4-hydroxyphenyl)4-amino-3-hydroxyphenylbenzamide, N-(4-amino-3-hydroxyphenyl)3-amino-4-hydroxyphenylbenzamide, 2,4'-bis(4-amino-3-hydroxyphenoxy)biphenyl, 2,4'-bis(3-amino-4-hydroxyphenoxy)biphenyl, 4,4'-bis(4-amino-3-hydroxyphenoxy)biphenyl, 4,4'-bis(3-amino-4-hydroxyphenoxy)biphenyl, di[4-(4-amino-3-hydroxyphenoxy)phenyl]ether, di[4-(3-amino-4-hydroxyphenoxy)phenyl]ether, 2,4'-bis(4-amino-3-hydroxyphenoxy)benzophenone, 2,4'-bis(3-amino-4-hydroxyphenoxy)benzophenone, 4,4'-bis(4-amino-3-hydroxyphenoxy)benzophenone, 4,4'-bis(3-amino-4-hydroxyphenoxy)benzophenone, 2,4'-bis(4-amino-3-hydroxyphenoxy)octafluorobiphenyl, 2,4'-bis(3-amino-4-hydroxyphenoxy)octafluorobiphenyl, 4,4'-bis(4-amino-3-hydroxyphenoxy)octafluorobiphenyl, 4,4'-bis(3-amino-4-hydroxyphenoxy)octafluorobiphenyl, 2,4'-bis(4-amino-3-hydroxyphenoxy)octafluorobenzophenone, 2,4'-bis(3-amino-4-hydroxyphenoxy)octafluorobenzophenone, 4,4'-bis(4-amino-3-hydroxyphenoxy)octafluorobenzophenone, 4,4'-bis(3-amino-4-hydroxyphenoxy)octafluorobenzophenone, 2,2-bis[4-(4-amino-3-hydroxyphenoxy)phenyl]propane, 2,2-bis[4-(3-amino-4-hydroxyphenoxy)phenyl]propane, 2,2-bis[4-(4-amino-3-hydroxyphenoxy)phenyl]hexafluoropropane, 2,2-bis[4-(3-amino-4-hydroxyphenoxy)phenyl]hexafluoropropane, 2,8-diamino-3,7-dihydroxydibenzofuran, 2,8-diamino-3,7-dihydroxyfluorene, 2,6-diamino-3,7-dihydroxyxanthone, 9,9-bis-(4-amino-3-hydroxyphenyl)fluorene, and 9,9-bis-(3-amino-4-hydroxyphenyl)fluorene.

Among these, 2,2-bis(3-amino-4-hydroxyphenyl)hexafluoropropane is preferable. (Dicarbonyl compound)

As synthetic raw material of a polybenzoxazole precursor, the above-described aromatic diamine diol and a dicarbonyl compound represented by the following formula (a03) are used together. The above-mentioned aromatic diamine diol and a dicarbonyl compound represented by the following formula (a03) are condensed to each other to obtain a polybenzoxazole precursor.

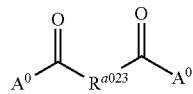

(a03)

In the formula (a03), $R^{a023}$ is a divalent organic group, and $A^0$ represents a hydrogen atom or a halogen atom.

$R^{a023}$ in the formula (a03) may be an aromatic group, or an aliphatic group, or a group combining an aromatic group and an aliphatic group. From the viewpoint that heat resistance, mechanical property, chemical resistance, or the like, of the obtained polybenzoxazole resin are excellent, $R^{a023}$ is preferably a group containing an aromatic group and/or an alicyclic group. The aromatic group contained in $R^{a023}$ may be an aromatic hydrocarbon group, or may be an aromatic heterocyclic group.

$R^{a023}$ can include, in addition to a carbon atom and a hydrogen atom, a halogen atom, an oxygen atom, and a sulfur atom. In a case in which $R^{a023}$ includes an oxygen atom, a nitrogen atom or a sulfur atom, the oxygen atom, the nitrogen atom or the sulfur atom can be included in $R^{a023}$ as a group selected from: a nitrogen-containing heterocyclic group; —CONH—; —NH—; —N=N—; —CH=N—; —COO—; —O—; —CO—; —SO—; —SO$_2$—; —S—; and —S—S—, and more preferably included in $R^{a023}$ as a group selected from: —O—; —CO—; —SO—; —SO$_2$—; —S—; and —S—S—.

In the formula (a03), one of two $A^0$ may be a hydrogen atom and the other may be a halogen atom, but it is preferable that both of two $A^0$ are hydrogen atoms, or both of two $A^0$ are halogen atoms. When $A^0$ is a halogen atom, chlorine, bromine, and iodine are preferable as $A^0$, and chlorine is more preferable.

When a dialdehyde compound in which two $A^0$ are hydrogen atoms is used as a dicarbonyl compound represented by the formula (a03), a polybenzoxazole precursor represented by the following formula (A2) is produced.

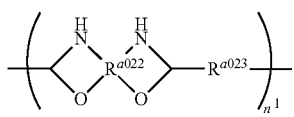
(A2)

In the formula (A2), $R^{a022}$ and $R^{a023}$ are the same as defined in the formulae (a02) and (a03), and $n^1$ is the number of repeating units represented by the formula (A2).

When dicarboxylic acid dihalide in which two $A^0$ are halogen atoms is used as the dicarbonyl compound represented by the formula (a03), the polybenzoxazole precursor represented by the following formula (A3) is produced.

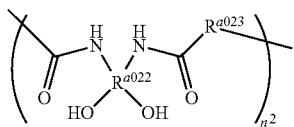
(A3)

In the formula (A3), $R^{a022}$ and $R^{a023}$ are the same as defined in the formulae (a02) and (a03), and $n^2$ is the number of repeating units represented by the formula (A3).

Hereinafter, a dialdehyde compound and a dicarboxylic acid dihalide as a compound suitable for a dicarbonyl compound will be described.

(Dialdehyde Compound)

A dialdehyde compound to be used as raw material for a polybenzoxazole precursor is a compound represented by the following formula (a02-I). The dialdehyde compound may be used alone or may be used in combination of two or more types thereof.

(a2-I)

In the formula (a2-I), $R^{a203}$ is the same as defined in the formula (a03).

An aromatic group or an aromatic ring-containing group suitable for $R^{a203}$ in the formula (a2-I) includes the following groups.

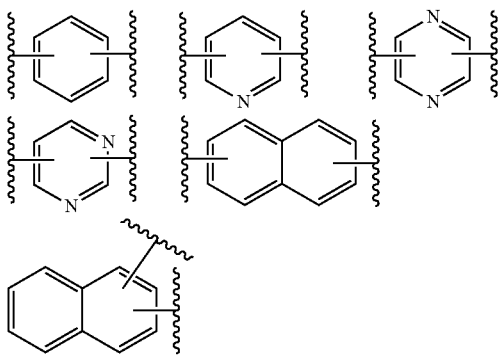

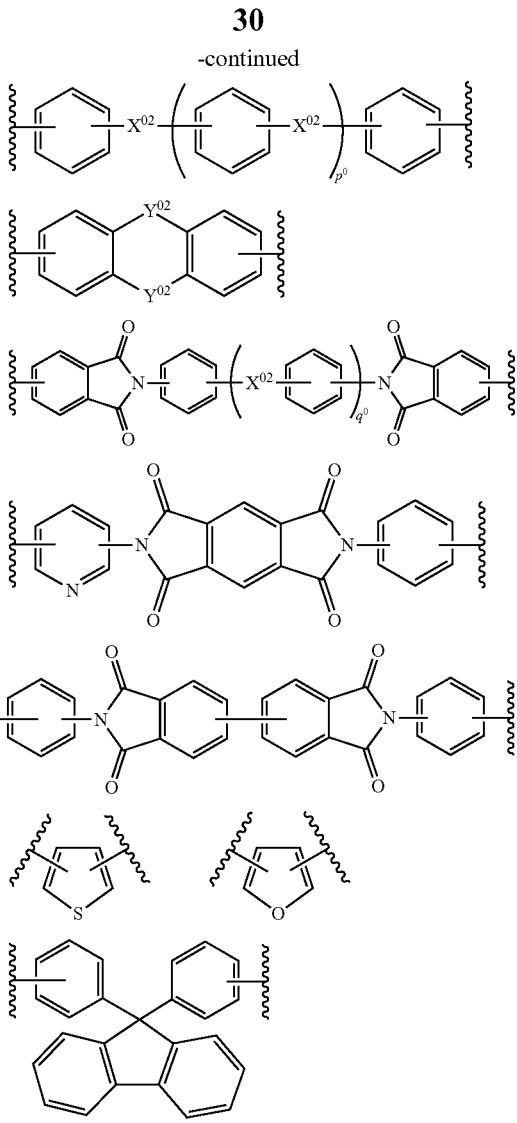

In the above-mentioned formula, $X^{02}$ is one selected from the group consisting of an alkylene group having 1 or more and 10 or less carbon atoms, a fluoridated alkylene group having 1 or more and 10 or less carbon atoms, —O—, —S—, —SO—, —SO$_2$—, —CO—, —COO—, —CONH—, and a single bond. When a plurality of $X^{02}$ are present, the plurality of $X^{02}$ may be the same as or different from each other. $Y^{02}$ may be the same as or different from each other, and are at least one selected from the group consisting of —CH$_2$—, —O—, —S—, —SO—, —SO$_2$—, —CO—, and a single bond. $p^0$ and $q^0$ are respectively an integer of 0 or more and 3 or less.

An alicyclic group or an alicycle-containing group suitable for $R^{a203}$ in the formula (a2-I) includes the following groups.

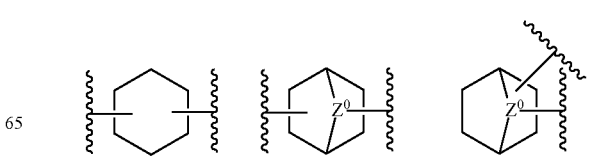

-continued

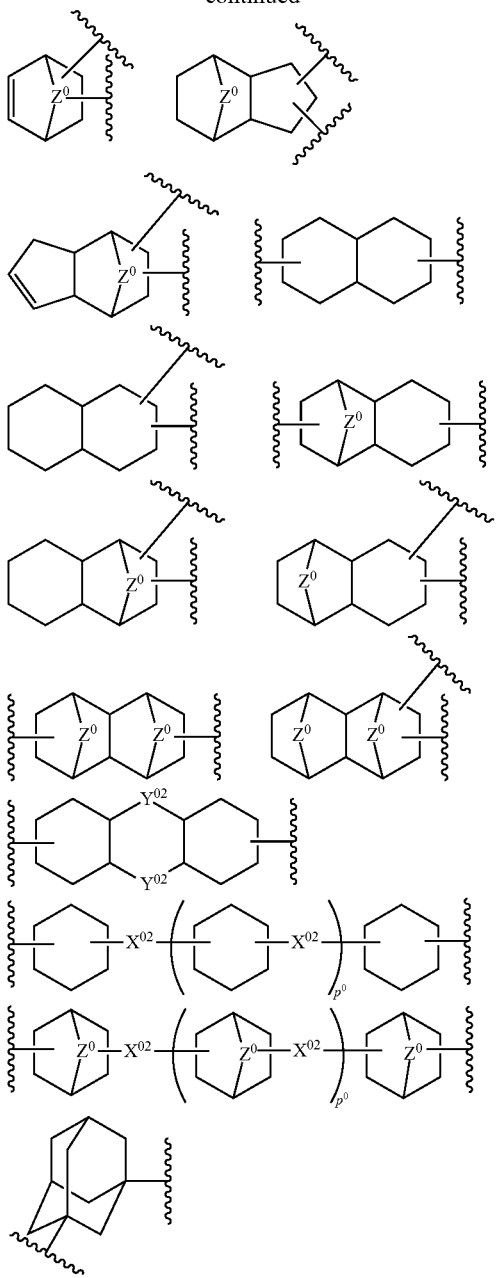

In the above-mentioned formula, $X^{02}$ is one selected from the group consisting of an alkylene group having 1 or more and 10 or less carbon atoms, a fluorinated alkylene group having 1 or more and 10 or less carbon atoms, —O—, —S—, —SO—, —SO$_2$—, —CO—, —COO—, —CONH—, and single bond. When a plurality of $X^{02}$ are present, the plurality of $X^{02}$ may be the same as or different from each other. $Y^{02}$ may be the same as or different from each other, and are at least one selected from the group consisting of —CH$_2$—, —O—, —S—, —SO—, —SO$_2$—, —CO—, and a single bond. $Z^0$ is at least one selected from the group consisting of —CH$_2$—, —CH$^2$CH$^2$—, and —CH═CH—. $P^0$ is a integer of 0 or more and 3 or less.

An aromatic ring or an aliphatic ring included in the suitable group as above-mentioned $R^{a023}$ may have one or more substituent on the ring thereof. Suitable examples of a substituent include a fluorine atom, an alkyl group having 1 or more and 6 or less carbon atoms, an alkoxy group having 1 or more and 6 or less carbon atoms, a fluorinated alkyl group having 1 or more and 6 or less carbon atoms, and a fluorinated alkoxy group having 1 or more and 6 or less carbon atoms. When substituent is a fluorinated alkyl group or a fluorinated alkoxy group, a perfluoroalkyl group or a perfluoroalkoxy group is preferable.

When a dialdehyde compound represented by the formula (a2-I) is an aromatic dialdehyde, suitable examples include benzene dialdehydes, pyridine dialdehydes, pyrazine dialdehydes, pyrimidine dialdehydes, naphthalene dialdehydes, biphenyl dialdehydes, diphenylether dialdehydes, diphenylsulfone dialdehydes, diphenylsulfide dialdehydes, bis(formylphenoxy)benzenes, [1,4-phenylenebis(1-methylethylidene)]bisbenzaldehydes, 2,2-bis[4-(formylphenoxy)phenyl]propanes, bis[4-(formylphenoxy)phenyl]sulfides, bis[4-(formylphenoxy)phenyl]sulfones, and fluorene-containing dialdehydes.

Specific examples of benzene dialdehydes include phthalaldehyde, isophthalaldehyde, terephthalaldehyde, 3-fluorophthalaldehyde, 4-fluorophthalaldehyde, 2-fluoroisophthalaldehyde, 4-fluoroisophthalaldehyde, 5-fluoroisophthalaldehyde, 2-fluoroterephthalaldehyde, 3-trifluoromethylphthalaldehyde, 4-trifluoromethylphthalaldehyde, 2-trifluoromethylisophthalaldehyde, 4-trifluoromethylisophthalaldehyde, 5-trifluoromethylisophthalaldehyde, 2-trifluoromethylterephthalaldehyde, 3,4,5,6-tetrafluorophthalaldehyde, 2,4,5,6-tetrafluoroisophthalaldehyde, 2,3,5,6-tetrafluoroterephthalaldehyde, and the like.

Specific examples of pyridine dialdehydes include pyridine-2,3-dialdehyde, pyridine-3,4-dialdehyde, pyridine-3,5-dialdehyde, and the like. Specific examples of pyrazine dialdehydes include pyrazine-2,3-dialdehyde, pyrazine-2,5-dialdehyde, pyrazine-2,6-dialdehyde, and the like. Specific examples of pyrimidine dialdehydes include pyrimidine-2,4-dialdehyde, pyrimidine-4,5-dialdehyde, pyrimidine-4,6-dialdehyde, and the like.

Specific examples of naphthalene dialdehydes include naphthalene-1,5-dialdehyde, naphthalene-1,6-dialdehyde, naphthalene-2,6-dialdehyde, naphthalene-3,7-dialdehyde, 2,3,4,6,7,8-hexafluoronaphthalene-1,5-dialdehyde, 2,3,4,5,6,8-hexafluoronaphthalene-1,6-dialdehyde, 1,3,4,5,7,8-hexafluoronaphthalene-2,6-dialdehyde, 1-trifluoromethylnaphthalene-2,6-dialdehyde, 1,5-bis(trifluoromethyl)naphthalene-2,6-dialdehyde, 1-trifluoromethylnaphthalene-3,7-dialdehyde, 1,5-bis(trifluoromethyl)naphthalene-3,7-dialdehyde, 1-trifluoromethyl-2,4,5,6,8-pentafluoronaphthalene-3,7-dialdehyde, 1-bis(trifluoromethyl)methoxy-2,4,5,6,8-pentafluoronaphthalene-3,7-dialdehyde, 1,5-bis(trifluoromethyl)-2,4,6,8-tetrafluoronaphthalene-3,7-dialdehyde, 1,5-bis[bis(trifluoromethyl)methoxy]-2,4,6,8-tetrafluoronaphthalene-3,7-dialdehyde, and the like.

Specific examples of biphenyl dialdehydes include biphenyl-2,2'-dialdehyde, biphenyl-2,4'-dialdehyde, biphenyl-3,3'-dialdehyde, biphenyl-4,4'-dialdehyde, 6,6'-difluorobiphenyl-3,4'-dialdehyde, 6,6'-difluorobiphenyl-2,4'-dialdehyde, 6,6'-difluorobiphenyl-3,3'-dialdehyde, 6,6'-difluorobiphenyl-3,4'-dialdehyde, 6,6'-difluorobiphenyl-4,4'-dialdehyde, 6,6'-ditrifluoromethylbiphenyl-2,2'-dialdehyde, 6,6'-ditrifluoromethylbiphenyl-2,4'-dialdehyde, 6,6'-ditrifluoromethylbiphenyl-3,3'-dialdehyde, 6,6'-ditrifluoromethylbiphenyl-3,4'-dialdehyde, 6,6'-ditrifluoromethybiphenyl-4,4'-dialdehyde, and the like.

Specific examples of diphenylether dialdehydes include diphenylether-2,4'-dialdehyde, diphenylether-3,3'-dialdehyde, diphenylether-3,4'-dialdehyde, diphenylether-4,4'-dialdehyde, and the like.

Specific examples of diphenylsulfone dialdehydes include diphenylsulfone-3,3'-dialdehyde, diphenylsulfone-3,4'-dialdehyde, diphenylsulfone-4,4'-dialdehyde, and the like.

Specific examples of diphenylsulfide dialdehydes include diphenylsulfide-3,3'-dialdehyde, diphenylsulfide-3,4'-dialdehyde, diphenylsulfide-4,4'-dialdehyde, and the like.

Specific examples of diphenylketone dialdehydes include diphenylketone-3,3'-dialdehyde, diphenylketone-3,4'-dialdehyde, diphenylketone-4,4'-dialdehyde, and the like.

Specific examples of bis(formylphenoxy)benzenes include 1,3-bis(3-formylphenoxy)benzene, 1,4-bis(3-formylphenoxy)benzene, 1,4-bis(4-formylphenoxy)benzene, and the like.

Specific examples of [1,4-phenylenebis(1-methylethylidene)]bisbenzaldehydes includes [1,4-phenylenebis(1-methylethylidene)]bisbenzaldehyde, 3,4'-[1,4-phenylenebis(1-methylethylidene)]bisbenzaldehyde, 4,4'-[1,4-phenylenebis(1-methylethylidene)]bisbenzaldehyde, and the like.

Specific examples of 2,2-bis[4-(formylphenoxy)phenyl]propanes include 2,2-bis[4-(2-formylphenoxy)phenyl]propane, 2,2-bis[4-(3-formylphenoxy)phenyl]propane, 2,2-bis[4-(4-formylphenoxy)phenyl]propane, 2,2-bis[4-(3-formylphenoxy)phenyl]hexafluoropropane, 2,2-bis[4-(4-formylphenoxy)phenyl]hexafluoropropane, and the like.

Specific examples of bis[4-(formylphenoxy)phenyl]sulfides include bis[4-(3-formylphenoxy)phenyl]sulfide, bis[4-(4-formylphenoxy)phenyl]sulfide, and the like.

Specific examples of bis[4-(formylphenoxy)phenyl]sulfones include bis[4-(3-formylphenoxy)phenyl]sulfone, bis[4-(4-formylphenoxy)phenyl]sulfone, and the like.

Specific examples of fluorene-containing dialdehydes include fluorene-2,6-dialdehyde, fluorene-2,7-dialdehyde, dibenzofuran-3,7-dialdehyde, 9,9-bis(4-formylphenyl)fluorene, 9,9-bis(3-formylphenyl)fluorine, 9-(3-formylphenyl)-9-(4'-formylphenyl)fluorene, and the like.

Diphenylalkanedialdehydes or diphenylfluoroalkanedialdehydes represented by the following formulae are also preferably used as an aromatic dialdehyde compound.

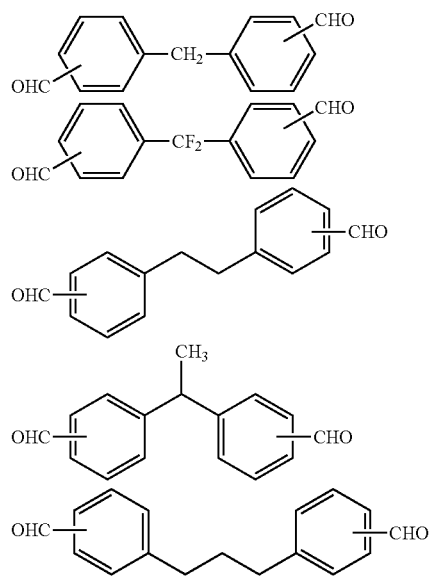

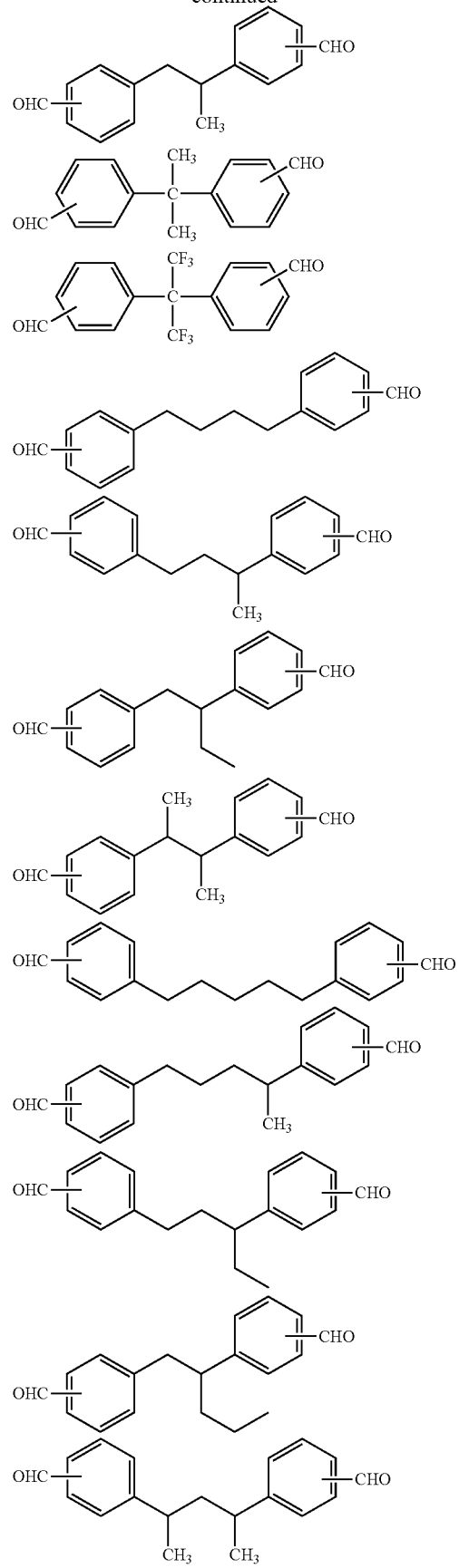

-continued

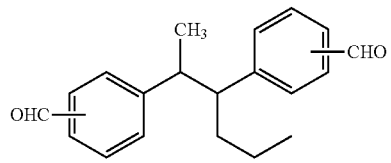
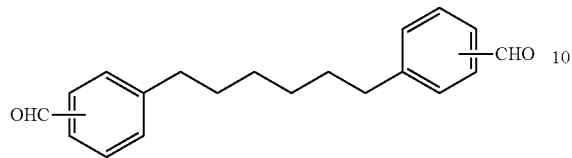
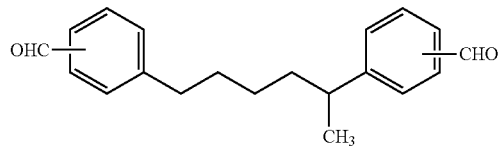
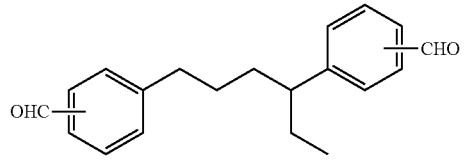
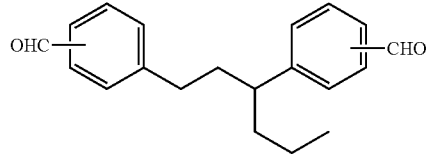

-continued

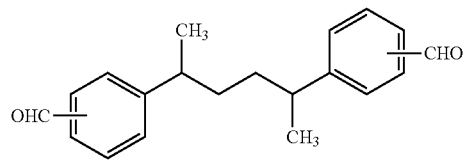
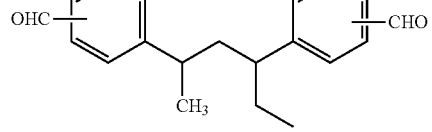
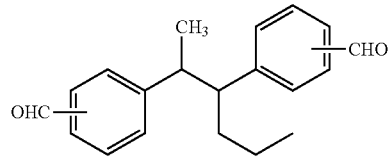

Furthermore, compounds represented by the following formulae including imide bond are also preferably used as an aromatic dialdehyde compound.

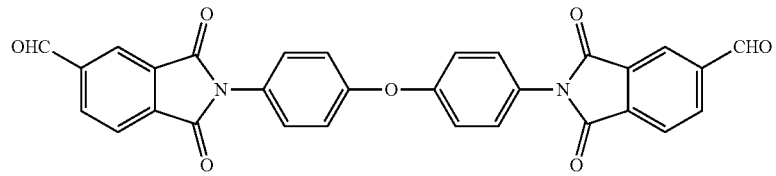
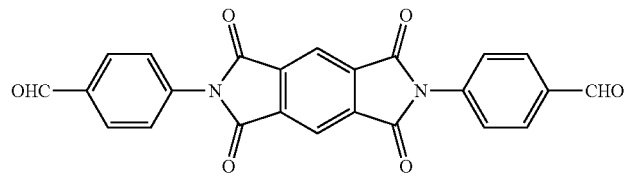
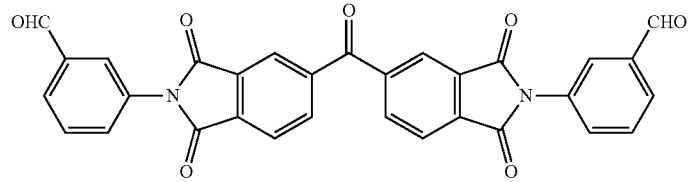

-continued

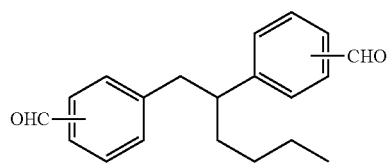

When a dicarbonyl compound represented by the formula (a2-I) is an alicyclic dialdehyde including an alicyclic group, suitable examples include cyclohexane-1,4-dialdehyde, cyclohexane-1,3-dialdehyde, bicyclo[2.2.1]heptane-2,5-dialdehyde, bicyclo[2.2.2]octane-2,5-dialdehyde, bicyclo[2.2.2]octa-7-en-2,5-dialdehyde, bicyclo[2.2.1]heptane-2,3-dialdehyde, bicyclo[2.2.1]hepta-5-en-2,3-dialdehyde, tricyclo[5.2.1.0$^{2,6}$]decane-3,4-dialdehyde, tricyclo[5.2.1.0$^{2,6}$]deca-4-en-8,9-dialdehyde, perhydronaphthalene-2,3- dialdehyde, perhydronaphthalene-1,4-dialdehyde, perhydronaphthalene-1,6-dialdehyde, perhydro-1,4-methanonaphthalene-2,3-dialdehyde, perhydro-1,4-methanonaphthalene-2,7-dialdehyde, perhydro-1,4-methanonaphthalene-7,8-dialdehyde, perhydro-1,4:5,8-dimethanonaphthalene-2,3-dialdehyde, perhydro-1,4:5,8-dimethanonaphthalene-2,7-dialdehyde, perhydro-1,4:5,8:9,10-trimethanoanthracene-2,3-dialdehyde, bicyclohexyl-4,4'-dialdehyde, dicyclohexylether-3,4'-dialdehyde, dicyclohexylmethane-3,3'-dialdehyde, dicyclohexylmethane-3,4'-dialdehyde, dicyclohexylmethane-4,4'-dialdehyde, dicyclohexyldifluoromethane-3,3'-dialdehyde, dicyclohexyldifluoromethane-3,4'-dialdehyde, dicyclohexyldifluoromethane-4,4'-dialdehyde, dicyclohexylsulfone-3,3'-dialdehyde, dicyclohexylsulfone-3,4'-dialdehyde, dicyclohexylsulfone-4,4'-dialdehyde, dicyclohexylsulfide-3,3'-dialdehyde, dicyclohexylsulfide-3,4'-dialdehyde, dicyclohexylsulfide-4,4'-dialdehyde, dicyclohexylketone-3,3'-dialdehyde, dicyclohexylketone-3,4'-dialdehyde, dicyclohexylketone-4,4'-dialdehyde, 2,2-bis(3-formylcyclohexyl)propane, 2,2-bis(4-formylcyclohexyl)propane, 2,2-bis(3-formylcyclohexyl)hexafluoropropane, 2,2-bis(4-formylcyclohexyl)hexafluoropropane, 1,3-bis(3-formylcyclohexyl)benzene, 1,4-bis(3-formylcyclohexyl)benzene, 1,4-bis(4-formylcyclohexyl)benzene, 3,3'-[1,4-cyclohexylenebis(1-methylethylidene)]biscyclohexanecarbaldehyde, 3,4'-[1,4-cyclohexylenebis(1-methylethylidene)]biscyclohexanecarbaldehyde, 4,4'-[1,4-cyclohexylenebis(1-methylethylidene)]biscyclohexanecarbaldehyde, 2,2-bis[4-(3-formylcyclohexyl)cyclohexyl]propane, 2,2-bis[4-(4-formylcyclohexyl)cyclohexyl]propane, 2,2-bis[4-(3-formylcyclohexyl)cyclohexyl]hexafluoropropane, 2,2-bis[4-(4-formylphenoxy)cyclohexyl]hexafluoropropane, bis[4-(3-formylcyclohexyloxy)cyclohexyl]sulfide, bis[4-(4-formylcyclohexyloxy)cyclohexyl]sulfide, bis[4-(3-formylcyclohexyloxy)cyclohexyl]sulfone, bis[4-(4-formylcyclohexyloxy)cyclohexyl]sulfone, 2,2'-bicyclo[2.2.1]heptane-5,6'-dialdehyde, 2,2'-bicyclo[2.2.1]heptane-6,6'-dialdehyde, 1,3-diformyladamantane, and the like.

Among the above-described dialdehyde compounds, because of ease of synthesis or availability, and ease of obtaining a polybenzoxazole precursor capable of providing a polybenzoxazole resin having excellent heat resistance and mechanical property, isophthalaldehyde is preferable.

(Dicarboxylic Acid Dihalide)

A dicarboxylic acid dihalide to be used as raw material for a polybenzoxazole precursor is a compound represented by the following formula (a2-II). The dicarboxylic acid dihalide may be used alone or may be used in combination of two or more types thereof.

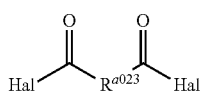

(a2-II)

In the formula (a2-II), $R^{a023}$ is the same as defined in the formula (a03), and Hal represents a halogen atom.

In the formula (a2-II), Hal is preferably chlorine, bromine, and iodine, and more preferably chlorine.

Preferable examples of the compounds suitable for the compound represented by the formula (a2-II) include a compound in which two aldehyde groups of the compound mentioned above as suitable examples of the dialdehyde compound are substituted with a halocarbonyl group, and preferably a chlorocarbonyl group.

Among the above-described dicarboxylic acid dihalides, because of ease of synthesis or availability, and ease of obtaining a polybenzoxazole precursor that provides polybenzoxazole resin having excellent heat resistance and mechanical property, terephthalic acid dichloride is preferable.

(Solvent)

A solvent to be used for preparation of a polyimide resin precursor or a polybenzoxazole precursor is not particularly limited, and can be appropriately selected from solvents that have conventionally been used for preparation of a polyimide resin precursor or a polybenzoxazole precursor. As the solvent to be used for preparation of the polyimide resin precursor or the polybenzoxazole precursor, a solvent containing the compound represented by the following formula (a04) is preferable.

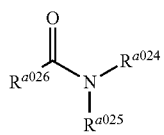

(a04)

In the formula (a04), $R^{a024}$ and $R^{a025}$ are each independently an alkyl group having 1 or more and 3 or less carbon atoms, and $R^{a026}$ is a group represented by the following formula (a04-1) or (a04-2).

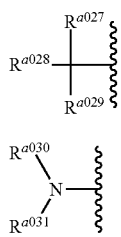

(a04-1)

(a04-2)

In the formula (a04-1), $R^{a027}$ is a hydrogen atom or a hydroxy group, and $R^{a028}$ and $R^{a029}$ are each independently an alkyl group having 1 or more and 3 or less carbon atoms. In the formula (a04-2), $R^{a030}$ and $R^{a031}$ are each independently a hydrogen atom or an alkyl group having 1 or more and 3 or less carbon atoms.

When the polybenzoxazole precursor is synthesized using a solvent containing a compound represented by the above-mentioned formula (a04), even when the polybenzoxazole precursor is heat-treated at a low temperature, it is possible to produce a polybenzoxazole resin having excellent mechanical property such as tensile elongation and chemical resistance while suppressing deterioration of transparency due to coloring of resin during heating of the polybenzoxazole precursor.

Furthermore, when a polybenzoxazole resin is produced by heating the polybenzoxazole precursor synthesized using a solvent containing a compound represented by the above formula (a04), it is possible to suppress generation of defects such as swelling, cracking, and foaming on the surface of polybenzoxazole resin. Therefore, when a film of a polybenzoxazole resin is produced by heating a film including the polybenzoxazole precursor synthesized using a solvent containing a compound represented by the above-mentioned formula (a04), a film having excellent appearance without defects such as cracking, blisters, and pin-holes, is easily manufactured.

When $R^{a026}$ is a group represented by the formula (a04-1), specific examples of compound represented by the formula (a04) include N,N,2-trimethylpropionamide, N-ethyl,N,2-dimethylpropionamide, N,N-diethyl-2-methylpropionamide, N,N,2-trimethyl-2-hydroxypropionamide, N-ethyl-N,2-dimethyl-2-hydroxypropionamide, N,N-diethyl-2-hydroxy-2-methylpropionamide, and the like.

When $R^{a026}$ is a group represented by the formula (a04-2), specific examples of compound represented by the formula (a04) include N,N,N',N'-tetramethylurea, N,N,N'N'-tetraethylurea, and the like.

Particularly preferable examples of the compound represented by the formula (a4) include N,N,2-trimethyl propionamide and N,N,N',N'-tetramethylurea. The boiling point of N,N,2-trimethyl propionamide under atmospheric pressure is 175° C., and the boiling point of N,N,N',N'-tetramethylurea under atmospheric pressure is 177° C. Thus, N,N,2-trimethyl propionamide and N,N,N',N'-tetramethylurea have relatively low boiling points among the solvents capable of dissolving aromatic diamine diol, a dicarbonyl compound, and the generated polybenzoxazole precursor. Therefore, when a polybenzoxazole resin is formed using the polybenzoxazole precursor synthesized using a solvent including at least one selected from N,N,2-trimethyl propionamide and N,N,N',N'-tetramethylurea, the solvent is less likely to remain in a generated polybenzoxazole resin at the time of heating the polybenzoxazole precursor, and tensile elongation of the resulting polybenzoxazole resin is less likely to be deteriorated.

In addition, N,N,2-trimethyl propionamide and N,N,N',N'-tetramethylurea are not identified as SVHCs (Substances of Very High Concern) with concerns about harmful effects under the EU (European Union) REACH regulation, and therefore they are useful as less harmful substances.

When a solvent to be used for preparing the polybenzoxazole precursor includes a compound represented by the formula (a04), the content of the compound represented by the formula (a04) in the solvent is preferably 70 mass % or more, more preferably 80 mass % or more, particularly preferably 90 mass % or more, and the most preferably 100 mass %.

When the solvent contains the compound represented by the formula (a04), examples of organic solvent which can be used with the compound represented by the formula (a04) include nitrogen-containing polar solvents such as N,N-dimethylformamide, N,N-dimethylacetamide, N-methyl-2-pyrrolidone, hexamethylphosphoramide, and 1,3-diemthyl-2-imidazolidinone; ketones such as methylethylketone, methylisobutylketone, cyclohexanone, and isophorone; esters such as γ-butyrolactone, γ-valerolactone, δ-valerolactone, γ-caprolactone, ε-caprolactone, α-methyl-γ-butyrolactone, ethyl lactate, methyl acetate, ethyl acetate, and n-butyl acetate; cyclic ethers such as dioxane, and tetrahydrofuran; cyclic esters such as ethylene carbonate, and propylene carbonate; aromatic hydrocarbons such as toluene, and xylene; and sulfoxides such as dimethylsulfoxyide.

(Method for Producing Polybenzoxazole Precursor)

A polybenzoxazole precursor is produced by reacting the aromatic diamine diol and the dicarbonyl compound mentioned above in a solvent by a well-known method. Hereinafter, as typical examples of a producing method for the polybenzoxazole precursor, a producing method in a case where the dicarbonyl compound is a dialdehyde compound, and a producing method in a case where the dicarbonyl compound is dicarboxylic halide will be described.

Reaction Between Aromatic Diamine Diol and a Dialdehyde Compound

A reaction between aromatic diamine diol and a dialdehyde compound is a formation reaction of a Schiff base, and can be carried out according to a well-known method. A reaction temperature is not particularly limited, but the temperature is usually preferably 20° C. or higher and 200° C. or lower, more preferably 20° C. or higher and 160° C. or lower, and particularly preferably 100° C. or higher and 160° C. or lower.

The reaction between the aromatic diamine diol and the dialdehyde compound may be carried out while an entrainer is added into the solvent and reflux dehydration is carried out. The entrainer is not particularly limited, and it is appropriately selected from organic solvents forming an azeotropic mixture with water, and forming a two-phase system with water at room temperature. Suitable examples of the entrainer include esters such as isobutyl acetate, allyl acetate, n-propyl propionate, isopropyl propionate, n-butyl propionate, and isobutyl propionate; ethers such as dichloromethylether, and ethylisoamylether; ketones such as ethylpropylketone; and aromatic hydrocarbons such as toluene.

Time of the reaction between the aromatic diamine diol and the dialdehyde compound is not particularly limited, but it is typically preferably about 2 hours or more and 72 hours or less.

An amount of the dialdehyde compound to be used in producing the polybenzoxazole precursor is preferably 0.5 moles or more and 1.5 moles or less, and more preferably 0.7 moles or more and 1.3 moles or less relative to 1 mole of the aromatic diamine diol.

An amount of a solvent to be used is not particularly limited as long as the reaction between the aromatic diamine diol and the dialdehyde compound proceeds well. Typically, it is preferable to use 1 time or more and 40 times or less, preferably 1.5 times or more and 20 times or less as the mass of solvent relative to the total of a mass of the aromatic diamine diol and a mass of the dialdehyde compound.

The reaction between the aromatic diamine diol and the dialdehyde compound is carried out preferably until the number average molecular weight of the produced polybenzoxazole precursor becomes 1000 or more and 20000 or less, and preferably 1200 or more and 5000 or less.

Reaction Between Aromatic Diamine Diol and Dicarboxylic Acid Dihalide

A temperature at which a reaction between aromatic diamine diol and dicarboxylic acid dihalide is carried out is not particularly limited, but the temperature is usually preferably −20° C. or higher and 150° C. or lower, more preferably −10° C. or higher and 150° C. or lower, and particularly preferably −5° C. or higher and 70° C. or lower. In the reaction between aromatic diamine diol and dicarboxylic acid dihalide, halogenated hydrogen is generated as a by-product. In order to neutralize such halogenated hydrogen, an organic base such as triethylamine, pyridine, and N,N-dimethyl-4-aminopyridine, and alkali metal hydroxide such as sodium hydroxide and potassium hydroxide may be added into a reaction solution in a small amount.

Time of the reaction between aromatic diamine diol and dicarboxylic acid dihalide is not particularly limited, but it is typically preferably about 2 hours or more and 72 hours or less.

An amount of dicarboxylic acid dihalide to be used in producing a polybenzoxazole precursor is preferably 0.5 moles or more and 1.5 moles or less, and more preferably 0.7 moles or more and 1.3 moles or less relative to 1 mole of aromatic diamine diol.

An amount of the solvent to be used is not particularly limited as long as the reaction between aromatic diamine diol and dicarboxylic acid dihalide proceeds well. Typically, it is preferable to use 1 time or more and 40 times or less, preferably 1.5 times or more and 20 times or less as the mass of solvent relative to the total of a mass of aromatic diamine diol and a mass of dicarboxylic acid dihalide.

The reaction between aromatic diamine diol and dicarboxylic acid dihalide is carried out preferably until the number average molecular weight of the produced polybenzoxazole precursor becomes 1,000 or more and 20000 or less, and preferably 1,200 or more and 5,000 or less.

A solution of the polybenzoxazole precursor is obtained by the method as described above. When the hydrogen barrier film forming composition is prepared, a solution of the polybenzoxazole precursor may be used as it is. Furthermore, it is possible to use the polybenzoxazole precursor in a form of paste or solid obtained by removing at least a part of a solvent from a solution of the polybenzoxazole precursor under reduced pressure, at a low temperature such that conversion of the polybenzoxazole precursor into a polybenzoxazole resin does not occur, for preparing a hydrogen barrier film forming composition.

[Polybenzothiazole Precursor]

A polybenzothiazole precursor is produced typically by reacting aromatic diamine dithiol and a dicarbonyl compound having a specific structure with each other. As the aromatic diamine dithiol, it is possible to use a compound in which a hydroxy group of an aromatic diamine diol to be used for synthesis of a polybenzoxazole precursor is substituted with a mercapto group. As the dicarbonyl compound, it is possible to use a compound similar to the compound to be used for synthesis of a polybenzoxazole precursor.

Reaction methods, reaction conditions, and the like, when the aromatic diamine dithiol and the dicarbonyl compound are reacted to each other to synthesize a polybenzothiazole precursor are the same as those when the aromatic diamine diol and the dicarbonyl compound are reacted to each other to synthesize the polybenzoxazole precursor.

[Polybenzimidazole Precursor]

A polybenzimidazole precursor is produced typically by reacting aromatic tetraamine and dicarboxylic acid dihalide with each other. As the aromatic tetraamine, a compound in which a hydroxy group of an aromatic diamine diol to be used for synthesis of a polybenzoxazole precursor is substituted with an amino group can be used. As the dicarboxylic acid dihalide, a compound similar to the compound to be used for synthesis of the polybenzoxazole precursor can be used.

Reaction methods, reaction conditions, and the like, when the aromatic tetraamine and dicarboxylic acid dihalide are reacted to each other to synthesize a polybenzimidazole precursor are the same as those in the case where the aromatic diamine diol and the dicarboxylic acid dihalide are reacted with each other to synthesize the polybenzoxazole precursor.

[Styrene-Maleic Acid Copolymer]

Types of a styrene-maleic acid copolymer are not particularly limited within a range where the objects of the present invention are not impaired. The copolymerization ratio (mass ratio) of styrene/maleic acid in the styrene-maleic acid copolymer is preferably 1/9 or more and 9/1 or less, more preferably 2/8 or more and 8/1 or less, and particularly preferably 1/1 or more and 8/1 or less. The molecular weight of the styrene-maleic acid copolymer is not particularly limited, but the mass average molecular weight based on polystyrene is preferably 1,000 or more and 100,000 or less, and more preferably 5,000 or more and 12,000 or less.

[Epoxy Group-Containing Resin]

When an epoxy group-containing resin is used as a base material component (A), epoxy groups of the epoxy group-containing resin are crosslinked to each other by heating in the presence of a curing agent and a curing accelerator if necessary. As a result, a cured product having excellent heat resistance or mechanical property can be obtained. The epoxy group-containing resin is not particularly limited as long as it is a resin constituted by molecules having an epoxy group.

The epoxy group-containing resin may be a polymer obtained by polymerizing a monomer having an epoxy group or a monomer mixture including a monomer having an epoxy group. The epoxy group-containing resin may be one in which an epoxy group is introduced into a polymer having a functional group having reactivity, for example, a hydroxy group, a carboxy group, an amino group, and the like, using a compound having an epoxy group, for example, epichlorohydrin. Because of ease of availability, preparation, adjustment of an amount of an epoxy group in the polymer, as the polymer having an epoxy group, a polymer obtained by polymerizing a monomer having an epoxy group or a monomer mixture including a monomer having an epoxy group is preferable.

Suitable examples of the epoxy group-containing resin include novolak type epoxy resins such as phenolnovolak type epoxy resin, brominated phenolnovolak type epoxy resin, orthocresolnovolak type epoxy resin, bisphenol A novolak type epoxy resin, and bisphenol AD novolak type epoxy resin; cycloaliphatic epoxy resins such as epoxidized dicyclopentadiene type phenol resin; aromatic epoxy resins such as epoxidized naphthalene type phenol resin.

Furthermore, among the epoxy group-containing resins, because of ease of preparation, or ease of adjustment of properties of the hydrogen barrier film, a homopolymer of a (meth)acrylic acid ester having an epoxy group, or a copolymer of a (meth)acrylic acid ester having an epoxy group and other monomers are preferable.

The (meth)acrylic acid ester having an epoxy group may be either a chain aliphatic (meth)acrylic acid ester having an epoxy group, or the below-mentioned (meth)acrylic acid ester having an alicyclic epoxy group. The (meth)acrylic acid ester having an epoxy group may have an aromatic group. The (meth)acrylic acid ester having an epoxy group is preferably an aliphatic (meth)acrylic acid ester having a chain aliphatic epoxy group or an aliphatic (meth)acrylic acid ester having an alicyclic epoxy group, and more preferably an aliphatic (meth)acrylic acid ester having an alicyclic epoxy group. In view of patterning property, an aliphatic (meth) acrylic acid ester including polycyclic structure in ring structure of an alicyclic epoxy group is further preferable.

Examples of the (meth)acrylic acid ester, which has an aromatic group and an epoxy group, include 4-glycidyloxyphenyl (meth)acrylate, 3-glycidyloxyphenyl (meth)acrylate, 2-glycidyloxyphenyl (meth)acrylate, 4-glycidyloxyphenylmethyl (meth)acrylate, 3-glycidyloxyphenylmethyl (meth)acrylate, and 2-glycidyloxyphenylmethyl (meth)acrylate.

Examples of the aliphatic (meth)acrylic acid ester having a chain aliphatic epoxy group include (meth)acrylic acid esters in which a chain aliphatic epoxy group is combined with an oxy group (—O—) in an ester group (—O—CO—), such as epoxyalkyl (meth)acrylate and epoxyalkyloxyalkyl (meth)acrylate. Such a chain aliphatic epoxy group possessed by the (meth)acrylic acid ester may have one or plural oxy group(s) (—O—) in a chain. The number of carbon atoms of the chain aliphatic epoxy group is not particularly limited, and is preferably 3 or more and 20 or less, more preferably 3 or more and 15 or less, and particularly preferably 3 or more and 10 or less.

Specific examples of the aliphatic (meth)acrylic acid ester having a chain aliphatic epoxy group include epoxyalkyl (meth)acrylates such as glycidyl (meth)acrylate, 2-methyl glycidyl (meth)acrylate, 3,4-epoxybutyl (meth)acrylate, and 6,7-epoxyheptyl (meth)acrylate; and epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-hexyl (meth)acrylate, and 6-glycidyloxy-n-hexyl (meth)acrylate.

Specific examples of the aliphatic (meth)acrylic acid ester having an alicyclic epoxy group include compounds represented by the following formulae (a05-1) to (a05-15). Of these compounds, compounds represented by the following formulae (a05-1) to (a05-5) are preferable, and compounds represented by the following formulae (a05-1) to (a05-2) are more preferable. Furthermore, as to each of these compounds, a bonding site on which an oxygen atom of an ester group is positioned to an alicyclic ring is not necessarily limited to the position shown herein, and may partially include a position isomer.

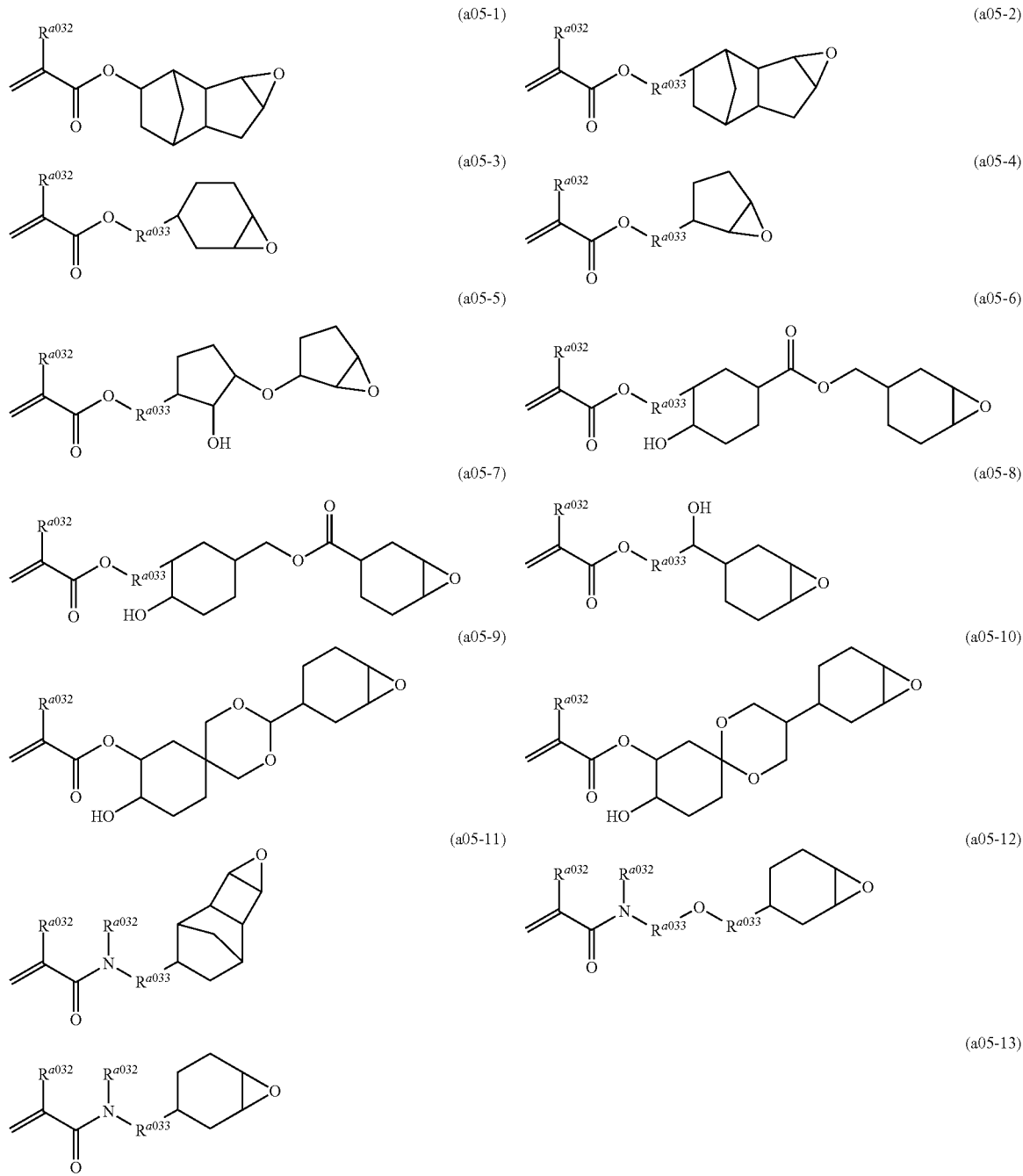

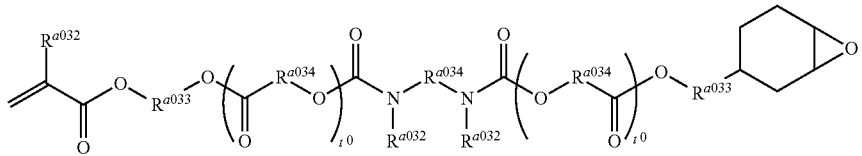

(a05-14)

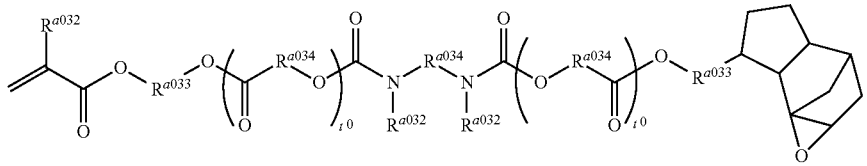

(a05-15)

In the above formulae, $R^{a032}$ is a hydrogen atom or a methyl group; $R^{a033}$ is a divalent aliphatic saturated hydrocarbon group having 1 or more and 6 or less carbon atoms; $R^{a034}$ is a divalent hydrocarbon group having 1 or more and 10 or less carbon atoms; and $t^0$ represents an integer of 0 or more and 10 or less. $R^{a033}$ is a linear or branched alkylene group and is preferably, for example, a methylene group, an ethylene group, a propylene group, a tetramethylene group, an ethylethylene group, a pentamethylene group, or a hexamethylene group. $R^{a034}$ is preferably, for example, a methylene group, an ethylene group, a propylene group, a tetramethylene group, an ethylethylene group, a pentamethylene group, a hexamethylene group, a phenylene group, or a cyclohexylene group.

It is possible to use, as the polymer having an epoxy group, both of a homopolymer of a (meth)acrylic acid ester having an epoxy group, and a copolymer of a (meth)acrylic acid ester having an epoxy group with the other monomer. The content of a unit derived from the (meth)acrylic acid ester having an epoxy group in the polymer having an epoxy group is for example 1% by mass or more and 100% by mass or less, preferably 10% by mass or more and 90% by mass or less, more preferably 30% by mass or more and 80% by mass or less, particularly preferably 50% by mass or more and 75% by mass or less.

When the polymer having an epoxy group is a copolymer of the (meth)acrylic acid ester having an epoxy group with the other monomer, examples of the other monomer include an unsaturated carboxylic acid, a (meth)acrylic acid ester having no epoxy group, (meth)acrylamides, an allyl compound, vinyl ethers, vinyl esters, styrenes, and the like. These compounds can be used alone, or two or more thereof can be used in combination. In view of storage stability of a hydrogen barrier film forming composition, and chemical resistance of a hydrogen barrier film formed using the hydrogen barrier film forming composition against alkali, it is preferred that the copolymer of the (meth)acrylic acid ester having an epoxy group with the other monomer does not include a unit derived from an unsaturated carboxylic acid.

Examples of the unsaturated carboxylic acid include (meth)acrylic acid; (meth)acrylic acid amide; crotonic acid; maleic acid, fumaric acid, citraconic acid, mesaconic acid, itaconic acid, and anhydrides of these dicarboxylic acids.

Examples of the (meth)acrylic acid ester having no epoxy group include linear or branched alkyl (meth)acrylates such as methyl (meth)acrylate, ethyl (meth)acrylate, propyl (meth)acrylate, amyl (meth)acrylate, and t-octyl (meth)acrylate; chloroethyl (meth)acrylate, 2,2-dimethylhydroxypropyl (meth)acrylate, 2-hydroxyethyl (meth)acrylate, trimethylolpropane mono(meth)acrylate, benzyl (meth)acrylate, furfuryl (meth)acrylate; and a (meth)acrylic acid ester having a group with an alicyclic skeleton. Of (meth)acrylic acid esters having no epoxy group, a (meth)acrylic acid ester having a group with an alicyclic skeleton is preferable in view of transparency of a cured article formed using a curable composition.

In a (meth)acrylic acid ester having a group with an alicyclic skeleton, an alicyclic group composing the alicyclic skeleton may be either monocyclic or polycyclic. Examples of the monocyclic alicyclic group include a cyclopentyl group, a cyclohexyl group, and the like. Examples of the polycyclic alicyclic group include a norbornyl group, an isobornyl group, a tricyclononyl group, a tricyclodecyl group, a tetracyclododecyl group, and the like.

Examples of the (meth)acrylic acid ester having a group with an alicyclic skeleton include compounds represented by the following formulae (a06-1) to (a06-8). Of these compounds, compounds represented by the following formulae (a06-3) to (a06-8) are preferable, and compounds represented by the following formulae (a06-3) or (a06-4) are more preferable.

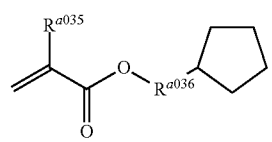

(a06-1)

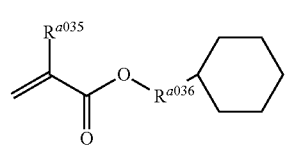

(a06-2)

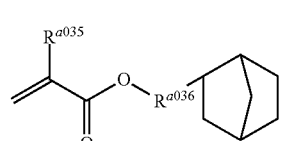

(a06-3)

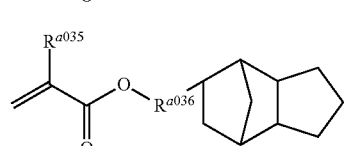

(a06-4)

-continued (a06-5)
(a06-6)
(a06-7)
(a06-8)

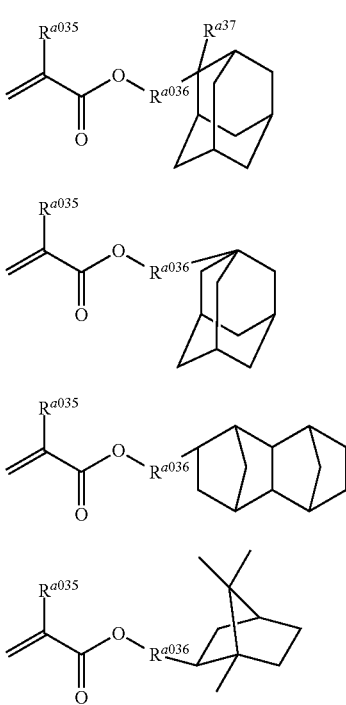

In the above formulae, $R^{a035}$ represents a hydrogen atom or a methyl group; $R^{a036}$ represents a single bond or a divalent aliphatic saturated hydrocarbon group having 1 or more and 6 or less carbon atoms; and $R^{a037}$ represents a hydrogen atom or an alkyl group having 1 or more and 5 or less carbon atoms. $R^{a036}$ is preferably a single bond, or a linear or branched alkylene group, for example, a methylene group, an ethylene group, a propylene group, a tetramethylene group, an ethylethylene group, a pentamethylene group, or a hexamethylene group. $R^{a037}$ is preferably a methyl group or an ethyl group.

Examples of (meth)acrylamides include (meth)acrylamide, N-alkyl(meth)acrylamide, N-aryl(meth)acrylamide, N,N-dialkyl(meth)acrylamide, N,N-aryl(meth)acrylamide, N-methyl-N-phenyl(meth)acrylamide, N-hydroxyethyl-N-methyl(meth)acrylamide, and the like.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; allyloxyethanol, and the like.

Examples of vinyl ethers include alkyl vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether; vinylaryl ethers such as vinyl phenyl ether, vinyl tolyl ether, vinyl chlorophenyl ether, vinyl-2,4-dichlorophenyl ether, vinyl naphthyl ether, and vinyl anthranyl ether; and the like.

Examples of vinyl esters include vinyl butyrate, vinyl isobutyrate, vinyl trimethyl acetate, vinyl diethyl acetate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenyl butyrate, vinyl benzoate, vinyl salicylate, vinyl chlorobenzoate, vinyl tetrachlorobenzoate, vinyl naphthoate, and the like.

Examples of styrenes include styrene; alkylstyrenes such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethylstyrene; alkoxystyrenes such as methoxystyrene, 4-methoxy-3-methylstyrene, and dimethoxystyrene; halostyrenes such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, and 4-fluoro-3-trifluoromethylstyrene; and the like.

The molecular weight of the polymer having an epoxy group is not particularly limited as long as the object of the present invention is not impaired, and is preferably 3,000 or more and 30,000 or less, and more preferably 5,000 or more and 15,000 or less, in terms of a polystyrene-equivalent weight average molecular weight.

When the above-mentioned thermosetting material is used as the base material component (A), a hydrogen barrier film forming composition may include, if necessary, additives and reinforcement materials, such as a curing agent, a curing accelerator, a dehydration-condensation agent, an antioxidant, an ultraviolet absorber, a flame retardant, a mold release agent, a plasticizer, a filler, and a reinforcement material. Furthermore, in order to facilitate film formation, the hydrogen barrier film forming composition may include a solvent. Types of the solvents are appropriately selected depending upon types of the thermosetting materials.

When the hydrogen barrier film forming composition includes the above-mentioned thermosetting material, and the hydrogen barrier agent (B), the content of the hydrogen barrier agent is preferably 0.01 mass % or more and 30 mass % or less, more preferably 0.05 mass % or more and 20 mass % or less, and particularly preferably 0.1 mass % or more and 10 mass % or less with respect to the mass of a thermosetting material of the hydrogen barrier film forming composition.

As the hydrogen barrier film forming composition, in addition to the compositions including the base material component (A) mentioned above, a photosensitive composition known as a so-called photoresist composition is preferable. By adding a predetermined amount of the hydrogen barrier agent (B) to conventionally known various photosensitive compositions, a photosensitive hydrogen barrier film forming composition is obtained. Conventionally known photosensitive compositions include various photocurable compounds or an alkali-soluble resin, resin whose alkali solubility is enhanced by exposure, and the like, as the base material component (A). The photosensitive hydrogen barrier film forming composition may be a negative photosensitive composition insolubilized in a developing solution by exposure, or a positive photosensitive composition solubilized in a developing solution by exposure. Hereinafter, suitable photosensitive compositions are described.

(1) Photosensitive Composition of First Aspect

A photosensitive composition of a first aspect is a negative photosensitive composition containing a hydrogen barrier agent (B), and an organic solvent together with an alkali-soluble resin (A1), a photopolymerizable compound (A2), and a photopolymerization initiator (C). In the photosensitive composition of the first aspect, the alkali-soluble resin (A1) and the photopolymerizable compound (A2) correspond to the base material component (A).

The alkali-soluble resin (A1) in the photosensitive composition of the first aspect is not particularly limited, and conventionally known alkali-soluble resins can be used. The alkali-soluble resin (A1) may have an ethylene unsaturated group, or may not have an ethylene unsaturated group. Note here that in the present specification the alkali-soluble resin is a resin that is dissolved in a film thickness of 0.01 μm or more when a resin solution (solvent: propylene glycol monomethyl ether acetate) having a resin concentration of 20 mass % is formed into a 1-μm resin film on a substrate, and immersed in 2.38 mass % aqueous solution of tetramethylammonium hydroxide (TMAH) for one minute.

As the alkali-soluble resin (A1) having an ethylene unsaturated group, for example, a resin obtained by further reacting a reaction product of an epoxy compound and unsaturated carboxylic acid with polyfunctional acid anhydride.

Among them, a resin represented by the following formula (a-1) is preferable. The resin represented by the following formula (a-1) is preferable because the resin itself is highly photo curable.

In the formula (a-1), $Z^a$ is a residue obtainable by removing 2 acid anhydride groups from tetracarboxylic acid dianhydride. Examples of the tetracarboxylic acid dianhydride include pyromellitic dianhydride, benzophenonetetracarboxylic dianhydride, biphenyltetracarboxylic dianhydride, biphenylethertetracarboxylic dianhydride, and the like. In the above formula (a-1), m is an integer of 0 or more and 20 or less.

Furthermore, as the alkali-soluble resin (A1) having an ethylene unsaturated group, it is possible to use polyester (meth)acrylate obtained by reacting a polyester prepolymer obtained by condensing polyalcohols and monobasic acid or polyfunctional acid with (meth)acrylic acid; polyurethane (meth)acrylate obtained by reacting polyol and a compound having two isocyanate groups with each other, followed by reacting thereto with (meth)acrylic acid; and epoxy (meth)acrylate resin obtained by reacting epoxy resins such as bisphenol A epoxy resin, bisphenol F epoxy resin, bisphenol S epoxy resin, phenol or cresol novolac epoxy resin, resol epoxy resin, triphenol methane epoxy resin, polycarboxylic acid polyglycidyl ester, polyol polyglycidyl ester, aliphatic

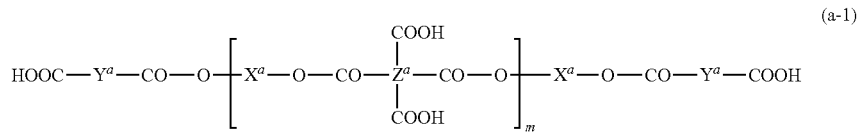

(a-1)

wherein, in the above-mentioned formula (a-1), $X^a$ represents a group represented by the following formula (a-2).

or alicyclic epoxy resin, an amine epoxy resin, and dihydroxy benzene epoxy resin with (meth)acrylic acid, and the

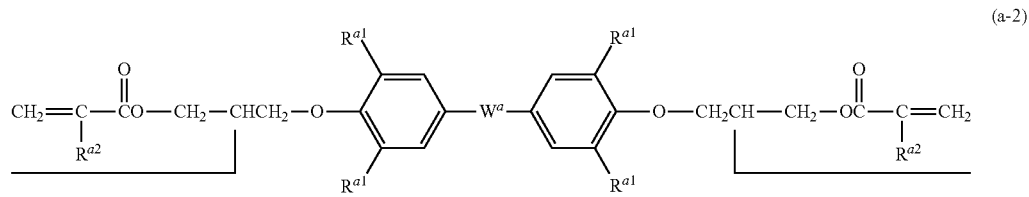

(a-2)

In the above formula (a-2), $R^{a1}$s are each independently a hydrogen atom, a hydrocarbon group having 1 or more and 6 or less carbon atoms, or a halogen atom, $R^{a2}$s are each independently a hydrogen atom or a methyl group, and $W^a$ is a single bond or a group represented by the following formula (a-3).

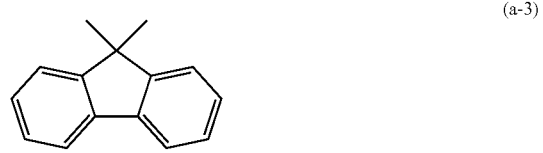

(a-3)

In the above formula (a-1), $Y^a$ is a residue obtainable by removing an acid anhydride group (—CO—O—CO—) from dicarboxylic acid anhydride. Examples of the dicarboxylic anhydride include maleic anhydride, succinic anhydride, itaconic anhydride, phthalic anhydride, tetrahydrophthalic anhydride, hexahydrophthalic anhydride, methylendomethylenetetrahydrophthalic anhydride, chlorendic anhydride, methyltetrahydrophthalic anhydride, anhydrous glutaric acid, and the like.

like. Note here that in the present specification "(meth) acrylic acid" means both acrylic acid and methacrylic acid. Similarly, "(meth)acrylate" means both acrylate and methacrylate.

On the other hand, as the alkali-soluble resin (A1) which does not have an ethylene unsaturated group, it is possible to use a resin obtained by copolymerizing unsaturated carboxylic acid and other unsaturated compounds with each other. Preferable examples of the other unsaturated compounds include at least one selected from an epoxy group-containing unsaturated compound, and an alicyclic group-containing unsaturated compound.

Examples of the unsaturated carboxylic acid include a monocarboxylic acid such as (meth)acrylic acid, and crotonic acid; a dicarboxylic acid such as maleic acid, fumaric acid, citraconic acid, mesaconic acid, and itaconic acid; and anhydrides of these dicarboxylic acids. Among these, (meth) acrylic acid and maleic anhydride are preferable from the viewpoint of reactivity in copolymerization, alkali-solubility of obtainable resin, availability, or the like. These unsaturated carboxylic acids can be used alone or in combination of two or more types thereof.

As the epoxy group-containing unsaturated compound, an epoxy group-containing unsaturated compound having no alicyclic group and an epoxy group-containing unsaturated compound having alicyclic group may be exemplified. As the epoxy group-containing unsaturated compound having alicyclic group, compounds represented by aforementioned formulae (a05-1) to (a05-15) may be exemplified. Examples of epoxy group-containing unsaturated compound having no alicyclic group include epoxyalkyl (meth)acrylates such as glycidyl (meth)acrylate, 2-methylglycidyl (meth)acrylate, 3,4-epoxybutyl (meth)acrylate, and 6,7-epoxyheptyl (meth)acrylate; epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-pentyl(meth)acrylate, (meth)acrylate, and 6-glycidyloxy-n-hexyl; epoxyalkyl α-alkylacrylate such as glycidyl α-ethylacrylate, glycidyl α-n-propylacrylate, glycidyl α-n-butylacrylate, 6,7-epoxyheptyl α-ethylacrylate; and glycidyl ethers such as o-vinylbenzyl glycidyl ether, m-vinylbenzyl glycidyl ether, and p-vinylbenzyl glycidyl ether. Among these, glycidyl (meth)acrylate, 2-methylglycidyl (meth)acrylate, 6,7-epoxyheptyl (meth)acrylate, o-vinylbenzyl glycidyl ether, m-vinylbenzyl glycidyl ether, and p-vinylbenzyl glycidyl are preferable from the viewpoint of reactivity in copolymerization, strength of cured resin, or the like. These epoxy group-containing unsaturated compounds can be used alone or in combination of two or more types thereof.

The alicyclic group-containing unsaturated compound is not particularly limited as long as it is a unsaturated compound having an alicyclic group. An alicyclic group may be either monocyclic or polycyclic. As a monocyclic alicyclic group, cyclopentyl group and cyclohexyl group may be exemplified. As a polycyclic alicyclic group, adamantyl group, norbornyl group, isobornyl group, tricyclononyl group, tricyclodecyl group, and tricyclododecyl group may be exemplified. Specifically, as the alicyclic group-containing unsaturated compound, compounds represented by aforementioned formulae (a06-1) to (a06-8) may be exemplified.

It is also preferable that compounds other than the above are further polymerized to the unsaturated carboxylic acid. Examples of such other compounds include (meth)acrylic acid esters, (meth)acrylamides, aryl compounds, vinyl ethers, vinyl esters, styrenes, maleimides, and the like. These compounds can be used alone or in combination of two or more types thereof.

Examples of the (meth)acrylic acid ester include linear or branched alkyl (meth)acrylates such as methyl (meth)acrylate, ethyl (meth)acrylate, propyl (meth)acrylate, amyl (meth)acrylate, and t-octyl (meth)acrylate; and chloroethyl (meth)acrylate, 2,2-dimethylhydroxypropyl (meth)acrylate, 2-hydroxyethyl (meth)acrylate, trimethylolpropane mono (meth)acrylate, benzyl (meth)acrylate, and furfuryl (meth) acrylate.

Examples of (meth)acrylamides include (meth)acrylamide, N-alkyl(meth)acrylamide, N-aryl(meth)acrylamide, N,N-dialkyl(meth)acrylamide, N,N-aryl(meth)acrylamide, N-methyl-N-phenyl(meth)acrylamide, N-hydroxyethyl-N-methyl(meth)acrylamide, and the like.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; allyloxyethanol, and the like.

Examples of vinyl ethers include alkyl vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether; vinylaryl ethers such as vinyl phenyl ether, vinyl tolyl ether, vinyl chlorophenyl ether, vinyl-2,4-dichlorophenyl ether, vinyl naphthyl ether, and vinyl anthranyl ether; and the like.

Examples of vinyl esters include vinyl butyrate, vinyl isobutyrate, vinyl trimethyl acetate, vinyl diethyl acetate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenyl butyrate, vinyl benzoate, vinyl salicylate, vinyl chlorobenzoate, vinyl tetrachlorobenzoate, vinyl naphthoate, and the like.

Examples of styrenes include styrene; alkylstyrenes such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethylstyrene; alkoxystyrenes such as methoxystyrene, 4-methoxy-3-methylstyrene, and dimethoxystyrene; halostyrenes such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, and 4-fluoro-3-trifluoromethylstyrene; and the like.

Examples of maleimides includes maleimides N-substituted with an alkyl group having 1 or more and 10 or less carbon atoms such as N-methylmaleimide, N-ethylmaleimide, N-n-propylmaleimide, N-isopropylmaleimide, N-n-butylmaleimide, N-n-pentylmaleimide, and N-n-hexylmaleimide; maleimides N-substituted with an alicyclic group having 3 or more and 20 or less carbon atoms such as N-cyclopentylmaleimide, N-cyclohexylmaleimide, and N-cycloheptylmaleimide; maleimides N-substituted with an aryl group having 6 or more and 20 or less carbon atoms such as N-phenylmaleimide, N-α-naphtylmaleimide, and N-β-naphthylmaleimide; and N-aralkyl maleimide N-substituted with an aralkyl group having 7 or more and 20 or less carbon atoms such as N-benzylmaleimide, and N-phenethylmaleimide.

Furthermore, a copolymer including at least a constituent unit having a polymerizable site to the below-mentioned photopolymerizable compound (A2), together with a constituent unit derived from the unsaturated carboxylic acid, or a copolymer including at least a constituent unit derived from the unsaturated carboxylic acid, a constituent unit derived from an epoxy group-containing unsaturated compound, and a constituent unit having a polymerizable site to the below-mentioned photopolymerizable compound (A2) can be suitably used as the alkali-soluble resin (A1). Use of these alkali-soluble resins allows a hydrogen barrier film having excellent mechanical strength and adhesion to a substrate to be formed.

The copolymer including a constituent unit having a polymerizable site to the photopolymerizable compound (A2) mentioned above may further include one or more constituent units derived from the above-mentioned (meth) acrylic acid esters, (meth)acrylamides, aryl compounds, vinyl ethers, vinyl esters, styrenes, maleimides, and the like.

It is preferable that the constituent unit having a polymerizable site to the photopolymerizable compound (A2) has an ethylene unsaturated group as the polymerizable site to the photopolymerizable compound (A2). A copolymer having such a constituent unit can be prepared by reacting at least a part of a carboxy group included in a homopolymer of the unsaturated carboxylic acid and an epoxy group-containing unsaturated compound with each other. Furthermore, a copolymer having the constituent unit having a polymerizable site to the photopolymerizable compound (A2) can be prepared also by reacting at least a part of an epoxy group included in a copolymer including a constituent unit derived from unsaturated carboxylic acid and a constituent unit derived from an epoxy group-containing unsaturated compound, with the unsaturated carboxylic acid.

The proportion of the above-mentioned constituent unit derived from unsaturated carboxylic acid in the alkali-soluble resin (A1) is preferably 3 mass % or more and 25 mass % or less, and more preferably 5 mass % or more and 25 mass % or less. Furthermore, the proportion of the constituent unit derived from the above-mentioned epoxy group-containing unsaturated compound is preferably 30 mass % or more and 95 mass % or less, and more preferably 50 mass % or more and 90 mass % or less. Furthermore, the above-mentioned proportion of the constituent unit derived from the alicyclic group-containing unsaturated compound is preferably 1 mass % or more and 30 mass % or less, more preferably 3 mass % or more and 25 mass % or less, and further preferably 5 mass % or more and 20 mass % or less. When the proportion is in the above-mentioned range, it is possible to make the alkali solubility of the obtained resin appropriate, and enhance the adhesion property of the photosensitive composition to a substrate and the strength of the photosensitive composition after it is cured.

A mass average molecular weight of the alkali-soluble resin (A1) is preferably 1000 or more and 40000 or less, and more preferably 2000 or more and 30000 or less. When the mass average molecular weight is in the above-mentioned range, it is possible to obtain excellent developing property and sufficient heat resistance and film strength.

The content of the alkali-soluble resin (A1) is preferably 5 mass % or more and 80 mass % or less, and more preferably 15 mass % or more and 50 mass % or less with respect to the solid content of the photosensitive composition of the first aspect. When the content is in the above-mentioned range, a balance of developing property tends to be easily achieved.

In the photosensitive composition of first aspect, the photopolymerizable compound (A2) includes a monofunctional monomer and a polyfunctional monomer. Examples of the monofunctional monomer include (meth)acrylamide, methylol(meth)acrylamide, methoxymethyl(meth)acrylamide, ethoxymethyl(meth)acrylamide, propoxymethyl(meth)acrylamide, butoxymethoxymethyl(meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamidesulfonic acid, methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerin mono(meth)acrylate, tetrahydrofurfuryl (meth)acrylate, dimethylaminoethyl (meth)acrylate, glycidyl (meth)acrylate, 2,2,2-trifluoroethyl (meth)acrylate, 2,2,3,3-tetrafluoropropyl (meth)acrylate, a half (meth)acrylate of a phthalic acid derivative, and the like. These monofunctional monomers may be used alone, or two or more monofunctional monomers may be used in combination.

Examples of the polyfunctional monomer include ethylene glycol di(meth)acrylate, diethylene glycol di(meth)acrylate, triethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth)acrylate, 1,6-hexane glycol di(meth)acrylate, trimethylolpropane tri(meth)acrylate, glycerin di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloyloxypropyl (meth)acrylate, ethylene glycol diglycidyl ether di(meth)acrylate, diethylene glycol diglycidyl ether di(meth)acrylate, phthalic acid diglycidyl ester di(meth)acrylate, glycerin triacrylate, glycerin polyglycidyl ether poly (meth)acrylate, urethane (meth)acrylate (i.e., tolylene diisocyanate), a reaction product of trimethylhexamethylene diisocyanate, hexamethylene diisocyanate, and 2-hydroxyethyl (meth)acrylate, methylenebis(meth)acrylamide, (meth)acrylamide methylene ether, a polyfunctional monomer such as a fused product of polyvalent alcohol and N-methylol(meth)acrylamide, triacryl formal, and the like. These polyfunctional monomers may be used alone, or two or more polyfunctional monomers may be used in combination.

The content of the photopolymerizable compound (A2) is preferably 1 mass % or more and 30 mass % or less, and more preferably 5 mass % or more and 20 mass % or less with respect to the solid content of the photosensitive composition of the first aspect. When the content is in the above-mentioned range, a balance of sensitivity, developing property, and resolution tend to be easily achieved.

The photopolymerization initiator (C) in the photosensitive composition of the first aspect is not particularly limited, and conventionally known photopolymerization initiators can be used.

Specific examples of the photopolymerization initiator (C) include 1-hydroxycyclohexyl phenyl ketone; 2-hydroxy-2-methyl-1-phenylpropan-1-one; 1-[4-(2-hydroxyethoxy)phenyl]-2-hydroxy-2-methyl-1-propan-1-one; 1-(4-isopropylphenyl)-2-hydroxy-2-methylpropan-1-one; 1-(4-dodecylphenyl)-2-hydroxy-2-methylpropan-1-one; 2,2-dimethoxy-1,2-diphenylethan-1-one; bis(4-dimethylaminophenyl)ketone; 2-methyl-1-[4-(methylthio)phenyl]-2-morpholinopropan-1-one; 2-benzyl-2-dimethylamino-1-(4-morpholinophenyl)-butan-1-one; ethanone, 1-[9-ethyl-6-(2-methylbenzoyl)-9H-carbazol-3-yl],1-(O-acetyloxime); (9-ethyl-6-nitro-9H-carbazol-3-yl)[4-(2-methoxy-1-methylethoxy)-2-methylphenyl]methanone O-acetyl oxime; 2-(benzoyloxyimino)-1-[4-(phenylthio)phenyl]-1-octanone; 2,4,6-trimethylbenzoyl diphenylphosphine oxide; 4-benzoyl-4'-methyldimethyl sulfide; 4-dimethylaminobenzoic acid; methyl 4-dimethylaminobenzoate; ethyl 4-dimethylaminobenzoate; butyl 4-dimethylaminobenzoate; 4-dimethylamino-2-ethylhexylbenzoic acid; 4-dimethylamino-2-isoamylbenzoic acid; benzyl-β-methoxyethylacetal; benzyldimethylketal; 1-phenyl-1,2-propanedione-2-(O-ethoxycarbonyl)oxime; methyl o-benzoylbenzoate; 2,4-diethylthioxanthone; 2-chlorothioxanthone; 2,4-dimethylthioxanthone; 1-chloro-4-propoxythioxanthone; thioxanthone; 2-chlorothioxanthene; 2,4-diethylthioxanthene; 2-methylthioxanthene, 2-isopropylthioxanthene; 2-ethylanthraquinone; octamethylanthraquinone; 1,2-benzanthraquinone; 2,3-diphenylanthraquinone; azobisisobutyronitrile; benzoyl peroxide; cumene hydroperoxide; 2-mercaptobenzoimidazole; 2-mercaptobenzoxazole; 2-mercaptobenzothiazole; 2-(o-chlorophenyl)-4,5-di(m-methoxyphenyl)-imidazolyl dimer; benzophenone; 2-chlorobenzophenone; p,p'-bisdimethylaminobenzophenone; 4,4'-bisdiethylaminobenzophenone; 4,4'-dichlorobenzophenone; 3,3-dimethyl-4-methoxybenzophenone; benzyl; benzoin; benzoin methyl ether; benzoin ethyl ether; benzoin isopropyl ether; benzoin n-butyl ether; benzoin isobutyl ether; benzoin butyl ether; acetophenone; 2,2-diethoxyacetophenone; p-dimethylacetophenone; p-dimethylaminopropiophenone; dichloroacetophenone; trichloroacetophenone; p-tert-butylacetophenone; p-dimethylaminoacetophenone; p-tert-butyltrichloroacetophenone; p-tert-butyldichloroacetophenone; α,α-dichloro-4-phenoxyacetophenone; thioxanthone; 2-methylthioxanthone; 2-isopropylthioxanthone; dibenzosuberone; pentyl-4-dimethylaminobenzoate; 9-phenylacridine; 1,7-bis-(9-acridinyl)heptane; 1,5-bis-(9-acridinyl)pentane; 1,3-bis-(9-acridinyl)propane; p-methoxytriazine; 2,4,6-tris(trichloromethyl)-s-triazine; 2-methyl-4,6-bis(trichloromethyl)-s-triazine; 2-[2-(5-methylfuran-2-yl)ethenyl]-4,6-bis(trichloromethyl)-s-triazine; 2-[2-(furan-2-yl)ethenyl]-4,6-bis(trichloromethyl)-s-triazine; 2-[2-(4-diethylamino-2-methylphenyl)ethenyl]-4,6-bis(trichloromethyl)-s-triazine; 2-[2-(3,4-dimethoxyphenyl)ethenyl]-4,6-bis(trichloromethyl)-s-triazine; 2-(4-methoxyphenyl)-4,6-bis(trichloromethyl)-s-triazine; 2-(4-ethoxystyryl)-4,6-bis(trichloromethyl)-s-triazine; 2-(4-n-butoxyphenyl)-4,6-bis(trichloromethyl)-s-triazine; 2,4-bis-trichloromethyl-6-(3-bromo-4-methoxy)phenyl-s-triazine; 2,4-bis-trichloromethyl-6-(2-bromo-4-methoxy)phenyl-s-triazine; 2,4-bis-trichloromethyl-6-(3-bromo-4-methoxy)styrylphenyl-s-triazine; 2,4-bis-trichloromethyl-6-(2-bromo-4-methoxy)styrylphenyl-s-triazine; and the like. These photopolymerization initiators can be used alone, or two or more photopolymerization initiators can be used in combination.

Among these, an oxime-based photopolymerization initiator is particularly preferably used in view of the sensitivity. Among oxime-based photopolymerization initiators, O-acetyl-1-[6-(2-methylbenzoyl)-9-ethyl-9H-carbazol-3-yl]ethanone oxime; ethanone,1-[9-ethyl-6-(pyrrol-2-ylcarbonyl)-9H-carbazol-3-yl],1-(O-acetyloxime); and 1,2-octanedione,1-[4-(phenylthio)-,2-(O-benzoyloxime)] are particularly preferable.

It is also preferred to use, as the photopolymerization initiator, an oxime-based compound represented by the following formula (c1):

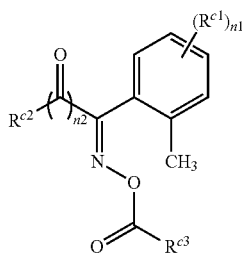

(c1)

wherein $R^{c1}$ is a group selected from the group consisting of a monovalent organic group, an amino group, halogen, a nitro group, and a cyano group,
n1 is an integer of 0 or more and 4 or less,
n2 is 0 or 1,
$R^{c2}$ is an optionally substituted phenyl group or an optionally substituted carbazolyl group, and
$R^{c3}$ is a hydrogen atom, or an alkyl group having 1 or more and 6 or less carbon atoms.

In the formula (c1), $R^{c1}$ is not particularly limited as long as the object of the present invention is not inhibited, and is appropriately selected from various organic groups. When $R^{c1}$ is an organic group, suitable examples include an alkyl group, an alkoxy group, an cycloalkyl group, an cycloalkoxy group, a saturated aliphatic acyl group, a saturated aliphatic acyloxy group, an alkoxycarbonyl group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclyl group which may have a substituent, an amino group, an amino group substituted with one or two organic groups, a morpholin-1-yl group, a piperazin-1-yl group, a halogen, a nitro group, a cyano group, and the like. When n1 is an integer of 2 or more and 4 or less, $R^{c1}$ may be the same or different. The number of carbon atoms of the substituent does not include the number of carbon atoms of the substituent possessed by the substituent.

When $R^{c1}$ is an alkyl group, the number of carbon atoms of the alkyl group is preferably 1 or more and 20 or less, and more preferably 1 or more and 6 or less. When $R^{c1}$ is an alkyl group, the alkyl group may be either one of a straight chain or branched chain alkyl group. When $R^{c1}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{c1}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{c1}$ is an alkoxy group, the number of carbon atoms of the alkoxy group is preferably 1 or more and 20 or less, and more preferably 1 or more and 6 or less. When $R^{c1}$ is an alkoxy group, the alkoxy group may be either one of a straight chain or branched chain alkoxy group. When $R^{c1}$ is an alkoxy group, specific examples include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. When $R^{c1}$ is an alkoxy group, the alkoxy group may include an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, a methoxypropyloxy group, and the like.

When $R^{c1}$ is a cycloalkyl group or a cycloalkoxy group, the number of carbon atoms of the cycloalkyl group or cycloalkoxy group is preferably 3 or more and 10 or less, and more preferably 3 or more and 6 or less. When $R^{c1}$ is a cycloalkyl group, specific examples include a cyclopropyl group, a cyclobutyl group, a cyclopentyl group, a cyclohexyl group, a cycloheptyl group, a cyclooctyl group, and the like. When $R^{c1}$ is a cycloalkoxy group, specific examples include a cyclopropyloxy group, a cyclobutyloxy group, a cyclopentyloxy group, a cyclohexyloxy group, a cycloheptyloxy group, a cyclooctyloxy group, and the like.

When $R^{c1}$ is a saturated aliphatic acyl group or a saturated aliphatic acyloxy group, the number of carbon atoms of the saturated aliphatic acyl group or saturated aliphatic acyloxy group is preferably 2 or more and 20 or less, and more preferably 2 or more and 7 or less. When $R^{c1}$ is a saturated aliphatic acyl group, specific examples include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, n-hexadecanoyl group, and the like. When $R^{c1}$ is a saturated aliphatic acyloxy group, specific examples include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group, and the like.

When $R^{c1}$ is an alkoxycarbonyl group, the number of carbon atoms of the alkoxycarbonyl group is preferably 2 or more and 20 or less, and more preferably 2 or more and 7 or less. When $R^{c1}$ is an alkoxycarbonyl group, specific examples include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group, and the like.

When $R^{c1}$ is a phenylalkyl group, the number of carbon atoms of the phenylalkyl group is preferably 7 or more and 20 or less, and more preferably 7 or more and 10 or less. When $R^{c1}$ is a naphthylalkyl group, the number of carbon atoms of the naphthylalkyl group is preferably 11 or more and 20 or less, and more preferably 11 or more and 14 or less. When $R^{c1}$ is a phenylalkyl group, specific examples include a benzyl group, a 2-phenylethyl group, a 3-phenylpropyl group, and a 4-phenylbutyl group. When $R^{c1}$ is a naphthylalkyl group, specific examples include an α-naphthylmethyl group, a β-naphthylmethyl group, a 2-(α-naphthyl)ethyl group, and a 2-(β-naphthyl)ethyl group. When $R^{c1}$ is a phenylalkyl group or naphthylalkyl group, $R^{c1}$ may further have a substituent on a phenyl group or a naphthyl group.

When $R^{c1}$ is a heterocyclyl group, the heterocyclyl group is a 5- or 6-membered single ring containing one or more N, S, and O, or a heterocyclyl group in which single rings are fused each other, or a single ring is fused with a benzene ring. When the heterocyclyl group is a fused ring, the number of rings in the fused ring is 3 or less. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline, and the like. When $R^{c1}$ is a heterocyclyl group, the heterocyclyl group may have a substituent.

When $R^{c1}$ is an amino group substituted with one or two organic groups, suitable examples of the organic group include an alkyl group having 1 or more and 20 or less carbon atoms, a cycloalkyl group having 3 or more and 10 or less carbon atoms, a saturated aliphatic acyl group having 2 or more and 20 or less carbon atoms, a phenyl group which may have a substituent, a benzoyl group which may have a substituent, a phenylalkyl group having 7 or more and 20 or less carbon atoms which may have a substituent, a naphthyl group which may have a substituent, a naphthoyl group which may have a substituent, a naphthylalkyl group having 11 or more and 20 or less carbon atoms which may have a substituent, a heterocyclyl group, and the like. Specific examples of suitable organic group are the same as those in $R^{c1}$. Specific examples of the amino group substituted with one or two organic group include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, an propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, a β-naphthoylamino group, and the like.

When an phenyl group, an naphthyl group, and a heterocyclyl group included in $R^{c1}$ further have a substituent, examples of the substituent include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group which has an alkyl group having 1 or more and 6 or less carbon atoms, a dialkylamino group which has two alkyl groups having 1 or more and 6 or less carbon atoms, a morpholin-1-yl group, an piperazin-1-yl group, halogen, a nitro group, a cyano group, and the like. When a phenyl group, a naphthyl group, and a heterocyclyl group included in $R^{c1}$ further have a substituent, the number of substituents is not particularly limited as long as the object of the present invention is not inhibited, and is preferably 1 or more and 4 or less. When a phenyl group, a naphthyl group, and a heterocyclyl group included in $R^{c1}$ have plural substituents, plural substituents may be the same as or different each other.

Among $R^{c1}$, a group selected from the group consisting of an alkyl group having 1 or more and 6 or less carbon atoms, an alkoxy group having 1 or more and 6 or less carbon atoms, and a saturated aliphatic acyl group having 2 or more and 7 or less carbon atoms is preferred, an alkyl group having 1 or more and 6 or less carbon atoms is more preferred, and a methyl group is particularly preferable from the viewpoint of chemical stability and ease of synthesis of an oxime ester compound because of less steric hindrance.

When the position of a bond of a phenyl group and a main skeleton of an oxime ester compound is regarded as the 1-position and the position of a methyl group is regarded as the 2-position with respect to the phenyl group to which $R^{c1}$ is bonded, the position at which $R^{c1}$ is bonded to a phenyl group is preferably the 4-position or the 5-position, more preferably the 5-position. n1 is preferably an integer of 0 or more and 3 or less, more preferably an integer of 0 or more and 2 or less, and particularly preferably 0 or 1.

$R^{c2}$ is a phenyl group which may have a substituent, or a carbazolyl group which may have a substituent. When $R^{c2}$ is a carbazolyl group which may have a substituent, the nitrogen atom on the carbazolyl group may be substituted with an alkyl group having 1 or more and 6 or less carbon atoms.

For $R^{c2}$, there is no particular limitation for substituents on the phenyl group or the carbazolyl group as long as they do not interfere with the object of the present invention. Examples of suitable substituents which the phenyl group or carbazolyl group may have on the carbon atom include an alkyl group having 1 or more and 20 or less carbon atoms, an alkoxy group having 1 or more and 20 or less carbon atoms, a cycloalkyl group having 3 or more and 10 or less carbon atoms, a cycloalkoxy group having 3 or more and 10 or less carbon atoms, a saturated aliphatic acyl group having 2 or more and 20 or less carbon atoms, an alkoxycarbonyl group having 2 or more and 20 or less carbon atoms, a saturated aliphatic acyloxy group having 2 or more and 20 or less carbon atoms, an optionally substituted phenyl group, an optionally substituted phenoxy group, an optionally substituted phenylthio group, an optionally substituted benzoyl group, an optionally substituted phenoxycarbonyl group, an optionally substituted benzoyloxy group, an optionally substituted phenylalkyl group having 7 or more and 20 or less carbon atoms, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group having 11 or more and 20 or less carbon atoms, an optionally substituted heterocyclyl group, an optionally substituted heterocyclylcarbonyl group, an amino group, an amino group substituted with 1 or 2 organic groups, a morpholine-1-yl group, a piperazine-1-yl group, halogen, a nitro group, a cyano group and the like.

In a case where $R^{c2}$ is a carbazolyl group, examples of suitable substituent which the carbazolyl group may have on the nitrogen atom include an alkyl group having 1 or more and 20 or less carbon atoms, a cycloalkyl group having 3 or more and 10 or less carbon atoms, a saturated aliphatic acyl group having 2 or more and 20 or less carbon atoms, an alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthyl group, an optionally substituted naphthoyl group, an optionally substituted naphthoxycarbonyl group, an optionally substituted naphthylalkyl group having 11 or more and 20 or less carbon atoms, an optionally substituted heterocyclyl group, an optionally substituted heterocyclylcarbonyl group and the like. Among these substituents, an alkyl group having 1 or more and 20 or less carbon atoms is preferred, and an alkyl group having 1 or more and 6 or less carbon atoms is more preferred, and in particular an ethyl group is preferred.

For an alkyl group, an alkoxy group, a cycloalkyl group, a cycloalkoxy group, a saturated aliphatic acyl group, an alkoxycarbonyl group, a saturated aliphatic acyloxy group, an optionally substituted phenylalkyl group, an optionally substituted naphthylalkyl group, an optionally substituted heterocyclyl group and an amino group substituted with 1 or 2 organic groups, specific examples of optional substituents on the phenyl group or the carbazolyl group are same as those in $R^{c1}$.

In a case where the phenyl group, the naphthyl group and the heterocyclyl group included in the substituent on the phenyl group or the carbazolyl group in $R^{c2}$ further have a substituent, examples of the substituent include an alkyl group having 1 or more and 6 or less carbon atoms; an alkoxy group having 1 or more and 6 or less carbon atoms; a saturated aliphatic acyl group having 2 or more and 7 or less carbon atoms; an alkoxycarbonyl group having 2 or more and 7 or less carbon atoms; a saturated aliphatic acyloxy group having 2 or more and 7 or less carbon atoms; a phenyl group; a naphthyl group; a benzoyl group; a naphthoyl group; a benzoyl group substituted with a group selected from the group consisting of an alkyl group having 1 or more and 6 or less carbon atoms, a morpholine-1-yl group, a piperazine-1-yl group and a phenyl group; a monoalkylamino group having an alkyl group having 1 or more and 6 or less carbon atoms; a dialkylamino group having alkyl groups having 1 or more and 6 or less carbon atoms; a morpholine-1-yl group; a piperazine-1-yl group; halogen; a nitro group; and a cyano group. In a case where the phenyl group, the naphthyl group and the heterocyclyl group included in the substituent on the phenyl group or the carbazolyl group further have a substituent, the number of the substituent is not limited as far as objects of the present invention are not inhibited, but 1 or more and 4 or less is preferred. In a case where the phenyl group, the naphthyl group and the heterocyclyl group have multiple substituents, the substituents may be different from or the same as each other.

Among $R^{c2}$(s), a group represented by the following formula (c2) or (c3) is preferable, a group represented by the following formula (c2) is more preferable, and a group represented by the following formula (c2) in which A is S is particularly preferable, since a photopolymerization initiator with excellent sensitivity is easily obtained.

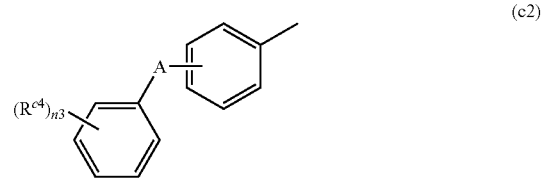

(c2)

$R^{c4}$ is a group selected from the group consisting of a monovalent organic group, an amino group, halogen, a nitro group and a cyano group; A is S or O; and n3 is an integer of 0 or more and 4 or less.

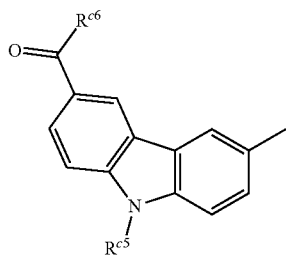

(c3)

$R^{c5}$ and $R^{c6}$ each are a monovalent organic group.

When $R^{c4}$ in formula (c2) is an organic group, $R^{c4}$ can be selected from various kinds of organic groups as far as objects of the present invention are not inhibited. Preferred examples when $R^{c4}$ is an organic group in formula (c2) include alkyl groups having 1 or more and 6 or less carbon atoms; alkoxy groups having 1 or more and 6 or less carbon atoms; saturated aliphatic acyl groups having 2 or more and 7 or less carbon atoms; alkoxycarbonyl groups having 2 or more and 7 or less carbon atoms; saturated aliphatic acyloxy groups having 2 or more and 7 or less carbon atoms; a phenyl group; a naphthyl group; a benzoyl group; a naphthoyl group; benzoyl groups substituted with a group selected from the group consisting of an alkyl group having 1 or more and 6 or less carbon atoms, a morpholine-1-yl group, a piperazine-1-yl group and a phenyl group; monoalkylamino groups having an alkyl group having 1 or more and 6 or less carbon atoms; dialkylamino groups having alkyl groups having 1 or more and 6 or less carbon atoms; a morpholine-1-yl group; a piperazine-1-yl group; halogen; a nitro group; and a cyano group.

Among $R^{c4}$, a benzoyl group; a naphthoyl group; a benzoyl groups substituted with a group selected from the group consisting of an alkyl group having 1 or more and 6 or less carbon atoms, a morpholine-1-yl group, a piperazine-1-yl group, and a phenyl group; and a nitro group are preferred, and a benzoyl group; a naphthoyl group; a 2-methylphenyl carbonyl group; a 4-(piperazine-1-yl) phenyl carbonyl group; and a 4-(phenyl) phenyl carbonyl group are more preferred.

In formula (c2), n3 is preferably an integer of 0 or more and 3 or less, more preferably an integer of 0 or more and 2 or less, and particularly preferably 0 or 1. When n3 is 1, the position at which $R^{c4}$ bonds is preferably the para-position to the bonding through which the phenyl group (to which $R^{b4}$ bonds) bonds to an oxygen atom or a sulfur atom.

$R^{c5}$ in the formula (c3) can be selected from various organic groups as long as they do not interfere with the object of the present invention. Suitable examples of $R^{c5}$ include an alkyl group having 1 or more and 20 or less carbon atoms, a cycloalkyl group having 3 or more and 10 or less carbon atoms, a saturated aliphatic acyl group having 2 or more and 20 or less carbon atoms, an alkoxycarbonyl group having 2 or more and 20 or less carbon atoms, an optionally substituted phenyl group, an optionally substituted benzoyl group, an optionally substituted phenoxycarbonyl group, an optionally substituted phenylalkyl group having 7 or more and 20 or less carbon atoms, an optionally substituted naphthyl group, an optionally substituted naphthoyl group, an optionally substituted naphthoxycarbonyl group, an optionally substituted naphthylalkyl group having 11 or more and 20 or less carbon atoms, an optionally substituted heterocyclyl group, an optionally substituted heterocyclylcarbonyl group, and the like.

Among $R^{c5}$, an alkyl group having 1 or more and 20 or less carbon atoms is preferred, an alkyl group having 1 or more and 6 or less carbon atoms is more preferred, and an ethyl group is particularly preferred.

There is no particular limitation for $R^{c6}$ in the formula (c3) as long as they do not interfere with the object of the present invention, and it can be selected from various organic groups. Specific examples of the suitable group for $R^{c6}$ include an alkyl group having 1 or more and 20 or less carbon atoms, an optionally substituted phenyl group, an optionally substituted naphthyl group and an optionally substituted heterocyclyl group. Among these groups, $R^{c6}$ is more preferably an optionally substituted phenyl group, and in particular preferably a 2-methylphenyl group.

when a phenyl group, a naphthyl group, and a heterocyclyl group included in $R^{c4}$, $R^{c5}$, or $R^{c6}$ further has a substituent, examples of the substituent include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group having an alkyl group which has 1 or more and 6 or less carbon atoms, a dialkylamino group having an alkyl group which has 1 or more and 6 or less carbon atoms, a morpholin-1-yl group, a piperazin-1-yl group, halogen, a nitro group, and a cyano group. When the phenyl group, naphthyl group, and heterocyclyl group included in $R^{c4}$, $R^{c5}$, or $R^{c6}$ further has a substituent, the number of substituents is not particularly limited as long as it does not interfere with the object of the present invention, but is preferably 1 or more and 4 or less. When the phenyl group, naphthyl group, and heterocyclyl group included in $R^{c4}$, $R^{c5}$, or $R^{c6}$ further has plural substituents, plural substituents may be the same or different.

$R^{c3}$ in the formula (c1) is a hydrogen atom, or an alkyl group having 1 or more and 6 or less carbon atoms. $R^{c3}$ is preferably a methyl group or an ethyl group, and more preferably a methyl group.

The oxime ester compound represented by the formula (c1) can be synthesized according to, for example, the following scheme 1 when p is 0. Specifically, the aromatic compound represented by the following formula (c1-1) is acylated by Friedel-Crafts reaction using a halocarbonyl compound represented by the following formula (c1-2) to obtain a ketone compound represented by the following formula (c1-3). The obtained ketone compound (c1-3) is oximated by hydroxyl amine to obtain an oxime compound represented by the following formula (c1-4), then, a hydroxy group in the oxime ester compound represented by the formula (c1-4) is acylated. Thus, an oxime ester compound represented by the following formula (c1-7) can be obtained. Preferable examples of the acylation agents include acid anhydride (($R^{c3}$CO)$_2$O) represented by the following formula (c1-5), or acid halide ($R^{c3}$COHal, wherein Hal is halogen) represented by the following formula (c1-6). Note here that in the following formula (c1-2), Hal is halogen; in the following formulae (c1-1), (c1-2), (c1-3), (c1-4), and (c1-7), $R^{c1}$, $R^{c2}$, $R^{c3}$, and n1 are the same as defined in the formula (c1).

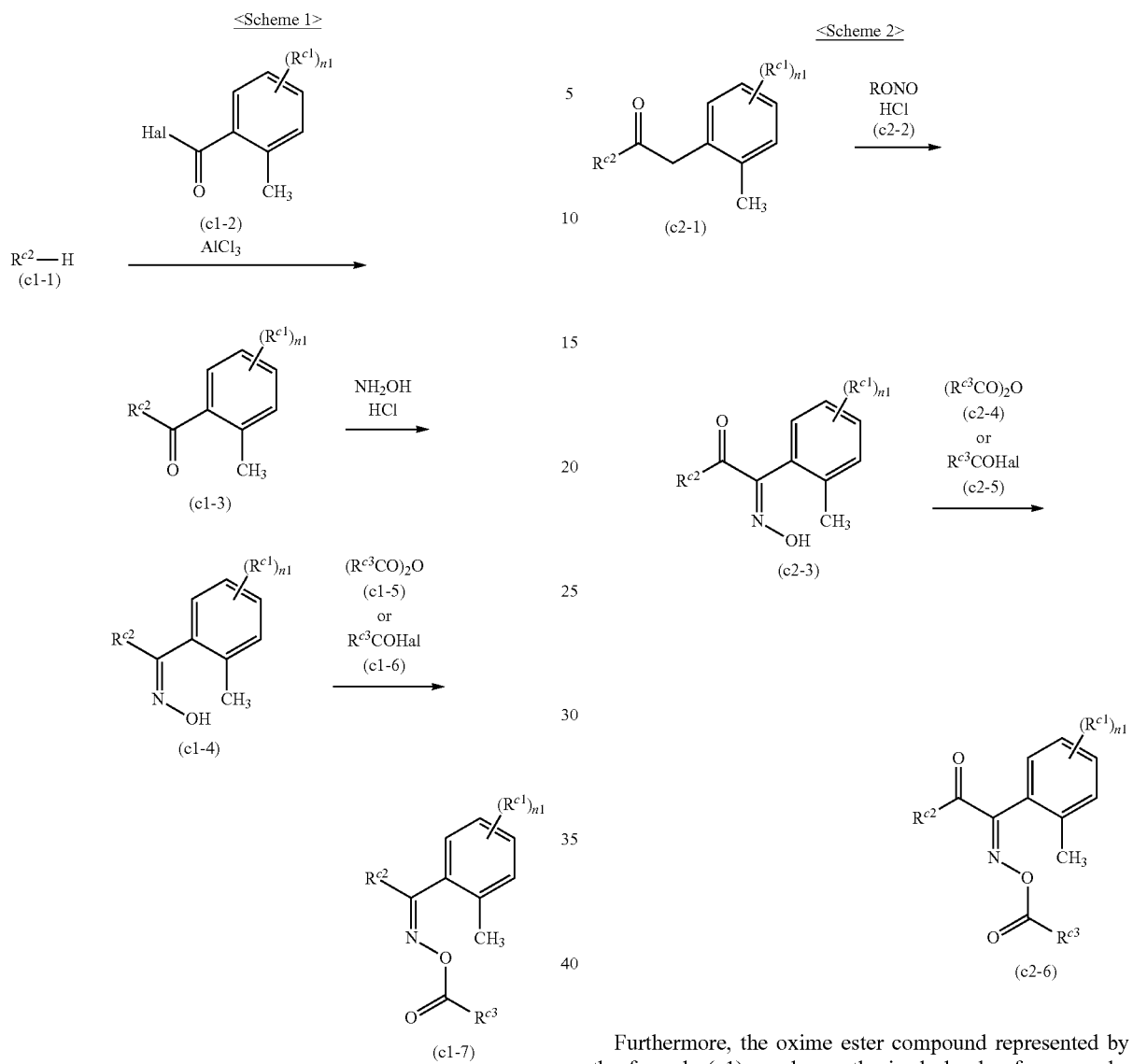

The oxime ester compound represented by the formula (c1) can be synthesized according to, for example, the following scheme 2 when n2 is 1. Specifically, a ketone compound represented by the following formula (c2-1) is reacted with nitrous acid ester (RONO, R is an alkyl group having 1 or more and 6 or less carbon atoms) represented by the following formula (c2-2) in the presence of hydrochloric acid to obtain a ketoxime compound represented by the following formula (c2-3), and then the hydroxy group represented by the following formula (c2-3) in the ketoxime compound is acylated. Thus, an oxime ester compound represented by the following formula (c2-6) can be obtained. Preferable examples of the acylation agents include acid anhydride (($R^{c3}CO)_2O$) represented by the following formula (c2-4), or acid halide ($R^{c3}COHal$, wherein Hal is halogen) represented by the following formula (c2-5). Note here that in the following formulae (c2-1), (c2-3), (c2-4), (c2-5), and (c2-6), $R^{c1}$, $R^{c2}$, $R^{c3}$, and n1 are the same as defined in the formula (c1).

Furthermore, the oxime ester compound represented by the formula (c1) can be synthesized also by, for example, subjecting a compound represented by the formula (c2-7) to oximation and acylation by the same method as in scheme 1, when n2 is 1, $R^{c1}$ is a methyl group, and $R^{c1}$ bonds to the a para-position with respect to a methyl group bonding to a benzene ring to which $R^{c1}$ bonds. Note here that in the following formula (c2-7), $R^{c2}$ is the same as defined in the formula (c1).

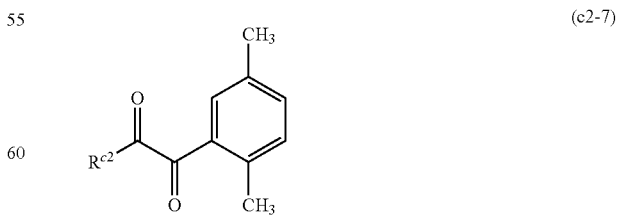

Among the oxime ester compounds represented by the formula (c1), the particularly suitable compounds include the following PI-1 to PI-42.

PI-1
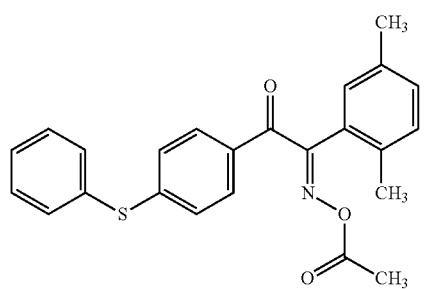
PI-2
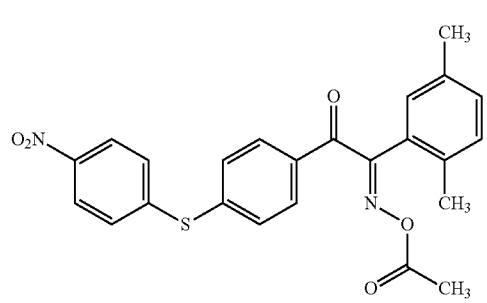
PI-3
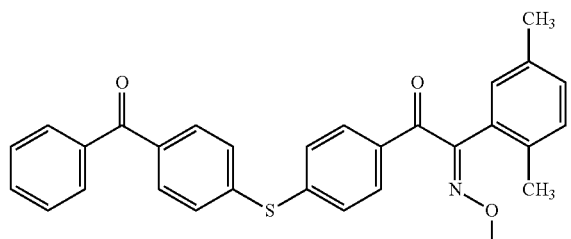
PI-4
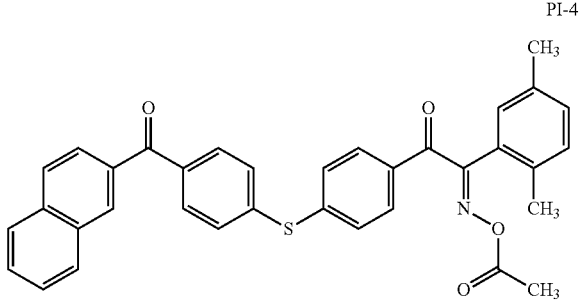
PI-5
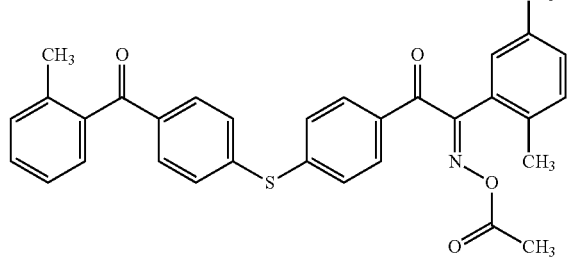
-continued
PI-6
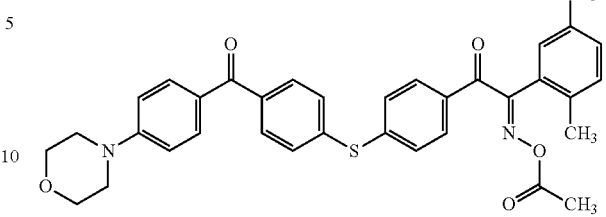
PI-7
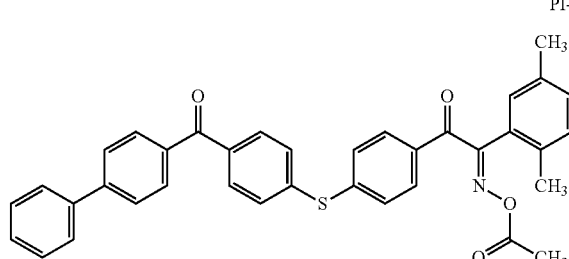
PI-8
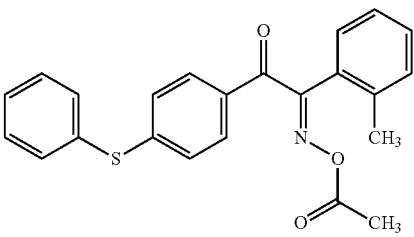
PI-9
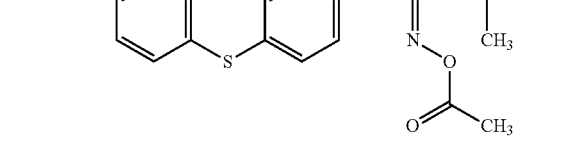
PI-10
PI-11
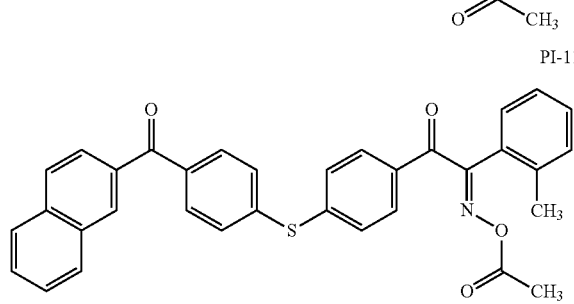

-continued
PI-12
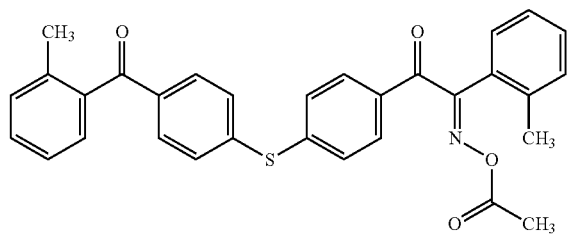
PI-13
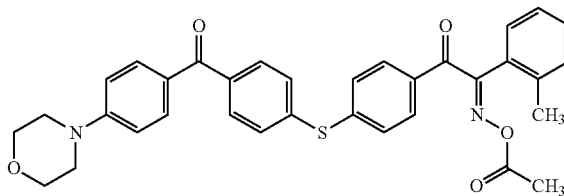
PI-14
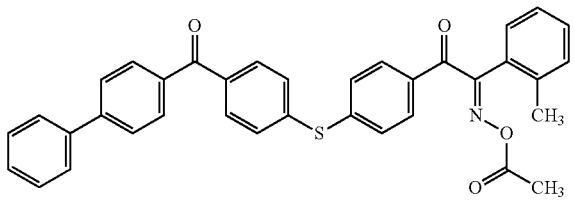
PI-15
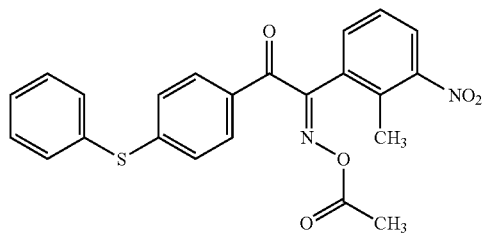
PI-16
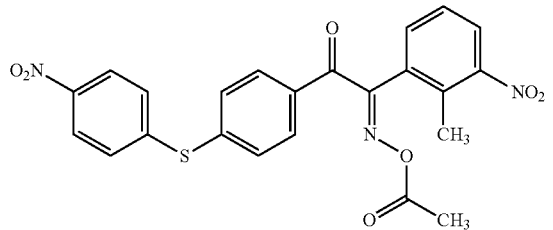
PI-17
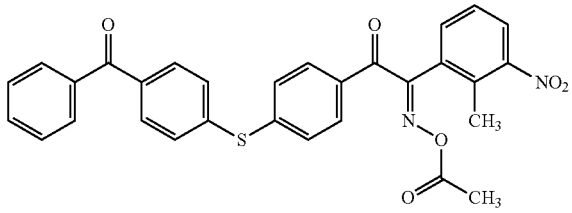
-continued
PI-18
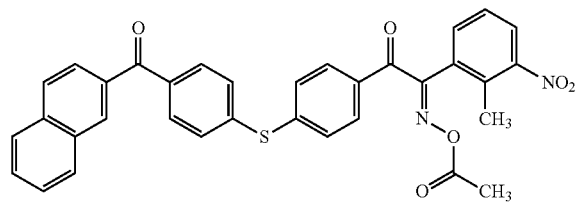
PI-19
PI-20
PI-21
PI-22
PI-23

-continued
PI-24
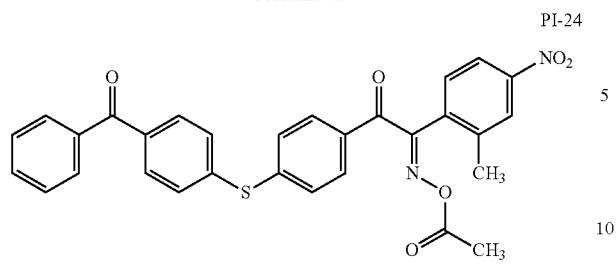
PI-25
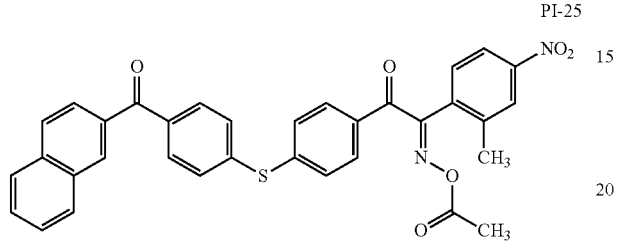
PI-26
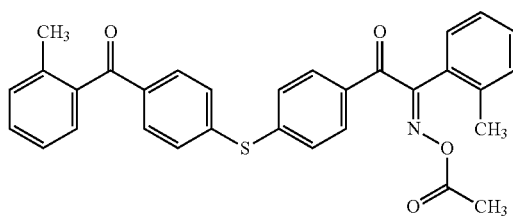
PI-27
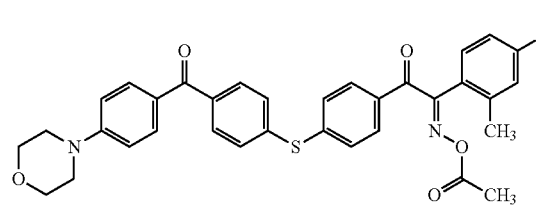
PI-28
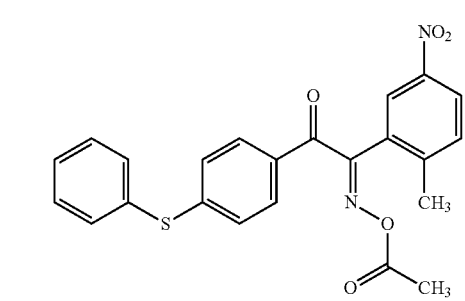
PI-29
-continued
PI-30
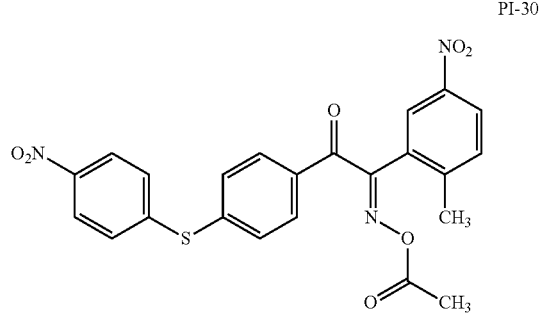
PI-31
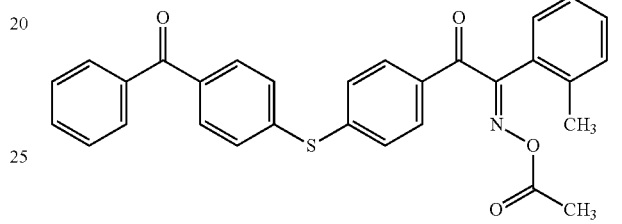
PI-32
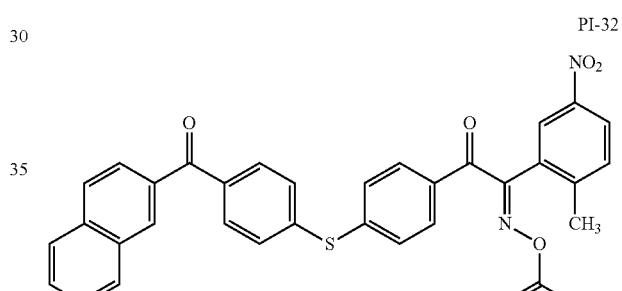
PI-33
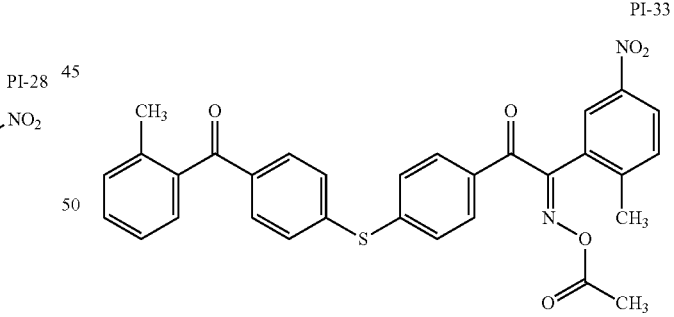
PI-34
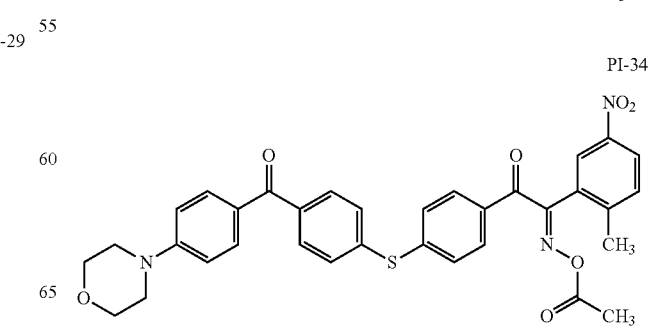

PI-35
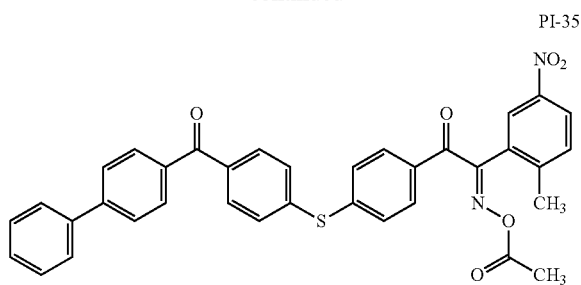

PI-36
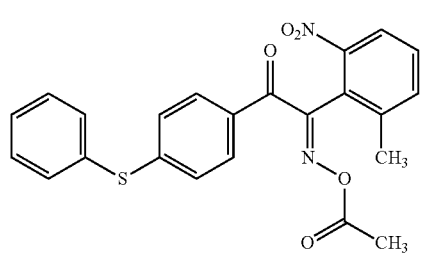

PI-37
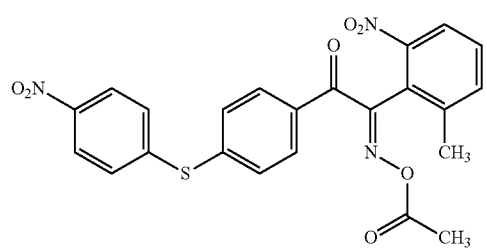

PI-38
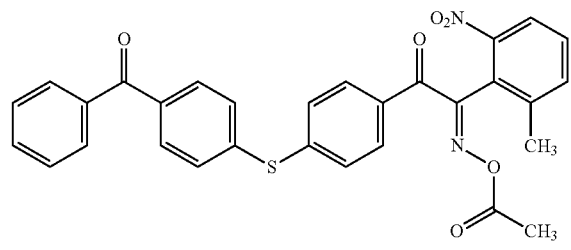

PI-39
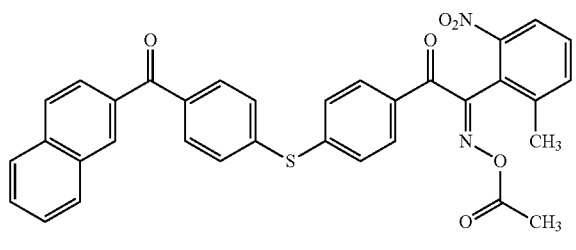

PI-40
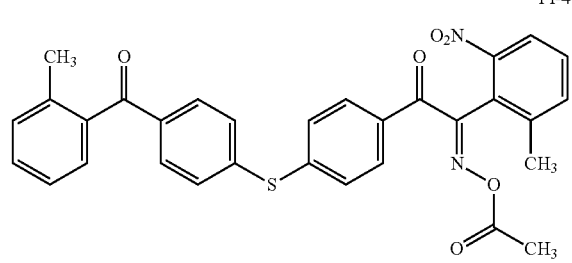

PI-41
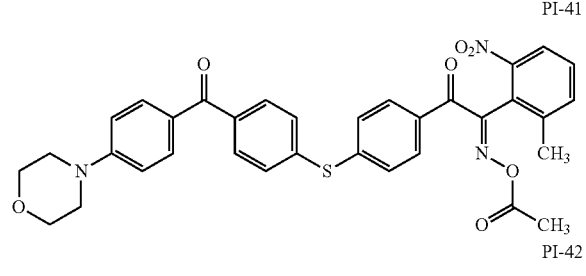

PI-42

Also preferable as a photopolymerization initiator is an oxime ester compound represented by the following formula (c4).

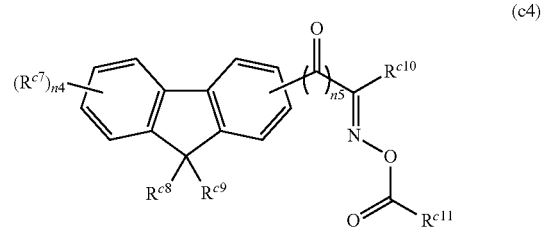 (c4)

$R^{c7}$ is a hydrogen atom, a nitro group, or a monovalent organic group, $R^{c8}$ and $R^{c9}$ each represent an optionally substituted chain alkyl group, an optionally substituted cyclic organic group, or a hydrogen atom, $R^{c8}$ and $R^{c9}$ may be bonded to one another to form a ring, $R^{c10}$ is a monovalent organic group, $R^{c11}$ is a hydrogen atom, an optionally substituted alkyl group having 1 or more and 11 or less carbon atoms, or an optionally substituted aryl group, n4 is an integer of 0 or more and 4 or less, and n5 is 0 or 1.

An oxime compound for producing an oxime ester compound of the formula (c4) is suitably a compound represented by the following formula (c5).

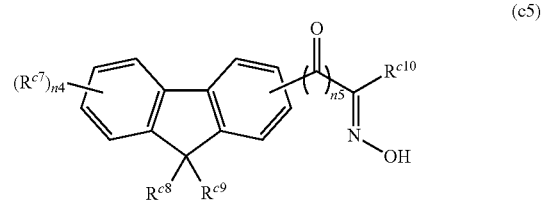 (c5)

$R^{c7}$, $R^{c8}$, $R^{c9}$, $R^{c10}$, n4, and n5 are the same as defined in the formula (c4).

In the formulae (c4) and (c5), $R^{c7}$ is a hydrogen atom, a nitro group, or a monovalent organic group. $R^{c7}$ is bonded to a 6-membered aromatic ring which is different from the 6-membered aromatic ring bonded to a group represented as —(CO)$_{n5}$— on a fluorene ring in the formula (c4). In the formula (c4), the bond position of $R^{c7}$ to a fluorene ring is not particularly limited. When a compound represented by the formula (c4) has 1 or more $R^{c7}$(s), one of the one or more $R^{c7}$(s) is preferably bonded at the 2-position in the fluorene ring since the synthesis of the compound represented by the formula (c4) becomes easy. When plural $R^{c7}$s exist, the plural $R^{c7}$s may be the same or different.

When $R^{c7}$ is an organic group, $R^{c7}$ is not particularly limited as long as it does not interfere with the object of the present invention, and is appropriately selected from various organic groups. When $R^{c7}$ is an organic group, suitable examples include an alkyl group, an alkoxy group, a cycloalkyl group, a cycloalkoxy group, a saturated aliphatic acyl group, a saturated aliphatic acyloxy group, an alkoxycarbonyl group, an optionally substituted phenyl group, an optionally substituted phenoxy group, an optionally substituted benzoyl group, an optionally substituted phenoxycarbonyl group, an optionally substituted benzoyloxy group, an optionally substituted phenylalkyl group, an optionally substituted naphthyl group, an optionally substituted naphthoxy group, an optionally substituted naphthoyl group, an optionally substituted naphthoxycarbonyl group, an optionally substituted naphthoyloxy group, an optionally substituted naphthylalkyl group, an optionally substituted heterocyclyl group, an optionally substituted heterocyclylcarbonyl group, an amino group substituted with one or two organic groups, a morpholin-1-yl group, and a piperazin-1-yl group.

When $R^{c7}$ is an alkyl group, the number of carbon atoms of the alkyl group is preferably 1 or more and 20 or less, and more preferably 1 or more and 6 or less. When $R^{c7}$ is an alkyl group, the alkyl group may be either one of a straight chain or branched chain alkyl group. When $R^{c7}$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{c7}$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, a methoxypropyl group, and the like.

When $R^{c7}$ is an alkoxy group, the number of carbon atoms of the alkoxy group is preferably 1 or more and 20 or less, and more preferably 1 or more and 6 or less. When $R^{c7}$ is an alkoxy group, the alkoxy group may be a straight-chain or branched-chain group. When $R^{c7}$ is an alkoxy group, specific examples thereof include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, an isodecyloxy group, and the like. When $R^{c7}$ is an alkoxy group, the alkoxy group may contain an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, a methoxypropyloxy group, and the like.

When $R^{c7}$ is a cycloalkyl group or a cycloalkoxy group, the number of carbon atoms of the cycloalkyl group or cycloalkoxy group is preferably 3 or more and 10 or less, and more preferably 3 or more and 6 or less. When $R^{c7}$ is a cycloalkyl group, specific examples thereof include a cyclopropyl group, a cyclobutyl group, a cyclopentyl group, a cyclohexyl group, a cycloheptyl group, a cyclooctyl group, and the like. When $R^{c7}$ is a cycloalkoxy group, specific examples thereof include a cyclopropyloxy group, a cyclobutyloxy group, a cyclopentyloxy group, a cyclohexyloxy group, a cycloheptyloxy group, a cyclooctyloxy group, and the like.

When $R^{c7}$ is a saturated aliphatic acyl group or a saturated aliphatic acyloxy group, the number of carbon atoms of the saturated aliphatic acyl group or saturated aliphatic acyloxy group is preferably 2 or more and 21 or less, and more preferably 2 or more and 7 or less. When $R^{c7}$ is a saturated aliphatic acyl group, specific examples thereof include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, an n-hexadecanoyl group, and the like. When $R^{c7}$ is a saturated aliphatic acyloxy group, specific examples thereof include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, an n-hexadecanoyloxy group, and the like.

When $R^{c7}$ is an alkoxycarbonyl group, the number of carbon atoms of the alkoxycarbonyl group is preferably 2 or more and 20 or less, and preferably 2 or more and 7 or less. When $R^{c7}$ is an alkoxycarbonyl group, specific examples thereof include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, an isodecyloxycarbonyl group, and the like.

When $R^{c7}$ is a phenylalkyl group, the number of carbon atoms of the phenylalkyl group is preferably 7 or more and 20 or less, and more preferably 7 or more and 10 or less. When $R^{c7}$ is a naphthylalkyl group, the number of carbon atoms of the naphthylalkyl group is preferably 11 or more and 20 or less, and more preferably 11 or more and 14 or less. When $R^{c7}$ is a phenylalkyl group, specific examples thereof include a benzyl group, a 2-phenylethyl group, a 3-phenylpropyl group, and a 4-phenylbutyl group. When $R^{c7}$ is a naphthylalkyl group, specific examples thereof include an α-naphthylmethyl group, a β-naphthylmethyl group, a 2-(α-naphthyl)ethyl group, and a 2-(β-naphthyl)ethyl group.

When $R^{c7}$ is a phenylalkyl group or a naphthylalkyl group, $R^{c7}$ may further have a substituent on a phenyl group or a naphthyl group.

When $R^{c7}$ is a heterocyclyl group, the heterocyclyl group is a 5- or 6-membered single ring containing one or more N, S, and O, or a heterocyclyl group in which single rings are fused each other, or a single ring is fused with a benzene ring. When the heterocyclyl group is a fused ring, the number of fused ring is 3 or less. The heterocyclyl group may be any one of an aromatic group (heteroaryl group) and a non-aromatic group. Examples of the heterocycle constituting the heterocyclyl group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, tetrahydrofuran, and the like. When $R^{c7}$ is a heterocyclyl group, the heterocyclyl group may further have a substituent.

When $R^{c7}$ is a heterocyclylcarbonyl group, a heterocyclyl group included in the heterocyclylcarbonyl group is the same as that in the case where $R^{c7}$ is a heterocyclyl group.

When $R^{c7}$ is an amino group substituted with one or two organic group(s), suitable examples of the organic group(s) include an alkyl group having 1 or more and 20 or less carbon atoms, a cycloalkyl group having 3 or more and 10 or less carbon atoms, a saturated aliphatic acyl group having 2 or more and 21 or less carbon atoms, an optionally substituted phenyl group, an optionally substituted benzoyl group, an optionally substituted phenylalkyl group having 7 or more and 20 or less carbon atoms, an optionally substituted naphthyl group, an optionally substituted naphthoyl group, an optionally substituted naphthylalkyl group having 11 or more 20 or less carbon atoms, a heterocyclyl group, and the like. The specific examples of these suitable organic groups are the same as those of $R^{c7}$. Specific examples of the amino group substituted with one or two organic groups include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, a propanoylamino group, an n-butanoylamino group, an n-pentanoylamino group, an n-hexanoylamino group, an n-heptanoylamino group, an n-octanoylamino group, an n-decanoylamino group, an benzoylamino group, an α-naphthoylamino group, a β-naphthoylamino group, and the like.

When the phenyl group, the naphthyl group, and the heterocyclyl group included in $R^{c7}$ further have a substituent, examples thereof include an alkyl group having 1 or more and 6 or less carbon atoms, an alkoxy group having 1 or more and 6 or less carbon atoms, a saturated aliphatic acyl group having 2 or more and 7 or less carbon atoms, an alkoxycarbonyl group having 2 or more and 7 or less carbon atoms, a saturated aliphatic acyloxy group having 2 or more and 7 or less carbon atoms, a monoalkylamino group having an alkyl group which has 1 or more and 6 or less carbon atoms, a dialkylamino group having an alkyl group which has 1 or more and 6 or less carbon atoms, a morpholin-1-yl group, a piperazin-1-yl group, halogen, a nitro group, a cyano group, and the like. When a phenyl group, a naphthyl group, and a heterocyclyl group included in $R^{c7}$ further have substituents, the number of substituents is not particularly limited as long as it does not interfere with the object of the present invention, but is preferably 1 or more 4 or less. When a phenyl group, a naphthyl group, and a heterocyclyl group included in $R^{c7}$ have plural substituents, the plural substituents may be the same or different.

Among the above-described groups, $R^{c7}$ is preferably a nitro group or a group represented as $R^{c12}$—CO— since the sensitivity tends to be improved. $R^{c12}$ is not particularly limited as long as it does not interfere with the object of the present invention, and can be selected from various organic groups. Examples of the group suitable as $R^{c12}$ include an alkyl group having 1 or more and 20 or less carbon atoms, an optionally substituted phenyl group, an optionally substituted naphthyl group, and an optionally substituted heterocyclyl group. Among these groups, $R^{c12}$ is particularly preferably a 2-methylphenyl group, a thiophen-2-yl group, and an α-naphthyl group. Moreover, it is preferred that $R^{c7}$ is a hydrogen atom since the transparency tends to be satisfactory. When $R^{c7}$ is a hydrogen atom and $R^{c10}$ is a group represented by the formula (c4a) or (c4b) mentioned later, the transparency tends to be even more satisfactory.

In the formula (c4), $R^{c8}$ and $R^{c9}$ each represent an optionally substituted chain alkyl group, an optionally substituted cyclic organic group, or a hydrogen atom. $R^{c8}$ and $R^{c9}$ may be bonded to one another to form a ring. Among these, preferably, $R^{c8}$ and $R^{c9}$ are optionally substituted chain alkyl groups. When $R^{c8}$ and $R^{c9}$ are optionally substituted chain alkyl groups, a chain alkyl group may be either a straight-chain alkyl group or a branched-chain alkyl group.

When $R^{c8}$ and $R^{c9}$ are chain alkyl groups having no substituent, the number of carbon atoms of the chain alkyl group is preferably 1 or more and 20 or less, more preferably 1 or more and 10 or less, and particularly preferably 1 or more and 6 or less. When $R^{c8}$ and $R^{c9}$ are chain alkyl groups, specific examples thereof include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, an isodecyl group, and the like. When $R^{c8}$ and $R^{c9}$ are alkyl groups, the alkyl group may have an ether bond (—O—) in a carbon chain. Examples of the alkyl group having an ether bond in a carbon chain include a methoxyethyl group, an ethoxyethyl group, a methoxyethoxyethyl group, an ethoxyethoxyethyl group, a propyloxyethoxyethyl group, and a methoxypropyl group.

When $R^{c8}$ and $R^{c9}$ are chain alkyl groups having a substituent, the number of carbon atoms of the chain alkyl group is preferably 1 or more and 20 or less, more preferably 1 or more and 10 or less, and particularly preferably 1 or more and 6 or less. In this case, the number of carbon atoms of the substituent is not included in the number of carbon atoms of the chain alkyl group. The chain alkyl group having a substituent is preferably a straight-chain group. The substituent, with which the alkyl group is optionally substituted, is not particularly limited as long as it does not interfere with the object of the present invention. Suitable examples of the substituent include a cyano group, a halogen atom, a cyclic organic group, and an alkoxycarbonyl group. Examples of the halogen atom include a fluorine atom, a chlorine atom, a bromine atom, and an iodine atom. Among these, a fluorine atom, a chlorine atom, and a bromine atom are preferable. Examples of the cyclic organic group include a cycloalkyl group, an aromatic hydrocarbon group, and a heterocyclyl group. Specific examples of the cycloalkyl group are the same as suitable examples in case $R^{c7}$ is a cycloalkyl group. Specific examples of the aromatic hydrocarbon group include a phenyl group, a naphthyl group, a biphenylyl group, an anthryl group, a phenanthryl group, and the like. Specific examples of the heterocyclyl group are the same as suitable examples in case $R^{c7}$ is a heterocyclyl group. When $R^{c7}$ is an alkoxycarbonyl group, an alkoxy group included in the alkoxycarbonyl group may be either a straight-chain or branched-chain group, and preferably a straight-chain group. The number of carbon atoms of an alkoxy group included in the alkoxycarbonyl group is preferably 1 or more and 10 or less, and more preferably 1 or more and 6 or less.

When the chain alkyl group has a substituent, the number of substituents is not particularly limited. The number of substituents preferably varies depending on the number of carbon atoms of the chain alkyl group. The number of substituents is typically 1 or more and 20 or less, preferably 1 or more and 10 or less, and more preferably 1 or more and 6 or less.

When $R^{c8}$ and $R^{c9}$ are cyclic organic groups, the cyclic organic group may be either an alicyclic group or an aromatic group. Examples of the cyclic organic group include an aliphatic cyclic hydrocarbon group, an aromatic hydrocarbon group, and a heterocyclyl group. When $R^{c8}$ and $R^{c9}$ are cyclic organic groups, the substituent, with which the cyclic organic group is optionally substituted, is the same as in case $R^{c8}$ and $R^{c9}$ are chain alkyl groups.

When $R^{c8}$ and $R^{c9}$ are aromatic hydrocarbon groups, the aromatic hydrocarbon group is preferably a phenyl group, or a group formed by bonding plural benzene rings through a carbon-carbon bond, or a group formed by condensing plural benzene rings. When the aromatic hydrocarbon group is a phenyl group, or a group formed by bonding or condensing plural benzene rings, the number of rings of a benzene ring included in the aromatic hydrocarbon group is not particularly limited, and is preferably 3 or less, more preferably 2 or less, and particularly preferably 1. Preferred specific examples of the aromatic hydrocarbon group include a phenyl group, a naphthyl group, a biphenylyl group, an anthryl group, a phenanthryl group, and the like.

When $R^{c8}$ and $R^{c9}$ are aliphatic cyclic hydrocarbon groups, the aliphatic cyclic hydrocarbon group may be either a monocyclic or polycyclic group. The number of carbon atoms of the aliphatic cyclic hydrocarbon group is not particularly limited, and is preferably 3 or more 20 or less, and more preferably 3 or more and 10 or less. Examples of the monocyclic cyclic hydrocarbon group include cyclopropyl group, a cyclobutyl group, a cyclopentyl group, a cyclohexyl group, a cycloheptyl group, a cyclooctyl group, a norbornyl group, a isobornyl group, a tricyclononyl group, a tricyclodecyl group, a tetracyclododecyl group, an adamantyl group, and the like.

When $R^{c8}$ and $R^{c9}$ are heterocyclyl groups, the heterocyclyl group is a 5-membered or 6-membered monocycle containing one or more N, S, and O, or a heterocyclyl group in which these monocycles are condensed, or the monocycle and a benzene ring are condensed. When the heterocyclyl group is a condensation ring, the number of rings is 3 or less. The heterocyclyl group may be either an aromatic group (heteroaryl group) or a non-aromatic group. Examples of the heterocycle constituting the heterocyclic group include furan, thiophene, pyrrole, oxazole, isoxazole, triazole, thiadiazole, isothiazole, imidazole, pyrazole, triazole, pyridine, pyrazine, pyrimidine, pyridazine, benzofuran, benzothiophene, indole, isoindole, indolizine, benzimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, tetrahydrofuran, and the like.

$R^{c8}$ and $R^{c9}$ may be bonded to one another to form a ring. The group composed of the ring formed by $R^{c8}$ and $R^{c9}$ is preferably a cycloalkylidene group. When $R^{c8}$ and $R^{c9}$ are bonded to form a cycloalkylidene group, the ring constituting the cycloalkylidene group is preferably a 5- to 6-membered ring, and more preferably a 5-membered ring.

When the group formed by bonding $R^{c8}$ and $R^{c9}$ is a cycloalkylidene group, the cycloalkylidene group may be fused with one or more other rings. Examples of the ring which may be fused with the cycloalkylidene group include a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, a pyrimidine ring, and the like.

Examples of suitable group among $R^{c8}$ and $R^{c9}$ descried above include a group represented by the formula: $-A^1-A^2$. In the formula, $A^1$ is a straight chain alkylene group, and $A^2$ is an alkoxy group, a cyano group, a halogen atom, a halogenated alkyl group, a cyclic organic group, or an alkoxycarbonyl group.

The number of carbon atoms of the straight chain alkylene group for $A^1$ is preferably 1 or more and 10 or less, and more preferably 1 or more and 6 or less. When $A^2$ is an alkoxy group, the alkoxy group may be any one of straight chain and branched chain alkoxy groups, and preferably a straight chain alkoxy group. The number of carbon atoms of the alkoxy group is preferably 1 or more and 10 or less, and more preferably 1 or more and 6 or less. When $A^2$ is a halogen atom, a fluorine atom, a chlorine atom, a bromine atom, or an iodine atom is preferable, and a fluorine atom, a chlorine atom, or a bromine atom is more preferable. When $A^2$ is a halogenated alkyl group, a halogen atom included in the halogenated alkyl group is preferably a fluorine atom, a chlorine atom, a bromine atom, or an iodine atom, and more preferably is a fluorine atom, a chlorine atom, or a bromine atom. The halogenated alkyl group may be any one of straight chain and branched chain halogenated alkyl groups, and preferably a straight chain halogenated alkyl group. When $A^2$ is a cyclic organic group, examples of the cyclic organic group are the same as the cyclic organic group possessed by $R^{c8}$ and $R^{c9}$ as the substituent. When $A^2$ is an alkoxycarbonyl group, examples of the alkoxycarbonyl group are the same as the alkoxycarbonyl group possessed by $R^{c8}$ and $R^{c9}$ as the substituent.

Suitable specific examples of $R^{c8}$ and $R^{c9}$ include alkyl groups such as an ethyl group, an n-propyl group, an n-butyl group, an n-hexyl group, an n-heptyl group, and an n-octyl group; alkoxyalkyl groups such as a 2-methoxyethyl group, a 3-methoxy-n-propyl group, a 4-methoxy-n-butyl group, a 5-methoxy-n-pentyl group, a 6-methoxy-n-hexyl group, a 7-methoxy-n-heptyl group, a 8-methoxy-n-octyl group, a 2-ethoxyethyl group, a 3-ethoxy-n-propyl group, a 4-ethoxy-n-butyl group, a 5-ethoxy-n-pentyl group, a 6-ethoxy-n-hexyl group, a 7-ethoxy-n-heptyl group, and a 8-ethoxy-n-octyl group; cyanoalkyl groups such as a 2-cyanoethyl group, a 3-cyano-n-propyl group, a 4-cyano-n-butyl group, a 5-cyano-n-pentyl group, a 6-cyano-n-hexyl group, a 7-cyano-n-heptyl group, and a 8-cyano-n-octyl group; phenylalkyl groups such as a 2-phenylethyl group, a 3-phenyl-n-propyl group, a 4-phenyl-n-butyl group, a 5-phenyl-n-pentyl group, a 6-phenyl-n-hexyl group, a 7-phenyl-n-heptyl group, and a 8-phenyl-n-octyl group; cycloalkylalkyl groups such as a 2-cyclohexylethyl group, a 3-cyclohexyln-propyl group, a 4-cyclohexyl-n-butyl group, a 5-cyclohexyl-n-pentyl group, a 6-cyclohexyl-n-hexyl group, a 7-cyclohexyl-n-heptyl group, a 8-cyclohexyl-n-octyl group, a 2-cyclopentylethyl group, a 3-cyclopentyl-n-propyl group, a 4-cyclopentyl-n-butyl group, a 5-cyclopentyl-n-pentyl group, a 6-cyclopentyl-n-hexyl group, a 7-cyclopentyl-n-heptyl group, and a 8-cyclopentyl-n-octyl group; alkoxycarbonylalkyl groups such as a 2-methoxycarbonylethyl group, a 3-methoxycarbonyl-n-propyl group, a 4-methoxycarbonyl-n-butyl group, a 5-methoxycarbonyl-n-pentyl group, a 6-methoxycarbonyl-n-hexyl group, a 7-methoxycarbonyl-n-heptyl group, a 8-methoxycarbonyl-n-octyl group, a 2-ethoxycarbonylethyl group, a 3-ethoxycarbonyl-n-propyl group, a 4-ethoxycarbonyl-n-butyl group, a 5-ethoxycarbonyl-n-pentyl group, a 6-ethoxycarbonyl-n-hexyl group, a 7-ethoxycarbonyl-n-heptyl group, and a 8-ethoxycarbonyl-n-octyl group; and halogenated alkyl groups such as a 2-chloroethyl group, a 3-chloro-n-propyl group, a 4-chloro-n-butyl group, a 5-chloro-n-pentyl group, a 6-chloro-n-hexyl group, a 7-chloro-n-heptyl group, a 8-chloro-n-octyl group, a 2-bromoethyl group, a 3-bromo-n-propyl group, a 4-bromo-n-butyl group, a 5-bromo-n-pentyl group, a 6-bromo-n-hexyl group, a 7-bromo-n-heptyl group, a 8-bromo-n-octyl group, a 3,3,3-trifluoropropyl group, and a 3,3,4,4,5,5,5-heptafluoro-n-pentyl group.

Among groups mentioned above, groups suitable as $R^{c8}$ and $R^{c9}$ are an ethyl group, an n-propyl group, an n-butyl group, an n-pentyl group, a 2-methoxyethyl group, a 2-cyanoethyl group, a 2-phenylethyl group, a 2-cyclohexylethyl group, a 2-methoxycarbonylethyl group, a 2-chloroethyl group, a 2-bromoethyl group, a 3,3,3-trifluoropropyl group, and a 3,3,4,4,5,5,5-heptafluoro-n-pentyl group.

In the same manner as $R^{c7}$, examples of suitable organic group for $R^{c10}$ include an alkyl group, an alkoxy group, a cycloalkyl group, a cycloalkoxy group, a saturated aliphatic acyl group, an alkoxycarbonyl group, a saturated aliphatic acyloxy group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclyl group which may have a substituent, a heterocyclylcarbonyl group which may have a substituent, an amino group substituted with one or two organic groups, a morpholin-1-yl group, a piperazin-1-yl group, and the like. Specific examples of these groups are the same as those described for $R^{c7}$. $R^{c10}$ is also preferably a cycloalkylalkyl group, a phenoxyalkyl group which may have a substituent on an aromatic ring, and a phenylthioalkyl group which may have a substituent on an aromatic ring. The substituent which may be possessed by a phenoxyalkyl group and phenylthioalkyl group is the same as the substituent which may be possessed by a phenyl group included in $R^{c7}$.

Among organic groups, $R^{c10}$ is preferably an alkyl group, a cycloalkyl group, a phenyl group which may have a substituent or cycloalkylalkyl group, or a phenylthioalkyl group which may have a substituent on an aromatic ring. The alkyl group is preferably an alkyl group having 1 or more and 20 or less carbon atoms, more preferably, an alkyl group having 1 or more and 8 or less carbon atoms, particularly preferably, an alkyl group having 1 or more and 4 or less carbon atoms, and most preferably a methyl group. Among phenyl groups which may have a substituent, a methylphenyl group is preferable and a 2-methylphenyl group is more preferable. The number of carbon atoms of the cycloalkyl group included in the cycloalkylalkyl group is preferably 5 or more and 10 or less, more preferably 5 or more and 8 or less, and particularly preferably 5 or 6. The number of carbon atoms of the alkylene group included in the cycloalkylalkyl group is preferably 1 or more and 8 or less, more preferably 1 or more and 4 or less, and particularly preferably 2. Among cycloalkylalkyl groups, a cyclopentylethyl group is preferable. The number of carbon atoms of the alkylene group which may have a substituent on an aromatic ring included in the phenylthioalkyl group, is preferably 1 or more and 8 or less, more preferably 1 or more and 4 or less, and particularly preferably 2. Among the phenylthioalkyl group which may have a substituent on an aromatic ring, a 2-(4-chlorophenylthio)ethyl group is preferable.

$R^{c10}$ is also preferably a group represented by -$A^3$-CO—O-$A^4$. $A^3$ is a divalent organic group, preferably a divalent hydrocarbon group, and more preferably an alkylene group. $A^4$ is a monovalent organic group, and preferably a monovalent hydrocarbon group.

When $A^3$ is an alkylene group, alkylene group may be any one of straight chain and branched chain alkylene groups, and preferably a straight chain alkylene group. When $A^3$ is an alkylene group, the number of carbon atoms of the alkylene group is preferably 1 or more and 10 or less, more preferably 1 or more and 6 or less, and particularly preferably 1 or more and 4 or less.

Suitable examples of $A^4$ include an alkyl group having 1 or more and 10 or less carbon atoms, an aralkyl group having 7 or more and 20 or less carbon atoms, and an aromatic hydrocarbon group having 6 or more and 20 or less carbon atoms. Suitable specific examples of $A^4$ include a methyl group, an ethyl group, an n-propyl group, an isopropyl group, an n-butyl group, an isobutyl group, a sec-butyl group, an tert-butyl group, an n-pentyl group, an n-hexyl group, a phenyl group, a naphthyl group, a benzyl group, a phenethyl group, an α-naphthylmethyl group, a β-naphthylmethyl group, and the like.

Suitable specific examples of the group represented by -$A^3$-CO—O-$A^4$ include a 2-methoxycarbonylethyl group, a 2-ethoxycarbonylethyl group, a 2-n-propyloxycarbonylethyl group, a 2-n-butyloxycarbonylethyl group, a 2-n-pentyloxycarbonylethyl group, a 2-n-hexyloxycarbonylethyl group, a 2-benzyloxycarbonylethyl group, a 2-phenoxycarbonylethyl group, a 3-methoxycarbonyl-n-propyl group, a 3-ethoxycarbonyl-n-propyl group, a 3-n-propyloxycarbonyl-n-propyl group, a 3-n-butyloxycarbonyl-n-propyl group, a 3-n-pentyloxycarbonyl-n-propyl group, a 3-n-hexyloxycarbonyl-n-propyl group, a 3-benzyloxycarbonyl-n-propyl group, a 3-phenoxycarbonyl-n-propyl group, and the like.

While $R^{c10}$ has been described above, $R^{c10}$ is preferably a group represented by the following formula (c4a) or (c4b):

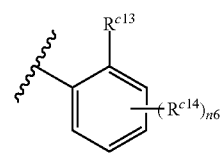

(c4a)

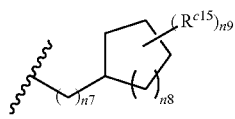
(c4b)

in which, in the formulas (c4a) and (c4b), $R^{c13}$ and $R^{c14}$ each are an organic group, n6 is an integer of 0 or more and 4 or less; when $R^{c13}$ and $R^{c14}$ exist at adjacent positions on a benzene ring, $R^{c13}$ and $R^{c14}$ may be bonded to one another to form a ring; n7 is an integer of 1 or more and 8 or less; n8 is an integer of 1 or more and 5 or less; n9 is an integer of 0 or more and (n8+3); and $R^{c15}$ is an organic group.

Examples of the organic group for $R^{c13}$ and $R^{c14}$ in the formula (c4a) are the same as those in $R^{c7}$. $R^{c13}$ is preferably an alkyl group or a phenyl group. When $R^{c13}$ is an alkyl group, the number of carbon atoms thereof is preferably 1 or more and 10 or less, more preferably 1 or more and 5 or less, preferably 1 or more and 3 or less, and most preferably 1. Namely, $R^{c13}$ is most preferably a methyl group. When $R^{c13}$ and $R^{c14}$ are bonded to form a ring, the ring may be either one of an aromatic ring or an aliphatic ring. Suitable examples of the group represented by the formula (c4a) in which $R^{c13}$ and $R^{c14}$ form a ring include a naphthalen-1-yl group, a 1,2,3,4-tetrahydronaphthalen-5-yl group, and the like. In the above formula (c4a), n6 is an integer of 0 or more and 4 or less, preferably 0 or 1, and more preferably 0.

In the above formula (c4b), $R^{c15}$ is an organic group. Examples of the organic group include the same group as the organic group described for $R^{c7}$. Among the organic groups, an alkyl group is preferable. The alkyl group may be any one of straight chain and branched chain alkyl groups. The number of carbon atoms of the alkyl group is preferably 1 or more and 10 or less, more preferably, 1 or more and 5 or less, and particularly preferably 1 or more and 3 or less. Preferable examples of $R^{c15}$ include a methyl group, an ethyl group, a propyl group, an isopropyl group, a butyl group, and the like. Among these, a methyl group is more preferable.

In the above formula (c4b), n8 is an integer of 1 or more and 5 or less, preferably 1 or more and 3 or less, and more preferably 1 or 2. In the formula (c4b), n9 is 0 or more and (n8+3) or less, preferably an integer of 0 or more and 3 or less, more preferably an integer of 0 or more and 2 or less, and particularly preferably 0. In the formula (c4b), n7 is an integer of 1 or more and 8 or less, preferably an integer of 1 or more and 5 or less, more preferably an integer of 1 or more and 3 or less, and particularly preferably 1 or 2.

In the formula (c4), $R^{c11}$ is a hydrogen atom, an alkyl group having 1 or more and 11 or less carbon atoms which may have a substituent, or an aryl group which may have a substituent. When $R^{c11}$ is an alkyl group, preferable examples of the substituent which may be possessed include a phenyl group, a naphthyl group, or the like. When $R^{c7}$ is an aryl group, preferable examples of the substituent which may be possessed include an alkyl group having 1 or more and 5 or less carbon atoms, an alkoxy group, a halogen atom, or the like.

In the formula (c4), preferable examples of $R^{c11}$ include a hydrogen atom, a methyl group, an ethyl group, an n-propyl group, an isopropyl group, an n-butyl group, a phenyl group, a benzyl group, a methylphenyl group, a naphthyl group, and the like. Among these, a methyl group or a phenyl group is more preferable.

The compound represented by the formula (c4) is produced by a method including the step of converting an oxime group ($>C=N-OH$) contained in a compound represented by the formula (c5) into an oxime ester group represented by $>C=N-O-COR^{c11}$. $R^{c11}$ is the same as $R^{c11}$ in the formula (c4).

Conversion of the oxime group ($>C=N-OH$) into the oxime ester group represented by $>C=N-O-COR^{c11}$ is performed by reacting a compound represented by the formula (c5) with an acylating agent. Examples of the acylating agent, which imparts an acyl group represented by $-COR^{c11}$, include an acid anhydride represented by $(R^{c11}CO)_2O$, and an acid halide represented by $R^{c11}COHal$ (Hal is a halogen atom).

When n5 is 0, a compound represented by the general formula (c4) can be synthesized according to, for example, the following scheme 3. In scheme 3, a fluorene derivative represented by the following formula (c3-1) is used as raw material. When $R^{c7}$ is a nitro group or a monovalent organic group, the fluorene derivative represented by the formula (c3-1) can be obtained by introducing a substituent $R^{c7}$ into a fluorene derivative substituted at position 9 with $R^{c8}$ and $R^{c9}$ by a well-known method. The fluorene derivative substituted at position 9 with $R^{c8}$ and $R^{c9}$, for example, when $R^{c8}$ and $R^{c9}$ are an alkyl group, can be obtained by reacting fluorene and an alkylating agent to each other in an aprotic polar organic solvent in the presence of alkali metal hydroxide as described in Japanese Unexamined Patent Application, Publication No. H06-234668. Furthermore, 9,9-alkyl substituted fluorene can be obtained by carrying out an alkylating reaction by adding an alkylating agent such as halogenated alkyl, an aqueous solution of alkali metal hydroxide, and a phase transfer catalyst such as tetrabutylammonium iodide and potassium tert-butoxide with the organic solvent solution of fluorene.

Fluorene derivatives represented by the formula (c3-3) are obtained by introducing an acyl group represented by $-CO-R^{c10}$ into fluorene derivatives represented by the formula (c3-1) by Friedel-Crafts acylation reaction. The acylating agent for introducing the acyl group represented by $-CO-R^{c10}$ may be a halocarbonyl compound, or may be an acid anhydride. As the acylating agent, a halocarbonyl compound represented by the formula (c3-2) is preferable. In the formula (c3-2), Hal represents a halogen atom. A position in which an acyl group is to be introduced on a fluorene ring can be selected by appropriately changing conditions of the Friedel-Crafts reaction, or carrying out protection and deprotection to a position other than the position to be acylated.

Then, a group represented by $-CO-R^{c10}$ in the resulting fluorene derivative represented by formula (c3-3) is converted into a group represented by $-C(=N-OH)-R^{c10}$ to obtain an oxime compound represented by the formula (c3-4). A method for converting the group represented by $-CO-R^{c10}$ into a group represented by $-C(=N-OH)-R^{c10}$ is not particularly limited, but oximation by hydroxyl amine is preferable. A compound represented by the following formula (c3-7) can be obtained by reacting an oxime compound of the formula (c3-4) and acid anhydride represented by the following formula (c3-5) (($R^{c11}CO)_2O$) or acid halide represented by the following formula (c3-6) ($R^{c11}COHal$, wherein Hal is a halogen atom) with each other.

Note here that in the formulae (c3-1), (c3-2), (c3-3), (c3-4), (c3-5), (c3-6), and (c3-7), $R^{c7}$, $R^{c8}$, $R^{c9}$, $R^{c10}$, and $R^{c11}$ are similar to those in the formula (c4).

Furthermore, in scheme 3, $R^{c10}$ included in each of the formula (c3-2), the formula (c3-3), and the formula (c3-4) may be the same as or different from each other. In other words, $R^{c10}$ included in the formula (c3-2), the formula (c3-3), and the formula (c3-4) may be subjected to chemical modification in the synthesis process shown as scheme 3. Examples of the chemical modification include esterification, etherification, acylation, amidation, halogenation, substitution of a hydrogen atom in an amino group by an organic group, and the like. Chemical modification which $R^{c10}$ may undergo is not limited to these examples.

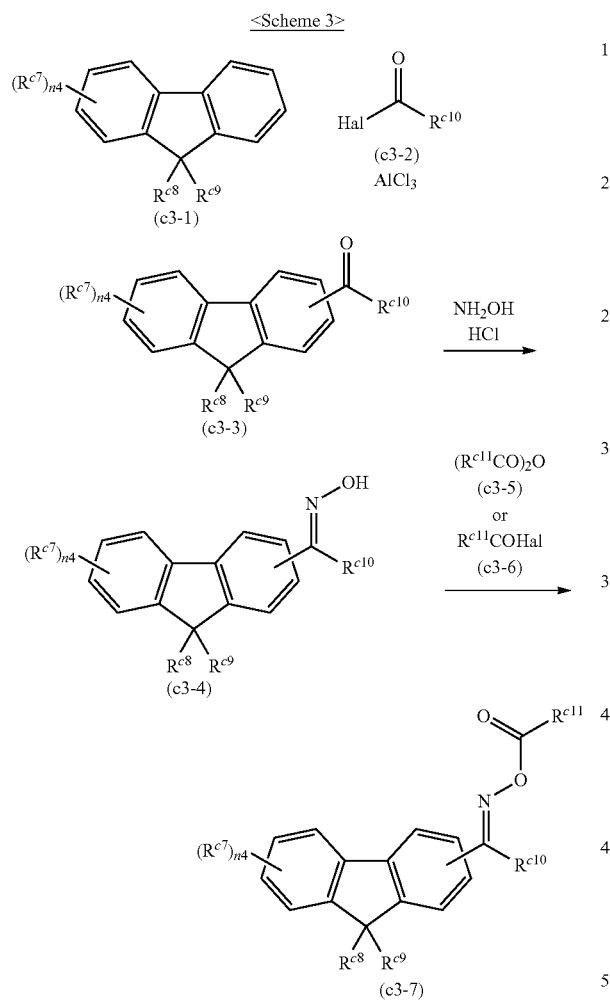

When n5 is 1, the compound represented by the formula (c4) can be synthesized according to, for example, the following scheme 4. In scheme 4, the fluorene derivative represented by the following formula (c4-1) is used as raw material. The fluorene derivative represented by the formula (c4-1) is obtained by introducing an acyl group represented by —CO—CH$_2$—$R^{c10}$ into the compound represented by the formula (c3-1) by Friedel-Crafts reaction by the same method as in scheme 3. As the acylating agent, carboxylic acid halide represented by the formula (c3-8): Hal-CO—CH$_2$—$R^{c10}$ is preferable. Subsequently, a methylene group existing between $R^{c10}$ and a carbonyl group in the compound represented by the formula (c4-1) is oximated to obtain a ketoxime compound represented by the following formula (c4-3). A method for oximating a methylene group is not particularly limited, but preferred is a method for reacting nitrous ester (RONO, R is an alkyl group having 1 or more and 6 or less carbon atoms) represented by the following general formula (c4-2) in the presence of hydrochloric acid. Next, a ketoxime compound represented by the following formula (c4-3), acid anhydride (($R^{c11}CO)_2O$)) represented by the following formula (c4-4), or acid halide ($R^{c11}$COHal, Hal is a halogen atom) represented by the following formula (c4-5) are reacted with each other to obtain a compound represented by the following formula (c4-6). Note here that in the following formulae (c4-1), (c4-3), (c4-4), (c4-5), and (c4-6), $R^{c7}$, $R^{c8}$, $R^{c9}$, $R^{c10}$, and $R^{c11}$ are the same as those in the formula (c4). When n5 is 1, generation of foreign matter in a pattern formed using a photosensitive composition containing a compound represented by the formula (c4) tends to be able to be reduced.

Furthermore, in scheme 4, $R^{c10}$ included in each of the formula (c3-8), the formula (c4-1), and the formula (c4-3) may be the same as or different from each other. In other words, $R^{c10}$ included in the formula (c3-8), the formula (c4-1), and the formula (c4-3) may be subjected to chemical modification in the synthesis process shown as scheme 4. Examples of the chemical modification include esterification, etherification, acylation, amidation, halogenation, substitution of a hydrogen atom in an amino group by an organic group, and the like. Chemical modification which $R^{c10}$ may undergo is not limited to these examples.

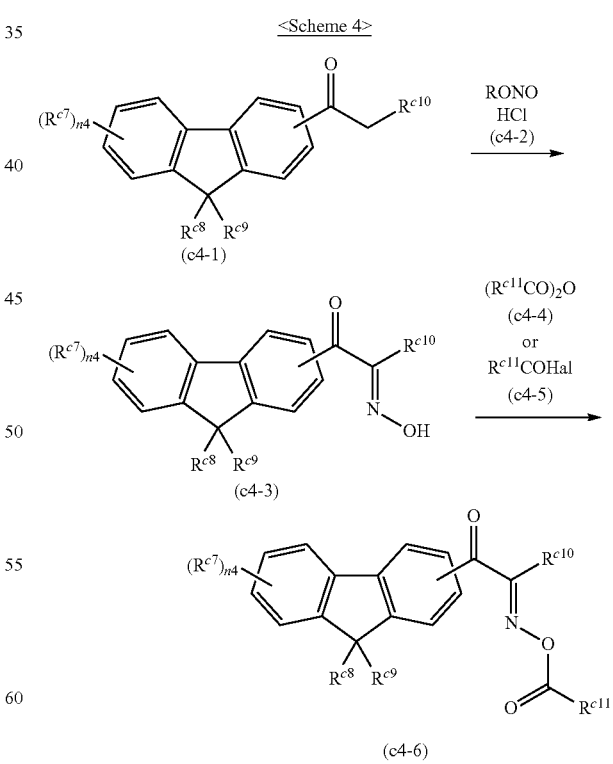

Suitable specific examples of the compound represented by the formula (c4) include the following compounds PI-43 to PI-83.

PI-43
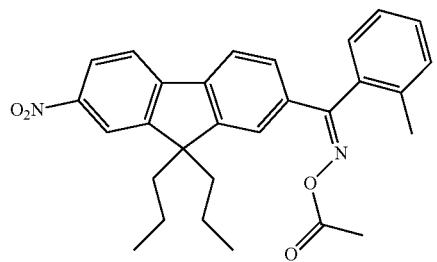
PI-44
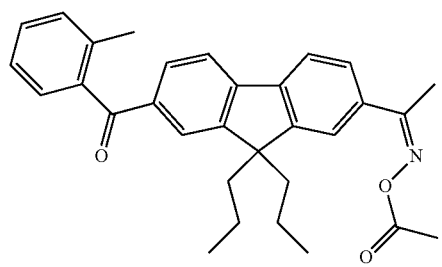
PI-45
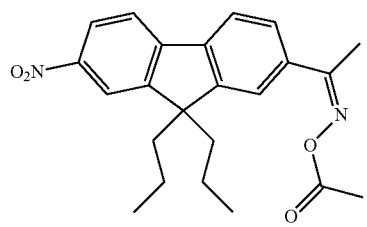
PI-46
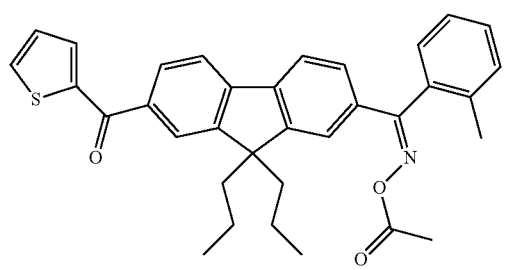
PI-47
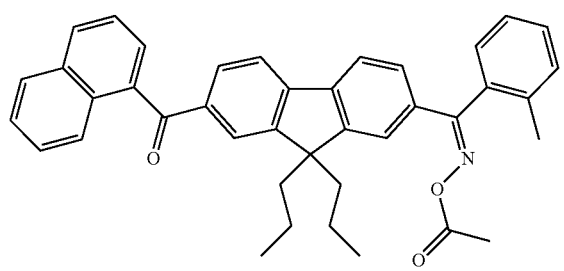
PI-48
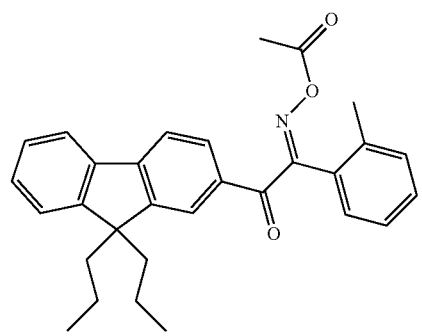
PI-49
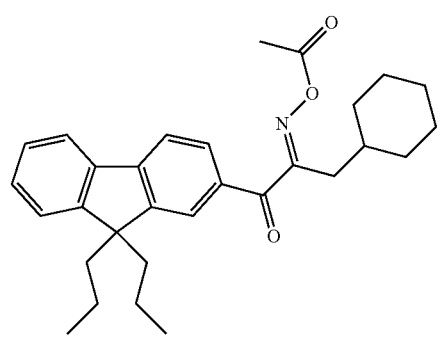
PI-50
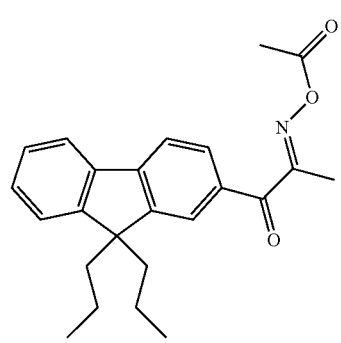
PI-51
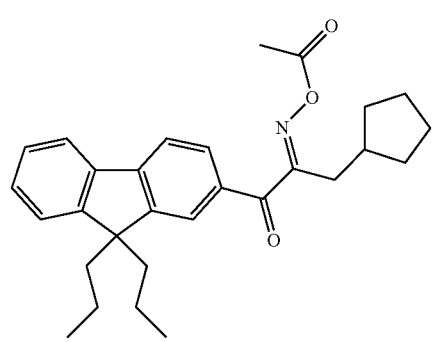

PI-52
PI-53
PI-54
PI-55
PI-56
PI-57
PI-58
PI-59

PI-60
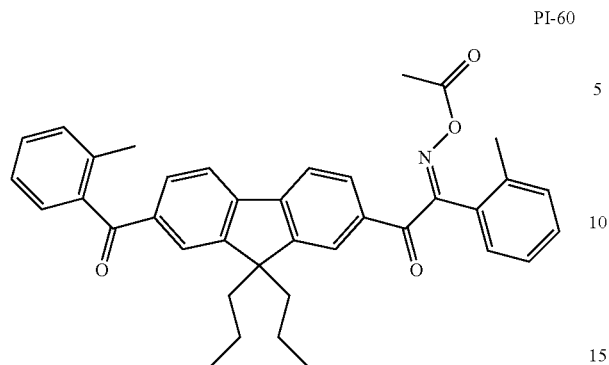
PI-61
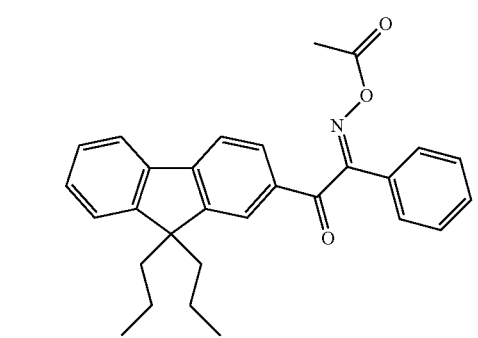
PI-62
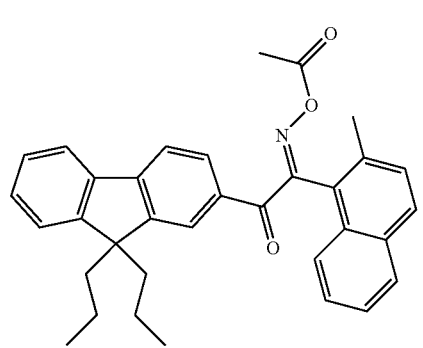
PI-63
PI-64
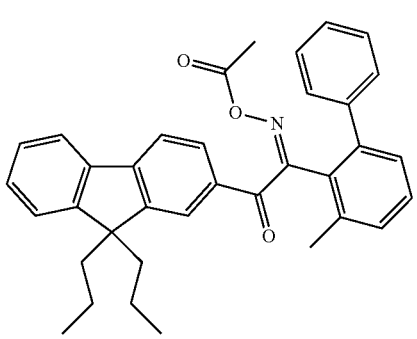
PI-65
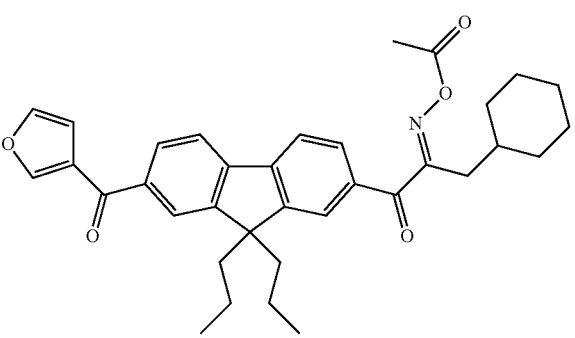
PI-66
PI-67
PI-68
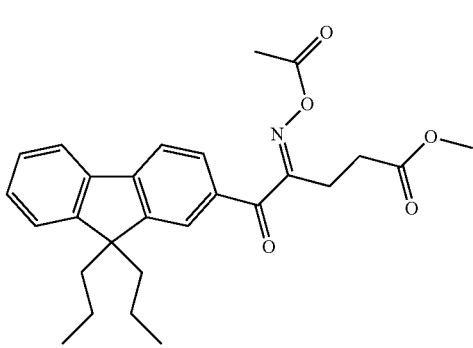

-continued
PI-69
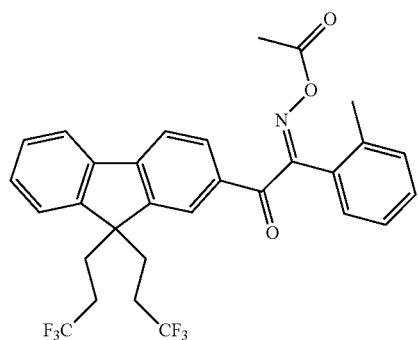
PI-70
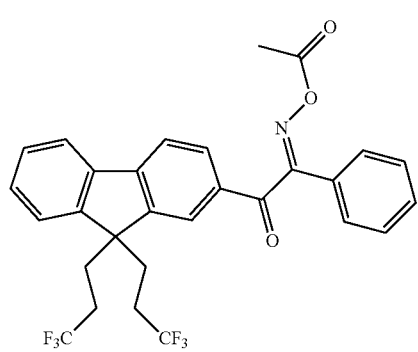
PI-71
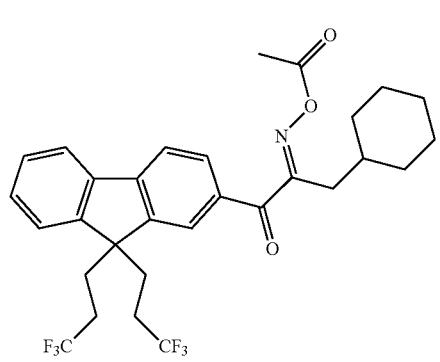
PI-72
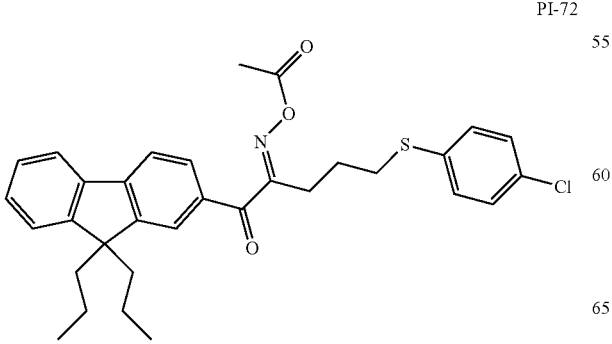
-continued
PI-73
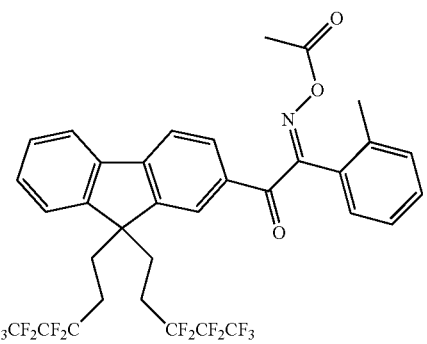
PI-74
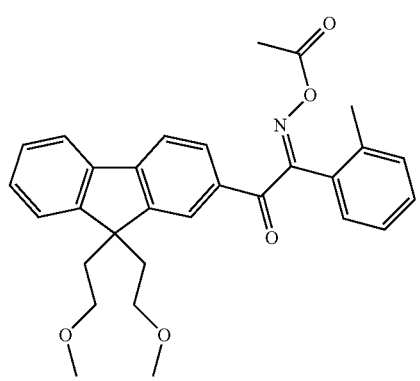
PI-75
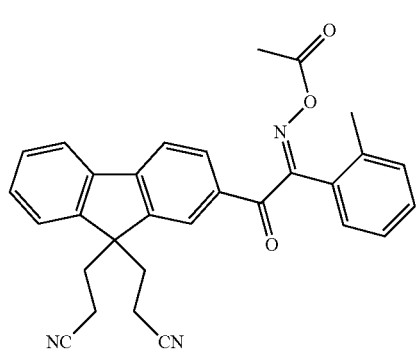
PI-76
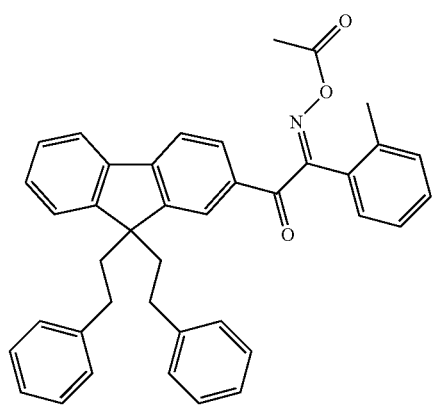

PI-77

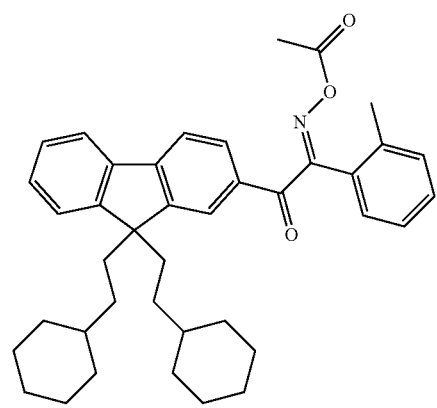

PI-78

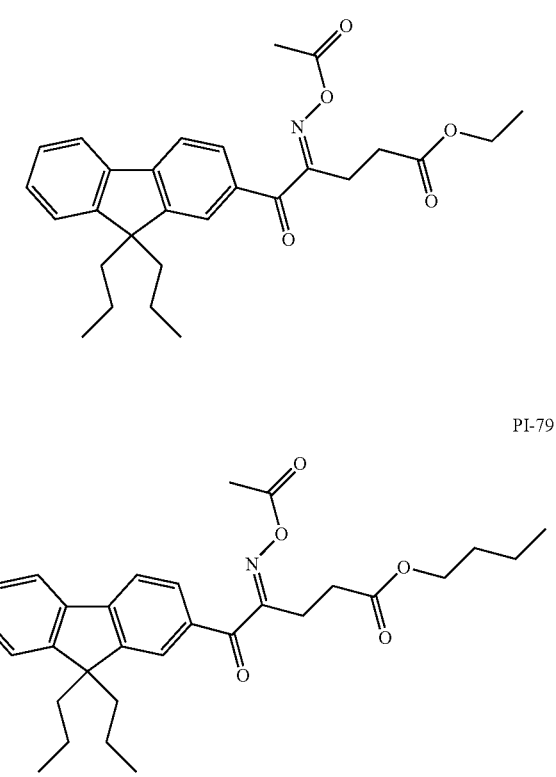

PI-79

PI-80

PI-81

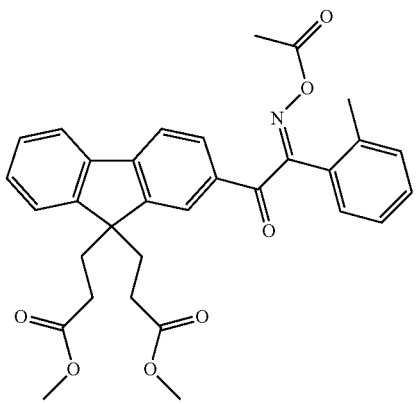

PI-82

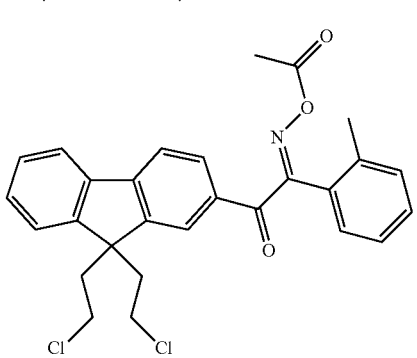

PI-83

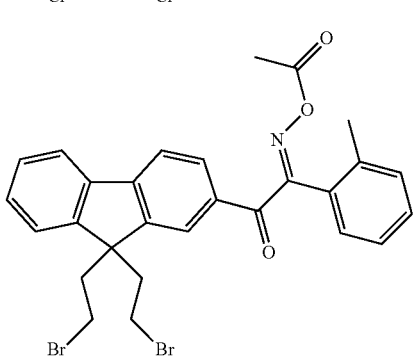

The content of the photopolymerization initiator is preferably 0.5 parts by mass or more and 20 parts by mass or less relative to 100 parts by mass of the solid content of the photosensitive composition of the first aspect. When the content is in the above-mentioned range, sufficient heat resistance and chemical resistance can be obtained, coating film forming capability can be improved, and curing failure can be suppressed.

The photosensitive composition of the first aspect contains the hydrogen barrier agent (B) as mentioned above. Containing this compound in the photosensitive composition enables a pattern having hydrogen barrier performance to be formed.

The content of the hydrogen barrier agent (B) is preferably 0.5 parts by mass or more and 95 parts by mass or less, and more preferably 1 part by mass or more and 50 parts by mass or less relative to 100 parts by mass of the photopolymerization initiator. When the content is in the above-mentioned range, a hydrogen barrier film having excellent hydrogen barrier property can be formed, and fine patterning property can be obtained while excellent developing property is obtained.

The photosensitive composition of the first aspect may further contain a coloring agent. When the coloring agent is contained, the photosensitive composition is preferably used for forming a color filter of, for example, image display devices such as a liquid crystal display and an organic EL display. Furthermore, when the photosensitive composition of the first aspect contains a light-shielding agent as a coloring agent, it is preferably used for forming, for example, a black matrix in a color filler.

The coloring agent is not particularly limited, but it is preferable to use, for example, compounds which are classified into Pigment in Color Index (C.I.; published by The Society of Dyers and Colorist), and specifically those having the following color index (C.I.) numbers.

Suitable examples include C.I. pigment yellow 1 (hereinafter, "C.I. pigment yellow" is the same, and only the numbers are listed), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, and 185;

C.I. pigment orange 1 (hereinafter, "C.I. pigment orange" is the same, and only the numbers are listed), 5, 13, 14, 16, 17, 24, 34, 36, 38, 40, 43, 46, 49, 51, 55, 59, 61, 63, 64, 71, and 73;

C.I. pigment violet 1 (hereinafter, "C.I. pigment violet" is the same, and only the numbers are listed), 19, 23, 29, 30, 32, 36, 37, 38, 39, 40, and 50;

C.I. pigment red 1 (hereinafter, "C.I. pigment red" is the same, and only the numbers are listed), 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, and 265;

C.I. pigment blue 1 (hereinafter, "C.I. pigment blue" is the same, and only the numbers are listed), 2, 15, 15:3, 15:4, 15:6, 16, 22, 60, 64, and 66;

C.I. pigment green 7, C.I. pigment green 36, and C.I. pigment green 37;

C.I. pigment brown 23, C.I. pigment brown 25, C.I. pigment brown 26, and C.I. pigment brown 28; and C.I. pigment black 1 and C.I. pigment black 7.

When the coloring agent is a light shielding agent, it is preferable to use a black pigment as the light shielding agent. Examples of the black pigment include various types of pigments irrespective of whether it is an organic substance or an inorganic substance, such as carbon black, titanium black, and a metal oxide, a composite oxide, a metal sulfide, a metal sulfate, and a metal carbonate of copper, iron, manganese, cobalt, chromium, nickel, zinc, calcium, silver, or the like. Among these, it is preferable to use a carbon black having high light shielding property.

As the carbon black, known carbon black such as channel black, furnace black, thermal black, and lamp black are usable. It is preferable to use a channel black having excellent light shielding property. Also, a resin-coated carbon black may be used.

Since the resin-coated carbon black having lower conductivity than that of carbon black without resin coating, in a case where it is used in a black matrix of a liquid crystal display, the display with low current leakage, high reliability and low power consumption can be produced.

Furthermore, in order to adjust the color tone of the carbon black, the above-mentioned organic pigment may be appropriately added as an auxiliary pigment.

Furthermore, in order to homogeneously disperse a coloring agent in a photosensitive composition, a dispersing agent may be further used. As such a dispersing agent, polyethylene imine, urethane resin, and acrylic resin high molecular dispersing agents are preferably used. In particular, when carbon black is used for the coloring agent, an acrylic resin dispersing agent is preferably used as the dispersing agent.

Furthermore, the inorganic pigment and the organic pigment may each be used alone or be used in combination. When the inorganic pigment and the organic pigment are used in combination, the organic pigment is preferably used in the range of 10 parts by mass or more and 80 parts by mass or less, and more preferably in the range of 20 parts by mass or more and 40 parts by mass or less relative to 100 parts by mass of the total amount of the inorganic pigment and the organic pigment.

The content of the coloring agent may be appropriately determined depending on the use of applications of the photosensitive composition of the first aspect, and, for example, the content is preferably 5 parts by mass or more and 70 parts by mass or less, and more preferably 25 parts by mass or more and 60 parts by mass or less relative to 100 parts by mass of the solid content of the photosensitive composition of the first aspect. In particular, when a black matrix is formed using the photosensitive composition of the first aspect, it is preferable that the amount of the light-shielding agent in the photosensitive composition is adjusted such that an OD value per 1 µm of a film thickness of the black matrix is 4 or more. When the OD value per 1 µm of the film thickness of the black matrix is 4 or more, in a case where it is used in a black matrix of a liquid crystal display, a sufficient display contrast can be obtained.

Note here that the coloring agent is preferably added to a photosensitive composition after it is dispersed using a dispersing agent at an appropriate concentration to form a dispersion liquid.

Examples of the organic solvent in the photosensitive composition of the first aspect include (poly)alkyleneglycol monoalkylethers such as ethyleneglycol monomethylether, ethyleneglycol monoethylether, ethyleneglycol mono-n-propylether, ethyleneglycol mono-n-butylether, diethyleneglycol monomethylether, diethyleneglycol monoethylether, diethyleneglycol mono-n-propylether, diethyleneglycol mono-n-butylether, triethyleneglycol monomethylether, triethyleneglycol monoethylether, propyleneglycol monomethylether, propyleneglycol monoethylether, propyleneglycol mono-n-propylether, propyleneglycol mono-n-butylether, dipropyleneglycol monomethylether, dipropyleneglycol monoethylether, dipropyleneglycol mono-n-propylether, dipropyleneglycol mono-n-butylether, tripropyleneglycol monomethylether, and tripropyleneglycol monoethylether; (poly)alkyleneglycol monoalkylether acetates such as ethyleneglycol monomethylether acetate, ethyleneglycol monoethylether acetate, diethyleneglycol monomethylether acetate, diethyleneglycol monoethylether acetate, propyleneglycol monomethylether acetate, and propyleneglycol monoethylether acetate; other ethers such as diethyleneglycol dimethylether, diethyleneglycol methylethylether, diethyleneglycol diethylether, and tetrahydrofuran; ketones such as methylethylketone, cyclohexanone, 2-heptanone, and 3-heptanone; lactic acid alkyl esters such as methyl 2-hydroxypropionate, and ethyl 2-hydroxypropionate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methyl-3-methoxybutyl acetate, 3-methyl-3-methoxybutyl propionate, ethyl acetate, n-propyl acetate, isopropyl acetate, n-butyl acetate, isobutyl acetate, n-pentyl formate, isopentyl acetate, n-butyl propionate, ethyl butanoate, n-propyl butanoate, isopropyl butanoate, n-butyl butanoate, methyl pyruvate, ethyl pyruvate, n-propyl pyruvate, methyl acetoacetate, ethyl acetoacetate, and ethyl 2-oxobutanoate; aromatic hydrocarbons such as toluene and xylene, and amides such as N-methylpyrrolidone, N,N-dimethylformamide, N,N-dimethylacetamide, and the solvents represented by the abovementioned formula (a04). These organic solvents can be used independently, or by combining two or more types.

Among the organic solvents, propyleneglycol monomethylether, ethyleneglycol monomethylether acetate, propyleneglycol monomethylether acetate, propyleneglycol monoethylether acetate, diethyleneglycol dimethylether, diethyleneglycol methylethylether, cyclohexanone, 3-methoxybutyl acetate, N-methylpyrrolidone, N,N-dimethylformamide, N,N-dimethylacetamide, and amides as solvents represented by the aforementioned formula (a04) are preferable, due to high solubility for the alkali-soluble resin (A1), the photopolymerizable compound (A2), photopolymerization initiator (C) and hydrogen barrier agent (B).

The content of the organic solvent is preferably an amount such that the solid content concentration of the photosensitive composition of the first aspect is 1 mass % or more and 50 mass % or less, and more preferably 5 mass % or more and 30 mass % or less.

The photosensitive composition of the first aspect may contain various additives if necessary. Examples of the additives include a sensitizer, a curing accelerator, a filler, an adhesion promoter, an antioxidant, an ultraviolet absorber, an aggregation inhibitor, a thermal polymerization inhibitor, an antifoaming agent, a surface active agent, and the like. As arbitrary additives, benzotriazole derivatives such as 1-(N, N-di(2-ethylhexyl)amino)methyl-1H-benzotriazole, 1-(N, N-di(2-ethylhexyl)amino)methyl-1H-methyl benzotriazole, carboxy benzotriazole, benzotriazole, methyl benzotriazole, dihydroxypropyl benzotriazole, and bis(aminomethyl)benzotriazole may be used alone or in combination of two or more types thereof. The addition amounts of various additives may be appropriately adjusted in a range from, for example, 0.001 mass % or more and 10 mass % or less, and preferably 0.1 mass % or more and 5 mass % or less with respect to the entire composition.

(2) Photosensitive Composition of Second Aspect

The photosensitive composition of second aspect is a positive type photosensitive composition. When the photosensitive composition of second aspect is a chemically amplified positive-type photosensitive composition, the photosensitive composition of second aspect contains an acid generator capable of producing an acid when irradiated with an active ray or radiation (hereinafter also referred to as the photo acid generator), and a resin whose solubility in alkali increases under the action of acid (hereinafter also referred to as the photosensitive resin). The photosensitive composition may comprise a component such as a n alkali soluble resin, an acid diffusion suppressing agent and an organic solvent, if desired. Examples of the other photosensitive compositions of the second aspect include positive photosensitive compositions including a quinone diazide group-containing compound, alkali-soluble resin such as novolak phenol resin, and the like (for example, the belowmentioned novolak resin (C1)).

There is no particular limitation for the film thickness of a resist pattern formed with the photosensitive composition of second aspect. The photosensitive composition of second aspect is preferably used for forming a thick resist pattern. The film thickness of a resist pattern formed with the photosensitive composition of second aspect is preferably 10 µm or more, more preferably 10 µm or more and 150 µm or less, in particular preferably 20 µm or more and 120 µm or less, and in particular preferably 20 µm or more and 80 µm or less.

Below, described are essential or optional components in the photosensitive composition of second aspect, and a method of manufacturing the photosensitive composition.

The photo acid generator is a compound capable of producing an acid when irradiated with an active ray or radiation, and is not particularly limited as long as it is a compound which directly or indirectly produces an acid under the action of light. Hereinafter, suitable examples among the photo acid generators that are suitably used in photosensitive composition of second aspect will be described.

The first example of the preferable photo acid generator may be a compound represented by the following formula (a1).

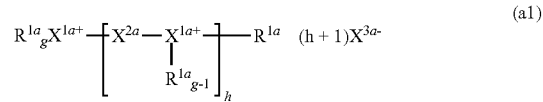

(a1)

In the formula (a1), $X^{1a}$ represents a sulfur atom or iodine atom respectively having a valence of g; g represents 1 or 2. h represents the number of repeating units in the structure within parentheses. $R^{1a}$ represents an organic group that is bonded to $X^{1a}$, and represents an aryl group having 6 or more and 30 or less carbon atoms, a heterocyclic group having 4 or more and 30 or less carbon atoms, an alkyl group having 1 or more and 30 or less carbon atoms, an alkenyl group having 2 or more and 30 or less carbon atoms, or an alkynyl group having 2 or more and 30 or less carbon atoms, and $R^{1a}$ may be substituted with at least one selected from the group consisting of an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocyclic group, an aryloxy group, an alkylsulfinyl group, an arylsulfinyl group, an alkylsulfonyl group, an arylsulfonyl group, an alkyleneoxy group, an amino group, a cyano group, a nitro group, and halogen atoms. The number of $R^{1a}$s is g+h(g-1)+1, and the $R^{1a}$s may be respectively identical to or different from each other. Furthermore, two or more $R^{1a}$s may be bonded to each other directly or via —O—, —S—, —SO—, —SO$_2$—, —NH—, —NR$^{2a}$—, —CO—, —COO—, —CONH—, an alkylene group having 1 or more and 3 or less carbon atoms, or a phenylene group, and may form a ring structure containing $X^{1a}$. $R^{2a}$ represents an alkyl group having 1 or more and 5 or less carbon atoms, or an aryl group having 6 or more and 10 or less carbon atoms.

$X^{2a}$ represents a structure represented by the following formula (a2).

(a2)

In the formula (a2), $X^{4a}$ represents an alkylene group having 1 or more and 8 or less carbon atoms, an arylene group having 6 or more and 20 or less carbon atoms, or a divalent group of a heterocyclic compound having 8 or more and 20 or less carbon atoms, and $X^{4a}$ may be substituted with at least one selected from the group consisting of an alkyl group having 1 or more and 8 or less carbon atoms, an alkoxy group having 1 or more and 8 or less carbon atoms, an aryl group having 6 or more and 10 or less carbon atoms, a hydroxy group, a cyano group, a nitro group, and halogen atoms. $X^{5a}$ represents —O—, —S—, —SO—, —SO$_2$—, —NH—, —NR$^{2a}$—, —CO—, —COO—, —CONH—, an alkylene group having 1 or more and 3 or less carbon atoms, or a phenylene group. h represents the number of repeating units of the structure in parentheses. $X^{4a}$s in the number of h+1 and $X^{5a}$s in the number of h may be identical to or different from each other. $R^{2a}$ has the same definition as described above.

$X^{3a-}$ represents a counterion of an onium, and examples thereof include a fluorinated alkylfluorophosphoric acid anion represented by the following formula (a17) or a borate anion represented by the following formula (a18).

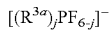
(a17)

In the formula (a17), $R^{3a}$ represents an alkyl group having 80% or more of the hydrogen atoms substituted by fluorine atoms.

j represents the number of $R^{1a}$s and is an integer from 1 or more and 5 or less. $R^{3a}$s in the number of j may be respectively identical to or different from each other.

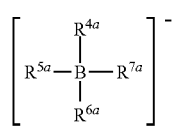
(a18)

In the formula (a18), $R^{4a}$ to $R^{7a}$ each independently represent a fluorine atom or a phenyl group, and a part or all of the hydrogen atoms of the phenyl group may be substituted by at least one selected from the group consisting of a fluorine atom and a trifluoromethyl group.

Examples of the onium ion in the compound represented by the formula (a1) include triphenylsulfonium, tri-p-tolylsulfonium, 4-(phenylthio)phenyldiphenylsulfonium, bis[4-(diphenylsulfonio)phenyl] sulfide, bis[4-{bis[4-(2-hydroxyethoxy)phenyl]sulfonio}phenyl] sulfide, bis{4-[bis(4-fluorophenyl)sulfonio]phenyl} sulfide, 4-(4-benzoyl-2-chlorophenylthio)phenylbis(4-fluorophenyl)sulfonium, 7-isopropyl-9-oxo-10-thia-9,10-dihydroanthran-2-yldi-p-tolylsulfonium, 7-isopropyl-9-oxo-10-thia-9,10-dihydroanthracen-2-yldiphenylsulfonium, 2-[(diphenyl)sulfonio]thioxanthone, 4-[4-(4-tert-butylbenzoyl)phenylthio]phenyldi-p-tolylsulfonium, 4-(4-benzoylphenylthio)phenyldiphenylsulfonium, diphenylphenacylsulfonium, 4-hydroxyphenylmethylbenzylsulfonium, 2-naphthylmethyl(1-ethoxycarbonyl)ethylsulfonium, 4-hydroxyphenylmethylphenacylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio) phenyl] diphenylsulfonium, octadecylmethylphenacylsulfonium, diphenyliodonium, di-p-tolyliodonium, bis(4-dodecylphenyl)iodonium, bis(4-methoxyphenyl)iodonium, (4-octyloxyphenyl)phenyliodonium, bis(4-decyloxy)phenyliodonium, 4-(2-hydroxytetradecyloxy)phenylphenyliodonium, 4-isopropylphenyl(p-tolyl)iodonium, and 4-isobutylphenyl(p-tolyl)iodonium.

Among the onium ions in the compound represented by the formula (a1), a preferred onium ion may be a sulfonium ion represented by the following formula (a19).

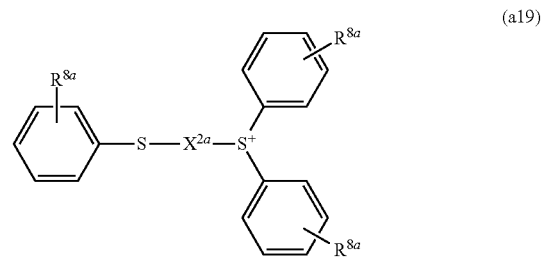
(a19)

In the formula (a19), $R^{8a}$s each independently represent a hydrogen atom or a group selected from the group consisting of alkyl, hydroxy, alkoxy, alkylcarbonyl, alkylcarbonyloxy, alkyloxycarbonyl, a halogen atom, an aryl, which may be substituted, and arylcarbonyl. $X^{2a}$ has the same definition as $X^{2a}$ in the formula (a1).

Specific examples of the sulfonium ion represented by the formula (a19) include 4-(phenylthio)phenyldiphenylsulfonium, 4-(4-benzoyl-2-chlorophenylthio)phenylbis(4-fluorophenyl)sulfonium, 4-(4-benzoylphenylthio)phenyldiphenylsulfonium, phenyl[4-(4-biphenylthio)phenyl]-4-biphenylsulfonium, phenyl[4-(4-biphenylthio)phenyl]-3-biphenylsulfonium, [4-(4-acetophenylthio)phenyl]diphenylsulfonium, and diphenyl[4-(p-terphenylthio)phenyl]diphenylsulfonium.

In regard to the fluorinated alkylfluorophosphoric acid anion represented by the formula (a17), $R^{3a}$ represents an alkyl group substituted with a fluorine atom, and a preferred number of carbon atoms is 1 or more and 8 or less, while a more preferred number of carbon atoms is 1 or more and 4 or less. Specific examples of the alkyl group include linear alkyl groups such as methyl, ethyl, propyl, butyl, pentyl and octyl; branched alkyl groups such as isopropyl, isobutyl, sec-butyl and tert-butyl; and cycloalkyl groups such as cyclopropyl, cyclobutyl, cyclopentyl, and cyclohexyl. The proportion of hydrogen atoms substituted by fluorine atoms in the alkyl groups is usually 80% or more, preferably 90% or more, and even more preferably 100%. If the substitution ratio of fluorine atoms is less than 80%, the acid strength of the onium fluorinated alkylfluorophosphate represented by the formula (a1) decreases.

A particularly preferred example of $R^{3a}$ is a linear or branched perfluoroalkyl group having 1 or more and 4 or less carbon atoms and a substitution ratio of fluorine atoms of 100%. Specific examples thereof include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$, and $(CF_3)_3C$. j which is the number of $R^{3a}$s represents an integer from 1 or more and 5 or less, and is preferably 2 or more and 4 or less, and particularly preferably 2 or 3.

Preferred specific examples of the fluorinated alkylfluorophosphoric acid anion include $[(CF_3CF_2)_2PF_4]^-$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)PF_4]^-$, and $[(CF_3CF_2CF_2)_3PF_3]^-$. Among these, $[(CF_3CF_2)_3PF_3]^-$, $[(CF_3CF_2CF_2)_3PF_3]^-$, $[((CF_3)_2CF)_3PF_3]^-$, $[((CF_3)_2

$CF_2)_2PF_4]^-$, $[((CF_3)_2CFCF_2)_3PF_3]^-$, and $[((CF_3)_2CFCF_2)_2PF_4]^-$ are particularly preferred.

Preferred specific examples of the borate anion represented by the formula (a18) include tetrakis(pentafluorophenyl)borate ($[B(C_6F_5)_4]^-$), tetrakis[(trifluoromethyl)phenyl]borate ($[B(C_6H_4CF_3)_4]^-$), difluorobis(pentafluorophenyl)borate ($[(C_6F_5)_2BF_2]^-$), trifluoro(pentafluorophenyl)borate ($[(C_6F_5)BF_3]^-$), and tetrakis(difluorophenyl)borate ($[B(C_6H_3F_2)_4]^-$). Among these, tetrakis(pentafluorophenyl)borate ($[B(C_6F_5)_4]^-$) is particularly preferred.

The second example of the preferable photo acid generator include halogen-containing triazine compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1,3,5-triazine and tris(2,3-dibromopropyl)-1,3,5-triazine, and halogen-containing triazine compounds represented by the following formula (a3) such as tris(2,3-dibromopropyl)isocyanurate.

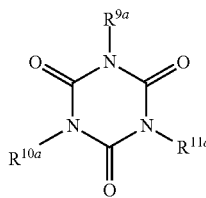

(a3)

In the formula (a3), $R^{9a}$, $R^{10a}$ and $R^{11a}$ each independently represent a halogenated alkyl group.

The third example of the preferable photo acid generator include α-(p-toluenesulfonyloxyimino)-phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile and α-(ethylsulfonyloxyimino)-1-cyclopentenylacetonitrile, and compounds represented by the following formula (a4) having an oximesulfonate group.

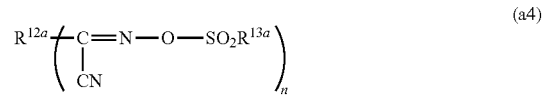

(a4)

In the formula (a4), $R^{12a}$ represents a monovalent, bivalent or trivalent organic group, $R^{13a}$ represents a substituted or unsubstituted saturated hydrocarbon group, an unsaturated hydrocarbon group, or an aromatic compound group, and n represents the number of repeating units of the structure in the parentheses.

In the formula (a4), the aromatic compound group indicates a group of compounds having physical and chemical properties characteristic of aromatic compounds, and examples thereof include aryl groups such as a phenyl group and a naphthyl group, and heteroaryl groups such as a furyl group and a thienyl group may be exemplified. These may have one or more appropriate substituents such as halogen atoms, alkyl groups, alkoxy groups and nitro groups on the rings. It is particularly preferable that $R^{13a}$ is an alkyl group having 1 or more and 6 or less carbon atoms such as a methyl group, an ethyl group, a propyl group, and a butyl group. In particular, compounds in which $R^{12a}$ represents an aromatic compound group, and $R^{13a}$ represents an alkyl group having 1 or more and 4 or less carbon atoms are preferred.

Examples of the photo acid generator represented by the formula (a4), include compounds in which $R^{12a}$ is any one of a phenyl group, a methylphenyl group and a methoxyphenyl group, and $R^{13a}$ is a methyl group, provided that n is 1, and specific examples thereof include α-(methylsulfonyloxyimino)-1-phenylacetonitrile, α-(methylsulfonyloxyimino)-1-(p-methylphenyl)acetonitrile, α-(methylsulfonyloxyimino)-1-(p-methoxyphenyl)acetonitrile, [2-(propylsulfonyloxyimino)-2,3-dihydroxythiophene-3-ylidene](o-tolyl)acetonitrile and the like. Provided that n is 2, the photo acid generator represented by the formula (a4) is specifically a photo acid generator represented by the following formulae.

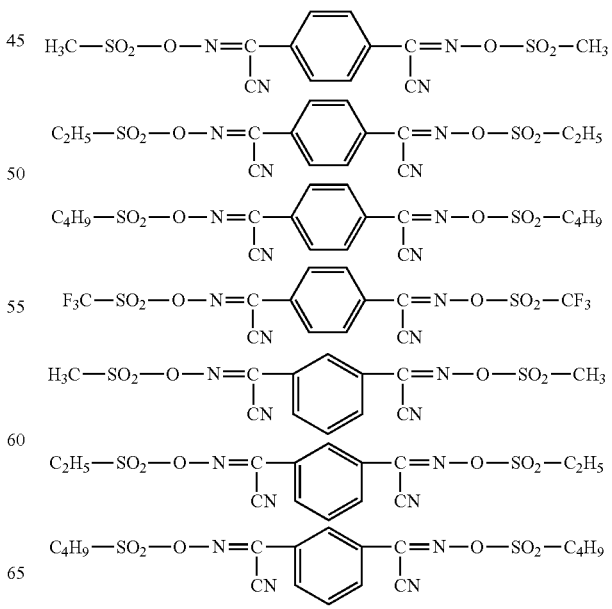

-continued

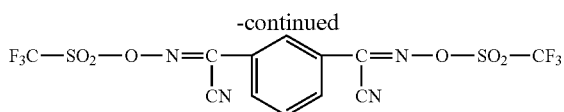

The fourth example of the preferable photo acid generator include onium salts that have a naphthalene ring at their cation moiety. The expression "have a naphthalene ring" indicates having a structure derived from naphthalene and also indicates at least two ring structures and their aromatic properties are maintained. The naphthalene ring may have a substituent such as a linear or branched alkyl group having 1 or more and 6 or less carbon atoms, a hydroxy group, a linear or branched alkoxy group having 1 or more and 6 or less carbon atoms or the like. The structure derived from the naphthalene ring, which may be of a monovalent group (one free valance) or of a bivalent group (two free valences), is desirably of a monovalent group (in this regard, the number of free valance is counted except for the portions connecting with the substituents described above). The number of naphthalene rings is preferably 1 or more and 3 or less.

Preferably, the cation moiety of the onium salt having a naphthalene ring at the cation moiety is of the structure represented by the following formula (a5).

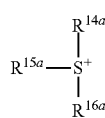

(a5)

In the formula (a5), at least one of $R^{14a}$, $R^{15a}$ and $R^{16a}$ represents a group represented by the following formula (a6), and the remaining represents a linear or branched alkyl group having 1 or more and 6 or less carbon atoms, a phenyl group which may have a substituent, a hydroxy group, or a linear or branched alkoxy group having 1 or more and 6 or less carbon atoms. Alternatively, one of $R^{14a}$, $R^{15a}$ and $R^{16a}$ is a group represented by the following formula (a6), and the remaining two are each independently a linear or branched alkylene group having 1 or more and 6 or less carbon atoms, and these terminals may bond to form a ring structure.

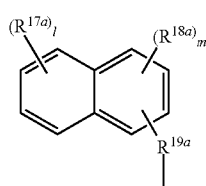

(a6)

In the formula (a6), $R^{17a}$ and $R^{18a}$ each independently represent a hydroxy group, a linear or branched alkoxy group having 1 or more and 6 or less carbon atoms, or a linear or branched alkyl group having 1 or more and 6 or less carbon atoms, and $R^{19a}$ represents a single bond or a linear or branched alkylene group having 1 or more and 6 or less carbon atoms that may have a substituent. l and m each independently represent an integer of 0 or more and 2 or less, and l+m is no greater than 3. In this regard, when there exists a plurality of $R^{17a}$, they may be identical or different from each other. Furthermore, when there exist a plurality of $R^{18a}$, they may be identical or different from each other.

Preferably, among $R^{14a}$, $R^{15a}$ and $R^{16a}$ as above, the number of groups represented by the formula (a6) is one in view of the stability of the compound, and the remaining are linear or branched alkylene groups having 1 or more and 6 or less carbon atoms of which the terminals may bond to form a ring. In this case, the two alkylene groups described above form a 3 to 9 membered ring including sulfur atom(s). Preferably, the number of atoms to form the ring (including sulfur atom(s)) is 5 or 6.

The substituent, which the alkylene group may have, is exemplified by an oxygen atom (in this case, a carbonyl group is formed together with a carbon atom that constitutes the alkylene group), a hydroxy group or the like.

Alternatively, the substituent, which the phenyl group may have, is exemplified by a hydroxy group, a linear or branched alkoxy groups having 1 or more and 6 or less carbon atoms, linear or branched alkyl groups having 1 or more and 6 or less carbon atoms, or the like.

Examples of suitable cation moiety include those represented by the following formulae (a7) and (a8), and the structure represented by the following formula (a8) is particularly preferable.

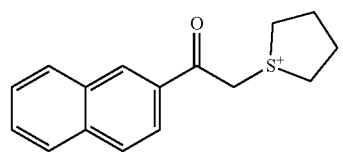

(a7)

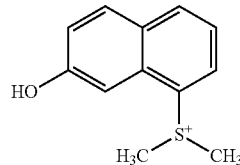

(a8)

The cation moieties, which may be of an iodonium salt or a sulfonium salt, are desirably of a sulfonium salt in view of acid-producing efficiency.

It is, therefore, desirable that the preferable anion moiety of the onium salt having a naphthalene ring at the cation moiety is an anion capable of forming a sulfonium salt.

The anion moiety of the photo acid generator is exemplified by fluoroalkylsulfonic acid ions, of which hydrogen atom(s) being partially or entirely fluorinated, or aryl sulfonic acid ions.

The alkyl group of the fluoroalkylsulfonic acid ions may be linear, branched or cyclic and have 1 or more and 20 or less carbon atoms. Preferably, the carbon number is 1 or more and 10 or less in view of bulkiness and diffusion distance of the produced acid. In particular, branched or cyclic groups are preferable due to shorter diffusion length. Also, methyl, ethyl, propyl, butyl, octyl groups and the like are preferable due to being inexpensively synthesizable.

The aryl group of the aryl sulfonic acid ions may be an aryl group having 6 or more and 20 or less carbon atoms, and is exemplified by a phenol group or a naphthyl group that may be unsubstituted or substituted with an alkyl group or a halogen atom. In particular, aryl groups having 6 or more and 10 or less carbon atoms are preferred since they can be synthesized inexpensively. Specific examples of preferable aryl group include phenyl, toluenesulfonyl, ethylphenyl, naphthyl, methylnaphthyl groups and the like.

When hydrogen atoms in the fluoroalkylsulfonic acid ion or the aryl sulfonic acid ion are partially or entirely substituted with a fluorine atom, the fluorination rate is preferably 10% or more and 100% or less, and more preferably 50% or more and 100% or less; it is particularly preferable that all hydrogen atoms are each substituted with a fluorine atom in view of higher acid strength. Specific examples thereof include trifluoromethane sulfonate, perfluorobutane sulfonate, perfluorooctane sulfonate, perfluorobenzene sulfonate, and the like.

Among these, the preferable anion moiety is exemplified by those represented by the following formula (a9).

$$R^{20a}SO_3^- \quad (a9)$$

In the formula (a9), $R^{20a}$ represents a group represented by the following formula (a10) or (a11), or a group represented by the following formula (a12).

(a10)

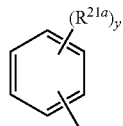

(a11)

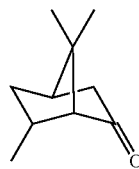

(a12)

In the formula (a10), x represents an integer of 1 or more and 4 or less. Also, in the formula (a11), $R^{21a}$ represents a hydrogen atom, a hydroxy group, a linear or branched alkyl group having 1 or more and 6 or less carbon atoms, or a linear or branched alkoxy group having 1 or more and 6 or less carbon atoms, and y represents an integer of 1 or more and 3 or less. Of these, trifluoromethane sulfonate, and perfluorobutane sulfonate are preferable in view of safety.

In addition, a nitrogen-containing moiety represented by the following formula (a13) or (a14) may be also be used for the anion moiety.

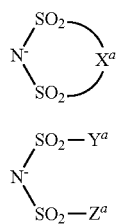

(a13)

(a14)

In the formulae (a13) and (a14), $X^a$ represents a linear or branched alkylene group of which at least one hydrogen atom is substituted with a fluorine atom, the carbon number of the alkylene group is 2 or more and 6 or less, preferably 3 or more and 5 or less, and most preferably the carbon number is 3. In addition, $Y^a$ and $Z^a$ each independently represent a linear or branched alkyl group of which at least one hydrogen atom is substituted with a fluorine atom, the number of carbon atoms of the alkyl group is 1 or more and 10 or less, preferably 1 or more and 7 or less, and more preferably 1 or more and 3 or less.

The smaller number of carbon atoms in the alkylene group of $X^a$, or in the alkyl group of $Y^a$ or $Z^a$ is preferred since the solubility into organic solvent is favorable.

In addition, a larger number of hydrogen atoms each substituted by a fluorine atom in the alkylene group of $X^a$, or in the alkyl group of $Y^a$ or $Z^a$ is preferred since the acid strength becomes greater. The percentage of fluorine atoms in the alkylene group or alkyl group, i.e., the fluorination rate is preferably 70% or more and 100% or less and more preferably 90% or more and 100% or less, and most preferable are perfluoroalkylene or perfluoroalkyl groups in which all of the hydrogen atoms are each substituted with a fluorine atom.

Preferable onium salts having a naphthalene ring at their cation moieties are exemplified by compounds represented by the following formulae (a15) and (a16).

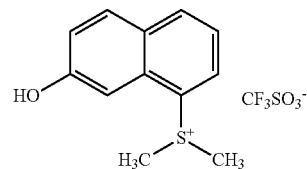

(a15)

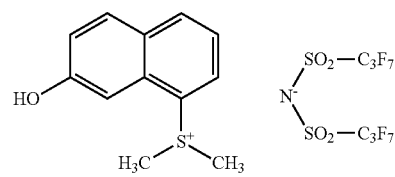

(a16)

Also, the sixth example of the preferable photo acid generator include bissulfonyldiazomethanes such as bis(p-toluenesulfonyl)diazomethane, bis(1,1-dimethyl ethylsulfonyl)diazomethane, bis(cyclohexylsulfonyl)diazomethane and bis(2,4-dimethylphenylsulfonyl)diazomethane; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate and dinitrobenzyl carbonate; sulfonates such as pyrogalloltrimesylate, pyrogalloltritosylate, benzyltosylate, benzylsulfonate, N-methylsulfonyloxysuccinimide, N-trichloromethylsulfonyloxysuccinimide, N-phenylsulfonyloxymaleimide and N-methylsulfonyloxyphthalimide; trifluoromethane sulfonates such as N-hydroxyphthalimide and N-hydroxynaphthalimide; onium salts such as diphenyliodonium hexafluorophosphate, (4-methoxyphenyl)phenyliodonium trifluoromethanesulfonate, bis(p-tert-butylphenyl)iodonium trifluoromethanesulfonate, triphenylsulfonium hexafluorophosphate, (4-methoxyphenyl)diphenylsulfonium trifluoromethanesulfonate and (p-tert-butylphenyl) diphenylsulfonium trifluoromethanesulfonate; benzointosylates such as benzointosylate and α-methylbenzointosylate; other diphenyliodonium salts, triphenylsulfonium salts, phenyldiazonium salts, benzylcarbonates and the like.

Particularly preferable photo acid generators used in combination with the hydrogen barrier agent (B) include naphthalic acid derivatives represented by the following formula (c-5).

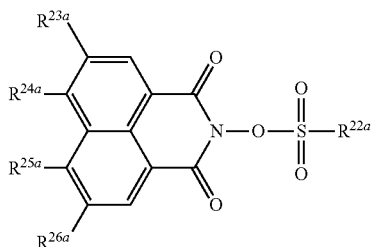
(c-5)

In the formula (c-5), $R^{22a}$ is a monovalent organic group, $R^{23a}$, $R^{24a}$, $R^{25a}$, and $R^{26a}$ are each independently a hydrogen atom or a monovalent organic group, and each of $R^{23a}$ and $R^{24a}$, $R^{24a}$ and $R^{25a}$, or $R^{25a}$ and $R^{26a}$, may be independently bonded to each other to form a ring.

The organic group as $R^{22a}$ is not particularly limited within a range in which the objects of the present invention are not impaired. The organic group may be a hydrocarbon group, and may include a heteroatom such as O, N, S, P, and a halogen atom. Furthermore, a structure of the organic group may be linear or branched or cyclic, and may be a combination thereof.

Examples of suitable organic group as $R^{22a}$ include an aliphatic hydrocarbon groups having 1 or more and 18 or less carbon atoms which may be substituted with a halogen atom and/or an alkylthio group, an aryl group having 6 or more and 20 or less carbon atoms which may have a substituent, an aralkyl group having 7 or more and 20 or less carbon atoms which may have a substituent, an alkylaryl group having 7 or more and 20 or less carbon atoms which may have a substituent, a camphor-10-yl group, and a group represented by the following formula (c-5a).

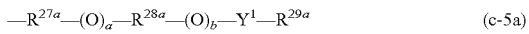
(c-5a)

In the formula (c-5a), $Y^1$ is a single bond or a alkanediyl group having 1 or more and 4 or less carbon atoms. $R^{27a}$ and $R^{28a}$ are each respectively an alkanediyl group having 2 or more and 6 or less carbon atoms which may be substituted with a halogen atom, or an arylene group having 6 or more and 20 or less carbon atoms which may be substituted with a halogen atom. $R^{29a}$ is an alkyl group having 1 or more and 18 or less carbon atoms which may be substituted with a halogen atom, an alicyclic hydrocarbon group having 3 or more and 12 or less carbon atoms which may be substituted with a halogen atom, or an aralkyl group having 7 or more and 20 or less carbon atoms which may be substituted with a halogen atom. a and b are each respectively 0 or 1, and at least one of a and b is 1.

When an organic group as $R^{22a}$ has a halogen atom as a substituent, examples of halogen atom include a chlorine atom, a bromine atom, an iodine atom, and a fluorine atom.

When an organic group as $R^{22a}$ is an alkyl group having 1 or more and 18 or less carbon atoms substituted with alkylthio group, the number of carbon atoms of an alkylthio group is preferably 1 or more and 18 or less. Examples of an alkylthio group having 1 or more and 18 or less carbon atoms include a methylthio group, a ethylthio group, an n-propylthio group, an isopropylthio group, an n-butylthio group, a sec-butylthio group, a tert-butylthio group, an isobutylthio group, an n-pentylthio group, an isopentylthio group, a tert-pentylthio group, an n-hexylthio group, an n-heptylthio group, an isoheptylthio group, a tert-heptylthio group, an n-octylthio group, an isooctylthio group, a tert-octylthio group, a 2-ethylhexylthio group, an n-nonylthio group, an n-decylthio group, an undecylthio group, an n-dodecylthio group, an n-tridecylthio group, an n-tetradecylthio group, an n-pentadecylthio group, an hexadecylthio group, an n-heptadecylthio group, and an n-octadecylthio group.

When the organic group as $R^{22a}$ is an aliphatic hydrocarbon group having 1 or more and 18 or less carbon atoms which may be substituted with a halogen atom, and/or an alkylthio group, the aliphatic hydrocarbon group may include an unsaturated double bond. Furthermore, a structure of the aliphatic hydrocarbon group is not particularly limited, and may be linear or branched or cyclic, and these structures may be combined.

When the organic group as $R^{22a}$ is an alkenyl group, suitable examples include an allyl group and a 2-methyl-2-propenyl group.

When the organic group as $R^{22a}$ is an alkyl group, suitable examples include a methyl group, an ethyl group, an n-propyl group, an isopropyl group, an n-butyl group, a sec-butyl group, a tert-butyl group, an isobutyl group, an n-pentyl group, an isopentyl group, a tert-pentyl group, an n-hexyl group, an n-hexane-2-yl group, an n-hexane-3-yl group, an n-heptyl group, an n-heptane-2-yl group, an n-heptane-3-yl group, an isoheptyl group, a tert-heptyl group, an n-octyl group, an isooctyl group, a tert-octyl group, a 2-ethylhexyl group, an n-nonyl group, an isononyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group.

When the organic group as $R^{22a}$ is an alicyclic hydrocarbon group, suitable examples of the alicyclic hydrocarbon composing a main skeleton of the alicyclic hydrocarbon groups include cyclopropane, cyclobutane, cyclopentane, cyclohexane, cycloheptane, cyclooctane, cyclodecane, bicycle[2.1.1]hexane, bicycle[2.2.1]heptane, bicycle[3.2.1]octane, bicycle[2.2.2]octane, and adamantine. As an alicyclic hydrocarbon groups is preferably a group in which one hydrogen atom is removed from these alicyclic hydrocarbons.

When the organic group as $R^{22a}$ is an aliphatic hydrocarbon group substituted with a halogen atom, suitable examples include a trifluoromethyl group, a pentafluoroethyl group, a 2-chloroethyl group, a 2-bromoethyl group, a heptafluoro-n-propyl group, a 3-bromopropyl group, a nonafluoro-n-butyl group, a tridecafluoro-n-hexyl group, a heptadecafluoro-n-octyl group, a 2,2,2-trifluoroethyl group, a 1,1-difluoroethyl group, a 1,1-difluoro-n-propyl group, a 1,1,2,2-tetrafluoro-n-propyl group, a 3,3,3-trifluoro-n-propyl group, a 2,2,3,3,3-pentafluoro-n-propyl group, a 2-norbornyl-1,1-difluoroethyl group, a 2-norborynyltetrafluoroethyl group, and a 3-adamantyl-1,1,2,2-tetrafluoropropyl group.

When the organic group as $R^{22a}$ is an aliphatic hydrocarbon group substituted with an alkylthio group, suitable examples include 2-methylthioethyl group, 4-methylthio-n-butyl group, and 2-n-butylthioethyl group.

When the organic group as $R^{22a}$ is an aliphatic hydrocarbon group substituted with a halogen atom and an alkylthio group, suitable example include 3-methylthio-1,1,2,2-tetrafluoro-n-propyl group.

When the organic group as $R^{22a}$ is an aryl group, suitable examples include a phenyl group, a naphthyl group, and biphenylyl group.

When the organic group as $R^{22a}$ is an aryl group substituted with a halogen atom, suitable examples include a pentafluorophenyl group, a chlorophenyl group, dichlorophenyl group, and trichlorophenyl group.

When the organic group as $R^{22a}$ is an aryl group substituted with an alkylthio group, suitable examples include a 4-methylthiophenyl group, a 4-n-butylthiophenyl group, a 4-n-octylthiophenyl group, and 4-n-dodecylthiophenyl group.

When the organic group as $R^{22a}$ is an aryl group substituted with a halogen atom and an alkylthio group, suitable example include a 1,2,5,6-tetrafluoro-4-methylthiophenyl group, a 1,2,5,6-tetrafluoro-4-n-butylthiophenyl group, and a 1,2,5,6-tetrafluoro-4-n-decylthiophenyl group.

When the organic group as $R^{22a}$ is an aralkyl group, suitable examples include a benzyl group, a phenethyl group, a 2-phenylpropane-2-yl group, a diphenylmethyl group, and a triphenyl methyl group.

When the organic group as $R^{22a}$ is an aralkyl group substituted with a halogen atom, suitable examples include a pentafluorophenylmethyl group, a phenyldifluoromethyl group, a 2-phenyltetrafluoroethyl group, and a 2-(pentafluorophenyl) ethyl group.

When the organic group as $R^{22a}$ is an aralkyl group substituted with an alkylthio group, suitable examples include a p-methylthiobenzyl group.

When the organic group as $R^{22a}$ is an aralkyl group substituted with a halogen atom and an alkylthio group, suitable examples include a 2-(2,3,5,6-tetrafluoro-4-methylthiophenyl) ethyl group.

When the organic group as $R^{22a}$ is an alkylaryl group, suitable examples include a 2-methylphenyl group, a 3-methylphenyl group, a 4-methylphenyl group, a 3-isopropylphenyl group, a 4-isopropylphenyl group, a 4-n-butylphenyl group, a 4-isobutylphenyl group, a 4-tert-butylphenyl group, a 4-n-hexylphenyl group, a 4-cyclohexylphenyl group, a 4-n-octylphenyl group, a 4-(2-ethyl-n-hexyl)phenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4-di-tert-butylphenyl group, a 2,5-di-tert-butylphenyl group, a 2,6-di-tert-butylphenyl group, a 2,4-di-tert-pentylphenyl group, a 2,5-di-tert-pentylphenyl group, a 2,5-di-tert-octylphenyl group, a 2-cyclohexylphenyl group, 3-cyclohexylphenyl group, 4-cyclohexylphenyl group, a 2,4,5-trimethylphenyl group, a 2,4,6-trimethylphenyl group, and 2,4,6-triisopropylphenyl group.

A group represented by the formula (c-5a) is a group containing an ether group. In the formula (c-5a), examples of an alkanediyl group having 1 or more and 4 or less carbon atoms represented by $Y^1$ include a methylene group, an ethane-1,2-diyl group, an ethane-1,1-diyl group, a propane-1,3-diyl group, a propane-1,2-diyl group, a butane-1,4-diyl group, a butane-1,3-diyl group, a butane-2,3-diyl group, and a butane-1,2-diyl group. In the formula (c-5a), examples of an alkanediyl group having 2 or more and 6 or less carbon atoms represented by $R^{27a}$ or $R^{28a}$ include an ethane-1,2-diyl group, a propane-1,3-diyl group, a propane-1,2-diyl group, a butane-1,4-diyl group, a butane-1,3-diyl group, a butane-2,3-diyl group, a butane-1,2-diyl group, a pentane-1,5-diyl group, a pentane-1,3-diyl group, a pentane-1,4-diyl group, a pentane-2,3-diyl group, a hexane-1,6-diyl group, a hexane-1,2-diyl group, a hexane-1,3-diyl group, a hexane-1,4-diyl group, a hexane-2,5-diyl group, a hexane-2,4-diyl group, and a hexane-3,4-diyl group.

In the formula (c-5a), when $R^{27a}$ or $R^{28a}$ is an alkanediyl group having 2 or more and 6 or less carbon atoms substituted with halogen atom(s), examples of the halogen atom include a chlorine atom, a bromine atom, an iodine atom, and a fluorine atom. Examples of alkanediyl group substituted with halogen atom(s) include a tetrafluoroethane-1,2-diyl group, a 1,1-difluoroethane-1,2-diyl group, a 1-fluoroethane-1,2-diyl group, a 1,2-difluoroethane-1,2-diyl group, a hexafluoropropane-1,3-diyl group, a 1,1,2,2-tetrafluoropropane-1,3-diyl group, and a 1,1,2,2-tetrafluoropentane-1,5-diyl group.

In the formula (c-5a), examples of an arylene group as $R^{27a}$ or $R^{28a}$ include a 1,2-phenylene group, a 1,3-phenylene group, a 1,4-phenylene group, a 2,5-dimethyl-1,4-phenylene group, a biphenyl-4,4'-diyl group, a diphenylmethane-4,4'-diyl group, a 2,2-diphenyl propane-4,4'-diyl group, a naphthalene-1,2-diyl group, a naphthalene-1,3-diyl group, a naphthalene-1,4-diyl group, a naphthalene-1,5-diyl group, a naphthalene-1,6-diyl group, a naphthalene-1,7-diyl group, a naphthalene-1,8-diyl group, a naphthalene-2,3-diyl group, a naphthalene-2,6-diyl group, an naphthalene-2,7-diyl group.

In the formula (c-5a), when $R^{27a}$ or $R^{28a}$ is an arylene group substituted with halogen atom(s), examples of the halogen atom include a chlorine atom, a bromine atom, an iodine atom, and a fluorine atom. Examples of an arylene group substituted with halogen atom(s) include 2,3,5,6-tetrafluoro-1,4-phenylene group.

In the formula (c-5a), examples of an optionally branched alkyl group having 1 or more and 18 or less carbon atoms include a methyl group, an ethyl group, an n-propyl group, an isopropyl group, an n-butyl group, a sec-butyl group, a tert-butyl group, an isobutyl group, an n-pentyl group, a isopentyl group, a tert-pentyl group, an n-hexyl group, an n-hexane-2-yl group, an n-hexane-3yl group, an n-heptyl group, an n-heptane-2-yl group, an n-heptane-3yl group, an isoheptyl group, a tert-heptyl group, an n-octyl group, an isooctyl group, a tert-octyl group, a 2-ethylhexyl group, an n-nonyl group, an isononyl group, an n-decyl group, an n-undecyl group, an n-dodecyl group, an n-tridecyl group, an n-tetradecyl group, an n-pentadecyl group, an n-hexadecyl group, an n-heptadecyl group, and an n-ocatadecyl group.

In the formula (c-5a), when $R^{29}$ is an alkyl group having 1 or more and 18 or less carbon atoms substituted with halogen atom(s), examples of the halogen atom include a chlorine atom, a bromine atom, an iodine atom, and a fluorine atom. Examples of an alkyl group substituted with a halogen atom include a trifluoromethyl group, a pentafluoroethyl group, a heptafluoro-n-propyl group, a nonafluoro-n-butyl group, a tridecafluoro-n-hexyl group, a heptadecafluoro-n-octyl group, a 2,2,2-trifluoroethyl group, a 1,1-difluoro-n-propyl group, a 1,1,2,2-tetrafluoro-n-propyl group, a 3,3,3-trifluoro-n-propyl group, a 2,2,3,3,3-pentafluoro-n-propyl group, and a 1,1,2,2-tetrafluorotetradecyl group.

In the formula (c-5a), when $R^{29a}$ is an alicyclic hydrocarbon group having 3 or more and 12 or less carbon atoms, examples of the alicyclic hydrocarbon composing a main skeleton of the alicyclic hydrocarbon groups include cyclopropane, cyclobutane, cyclopentane, cyclohexane, cycloheptane, cyclooctane, cyclodecane, bicycle[2.1.1]hexane, bicycle[2.2.1]heptane, bicycle[3.2.1]octane, bicycle[2.2.2]octane, and adamantine. As an alicyclic hydrocarbon groups is preferably a group in which one hydrogen atom is removed from these alicyclic hydrocarbons.

In the formula (c-5a), when $R^{29a}$ is an aryl group, a halogenated aryl group, an aralkyl group, and a halogenated aralkyl group, preferable examples of these groups are the same as the case where $R^{22}$ are these groups.

The suitable group among the groups represented by the formula (c-5a) is a group among the groups represented by $R^{27a}$ in which a carbon atom bonded to a sulfur atom is substituted with a fluorine atom. The number of carbon atoms of such a suitable group is preferably 2 or more and 18 or less.

$R^{22a}$ is preferably a perfluoroalkyl group having 1 or more and 8 or less carbon atoms. Furthermore, since highly minute resist patterns are easily formed, a camphor-10-yl group is also preferable as $R^{22a}$.

In the formula (c-5), $R^{23a}$ to $R^{26a}$ are a hydrogen atom or a monovalent organic group. Furthermore, $R^{23a}$ and $R^{24a}$, $R^{24a}$ and $R^{25a}$, or $R^{25a}$ and $R^{26a}$ may be bonded to each other respectively to form a ring. For example, $R^{25a}$ and $R^{26a}$ may be bonded to each other to form a five-membered ring together with a naphthalene ring, thereby forming an acenaphthene skeleton.

Preferable examples of the monovalent organic group include an alkoxy group having 4 or more and 18 or less carbon atoms which may be substituted with an alicyclic hydrocarbon group, a heterocyclic group (heterocyclyl group), or a halogen atom, and which may be branched; a heterocyclyl oxy group; an alkylthio group having 4 or more and 18 or less carbon atoms which may be substituted with an alicyclic hydrocarbon group, a heterocyclic group (heterocyclyl group), or a halogen atom and which may be branched; and a heterocyclylthio group. Furthermore, a group in which the methylene group at any position that is not adjacent to an oxygen atom of the alkoxy group is substituted with —CO— is also preferable. A group in which the alkoxy group is interrupted by an —O—CO— bond, or an —O—CO—NH-bond is also preferable. Note here that the left ends of the —O—CO— bond and the —O—CO—NH— bond are sides near the naphthalic acid mother nucleus in an alkoxy group. In addition, an alkylthio group having 4 or more and 18 or less carbon atoms, which may be substituted with an alicyclic hydrocarbon group, a heterocyclic group, or a halogen atom, and which may be branched, is also preferable as $R^{23a}$ to $R^{26a}$. A group in which the methylene group at any position that is not adjacent to a sulfur atom of the alkylthio group is substituted with —CO— is also preferable. A group in which the alkylthio group is interrupted by an —O—CO— bond, or an —O—CO—NH— bond is also preferable. Note here that the left ends of the —O—CO— bond and —O—CO—NH— bond are sides near the naphthalic acid mother nucleus in an alkylthio group.

As $R^{23a}$ to $R^{26a}$, it is preferable that $R^{23a}$ is an organic group, $R^{24a}$ to $R^{26a}$ are a hydrogen atom, $R^{24a}$ is an organic group, and $R^{23a}$, $R^{25a}$, and $R^{26a}$ are a hydrogen atom. Furthermore, all of $R^{23a}$ to $R^{26a}$ may be a hydrogen atom.

Examples of an unsubstituted alkoxy group as $R^{23a}$ to $R^{26a}$ includes an n-butyloxy group, a sec-butyloxy group, a tert-butyloxy group, an isobutyloxy group, an n-pentyloxy group, an isopentyloxy group, a tert-pentyloxy group, an n-hexyloxy group, an n-heptyloxy group, an isoheptyloxy group, a tert-heptyloxy group, an n-octyloxy group, an isooctyloxy group, a tert-octyloxy group, a 2-ethylhexyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, and an n-ocatdecyloxy group.

Examples of an unsubstituted alkylthio group as $R^{23a}$ to $R^{26a}$ includes an n-butylthio group, a sec-butylthio group, a tert-butylthio group, an isobutylthio group, an n-pentylthio group, an isopentylthio group, a tert-pentylthio group, an n-hexylthio group, an n-heptylthio group, an isoheptylthio group, a tert-heptylthio group, an n-octylthio group, an isooctylthio group, a tert-octylthio group, a 2-ethylhexylthio group, an n-nonylthio group, an n-decylthio group, an n-undecylthio group, an n-dodecylthio group, an n-tridecylthio group, an n-tetradecylthio group, an n-pentadecylthio group, an n-hexadecylthio group, an n-heptadecylthio group, and an n-ocatdecylthio group.

When $R^{23a}$ to $R^{26a}$ are an alkoxy group or an alkylthio group substituted with an alicyclic hydrocarbon group, examples of the alicyclic hydrocarbon composing a main skeleton of the alicyclic hydrocarbon group include cyclopropane, cyclobutane, cyclopentane, cyclohexane, cycloheptane, cyclooctane, cyclodecane, bicycle[2.1.1]hexane, bicycle[2.2.1]heptane, bicycle[3.2.1]octane, bicycle[2.2.2]octane, and adamantine. As an alicyclic hydrocarbon groups is preferably a group in which one hydrogen atom is removed from these alicyclic hydrocarbons.

When $R^{23a}$ to $R^{26a}$ are an alkoxy group or an alkylthio group substituted with a heterocyclic group, or when $R^{23a}$ to $R^{26a}$ are a heterocyclyloxy group, examples of heterocycle composing a main skeleton of the heterocyclic group or the heterocyclyloxy group include pyrrole, thiophene, furan, pyrane, thiopyrane, imidazole, pyrazole, triazole, isothiazole, oxazole, isoxazole, pyridine, pyrazine, pyrimidine, pyridazine, pyrrolidine, pyrazolidine, imidazolidine, isoxazolidine, isothiazolidine, piperidine, piperazine, morpholine, thiomorpholine, chroman, thiochroman, isochroman, isothiochroman, indoline, isoindoline, pyrindine, indolizine, indole, indazole, purine, quinolizine, isoquinoline, quinoline, naphthyridine, phthalazine, quinoxaline, quinazoline, cinnoline, pteridine, acridine, perimidine, phenanthroline, carbazole, carboline, phenazine, anthyridine, thiadiazole, oxadiazole, triazine, triazole, tetrazole, benzimidazole, benzoxazole, benzothiazole, benzothiadiazole, benzofuran, naphthoimidazole, benzotriazole, and tetraazaindene. Saturated heterocycles to which rings including conjugated bond(s) selected from these heterocycles are hydrogenated is also preferable. A group in which one hydrogen atom is removed from above-mentioned heterocycle is preferable as a heterocyclic group substituting the alkoxy group or the alkylthio group or a heterocyclic group included in the heterocyclyloxy group.

Examples of an alkoxy group containing an alicyclic hydrocarbon group as $R^{23a}$ to $R^{26b}$ include a cyclopentyloxy group, a methylcyclopnetyloxy group, a cyclohexyloxy group, a fluorocyclohexyloxy group, a chlorocyclohexyloxy group, a cyclohexylmethyloxy group, a methylcyclohexyloxy group, a norbornyloxy group, an ethylcyclohexyloxy group, a cyclohexylethyloxy group, a dimethylcyclohexyloxy group, a methylcyclohexylnethyloxy group, a norbornylmethyloxy group, a trimethylcyclohexyloxy group, a 1-cyclohexylbutyloxy group, an adamantyloxy group, a menthyloxy group, an n-butylcyclohexyloxy group, a tert-butylcyclohexyloxy group, a bornyloxy group, an isobornyloxy group, a decahydronaphthyloxy group, a dicyclopentadienoxy group, a 1-cyclohexylpentyloxy group, a methyladamantyloxy group, an adamantymethyloxy group, a 4-pentylcyclohexyloxy group, a cyclohexylcyclohexyloxy group, an adamantylethyloxy group, and a dimethyladamantyloxy group.

Examples of a heterocyclyloxy group as $R^{23a}$ to $R^{26b}$ include a tetrahydrofuranyloxy group, a furfuryloxy group, a tetrahydrofurfuryloxy group, a tetrahydropyranyloxy group, a butyrolactonyloxy group, and an indolyloxy group.

Examples of an alkylthio group containing an alicyclic hydrocarbon group as $R^{23a}$ to $R^{26b}$ include a cyclopentylthio group, a cyclohexylthio group, a cyclohexylmethylthio group, a norbornylthio group, and an isobornylthio group.

Examples of a heterocyclylthio group as $R^{23a}$ to $R^{26b}$ include a furfurylthio group, and a tetrahydrofuranylthio group.

When $R^{23a}$ to $R^{26b}$ are a group in which a methylene group is substituted with —CO— at any position except for a position adjacent to oxygen atom of an alkoxy group, examples include 2-ketobutyl-1-oxy group, 2-ketopentyl-1-oxy group, 2-ketohexyl-1-oxy group, 2-ketoheptyl-1-oxy group, 2-ketooctyl-1-oxy group, 3-ketobutyl-1-oxy group, 4-ketopentyl-1-oxy group, 5-ketohexyl-1-oxy group, 6-ketoheptyl-1-oxy group, 7-ketooctyl-1-oxy group, 3-methyl-2-ketopentane-4-oxy group, 2-ketopentane-4-oxy group, 2-methyl-2-ketopentane-4-oxy group, 3-ketoheptane-5-oxy group, and 2-adamantanone-5-oxy group.

When $R^{23a}$ to $R^{26b}$ are a group in which a methylene group is substituted with —CO— at any position except for a position adjacent to sulfur atom of an alkylthio group, examples include 2-ketobutyl-1-thio group, 2-ketopentyl-1-thio group, 2-ketohexyl-1-thio group, 2-ketoheptyl-1-thio group, 2-ketooctyl-1-thio group, 3-ketobutyl-1-thio group, 4-ketopentyl-1-thio group, 5-ketohexyl-1-thio group, 6-ketoheptyl-1-thio group, 7-ketooctyl-1-thio group, 3-methyl-2-ketopentane-4-thio group, 2-ketopentane-4-thio group, 2-methyl-2-ketopentane-4-thio group, and 3-ketoheptane-5-thio group.

As naphthalic acid derivatives represented by the formula (c-5), following compounds may be exemplified.

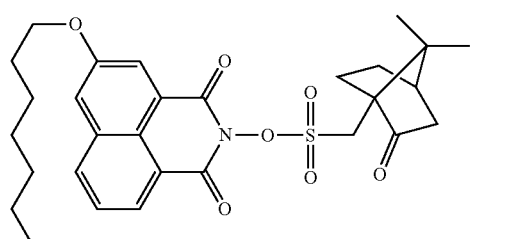

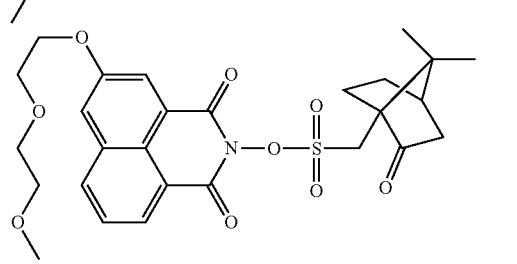

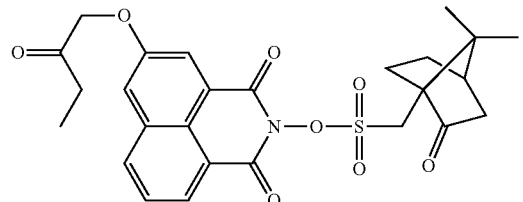

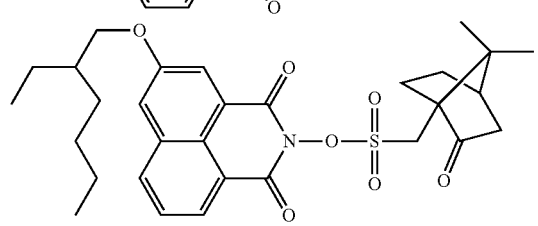

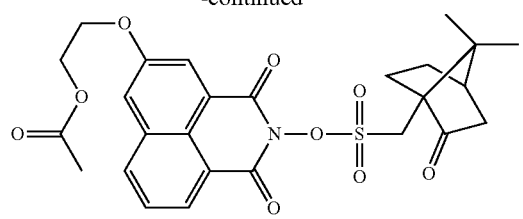

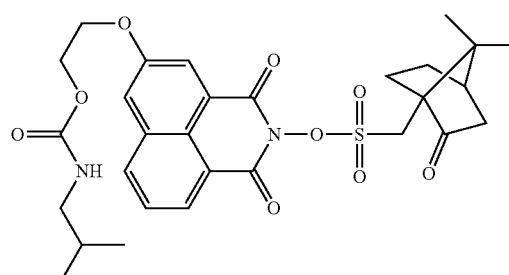

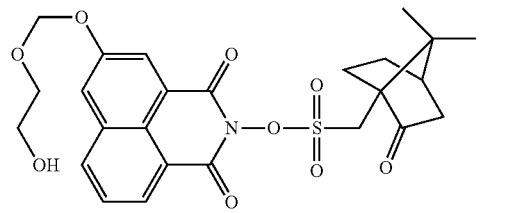

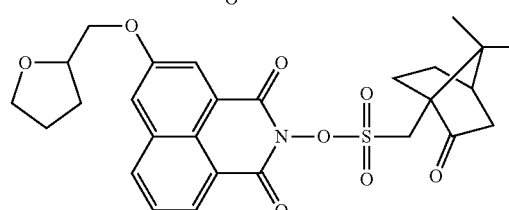

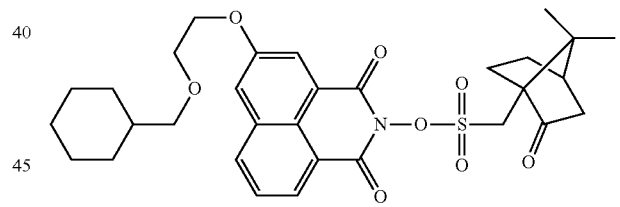

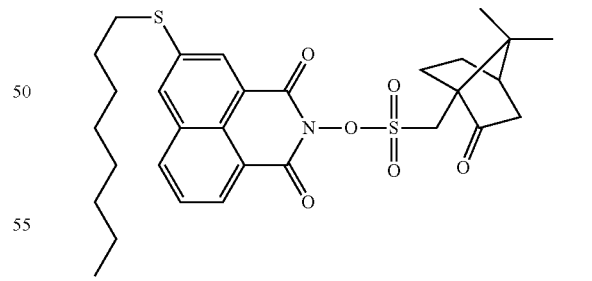

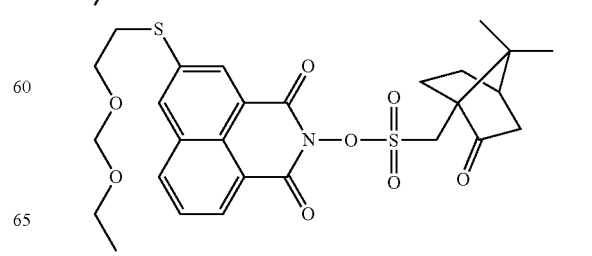

115
-continued
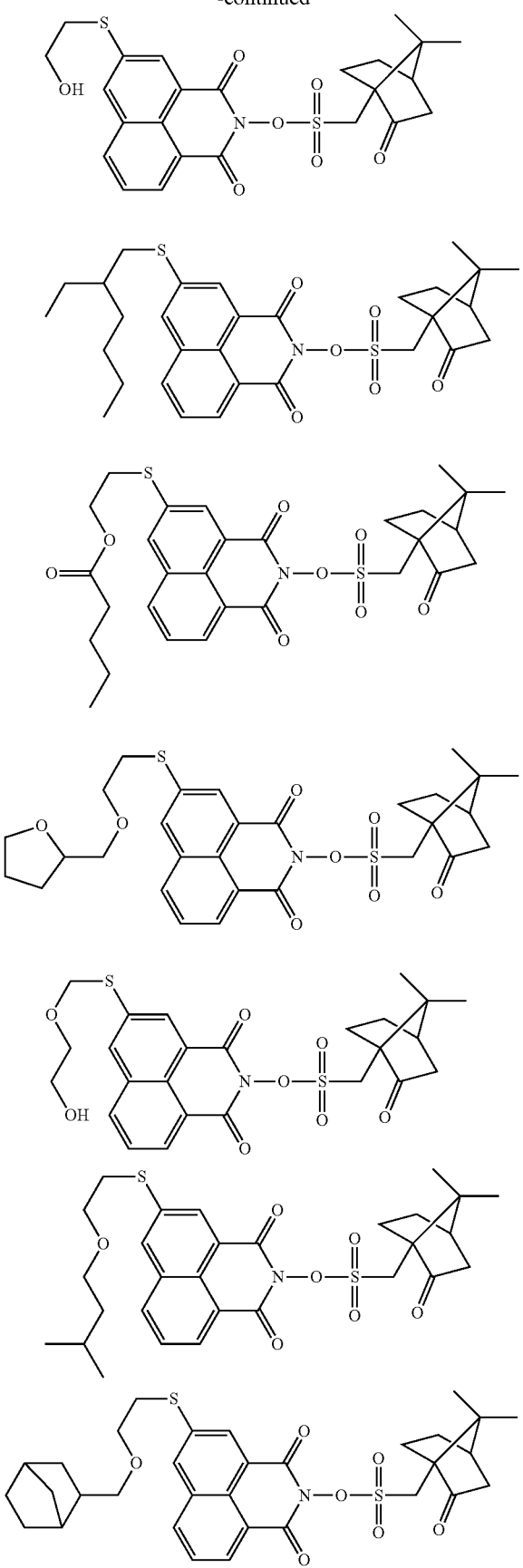
116
-continued
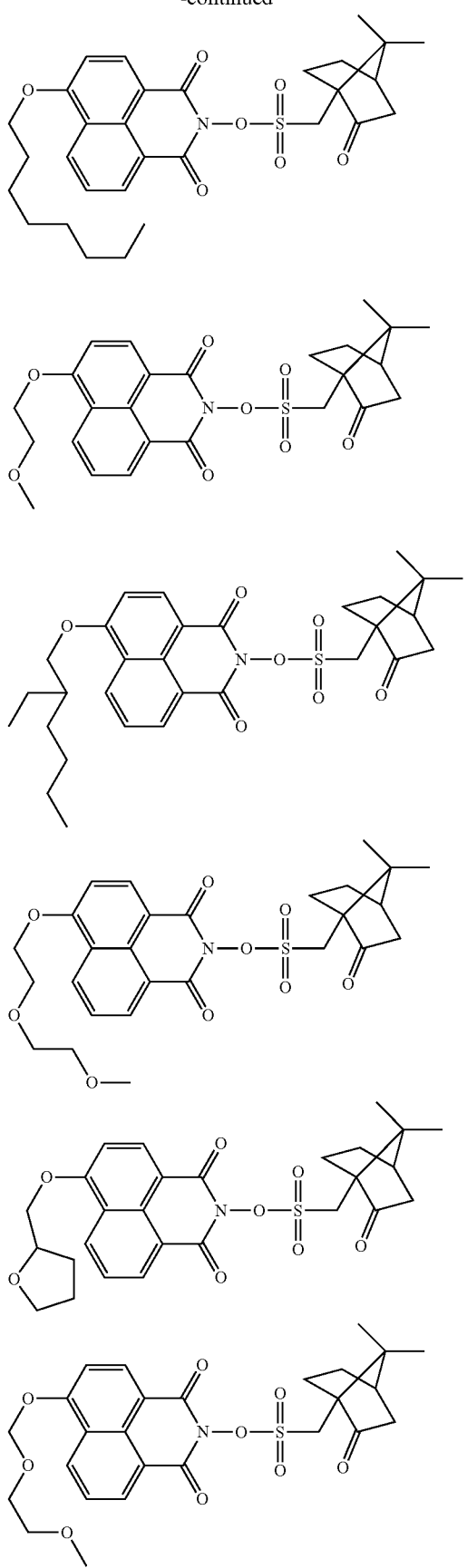

117
-continued
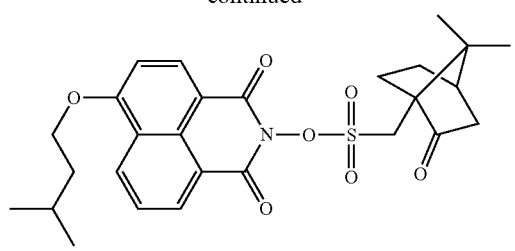
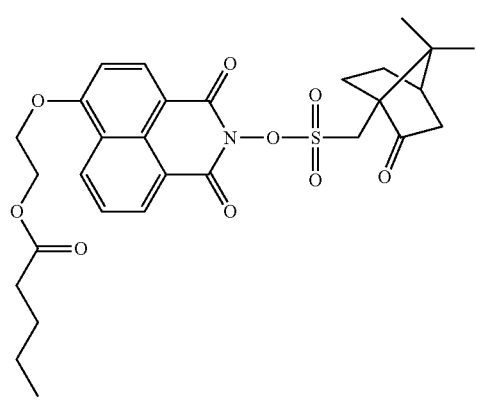
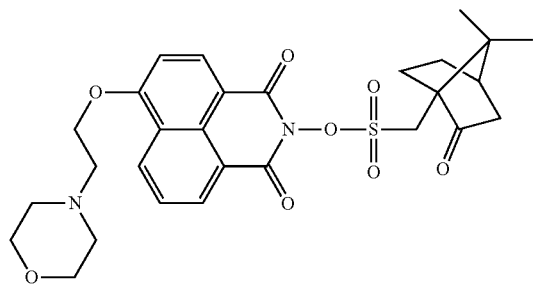
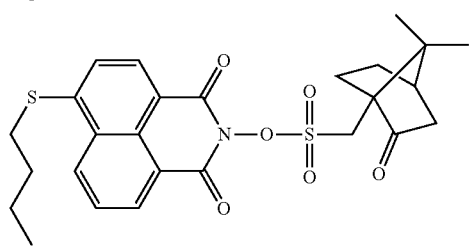
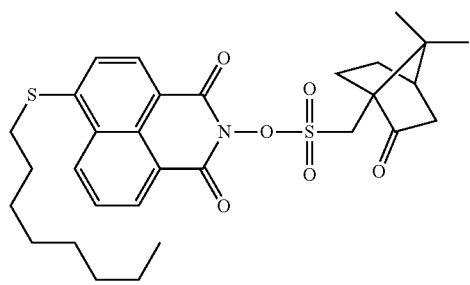
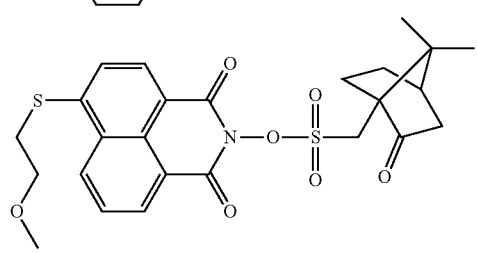
118
-continued
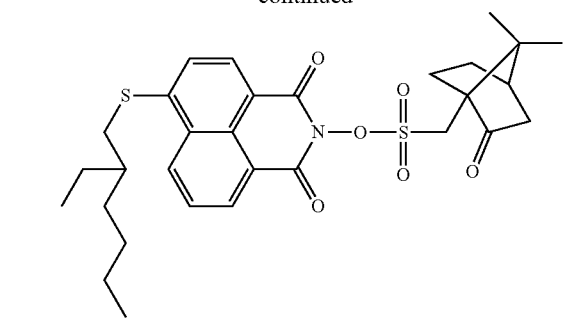
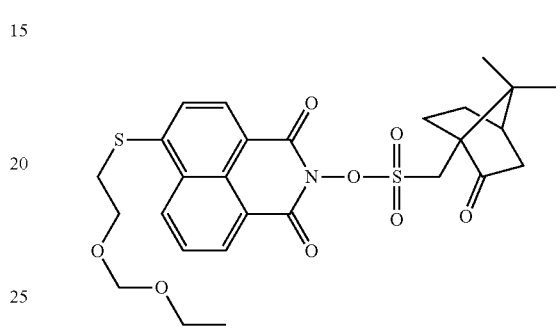
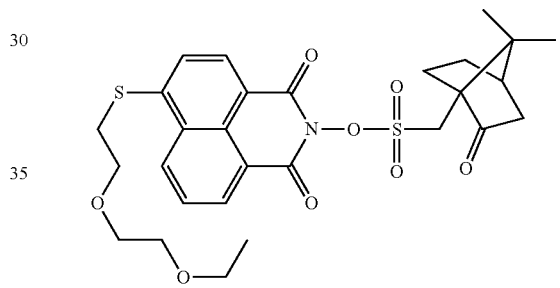
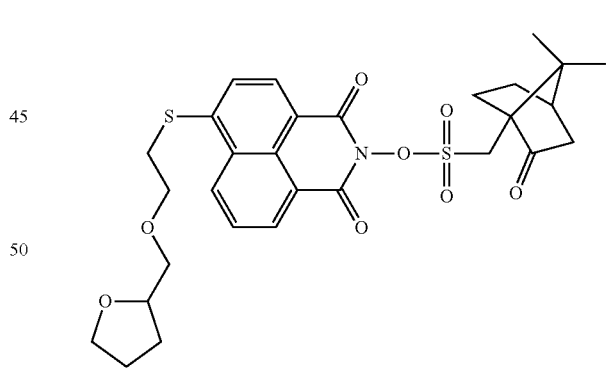
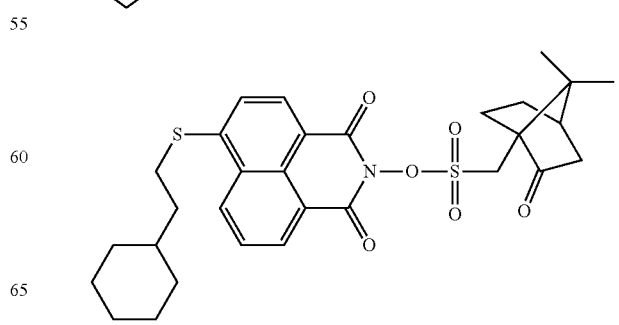

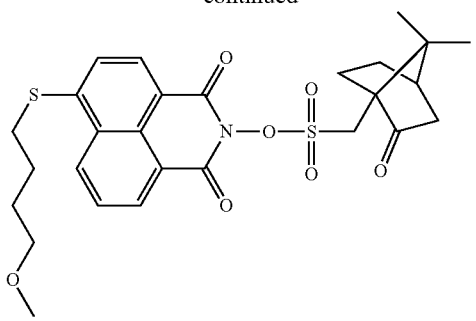
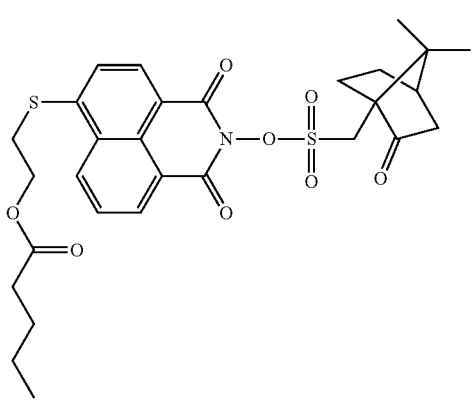
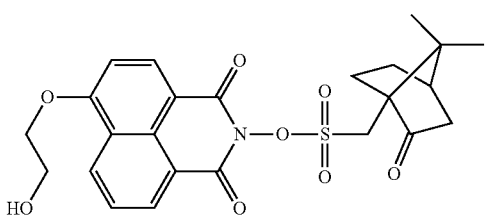
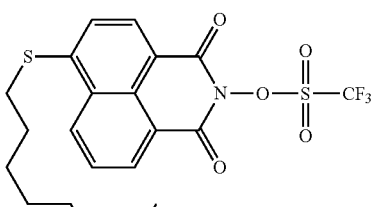
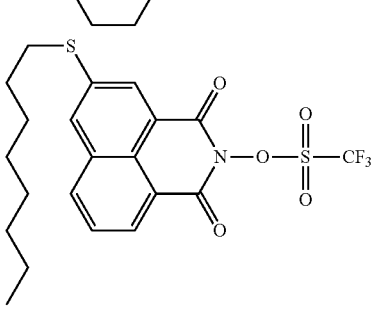
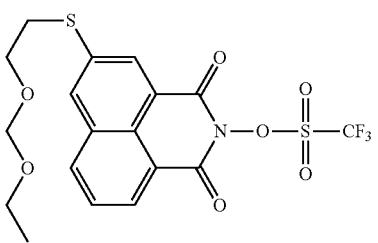
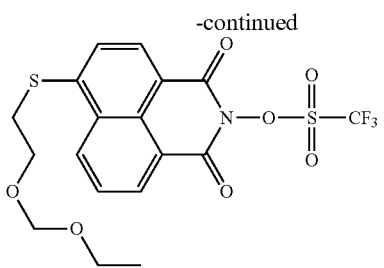
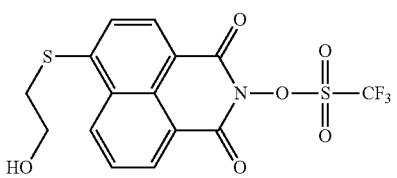
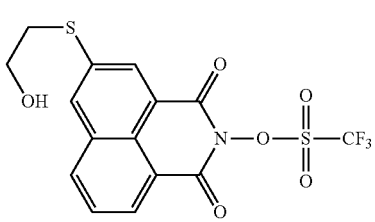
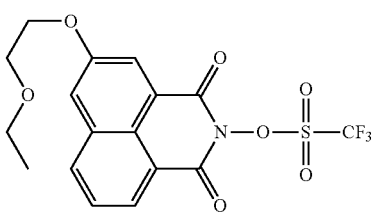
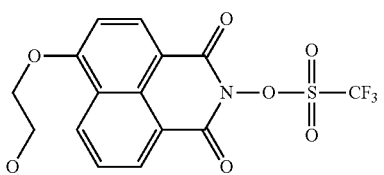
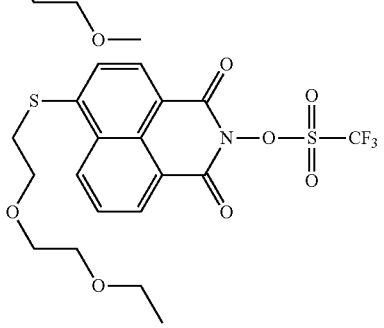
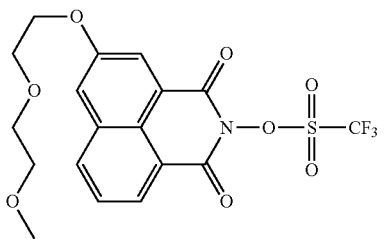

121
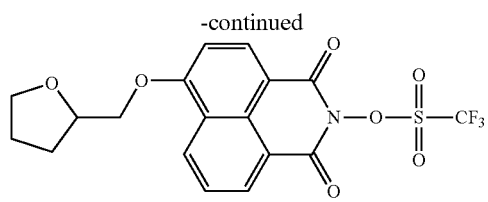
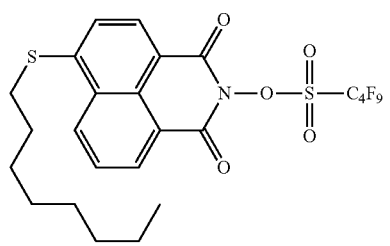
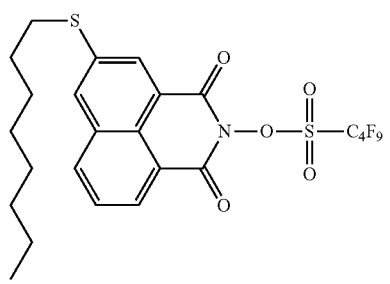
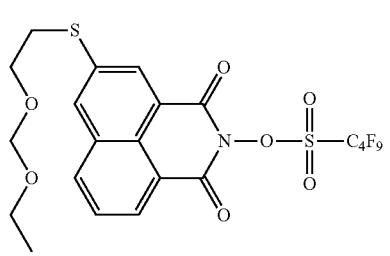
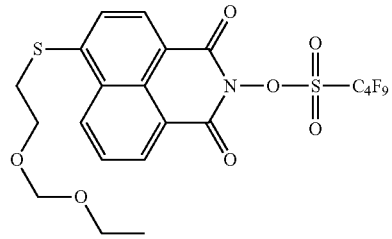
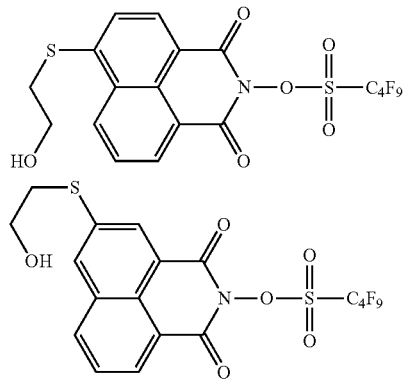
122
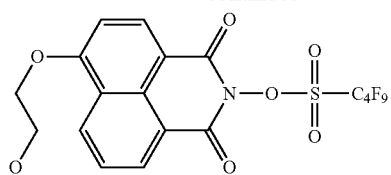
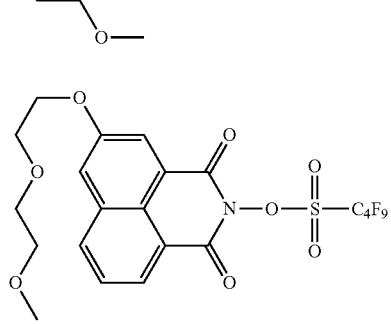
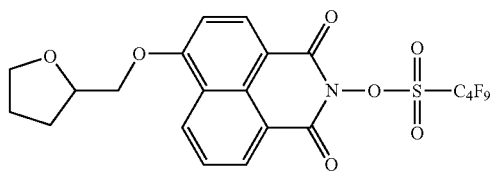
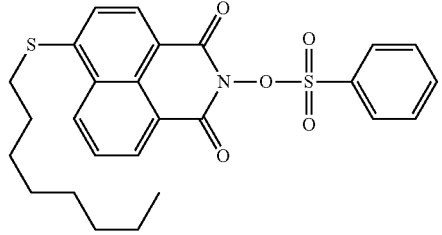
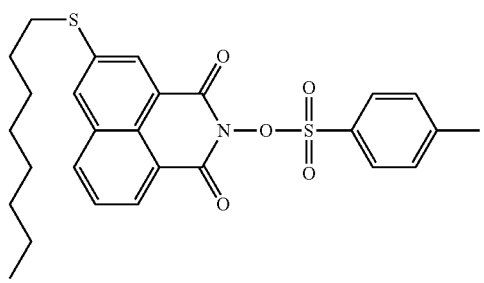
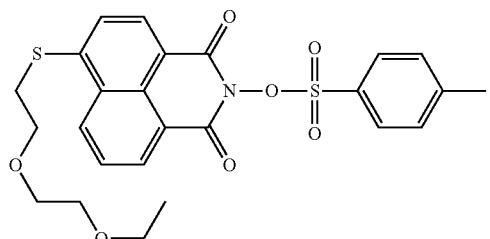
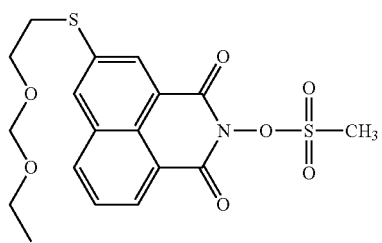

123
-continued
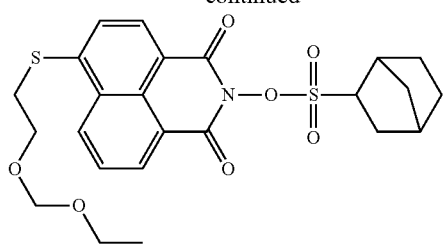
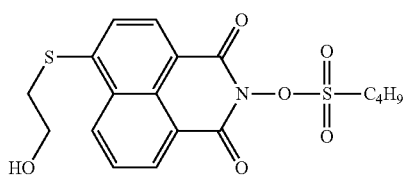
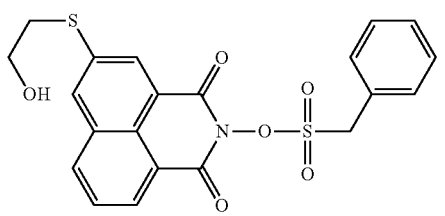
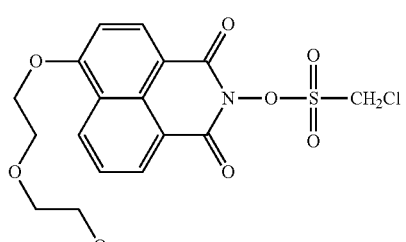
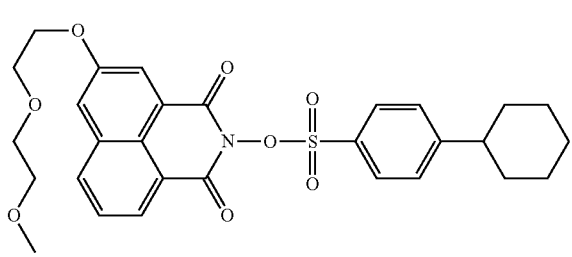
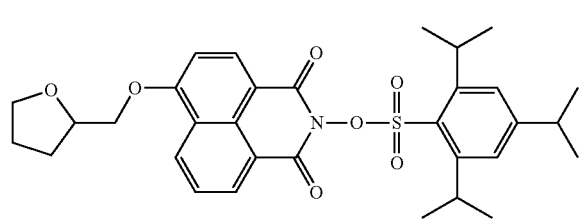
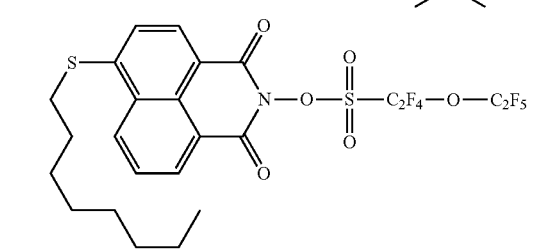
124
-continued
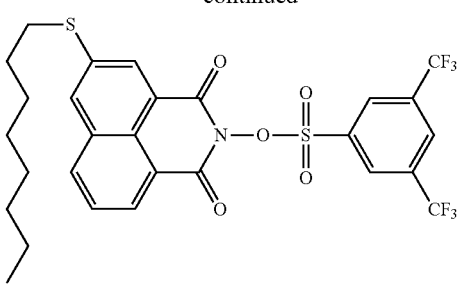
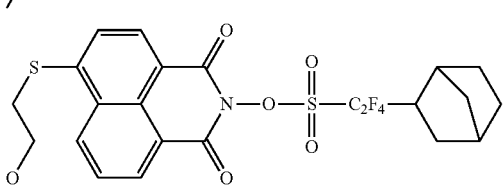
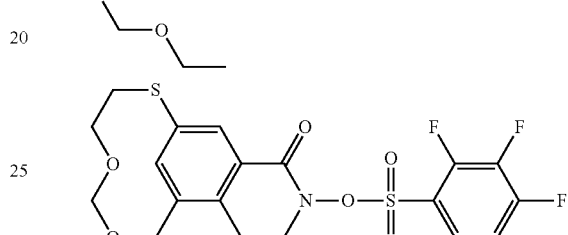
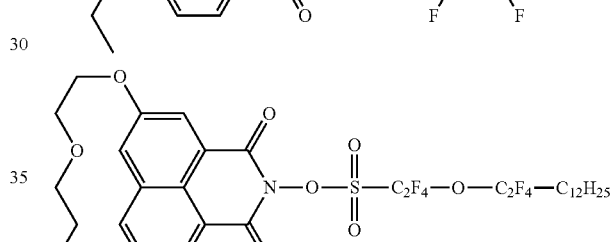
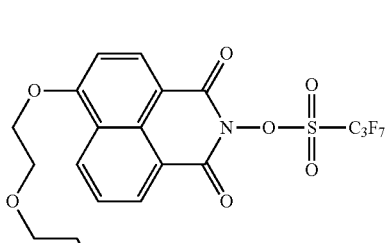
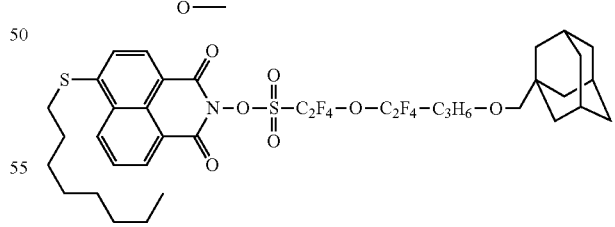
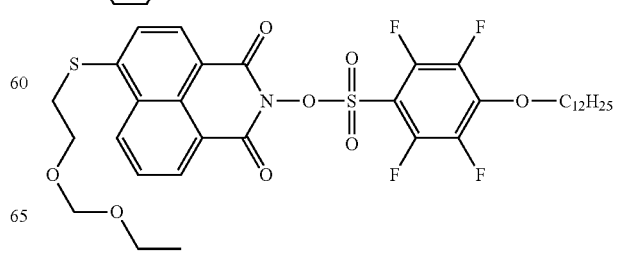

US 10,023,540 B2

-continued

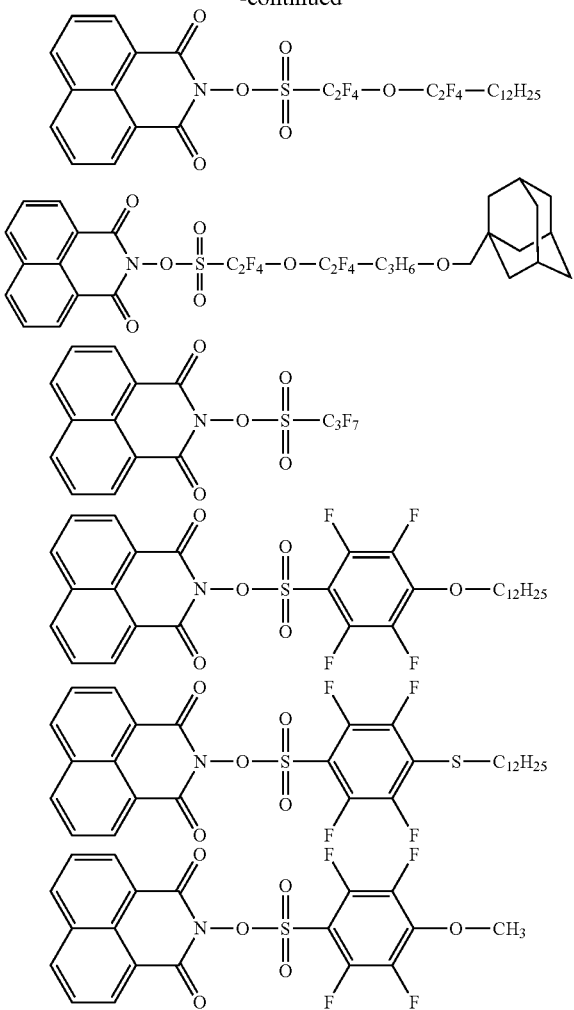

Examples of the other photo acid generators include bissulfonyldiazomethanes such as bis(p-toluenesulfonyl)diazomethane, methylsulfonyl-p-toluenesulfonyldiazomethane, 1-cyclohexylsulfonyl-1-(1,1-dimethylethylsulfonyl)diazomethane, bis(1,1-dimethylethylsulfonyl)diazomethane, bis-(1-methylethylsulfonyl)diazomethane, bis(cyclohexylsulfonyl)diazomethane, bis(2,4-dimethylphenylsulfonyl)diazomethane, bis(4-ethylphenylsulfonyl)diazomethane, bis(3-methylphenylsulfonyl)diazomethane, bis(4-methoxyphenylsulfonyl)diazomethane, bis(4-fluorophenylsulfonyl)diazomethane, bis(4-chlorophenylsulfonyl)diazomethane, and bis(4-tert-butylphenylsulfonyl)diazomethane; sulfonylcarbonylalkanes such as 2-methyl-2-(p-toluenesulfonyl)propiophenone, 2-(cyclohexylcarbonyl)-2-(p-toluenesulfonyl)propane, 2-methanesulfonyl-2-methyl-(p-methylthio)propiophenone, and 2,4-dimethyl-2-(p-toluenesulfonyl)pentane-3-one; sulfonylcarbonyldiazomethanes such as 1-p-toluenesulfonyl-1-cyclohexylcarbonyldiazomethane, 1-diazo-1-methylsulfonyl-4-phenyl-2-butanone, 1-cyclohexylsulfonyl-1-cyclohexylcarbonyldiazomethane, 1-diazo-1-cyclohexylsulfonyl-3,3-dimethyl-2-butanone, 1-diazo-1-(1,1-dimethylethylsulfonyl)-3,3-dimethyl-2-butanone, 1-acetyl-1-(1-methylethylsulfonyl)diazomethane, 1-diazo-1-(p-toluenesulfonyl)-3,3-dimethyl-2-butanone, 1-diazo-1-benzenesulfonyl-3,3-dimethyl-2-butanone, 1-diazo-1-(p-toluenesulfonyl)-3-methyl-2-butanone, cyclohexyl 2-diazo-2-(p-toluenesulfonyl)acetate, tert-butyl 2-diazo-2-benzenesulfonylacetate, isopropyl 2-diazo-2-methanesulfonylacetate, cyclohexyl 2-diazo-2-benzenesulfonylacetate, and tert-butyl 2-diazo2-(p-toluenesulfonyl)acetate; nitrobenzyl derivatives such as 2-nitrobenzyl p-toluenesulfonate, 2,6-dinitrobenzyl p-toluenesulfonate, and 2,4-dinitrobenzyl p-trifluoromethylbenzenesulfonate; and esters of polyhydroxy compound and aliphatic or aromatic sulfonic acid such as pyrogallol methanesulfonate, pyrogallol benzenesulfonate, pyrogallol p-toluenesulfonate, pyrogallol p-methoxybenzenesulfonate, pyrogallol mesitylenesulfonate, pyrogallol benzylsulfonate, alkyl gallate methanesulfonate, alkyl gallate benzenesulfonate, alkylgallate p-toluenesulfonate, alkyl gallate p-methoxybenzenesulfonate (the number of carbon atoms of alkyl group is 1 or more and 15 or less), alkylgallate mesitylenesulfonate, and alkylgallate benzylsulfonate. These photo acid generator may be used alone, or two or more kinds may be used in combination.

These photo acid generator may be used alone, or two or more kinds may be used in combination. Furthermore, the content of the photo acid generator is preferably adjusted to 0.1% by mass or more and 10% by mass or less, and more preferably 0.5% by mass or more and 3% by mass or less, relative to the total mass of the photosensitive composition of second aspect. When the amount of the photo acid generator used is adjusted to the range described above, a photosensitive composition that is a uniform solution having satisfactory sensitivity and exhibiting excellent storage stability can be readily prepared.

The resin whose alkali solubility increases by the action of an acid is not particularly limited, and an arbitrary resin whose alkali solubility increases by the action of an acid may be used. Of these, at least one resin selected from the group consisting of novolak resin (B1), polyhydroxystyrene resin (B2) and acrylic resin (B3) is preferably contained.

[Novolak Resin (B1)]

As the (B1) novolak resin, a resin including the constituent unit represented by the following formula (b1) may be used.

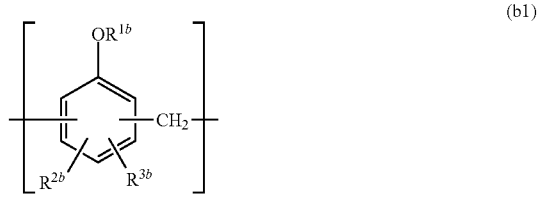

In the formula (b1), $R^{1b}$ represents an acid-dissociable dissolution-inhibiting group, and $R^{2b}$ and $R^{3b}$ each independently represent a hydrogen atom or an alkyl group having 1 or more and 6 or less carbon atoms.

The acid-dissociable dissolution-inhibiting group represented by the above $R^{1b}$ is preferably a group represented by the following formula (b2) or (b3), a linear, branched or cyclic alkyl group having 1 or more and 6 or less carbon atoms, a vinyloxyethyl group, a tetrahydropyranyl group, a tetrahydrofuranyl group, or a trialkylsilyl group.

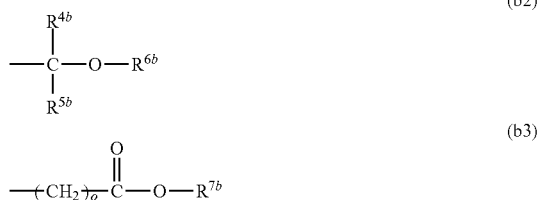

(b2)

(b3)

In the formulae (b2) and (b3), $R^{4b}$ and $R^{5b}$ each independently represent a hydrogen atom, or a linear or branched alkyl group having 1 or more and 6 or less carbon atoms, $R^{6b}$ represents a linear, branched or cyclic alkyl group having 1 or more and 10 or less carbon atoms, $R^{7b}$ represents a linear, branched or cyclic alkyl group having 1 or more and 6 or less carbon atoms, and o represents 0 or 1.

Examples of the linear or branched alkyl group include a methyl group, an ethyl group, a propyl group, an isopropyl group, a n-butyl group, an isobutyl group, a tert-butyl group, a pentyl group, an isopentyl group, a neopentyl group, and the like. Also, examples of the cyclic alkyl group include a cyclopentyl group, a cyclohexyl group, and the like.

Specific examples of the acid-dissociable dissolution-inhibiting group represented by the formula (b2) include a methoxyethyl group, ethoxyethyl group, n-propoxyethyl group, isopropoxyethyl group, n-butoxyethyl group, isobutoxyethyl group, tert-butoxyethyl group, cyclohexyloxyethyl group, methoxypropyl group, ethoxypropyl group, 1-methoxy-1-methylethyl group, 1-ethoxy-1-methylethyl group, and the like. Furthermore, specific examples of the acid-dissociable dissolution-inhibiting group represented by the formula (b3) include a tert-butoxycarbonyl group, tert-butoxycarbonylmethyl group, and the like. Examples of the trialkylsilyl group include a trimethylsilyl group and tri-tert-butyldimethylsilyl group in which each alkyl group has 1 or more and 6 or less carbon atoms.

[Polyhydroxystyrene Resin (B2)]

As the polyhydroxystyrene resin (B2), a resin including the constituent unit represented by the following formula (b4) may be used.

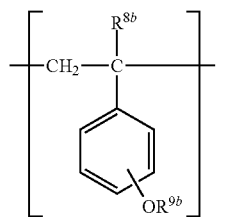

(b4)

In the formula (b4), $R^{8b}$ represents a hydrogen atom or an alkyl group having 1 or more and 6 or less carbon atoms, and $R^{9b}$ represents an acid-dissociable dissolution-inhibiting group.

The alkyl group having 1 or more and 6 or less carbon atoms may include, for example, linear, branched or cyclic alkyl groups having 1 or more and 6 or less carbon atoms. Examples of the linear or branched alkyl group include a methyl group, ethyl group, propyl group, isopropyl group, n-butyl group, isobutyl group, tert-butyl group, pentyl group, isopentyl group and neopentyl group, and examples of the cyclic alkyl group include a cyclopentyl group and cyclohexyl group.

The acid-dissociable dissolution-inhibiting group represented by the above $R^{9b}$ may be similar to the acid-dissociable dissolution-inhibiting groups exemplified in terms of the above formulae (b2) and (b3).

Furthermore, the polyhydroxystyrene resin (B2) may include another polymerizable compound as a structural unit in order to moderately control physical or chemical properties. The polymerizable compound is exemplified by conventional radical polymerizable compounds and anion polymerizable compounds. Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxy group and an ester bond such as 2-methacryloyloxyethyl succinic acid, 2-methacryloyloxyethyl maleic acid 2-methacryloyloxyethyl phthalic acid and 2-methacryloyloxyethyl hexahydrophthalic acid; (meth)acrylic acid alkyl esters such as methyl(meth)acrylate, ethyl (meth)acrylate and butyl (meth)acrylate; (meth)acrylic acid hydroxyalkyl esters such as 2-hydroxyethyl (meth)acrylate and 2-hydroxypropyl (meth)acrylate; (meth)acrylic acid aryl esters such as phenyl (meth)acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; and amide bond-containing polymerizable compounds such as acrylamide and methacrylamide.

[Acrylic Resin (B3)]

As the acrylic resin (B3), a resin including a constituent unit represented by the following formulae (b5) to (b7) may be used.

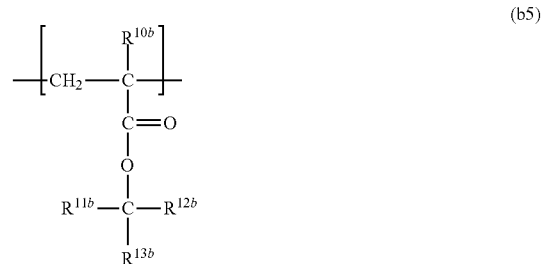

(b5)

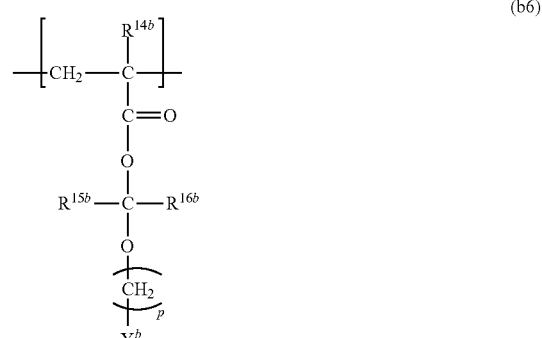

(b6)

131

-continued

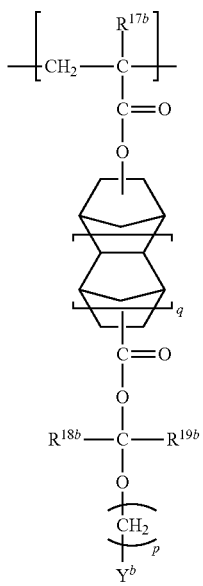

(b7)

$R^{10b}$ and $R^{14b}$ to $R^{19b}$ in the above formulae (b5) to (b7) are each independently a hydrogen atom, a linear or branched alkyl group having 1 or more and 6 or less carbon atoms, a fluorine atom or a linear or branched fluorinated alkyl group having 1 or more and 6 or less carbon atoms. $R^{11b}$ to $R^{13b}$ are each independently a linear or branched alkyl group having 1 or more and 6 or less carbon atoms, a linear or branched fluorinated alkyl group having 1 or more and 6 or less carbon atoms or an aliphatic cyclic group having 5 or more and 20 or less carbon atoms. $R^{12b}$ and $R^{13b}$ may join each other to form a hydrocarbon ring having 5 or more and 20 or less carbon atoms together with a carbon atom to which the both are attached. $Y^b$ represents an aliphatic cyclic group or an alkyl group optionally having a substituent. p is an integer of 0 or more and 4 or less, and q is 0 or 1.

Examples of the linear or branched alkyl group include a methyl group, ethyl group, propyl group, isopropyl group, n-butyl group, isobutyl group, tert-butyl group, pentyl group, isopentyl group, neopentyl group, and the like. The fluorinated alkyl group refers to the abovementioned alkyl groups of which the hydrogen atoms are partially or entirely substituted with fluorine atoms. Specific examples of the aliphatic cyclic group include a group in which one or more hydrogen atoms are removed from monocycloalkanes and polycycloalkanes such as bicycloalkanes, tricycloalkanes and tetracycloalkanes. Specific examples thereof include a group in which one hydrogen atom is removed from monocycloalkanes such as cyclopentane, cyclohexane, cycloheptane and cyclooctane, and polycycloalkanes such as adamantane, norbornane, isobornane, tricyclodecane and tetracyclododecane. In particular, cyclohexane and adamantane from which one hydrogen atom is removed (optionally further having a substituent) are preferable.

132

In a case where the above $R^{12b}$ and $R^{13b}$ do not form hydrocarbon ring by joining each other, a linear or branched alkyl group having 2 or more and 4 or less carbon atoms is preferred as the above $R^{11b}$, $R^{12b}$ and $R^{13b}$ in view of high contrast, good resolution, good focal depth-width and the like. As the above $R^{15b}$, $R^{16b}$, $R^{18b}$ and $R^{19b}$, preferred is a hydrogen atom or a methyl group.

The above $R^{12b}$ and $R^{13b}$ may form an aliphatic cyclic group having 5 or more and 20 or less carbon atoms together with a carbon atom to which the both are attached. Specific examples of such an aliphatic cyclic group include a group in which one or more hydrogen atoms are removed from monocycloalkane; and polycycloalkane such as bicycloalkane, tricycloalkane and tetracycloalkane. Specifically, they include a group in which one or more hydrogen atoms are removed from monocycloalkane such as cyclopentane, cyclohexane and cycloheptane; and polycycloalkane such as adamantane, norbornane, isobornane, tricyclodecane and tetracyclododecane; and the like. In particular, preferred is a group (optionally further having a substituent) in which one or more hydrogen atoms are removed from cyclohexane and adamantane.

Further, in a case where an aliphatic cyclic group to be formed with the above $R^{12b}$ and $R^{13b}$ has a substituent on the ring backbone thereof, examples of the above substituent include a polar group such as a hydroxy group, a carboxy group, a cyano group and an oxygen atom (=O), and a linear or branched alkyl group having 1 or more and 4 or less carbon atoms. As the polar group, an oxygen atom (=O) is particularly preferred.

The aforementioned $Y^b$ is an alicyclic group or an alkyl group; and examples thereof are a group in which one or more hydrogen atoms are removed from monocycloalkanes and polycycloalkanes such as bicycloalkanes, tricycloalkanes and tetracycloalkanes. Specific examples thereof are a group in which one or more hydrogen atoms are removed from monocycloalkanes such as cyclopentane, cyclohexane, cycloheptane and cyclooctane, and polycycloalkanes such as adamantane, norbornane, isobornane, tricyclodecane and tetracyclododecane. Particularly preferable is a group in which one or more hydrogen atoms are removed from adamantane (that may further have a substituent).

When the alicyclic group of the above-mentioned $Y^b$ has a substituent on the ring skeleton, the substituent is exemplified by polar groups such as a hydroxide group, carboxy group, cyano group and oxygen atom (=O), and linear or branched lower alkyl groups having 1 or more and 4 or less carbon atoms. The polar group is preferably an oxygen atom (=O) in particular.

When $Y^b$ is an alkyl group, it is preferably a linear or branched alkyl group having 1 or more and 20 or less carbon atoms, and more preferably 6 or more and 15 or less carbon atoms. Preferably, the alkyl group is an alkoxyalkyl group in particular; and examples of the alkoxyalkyl group include a 1-methoxyethyl group, 1-ethoxyethyl group, 1-n-propoxyethyl group, 1-isopropoxyethyl group, 1-n-butoxyethyl group, 1-isobutoxyethyl group, 1-tert-butoxyethyl group, 1-methoxypropyl group, 1-ethoxypropyl group, 1-methoxy-1-methylethyl group, 1-ethoxy-1-methylethyl group, and the like.

Preferable specific examples of the constituent unit represented by the above formula (b5) are those represented by the following formulae (b5-1) to (b5-33).

(b5-1) 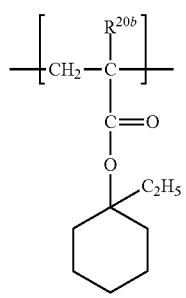
(b5-2) 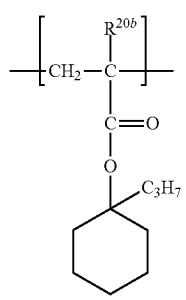
(b5-3) 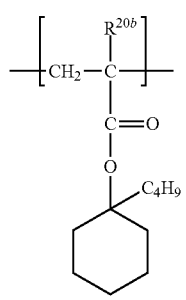
(b5-4) 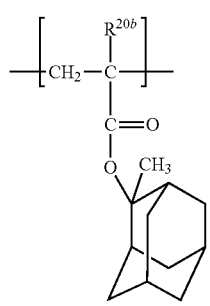
(b5-5) 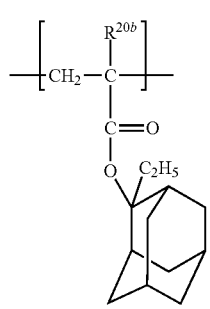
(b5-6) 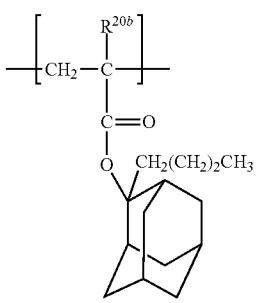
(b5-7) 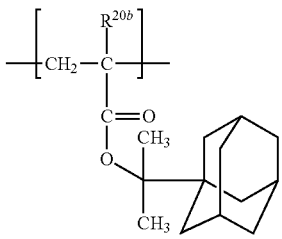
(b5-8) 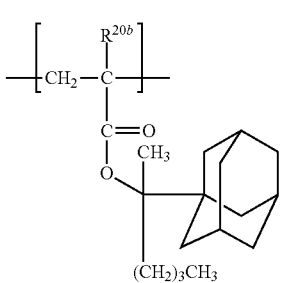
(b5-9) 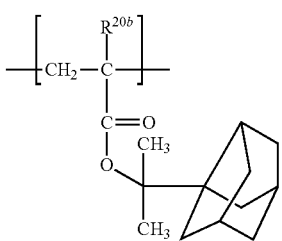
(b5-10) 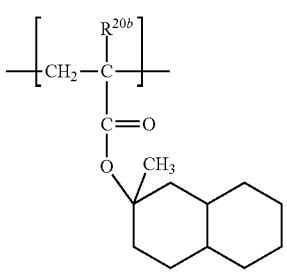
(b5-11) 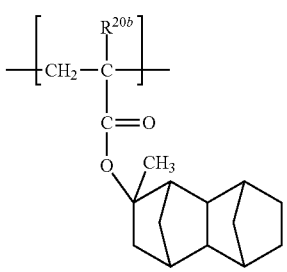

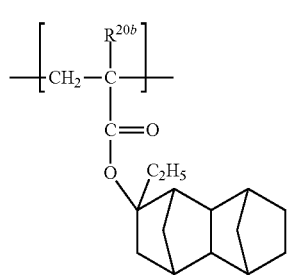
(b5-12)
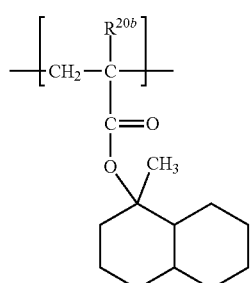
(b5-13)
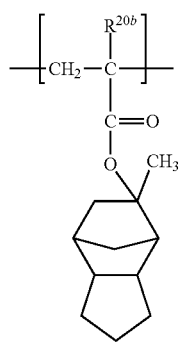
(b5-14)
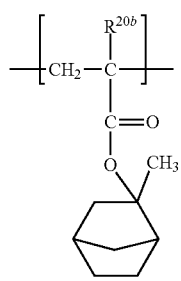
(b5-15)
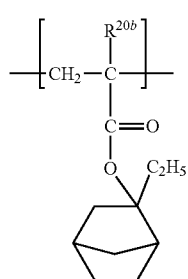
(b5-16)
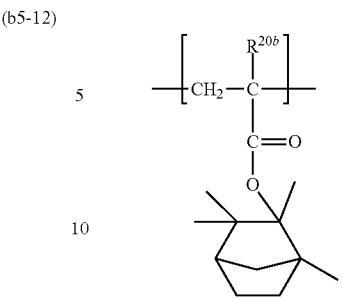
(b5-17)
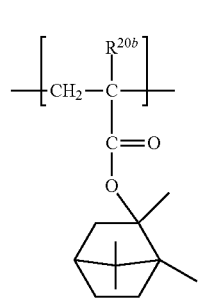
(b5-18)
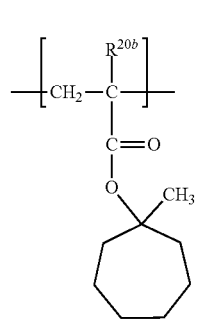
(b5-19)
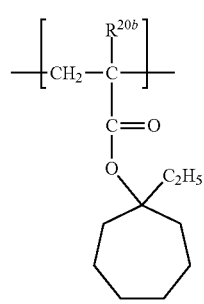
(b5-20)
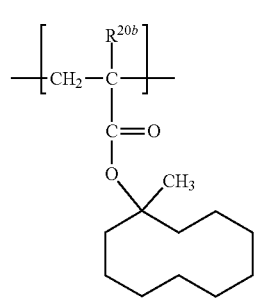
(b5-21)

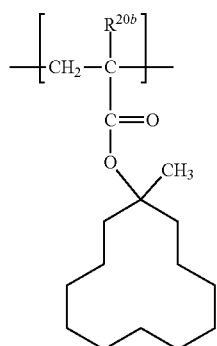 (b5-22)
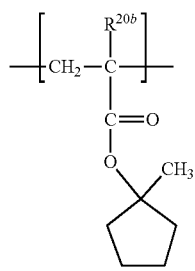 (b5-23)
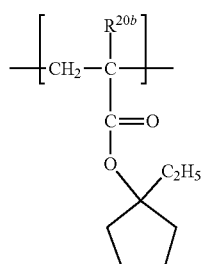 (b5-24)
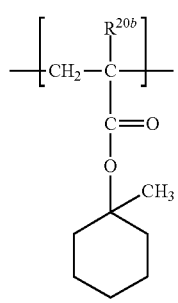 (b5-25)
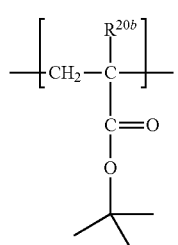 (b5-26)
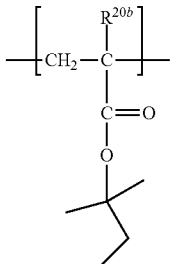 (b5-27)
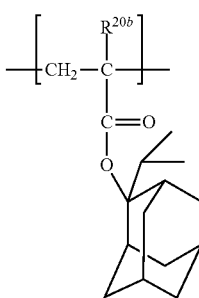 (b5-28)
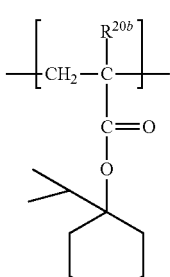 (b5-29)
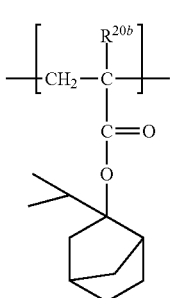 (b5-30)
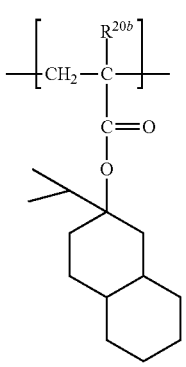 (b5-31)

(b5-32) 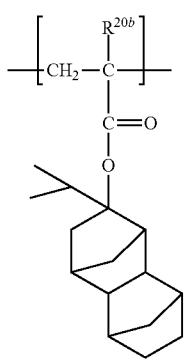
(b5-33) 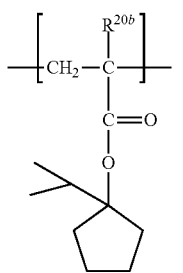
In the above formulae (b5-1) to (b5-33), $R^{20b}$ represents a hydrogen atom or a methyl group.
Preferable specific examples of the constituent unit represented by the above formula (b6) include those represented by the following formulae (b6-1) to (b6-25).
(b6-1) 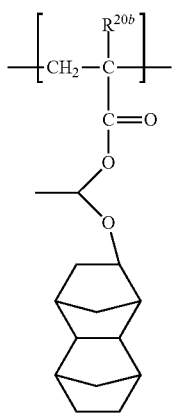
(b6-2) 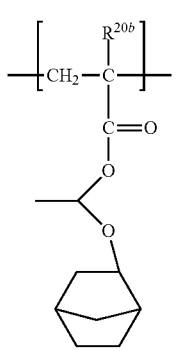
(b6-3) 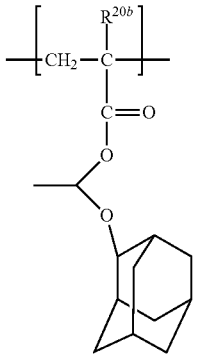
(b6-4) 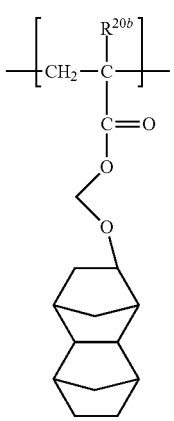
(b6-5) 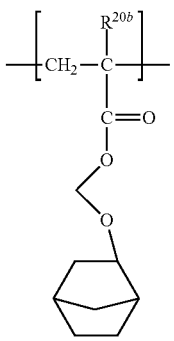
(b6-6) 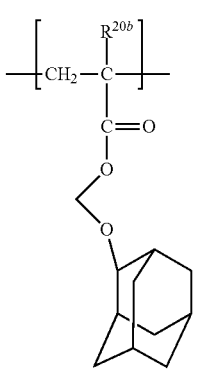

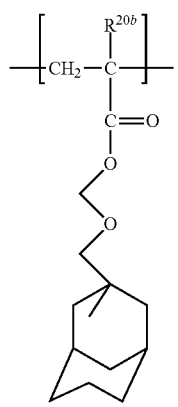
(b6-7)
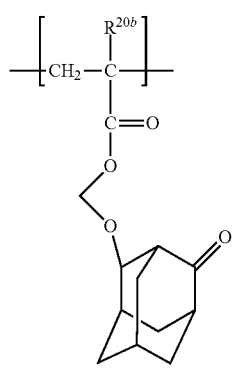
(b6-8)
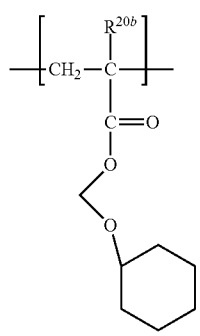
(b6-9)
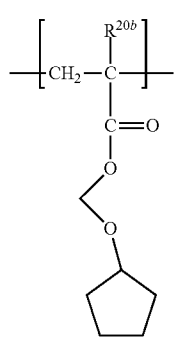
(b6-10)
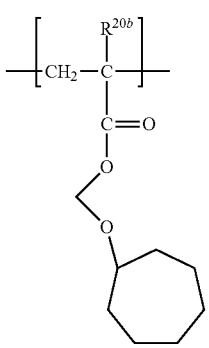
(b6-11)
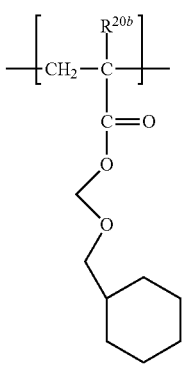
(b6-12)
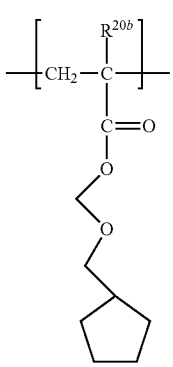
(b6-13)
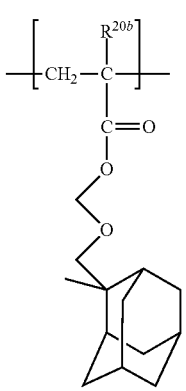
(b6-14)

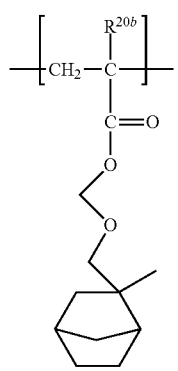
(b6-15)
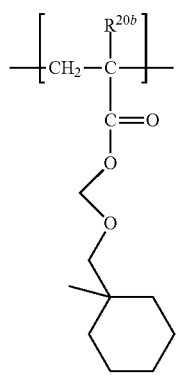
(b6-16)
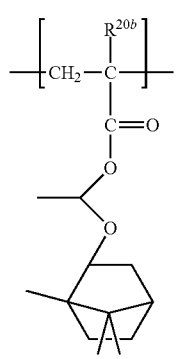
(b6-17)
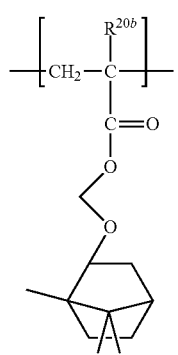
(b6-18)
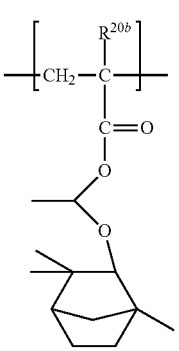
(b6-19)
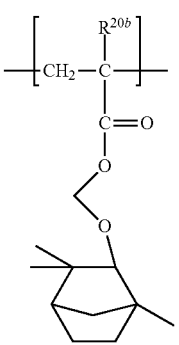
(b6-20)
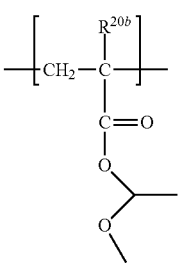
(b6-21)
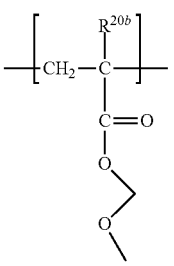
(b6-22)
(b6-23)

(b6-24)
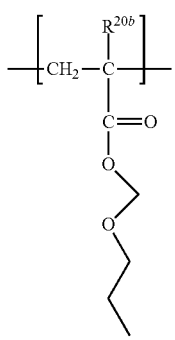
(b6-25)
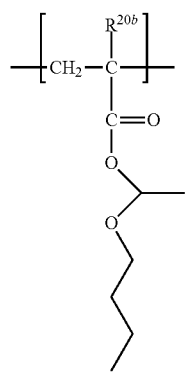
In the above formulae (b6-1) to (b6-25), $R^{20b}$ presents a hydrogen atom or a methyl group.
Preferable specific examples of the constituent unit represented by the above formula (b7) include those represented by the following formulae (b7-1) to (b7-15).
(b7-1)
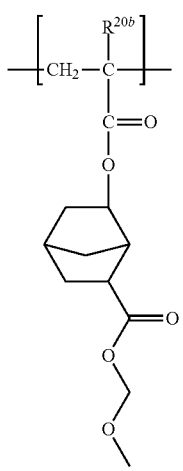
(b7-2)
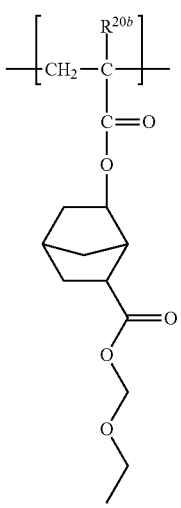
(b7-3)
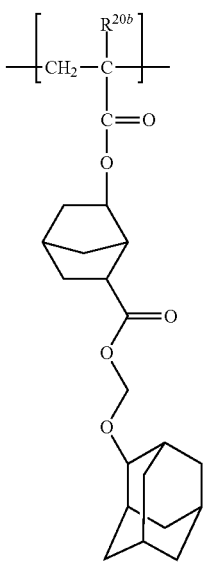

(b7-4)
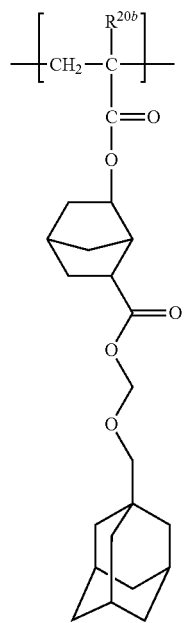
(b7-6)
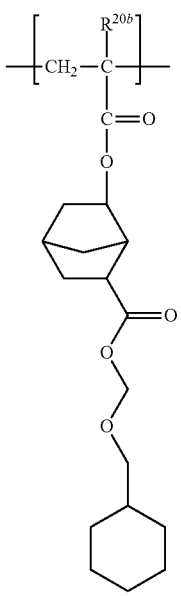
(b7-5)
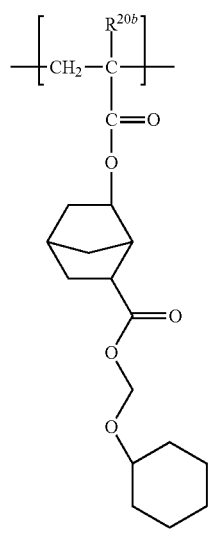
(b7-7)
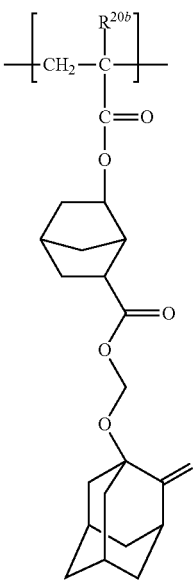

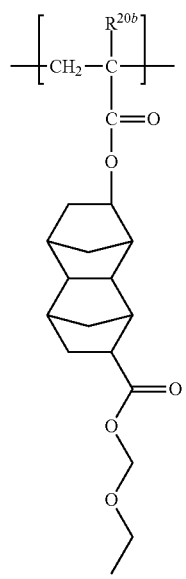
(b7-8)
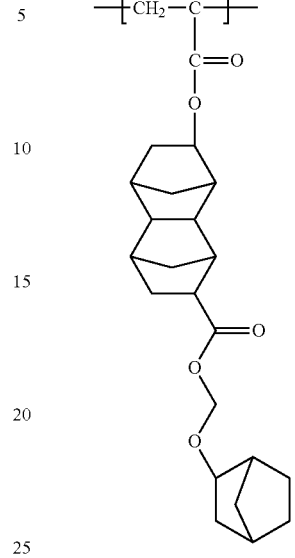
(b7-10)
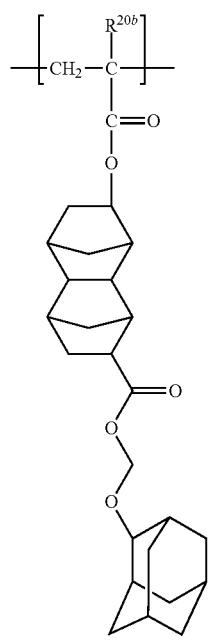
(b7-9)
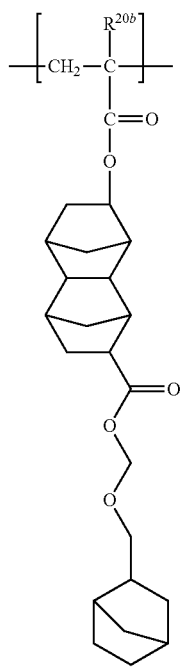
(b7-11)

(b7-12)
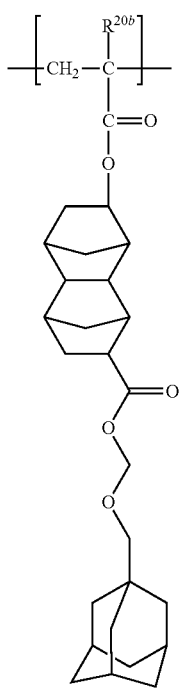

(b7-14)
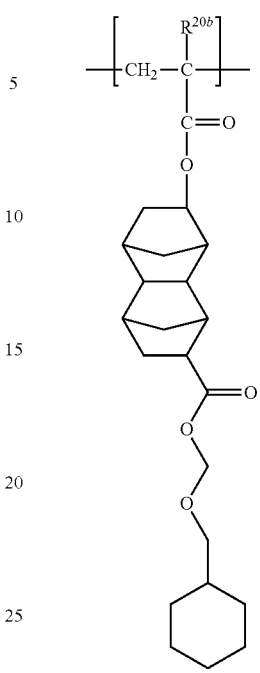

(b7-15)
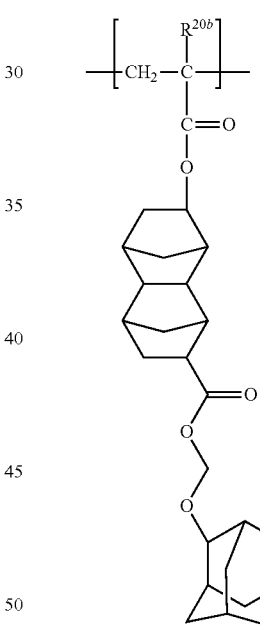

(b7-13)
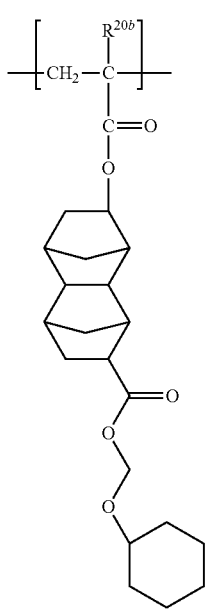

In the above formula (b7-1) to (b7-15), $R^{20b}$ resents a hydrogen atom or a methyl group.

It is also preferred that the acrylic resin (B3) includes a copolymer containing a constituent unit derived from a polymerizable compound having an ether bond in addition to the constituent unit represented by the above formulae (b5) to (b7).

Examples of the polymerizable compound having an ether bond include radical polymerizable compounds such as (meth)acrylic acid derivatives having an ether bond and an ester bond, and specific examples thereof include 2-methoxyethyl (meth)acrylate, 2-ethoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolyethylene glycol (meth)acrylate, methoxypolypropylene glycol (meth) acrylate, tetrahydrofurfuryl (meth)acrylate, and the like. Also, the polymerizable compound having an ether bond is preferably, 2-methoxyethyl (meth)acrylate, 2-ethoxyethyl (meth)acrylate, or methoxytriethylene glycol (meth)acrylate. These polymerizable compounds may be used alone, or in combinations of two or more thereof.

Furthermore, the acrylic resin (B3) may contain another polymerizable compound as a structural unit in order to moderately control physical or chemical properties. The polymerizable compound is exemplified by conventional radical polymerizable compounds and anion polymerizable compounds.

Examples of the polymerizable compound include monocarboxylic acids such as acrylic acid, methacrylic acid and crotonic acid; dicarboxylic acids such as maleic acid, fumaric acid and itaconic acid; methacrylic acid derivatives having a carboxy group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid; (meth) acrylic acid alkyl esters such as methyl(meth)acrylate, ethyl (meth)acrylate, butyl(meth)acrylate and cyclohexyl(meth) acrylate; (meth)acrylic acid hydroxyalkyl esters such as 2-hydroxyethyl (meth)acrylate and 2-hydroxypropyl (meth) acrylate; (meth)acrylic acid aryl esters such as phenyl (meth) acrylate and benzyl (meth)acrylate; dicarboxylic acid diesters such as diethyl maleate and dibutyl fumarate; vinyl group-containing aromatic compounds such as styrene, α-methylstyrene, chlorostyrene, chloromethylstyrene, vinyltoluene, hydroxystyrene, α-methylhydroxystyrene and α-ethylhydroxystyrene; vinyl group-containing aliphatic compounds such as vinyl acetate; conjugated diolefins such as butadiene and isoprene; nitrile group-containing polymerizable compounds such as acrylonitrile and methacrylonitrile; chlorine-containing polymerizable compounds such as vinyl chloride and vinylidene chloride; amide bond-containing polymerizable compounds such as acrylamide and methacrylamide; and the like.

Furthermore, examples of the polymerizable compound include (meth)acrylic acid esters having a non-acid-dissociable aliphatic polycyclic group, and vinyl group-containing aromatic compounds. As the non-acid-dissociable aliphatic polycyclic group, particularly, a tricyclodecanyl group, an adamantyl group, a tetracyclododecanyl group, an isobornyl group, a norbornyl group, and the like are preferred from the viewpoint of easy industrial availability. These aliphatic polycyclic groups may have a linear or branched alkyl group having 1 or more and 5 or less carbon atoms as a substituent.

Specific examples of the (meth)acrylic acid esters having a non-acid-dissociable aliphatic polycyclic group include compounds having structures represented by the following formulae (b8-1) to (b8-5).

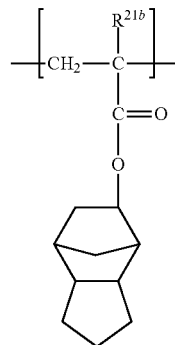
(b8-1)

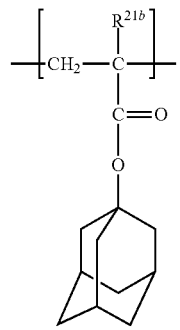
(b8-2)

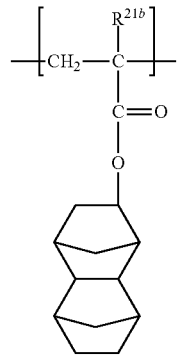
(b8-3)

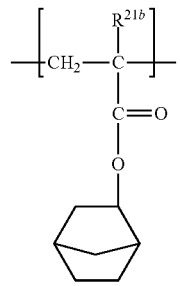
(b8-4)

-continued (b8-5)

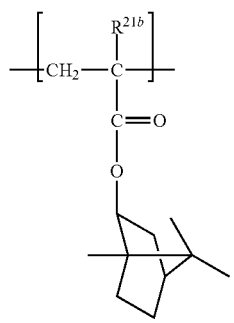

In the formulae (b8-1) to (b8-5) $R^{21b}$ represents a hydrogen atom or a methyl group.

Among the photosensitive resins, the acrylic resins (B3) are preferably used. Among such acrylic resins (B3), a copolymer having a constituent unit represented by formula (b5), a constituent unit derived from (meth)acrylic acid, a constituent unit derived from a (meth)acrylic acid alkyl ester, and a constituent unit derived from a (meth)acrylic acid aryl ester is preferred.

Such a copolymer is preferably a copolymer represented by the following formula (b9).

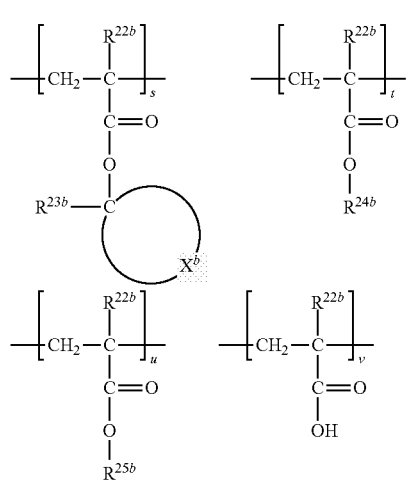

(b9)

In the formula (b9), $R^{22b}$ represents a hydrogen atom or a methyl group; $R^{23b}$ represents a linear or a branched alkyl group having 2 or more and 4 or less carbon atoms; $X^b$ represents a hydrocarbon ring having 5 or more and 20 or less carbon atoms formed together with a carbon atom to which it is attached; $R^{24b}$ represents a linear or branched alkyl group having 1 or more and 6 or less carbon atoms or an alkoxyalkyl group having 1 or more and 6 or less carbon atoms; and $R^{25b}$ represents an aryl group having 6 or more and 12 or less carbon atoms.

In regard to the copolymers represented by the above formula (b9), s, t, u and v represent each molar ratio of the constituent unit, with s being 8% by mole or more and 45% by mole or less, t being 10% by mole or more and 65% by mole or less, u being 3% by mole or more and 25% by mole or less, and v being 6% by mole or more and 25% by mole.

The polystyrene equivalent mass average molecular weight of the photosensitive resin is preferably 10,000 or more and 600,000 or less, more preferably 20,000 or more and 400,000 or less, and still more preferably 30,000 or more and 300,000 or less. By thus adjusting the mass average molecular weight, the photosensitive resin layer can maintain sufficient strength without deteriorating peel properties with supports, and also swelling of profiles in plating, and generation of cracks can be prevented.

It is also preferred that the photosensitive resin has a dispersivity of 1.05 or more. Dispersivity herein indicates a value of a mass average molecular weight divided by a number average molecular weight. A dispersivity in the range described above can avoid problems with respect to stress resistance on intended plating or possible swelling of metal layers resulting from the plating process.

The content of the resin is preferably 5% by mass or more and 60% by mass or less with respect to the total mass of the photosensitive rein composition according to the present invention.

It is preferred that the photosensitive composition of second aspect further contains a alkali-soluble resin in order to improve crack resistance. The alkali-soluble resin is preferably at least one selected from the group consisting of novolak resin (C1), polyhydroxystyrene resin (C2) and acrylic resin (C3).

[Novolak Resin (C1)]

The novolak resin (C1) may be prepared by addition condensation between, for example, aromatic compounds having a phenolic hydroxy group (hereinafter, merely referred to as "phenols") and aldehydes in the presence of an acid catalyst.

Examples of the phenols include phenol, o-cresol, m-cresol, p-cresol, o-ethylphenol, m-ethylphenol, p-ethylphenol, o-butylphenol, m-butylphenol, p-butylphenol, 2,3-xylenol, 2,4-xylenol, 2,5-xylenol, 2,6-xylenol, 3,4-xylenol, 3,5-xylenol, 2,3,5-trimethyl phenol, 3,4,5-trimethyl phenol, p-phenylphenol, resorcinol, hydroquinone, hydroquinone monomethyl ether, pyrogallol, phloroglycinol, hydroxydiphenyl, bisphenol A, gallic acid, gallic acid ester, α-naphthol, β-naphthol, and the like. Examples of the aldehydes include formaldehyde, furfural, benzaldehyde, nitrobenzaldehyde, acetaldehyde, and the like. The catalyst used in the addition condensation reaction, which is not specifically limited, is exemplified by hydrochloric acid, nitric acid, sulfuric acid, formic acid, oxalic acid, acetic acid, etc., in regards to acid catalyst.

The flexibility of the novolak resins can be enhanced still more when o-cresol is used, a hydrogen atom of a hydroxide group in the resins is substituted with other substituents, or bulky aldehydes are used.

The mass average molecular weight of novolac resin (C1) is not particularly limited as long as the purpose of the present invention is not impaired, but the mass average molecular weight is preferably 1,000 or more and 50,000 or less.

[Polyhydroxystyrene Resin (C2)]

The hydroxystyrene compound to constitute the polyhydroxystyrene resin (C2) is exemplified by p-hydroxystyrene, α-methylhydroxystyrene, α-ethylhydroxystyrene, and the like. Among these, the polyhydroxystyrene resin (C2) is preferably prepared to give a copolymer with a styrene resin. The styrene compound to constitute the styrene resin is exemplified by styrene, chlorostyrene, chloromethylstyrene, vinyltoluene, α-methylstyrene, and the like.

The mass average molecular weight of the polyhydroxystyrene resin (C2) is not particularly limited as long as the purpose of the present invention is not impaired, but the mass average molecular weight is preferably 1,000 or more and 50,000 or less.

[Acrylic Resin (C3)]

It is preferred that the acrylic resin (C3) includes a constituent unit derived from a polymerizable compound having an ether bond and a constituent unit derived from a polymerizable compound having a carboxy group.

Examples of the polymerizable compound having an ether bond include (meth)acrylic acid derivatives having an ether bond and an ester bond such as 2-methoxyethyl (meth)acrylate, methoxytriethylene glycol (meth)acrylate, 3-methoxybutyl (meth)acrylate, ethylcarbitol (meth)acrylate, phenoxypolyethylene glycol (meth)acrylate, methoxypolypropylene glycol (meth)acrylate, tetrahydrofurfuryl (meth)acrylate, and the like. The polymerizable compound having an ether bond is preferably, 2-methoxyethyl acrylate, and methoxytriethylene glycol acrylate. These polymerizable compounds may be used alone, or in combinations of two or more.

Examples of the polymerizable compound having a carboxy group include monocarboxylic acids such as acrylic acid, methacrylic acid and crotonic acid; dicarboxylic acids such as maleic acid, fumaric acid and itaconic acid; compounds having a carboxy group and an ester bond such as 2-methacryloyloxyethyl succinic acid, 2-methacryloyloxyethyl maleic acid, 2-methacryloyloxyethyl phthalic acid and 2-methacryloyloxyethyl hexahydrophthalic acid. The polymerizable compound having a carboxy group is preferably, acrylic acid and methacrylic acid. These polymerizable compounds may be used alone, or in combinations of two or more thereof.

The mass average molecular weight of the acrylic resin (C3) is not particularly limited as long as the purpose of the present invention is not impaired, but the mass average molecular weight is preferably 50,000 or more and 800,000 or less.

The content of alkali-soluble resin is such that when the total amount of the photosensitive resin and the alkali-soluble resin is taken as 100 parts by mass, the content is preferably 0 parts by mass or more and 80 parts by mass or less, and more preferably 0 parts by mass or more and 60 parts by mass or less. By adjusting the content of the alkali-soluble resin to the range described above, there is a tendency for resistance to cracking to increase, and film loss at the time of development can be prevented.

In order to improve the post-exposure delay stability and the like, it is preferred that the photosensitive composition of second aspect further contains an acid diffusion control agent. The acid diffusion control agent is preferably a nitrogen-containing compound (D1), and an organic carboxylic acid, or an oxo acid of phosphorus or a derivative thereof (D2) may be further included as needed.

[Nitrogen-Containing Compound (D1)]

Examples of the nitrogen-containing compound (D1) include trimethylamine, diethylamine, triethylamine, di-n-propylamine, tri-n-propylamine, tri-n-pentylamine, tribenzylamine, diethanolamine, triethanolamine, n-hexylamine, n-heptylamine, n-octylamine, n-nonylamine, ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, formamide, N-methylformamide, N,N-dimethylformamide, acetamide, N-methylacetamide, N,N-dimethylacetamide, propionamide, benzamide, pyrrolidone, N-methylpyrrolidone, methylurea, 1,1-dimethylurea, 1,3-dimethylurea, 1,1,3,3,-tetramethylurea, 1,3-diphenylurea, imidazole, benzimidazole, 4-methylimidazole, 8-oxyquinoline, acridine, purine, pyrrolidine, piperidine, 2,4,6-tri (2-pyridyl)-S-triazine, morpholine, 4-methylmorpholine, piperazine, 1,4-dimethylpiperazine, 1,4-diazabicyclo[2.2.2]octane, pyridine and the like. These may be used alone, or in combinations of two or more thereof.

The nitrogen-containing compound (D1) may be used in an amount typically in the range of 0 parts by mass or more and 5 parts by mass or less, and particularly in the range of 0 parts by mass or more and 3 parts by mass or less, with respect to 100 parts by mass of total mass of the photosensitive resin and the alkali-soluble resin.

[Organic Carboxylic Acid or Oxo Acid of Phosphorus or Derivative Thereof (D2)]

Among the organic carboxylic acid, or the oxo acid of phosphorus or the derivative thereof (D2), specific preferred examples of the organic carboxylic acid include malonic acid, citric acid, malic acid, succinic acid, benzoic acid, salicylic acid and the like, and salicylic acid is particularly preferred.

Examples of the oxo acid of phosphorus or derivatives thereof include phosphoric acid and derivatives such as esters thereof such as, e.g., phosphoric acid, phosphoric acid di-n-butyl ester, and phosphoric acid diphenyl ester; phosphonic acid and derivatives such as esters thereof such as, e.g., phosphonic acid, phosphonic acid dimethyl ester, phosphonic acid di-n-butyl ester, phenylphosphonic acid, phosphonic acid diphenyl ester, and phosphonic acid dibenzyl ester; and phosphinic acid and derivatives such as esters thereof such as, e.g., phosphinic acid and phenylphosphinic acid; and the like. Among these, phosphonic acid is particularly preferred. These may be used alone, or in combinations of two or more thereof.

The organic carboxylic acid, or the oxo acid of phosphorus or the derivative thereof (D2) may be used in an amount typically in the range of 0 parts by mass or more and 5 parts by mass or less, and particularly in the range of 0 parts by mass or more and 3 parts by mass or less, with respect to 100 parts by mass of total mass of the photosensitive resin and the alkali-soluble resin.

Moreover, in order to form a salt to allow for stabilization, the organic carboxylic acid, or the oxo acid of phosphorous or the derivative thereof (D2) is preferably used in an amount equivalent to that of the nitrogen-containing compound (D1).

The photosensitive composition of second aspect contains an organic solvent. The kind of the organic solvent is not particularly limited as long as the purpose of the present invention is not impaired, and the organic solvent can be appropriately selected for use from the organic solvents that have been conventionally used in positive-type photosensitive compositions.

Specific examples of the organic solvent include, in addition to solvents described as an example in the photosensitive composition of the first aspect, ketones such as acetone, methyl ethyl ketone, cyclohexanone, methyl isoamyl ketone, and 2-heptanone; polyhydric alcohols and derivatives thereof, like monomethyl ethers, monoethyl ethers, monopropyl ethers, monobutyl ethers and monophenyl ethers, such as ethylene glycol, ethylene glycol monoacetate, diethylene glycol, diethylene glycol monoacetate, propylene glycol, propylene glycol monoacetate, dipropylene glycol and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, methyl pyruvate, ethylethoxy acetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanate, 3-methoxybutyl acetate and 3-methyl-3-methoxybutyl acetate; aromatic hydrocarbons such as toluene and xylene; and the like. These may be used alone, or as a mixture of two or more thereof.

The content of the organic solvent is not particularly limited as long as the purpose of the present invention is not impaired. When the photosensitive composition is used for a thick-film application in which a photosensitive resin layer obtainable by a spin-coating method or the like has a film thickness of 10 μm or greater, it is preferable to use the organic solvent to the extent that the solid concentration of the photosensitive resin composition is 30% by mass or more and 55% by mass or less.

The photosensitive composition of second aspect may further contain a polyvinyl resin for improving plasticity. Specific examples of the polyvinyl resin include polyvinyl chloride, polystyrene, polyhydroxystyrene, polyvinyl acetate, polyvinylbenzoic acid, polyvinyl methyl ether, polyvinyl ethyl ether, polyvinyl alcohol, polyvinyl pyrrolidone, polyvinyl phenol, and copolymers thereof, and the like. The polyvinyl resin is preferably polyvinyl methyl ether in view of lower glass transition temperatures.

Further, the photosensitive composition of second aspect may also contain an adhesive auxiliary agent in order to improve the adhesiveness between a hydrogen barrier film formed with the photosensitive composition of second aspect and a substrate, particularly a metal substrate.

Also, the photosensitive composition of second aspect may further contain a surfactant for improving coating characteristics, defoaming characteristics, leveling characteristics and the like. Specific examples of the surfactant include commercially available fluorochemical surfactants such as BM-1000 and BM-1100 (both manufactured by B.M-Chemie Co., Ltd.), Megafac F142D, Megafac F172, Megafac F173 and Megafac F183 (all manufactured by Dainippon Ink And Chemicals, Incorporated), Flolade FC-135, Flolade FC-170C, Flolade FC-430 and Flolade FC-431 (all manufactured by Sumitomo 3M Ltd.), Surflon S-112, Surflon S-113, Surflon S-131, Surflon S-141 and Surflon S-145 (all manufactured by Asahi Glass Co., Ltd.), SH-28PA, SH-190, SH-193, SZ-6032 and SF-8428 (all manufactured by Toray Silicone Co., Ltd.), but not limited thereto.

Additionally, in order to finely adjust the solubility in a developing solution, the photosensitive composition of second aspect may further contain an acid, an acid anhydride, or a solvent having a high boiling point.

Specific examples of the acid and acid anhydride include monocarboxylic acids such as acetic acid, propionic acid, n-butyric acid, isobutyric acid, n-valeric acid, isovaleric acid, benzoic acid, and cinnamic acid; hydroxymonocarboxylic acids such as lactic acid, 2-hydroxybutyric acid, 3-hydroxybutyric acid, salicylic acid, m-hydroxybenzoic acid, p-hydroxybenzoic acid, 2-hydroxycinnamic acid, 3-hydroxycinnamic acid, 4-hydroxycinnamic acid, 5-hydroxyisophthalic acid, and syringic acid; polyvalent carboxylic acids such as oxalic acid, succinic acid, glutaric acid, adipic acid, maleic acid, itaconic acid, hexahydrophthalic acid, phthalic acid, isophthalic acid, terephthalic acid, 1,2-cyclohexanedicarboxylic acid, 1,2,4-cyclohexanetricarboxylic acid, butanetetracarboxylic acid, trimellitic acid, pyromellitic acid, cyclopentanetetracarboxylic acid, butanetetracarboxylic acid, and 1,2,5,8-naphthalenetetracarboxylic acid; acid anhydrides such as itaconic anhydride, succinic anhydride, citraconic anhydride, dodecenylsuccinic anhydride, tricarbanilic anhydride, maleic anhydride, hexahydrophthalic anhydride, methyltetrahydrophthalic anhydride, Himic anhydride, 1,2,3,4-butanetetracarboxylic acid, cyclopentanetetracarboxylic dianhydride, phthalic anhydride, pyromellitic anhydride, trimellitic anhydride, benzophenonetetracarboxylic anhydride, ethylene glycol bis anhydrous trimellitate, and glycerin tris anhydrous trimellitate; and the like.

Furthermore, specific examples of the solvent having a high boiling point include N-methylformamide, N,N-dimethylformamide, N-methylformanilide, N-methylacetamide, N,N-dimethylacetamide, N-methylpyrrolidone, dimethyl sulfoxide, benzyl ethyl ether, dihexyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, phenyl cellosolve acetate, and the like.

Moreover, the photosensitive composition of second aspect may further contain a sensitizer for improving the sensitivity.

The content of the hydrogen barrier agent (B) is preferably 0.01 mass % or more and 30 mass % or less, more preferably 0.05 mass % or more and 20 mass % or less, and particularly preferably 0.1 mass % or more and 10 mass % or less with respect to the mass of the resin corresponding to the base material component (A) in the photosensitive composition of the second aspect. When the content is in the above-defined range, a pattern having hydrogen barrier performance can be obtained and excellent developing property is obtained.

(3) Photosensitive Composition of Third Aspect

A photosensitive composition of a third aspect is a negative photosensitive composition containing an alkali-soluble resin including a phenolic hydroxy group, an acid crosslinking substance, a photo acid generator, a hydrogen barrier agent (B), and an organic solvent.

For the alkali-soluble resin having the phenolic hydroxy group of the photosensitive composition of the third aspect, for example, a polyhydroxy styrene resin can be used. The polyhydroxy styrene resin includes at least a constituent unit derived from hydroxy styrene. Herein, "hydroxy styrene" is intended as a concept that includes hydroxy styrene, and hydroxy styrene in which a hydrogen atom bonded to an α-position of hydroxy styrene is substituted with other substituents such as a halogen atom, an alkyl group, a halogenated alkyl group, as well as a hydroxy styrene derivative (monomer) of the derivatives thereof. Examples of the "hydroxy styrene derivative" include one in which at least a benzene ring and a hydroxy group bonded thereto are maintained and a hydrogen atom bonded to the α-position of hydroxy styrene is substituted with other substituents such as a halogen atom, an alkyl group having 1 or more and 5 or less carbon atoms, an halogenated alkyl group, and the like, as well as one in which an alkyl group having 1 or more and 5 or more carbon atoms is further bonded to a benzene ring to which a hydroxy group of hydroxy styrene is bonded, or one in which one or more and two or less hydroxy groups are further bonded to a benzene ring to which the hydroxy group is bonded (at this time, the total number of hydroxy groups is two or more and three or less), and the like. Preferable examples of the halogen atom include a chlorine atom, a fluorine atom, a bromine atom, and the like. A fluorine atom is preferable. Note here that the "α-position of hydroxy styrene" denotes a carbon atom to which a benzene ring is bonded unless otherwise particularly specified.

The constituent unit derived from the hydroxy styrene is represented by, for example, the following formula (b-1).

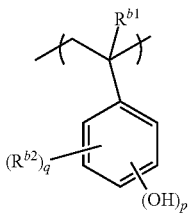

(b-1)

wherein, in the above-mentioned formula (b-1), $R^{b1}$ represents a hydrogen atom, an alkyl group, a halogen atom, or a halogenated alkyl group; $R^{b2}$ represents an alkyl group having 1 or more and 5 or less carbon atoms 1; p is an integer of 1 or more and 3 or less; and q is an integer of 0 or more and 2 or less.

The alkyl group of $R^{b1}$ preferably has 1 or more and 5 or less carbon atoms. Furthermore, a linear or branched alkyl group is preferable, and examples thereof include a methyl group, an ethyl group, a propyl group, an isopropyl group, an n-butyl group, an isobutyl group, a tert-butyl group, a pentyl group, an isopentyl group, a neopentyl group, and the like. Among them, a methyl group is industrially preferable. Examples of the halogen atom include a fluorine atom, a chlorine atom, a bromine atom, an iodine atom, and the like. A fluorine atom is preferable. The halogenated alkyl group is a group in which a part or entire part of the hydrogen atom of the above-mentioned alkyl group having 1 or more and 5 or less carbon atoms is substituted with a halogen atom. Among them, an alkyl group in which the entire part of the hydrogen atom is substituted with a fluorine atom is preferable. Furthermore, a linear or branched fluoridated alkyl group is preferable, a trifluoromethyl group, a hexafluoroethyl group, a heptafluoropropyl group, a nonafluorobutyl group, and the like, are more preferable, and a trifluoromethyl group (—$CF_3$) is the most preferable. $R^{b1}$ is preferably a hydrogen atom or a methyl group, and more preferably a hydrogen atom.

Examples of the alkyl group having 1 or more and 5 or less carbon atoms of $R^{b2}$ are the same groups as defined in the case of $R^{b1}$. q is an integer of 0 or more and 2 or less. Among them, q is preferably 0 or 1, and industrially particularly preferably 0. The substituted position of $R^{b2}$ may be any one of an ortho-position, a meta-position, and a para-position when q is 1, and arbitrary substituted positions can be combined when q is 2. p is an integer of 1 or more and 3 or less, and preferably 1. The substituted position of the hydroxy group may be any one of an ortho-position, a meta-position, and a para-position when p is 1, but a para-position is preferable because it is easily available and low priced. In addition, when p is 2 or 3, arbitrary substituted positions can be combined.

The constituent units represented by the above-mentioned formula (b-1) can be used alone or in combination of two or more types thereof.

The proportion of the constituent unit derived from hydroxy styrene in a polyhydroxy styrene resin is preferably 60 mol % or more and 100 mol % or less, and more preferably 70 mol % or more and 100 mol % or less, and further preferably 80 mol % or more and 100 mol % or less, with respect to the entire constituent units constituting the polyhydroxy styrene resin. When the proportion is in the above-mentioned range, appropriate alkali solubility can be obtained as the photosensitive composition.

The polyhydroxy styrene resin preferably further includes a constituent unit derived from styrene. Herein, the "constituent unit derived from styrene" is defined as encompassing a constituent unit obtained by cleaving an ethylene double bond between a styrene and styrene derivative (however, hydroxy styrene is not included). The "styrene derivative" is defined as encompassing a derivative in which a hydrogen atom bonded to the α-position of styrene is substituted with other substituents such as a halogen atom, an alkyl group, and a halogenated alkyl group, a derivate in which a hydrogen atom of a phenyl group of styrene is substituted with a substituent such as an alkyl group having 1 or more and 5 or less carbon atoms, or the like. Examples of the halogen atom include a chlorine atom, a fluorine atom, a bromine atom, and the like, and a fluorine atom is preferable. Note here that the "α-position of styrene" denotes a carbon atom in which a benzene ring is bonded unless otherwise particularly specified.

The constituent unit derived from the styrene is represented by, for example, the following formula (b-2). In the formula, $R^{b1}$, $R^{b2}$, and q are the same as defined in the above-mentioned formula (b-1).

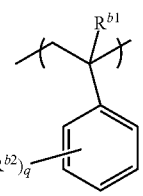

(b-2)

Examples of $R^{b1}$ and $R^{b2}$ include groups the same as those in $R^{b1}$ and $R^{b2}$ of the above-mentioned formula (b-1), respectively. q is an integer of 0 or more and 2 or less. Among them, q is preferably 0 or 1, and industrially particularly preferably 0. The substituted position of $R^{b2}$ may be any one of an ortho-position, a meta-position, and a para-position when q is 1, and further may be an arbitrary combination of substituted positions when q is 2.

The constituent units represented by the above-mentioned formula (b-2) can be used alone or in combination of two or more types thereof.

The proportion of the constituent unit derived from styrene in the polyhydroxy styrene resin is preferably 40 mol % or less, more preferably 30 mol % or less, and further preferably 20 mol % or less with respect to the entire constituent units constituting the polyhydroxy styrene resin. The above-specified range allows a photosensitive composition to have appropriate alkali solubility and to be well-balanced with other constituent units.

Note here that the polyhydroxy styrene resin may include constituent units other than the constituent unit derived from hydroxy styrene and the constituent unit derived from styrene. More preferably, the above-mentioned polyhydroxy styrene resin is a polymer including only a constituent unit derived from hydroxy styrene, or a copolymer including a constituent unit derived from hydroxy styrene and a constituent unit derived from styrene.

The mass average molecular weight of the polyhydroxy styrene resin is not particularly limited, but it is preferably 1500 or more and 40000 or less, and more preferably 2000 or more and 8000 or less.

Furthermore, as an alkali-soluble resin having a phenolic hydroxy group, novolak resin can be used. This novolak resin can be obtained by subjecting phenols and aldehydes to addition condensation in the presence of an acid catalyst.

Examples of the phenols include phenol; cresols such as o-cresol, m-cresol, and p-cresol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; alkylphenols such as 2-isopropylphenol, 3-isopropylphenol, 4-isopropylphenol, o-butylphenol, m-butylphenol, p-butylphenol, and p-tert-butylphenol; trialkylphenols such as 2,3,5-trimethylphenol, and 3,4,5-trimethylphenol; polyhydric phenol such as resorcinol, catechol, hydroquinone, hydroquinone monomethylether, pyrogallol, and phloroglucinol; alkyl polyhydric phenols such as alkylresorcinol, alkylcatechol, and alkylhydroquinone (number of carbon atoms of alkyl group included in the alkyl polyhydric phenols is 1 or more and 4 or less); α-naphthol; β-naphthol; hydroxydiphenyl; and bisphenol A. These phenols can be used alone, or two or more thereof can be used in combination. Among these phenols, m-cresol and p-cresol are preferable, and combinational use of m-cresol and p-cresol is more preferable. In this case, by adjusting the blending rate of both phenols, various properties such as sensitivity can be adjusted.

As aldehydes, formaldehyde, paraformaldehyde, furfural, benzaldehyde, nitrobenzaldehyde, and acetaldehyde may be exemplified. These aldehydes can be used alone, or two or more thereof can be used in combination.

Examples of the acid catalyst include inorganic acids such as hydrochloric acid, sulfuric acid, nitric acid, phosphoric acid, and phosphorous acid; organic acids such as formic acid, oxalic acid, acetic acid, diethyl sulfuric acid, and paratoluene sulfonic acid; metal salts such as zinc acetate, and the like. These acid catalysts can be used alone, or two or more thereof can be used in combination.

Specific examples of the novolak resins thus obtained include phenol/formaldehyde condensation novolak resin, cresol/formaldehyde condensation novolak resin, phenol-naphthol/formaldehyde condensation novolak resin, and the like.

The mass average molecular weight of the novolak resin is not particularly limited, but is preferably 1,000 or more and 30,000 or less, and preferably 3,000 or more and 25,000 or less.

Further, as the alkali-soluble resin having a phenolic hydroxy group, phenol-xylylene glycol condensation resin, cresol-xylylene glycol condensation resin, and phenol-dicyclopentadiene condensation resin and the like can be used.

The content of the alkali-soluble resin having a phenolic hydroxy group is preferably 20 mass % or more and 80 mass % or less, and more preferably 35 mass % or more and 65 mass % or less with respect to the solid content of the photosensitive composition of the third aspect. When the content is in the above-mentioned range, a balance of developing property tends to be easily achieved.

In the photosensitive composition of the third aspect, the acid crosslinking substance is not particularly limited, and conventionally known acid crosslinking substances can be used.

Specific examples of the acid crosslinking substance include an amino resin having a hydroxy group or an alkoxy group, for example, a melamine resin, a urea resin, a guanamine resin, an acetoguanamine resin, a benzoguanamine resin, a glycoluril-formaldehyde resin, a succinyl amide-formaldehyde resin, an ethylene urea-formaldehyde resin, and the like. These acid crosslinking substances are easily obtained by reacting melamine, urea, guanamine, acetoguanamine, benzoguanamine, glycoluril, succinyl amide, ethylene urea with formalin in boiling water to be methylolated, or further reacting these with a lower alcohol to be alkoxylated. Practically, they can be obtained as a melamine resin such as Nikalac MX-750, Nikalac MW-30, Nikalac MW100LM, and the like, or a urea resin such as Nikalac MX-290 and the like (all manufactured by Sanwa Chemical Co. Ltd.). Furthermore, benzoguanamine resins can also be obtained as commercial products such as Cymel 1123 and Cymel 1128 (manufactured by Mitsui Cyanade Co., Ltd.).

Furthermore, a benzene compound having an alkoxy group, such as 1,3,5-tris(methoxymethoxy)benzene, 1,2,4-tris(isopropoxymethoxy)benzene, and 1,4-bis(sec-butoxymethoxy)benzene, and a phenol compound having a hydroxy group, such as 2,6-dihydroxymethyl-p-tert-butylphenol or an alkoxy group may be used. These acid crosslinking substances can be used alone or in combination of two or more types thereof.

The content of the acid crosslinking substances is preferably 5 parts by mass or more and 50 parts by mass or less, and more preferably 10 parts by mass or more and 30 parts by mass or less, relative to 100 parts by mass of the alkali-soluble resin having a phenolic hydroxy group. When the content is in the above-defined range, the curability and patterning property of the photosensitive composition is improved.

In the photosensitive composition of the third aspect, the photo acid generator is not particularly limited, and conventionally known photo acid generators can be used. Preferable examples of the photo acid generator include the photo acid generator described for the second photosensitive composition.

The content of the photo acid generator is preferably 0.05 parts by mass or more and 30 parts by mass or less, and more preferably 0.1 parts by mass or more and 10 parts by mass or less relative to 100 parts by mass of the alkali-soluble resin having a phenolic hydroxy group. When the content is in the above-defined range, the curability of the photosensitive composition is improved.

As mentioned above, the photosensitive composition of the third aspect contains the hydrogen barrier agent (B). When this compound is contained in the photosensitive composition, pattern formation having hydrogen barrier performance can be carried out.

The content of the hydrogen barrier agent (B) is preferably 0.01 mass % or more and 30 mass % or less, more preferably 0.05 mass % or more and 20 mass % or less, and particularly preferably 0.1 mass % or more and 10 mass % or less with respect to the mass of the resin corresponding to the base material component (A) in the photosensitive composition of the third aspect. When the content is in the above-defined range, a pattern having hydrogen barrier performance can be obtained and excellent developing property is obtained.

The photosensitive composition of the third aspect may further contain a compound having four or more phenolic hydroxy groups and having a molecular weight of less than 2000.

Specific examples of these compounds include hydroxyaryl type compounds such as bis[2-hydroxy-3-(2'-hydroxy-5'-methylbenzyl)-5-methylphenyl]methane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3,5-dimethylphenyl)-2,4-dihydroxyphenylmethane, bis(4-hydroxy-2,5-dimethylphenyl)-2,4-dihydroxyphenylmethane, bis(3-cyclohexyl-4-hydroxy-6-methylphenyl)-3,4-dihydroxyphenylmethane, bis(3- cyclohexyl-6-hydroxy-4-methylphenyl)-3,4-dihydroxyphenylmethane, and bis(4-hydroxy-2,3,5-trimethylphenyl)-3,4-dihydroxyphenylmethane; bis(hydroxyphenyl)alkane type compounds such as 2-(2,3,4-trihydroxyphenyl)-2-(2',3',4'-trihydroxyphenyl)propane, and 2-(2,4-dihydroxyphenyl)-2-(2',4'-dihydroxyphenyl)propane; and polyhydroxystyrene type compounds having molecular weight of 2,000 or less such as poly(o-hydroxystyrene), poly(m-hydroxystyrene), poly(p-hydroxystyrene), poly(α-methyl-p-hydroxystyrene), and poly(4-hydroxy-3-methylstyrene), in addition to benzophenone compounds such a tetrahydroxybenzophenones, pentahydroxybenzophenones, and heptahydroxybenzophenones. Above mentioned benzophenone compounds, hydroxyaryl type compounds, bis(hydroxyphenyl)alkane type compounds may have substituent other than hydroxy group. These compounds can be used alone, or two or more thereof can be used in combination.

The content of the compound having four or more phenolic hydroxy groups and having a molecular weight of less than 2000 is preferably 0.5 parts by mass or more and 5 parts by mass or less relative to 100 parts by mass of an alkali-soluble resin having a phenolic hydroxy group. When the content is in the above-defined range, it is possible to suppress a tapering phenomenon when the photosensitive composition is patterned.

Examples of the organic solvents of the photosensitive composition of the third aspect include organic solvents described as an example in the photosensitive composition of the first aspect. The content of the organic solvent is an amount such that the solid content concentration of the photosensitive composition of the third aspect is preferably 1 mass % or more and 50 mass % or less, and more preferably 5 mass % or more and 30 mass % or less. The photosensitive composition of the third aspect may contain various additives as mentioned above if necessary, similar to the photosensitive composition of the first aspect.

(4) Photosensitive Composition of Fourth Aspect

A photosensitive composition of the fourth aspect is a negative photosensitive composition containing a photosensitive polyimide precursor, a photopolymerizable compound, a photopolymerization initiator, a hydrogen barrier agent (B), and an organic solvent.

As the photosensitive polyimide precursor of the photosensitive composition of the fourth aspect, it is possible to use, for example, a resin including a constituent unit represented by the following formula (d-1), and having an acid functional group and photosensitive group in a molecule.

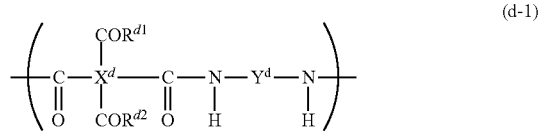
(d-1)

In the formula (d-1), $X^d$ represents a tetravalent organic group that does not contain an atom having an unshared electron pair in a skeleton connecting two amide groups bonded to $X^d$; $Y^d$ represents a divalent organic group that does not contain an atom having an unshared electron pair in a skeleton connecting two amide groups bonded to $Y^d$; and $R^{d1}$ and $R^{d2}$ each independently represent a hydroxy group or a monovalent organic group.

In the definitions of $X^d$ and $Y^d$, the "skeleton connecting two amide groups" means a skeleton consisting of only atoms constituting a chain of bonds connecting the two amide bonds. Accordingly, atoms which are present as terminals such as hydrogen atoms, fluorine atoms and the like, and which do not form a chain of bonds connecting the two amide bonds, are not included in the above "skeleton". However, in the case of including atoms constituting a ring (aromatic ring or aliphatic ring) in the skeleton, all of the atoms constituting the ring are defined as being included in the above "skeleton". For example, in the case where a chain connecting two amide bonds includes a benzene ring or a cyclohexyl ring, the 6 carbon atoms constituting the benzene ring or cyclohexyl ring themselves are considered to be included in the above "skeleton". Note here that substituents or hydrogen atoms bonded to the benzene ring or the cyclohexyl ring are not included in the "skeleton" as referred herein.

Accordingly, in the case where a carbonyl bond is present on the skeleton, since what constitutes the chain connecting the above two amide groups is only the carbon atom in the carbonyl group, the oxygen atom of the carbonyl group is not considered to be a constituent of the above "skeleton". Furthermore, as to a 2,2-propylidene bond or a hexafluoro-2,2-propylidene bond, only the carbon atom present in the center (2-position) constitutes the skeleton, and the carbon atoms at both ends (the 1-position or 3-position) do not constitute the above "skeleton". Examples of the "atom having an unshared electron pair" include an oxygen atom, a nitrogen atom, a sulfur atom, and the like; on the other hand, examples of the "atom not having an unshared electron pair" include a carbon atom and a silicon atom, and the like.

In the photosensitive polyimide precursor, it is preferable that $X^d$ does not contain an atom having an unshared electron pair in the skeleton as mentioned above, because swelling at the time of alkali-developing is small. For the same reason, it is preferable that $Y^d$ does not contain an atom having an unshared electron pair in the skeleton.

Furthermore, the photosensitive polyimide precursor having $Y^{d2}$ containing a silicon atom as a part thereof, instead of $Y^d$ in the constituent unit, for example, one including a siloxane bond is preferable, because a higher adhesion to a substrate can be provided. In this case, the proportion thereof is preferably 1 mol % or more and 20 mol % or less in all of the diamine residues forming the photosensitive polyimide precursor.

Preferable examples of $X^d$ and $Y^d$ in the above-mentioned formula (d-1) include an alkyl group or a cycloalkyl group having 4 or more and 20 or less carbon atoms, or an aromatic ring such as a benzene ring having 6 or more and 20 or less carbon atoms, or a naphthyl ring, or ones where 2 or more and 10 or less of these aromatic rings are bonded via a single bond, an alkylene group, a fluorinated alkylene group, a carbonyl group, or the like. Furthermore, these may have a substituent such as a hydrocarbon group, a halogenated hydrocarbon group, a halogen atom, or the like, on the aromatic ring. Note here that it is preferable that in $X^d$ and $Y^d$, atoms directly bonded to the atoms constituting the above-mentioned skeleton are also "atoms not having unshared electron pairs" because they have a higher effect. Note here that in this definition, those in which an oxygen atom is directly bonded to a carbon atom constituting the skeleton, for example, a carbonyl group, or those in which a fluorine atom is bonded to a carbon atom constituting the skeleton are excluded. Furthermore, $X^d$ and $Y^d$ preferably do not include a fluorine atom.

As the acid functional group contained in molecules of the photosensitive polyimide precursor, carboxy group, phenolic hydroxy group, and sulfonic acid group may be exemplified, and carboxy group is preferable. As a photosensitive group, groups having ethylenically unsaturated bond such as a vinyl group, a allyl group, acryloyl group, methacryloyl group, acryloxy group, and methacryloxy group are preferable, and acryloyl group, methacryloy group, acryloxy group, and methacryloxy group are more preferable.

In the photosensitive polyimide precursor, the acid functional group is preferably present as one in which $R^{d1}$ or $R^{d1}$ in the constituent unit of the formula (d-1) represents a hydroxy group (i.e., forming a carboxy group) or is present in a diamine residue represented by $Y^d$. The photosensitive group is preferably present in a side chain represented by $R^{d1}$ or $R^{d2}$ in the formula (d-1), or in a diamine residue represented by $Y^d$, for example, as a group bonded to an aromatic ring in a diamine residue having an aromatic ring.

In $R^{d1}$ and $R^{d2}$, as a monovalent organic group having photosensitive group, groups represented by the following formulae.

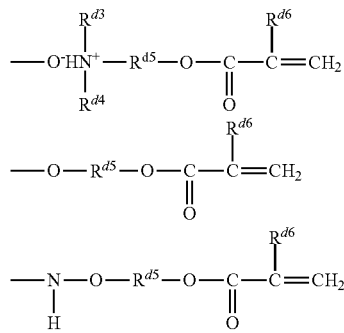

In the above formulae, $R^{d3}$ and $R^{d4}$ are each independently a monovalent hydrocarbon group having 1 or more and 6 or less carbon atoms, $R^{d5}$ is a divalent hydrocarbon group having 1 or more and 10 or less carbon atoms, and $R^{d6}$ is a hydrogen atom or a methyl group.

In $R^{d1}$ and $R^{d2}$, as a monovalent organic group having no photosensitive group, an alkoxy group or an alkylamino group respectively having 1 or more and 15 or less carbon atoms.

The photosensitive polyimide precursor preferably contains 50 mol % or more and 100 mol % or less of a constituent unit represented by the formula (d-1), and more preferably, the photosensitive polyimide precursor consists of only a constituent unit represented by the formula (d-1), or includes a constituent unit represented by the formula (d-1) and a constituent unit represented by the formula (d-1) in which $Y^d$ is a divalent organic group containing a silicon atom.

The photosensitive polyimide precursor can be obtained using a tetracarboxylic dianhydride, a diamine, and a compound having a photosensitive group as materials, and various known production methods can be applied.

Examples of a tetracarboxylic dianhydride providing $X^d$ include pyromellitic dianhydride, 3,3',4,4'-biphenyl tetracarboxylic dianhydride, 1,2,5,6-naphthalene tetracarboxylic dianhydride, 2,3,6,7-naphthalene tetracarboxylic dianhydride, 1,4,5,8-naphthalene tetracarboxylic dianhydride, 3,4,9,10-perylene tetracarboxylic dianhydride, m-terphenyl-3,3',4,4'-tetracarboxylic dianhydride, p-terphenyl-3,3',4,4'-tetracarboxylic dianhydride, 4,4'-hexafluoroisoproylidene diphthalic dianhydride, and 3,3',4,4'-benzophenone tetracarboxylic dianhydride. These tetracarboxylic dianhydrides can be used alone, or two or more thereof can be used in combination.

Examples of a diamine providing $Y^d$ include 2,2'-dimethyl-4,4'-diaminobiphenyl, 3,3'-dimethyl-4,4'-diaminobiphenyl, 2,2',6,6'-tetramethyl-4,4'-diaminobiphenyl, 3,3',5,5'-tetramethyl-4,4'-diaminobiphenyl, 4,4'- (or 3,4-, 3,3'-, 2,4-, or 2,2'-) diaminobiphenylmethane, p-xylylenediamine, m-xylylenediamine, 4,4'-methylene-bis-(2,6-diethylaniline), 4,4'-methylene-bis(2,6-diisopropylaniline), 1,5,-diaminonaphthalene, 3,3'-dimethyl-4,4'-diaminodiphenylmethane, 3,3',5,5'-tetramethyl-4,4'-diaminodiphenylmethane, 2,2-bis(4-aminophenyl)propane, 2,2'-hexafluorodimethyl-4,4'-diaminobiphenyl, 3,3'-hexafluorodimethyl-4,4'-diaminobiphenyl, 4,4'-hexafluoroisopropylidene dianiline, 1,1,1,3,3,3-hexafluoro-2,2-bis(4-aminophenyl)propane, 2,3,5,6-tetramethyl-1,4-phenylenediamin, 2,5-dimethyl-1,4-phenylenediamine, 2,4-diaminotoluene, 2,6-diaminotoluene, 2,4,6-trimethyl-1,3-phenylenediamine, 2,7-diaminofluorene, 4,4-diaminooctafluorobiphenyl, and 2,2-hexafluorodimethyl-4,4'-diaminobiphenyl. These diamines can be used alone, or two or more thereof can be used in combination.

Furthermore, $Y^d$ may have at least one phenolic hydroxy group or a carboxy group as the acid functional group as long as it is a bifunctional amine which does not include an atom having an unshared electron pair at the skeleton connecting the amino groups. Suitable examples include 2,5-diaminobenzoic acid, 3,4-diaminobenzoic acid, 3,5-diaminobenzoic acid, 2,5-diaminoterephthalic acid, bis(4-amino-3-carboxyphenyl)methylene, 4,4'-diamino-3,3'-dicarboxybiphenyl, 4,4'-diamino-5,5'-dicarboxy-2,2'-dimethylbiphenyl, 1,3-diamino-4-hydroxybenzene, 1,3-diamino-5-hydroxybenzene, 3,3'-diamino-4,4'-dihydroxybiphenyl, 4,4'-diamino-3,3'-dihydroxybiphenyl, bis(3-amino-4-hydroxyphenyl)hexafluoropropane, bis(4-amino-3-hydroxyphenyl)hexafluoropropane, bis(4-amino-3-carboxyphenyl)methane, and 4,4'-diamino-2,2'-dicarboxybiphenyl. These can be used alone, or two or more thereof can be used in combination, with diamines.

Furthermore, examples of the diamine providing $Y^{2d}$ including a silicon atom include an aliphatic diamine such as diaminopolysiloxane represented by the following formula (d-2).

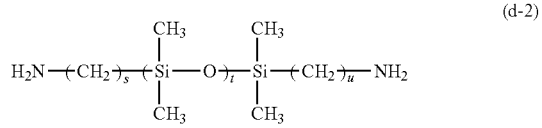

In the above formula (d-2), s, t, and u are each independently integers of 1 or more and 10 or less. When this aliphatic diamine is used, its blending amount is preferably 20 mol % or less with respect to the entire diamine, because less swelling occurs at the time of developing and from the viewpoint of heat resistance of the film to be formed, and the like.

Examples of the methods for making the polyimide precursor having the photosensitive group include a method of making the polyimide precursor in which a compound having an ethylenically unsaturated bond and an amino group or a quaternary salt group thereof is ionically bonded with a carboxylic group of a polyamic acid at a portion of the amino group or the quaternary salt group thereof, or a method of introducing an ethylenically unsaturated bond at a side chain via a covalent bond such as an ester bond, an amide bond or the like.

Among them, in particular, a photosensitive polyimide precursor (polyamic ester) in a form in which an ethylenically unsaturated bond is introduced by an ester bond is suitable for alkali developing. In the case of introducing the ethylenically unsaturated bond by an ester bond, the introduced amount of the compound having the ethylenically unsaturated bond is preferably an amount of 85 mol % or more and 25 mol % or less with respect to the total amount of the carboxy groups belonging to the polyamic acid, and the remainder is left as carboxy groups (namely, a polyamic partial ester) from the viewpoint of compatibility of alkali solubility, curing property, heat resistance, and the like, with reactivity.

Examples of compounds capable of introducing ethylenically unsaturated bond via ester bond include 2-hydroxyethyl acrylate, 3-hydroxypropyl acrylate, 2-hydroxyethyl methacrylate, 3-hydroxypropyl methacrylate, 4-hydroxybutyl acrylate, 4-hydroxybutyl methacrylate, pentaerythritol diacrylate monostearate, pentaerythritol triacrylate, pentaerythritol trimethacrylate, caprolactone 2-(methacryloyloxy) ethyl ester, dicaprolactone 2-(methacryloyloxy) ethyl ester, caprolactone 2-(acryloyloxy) ethyl ester, and dicaprolactone 2-(acryloyloxy) ethyl ester.

Mass average molecular weight of the photosensitive polyimide precursor is preferably 5,000 or more and 80,000 or less.

The content of the photosensitive polyimide precursor is preferably 40 mass % or more 95 mass % or less, and more preferably 55 mass % or more and 90 mass % or less, with respect to the solid content of the photosensitive composition of the fourth aspect. When the content is in the above-defined range, a balance of developing property tends to be easily achieved.

Examples of the photopolymerizable compounds in the photosensitive composition of the fourth aspect include those exemplified in the photosensitive composition of the first aspect. The content of the photopolymerizable compound is preferably 5 parts by mass or more and 100 parts by mass or less, and more preferably 5 parts by mass or more and 40 parts by mass or less, relative to 100 parts by mass of the photosensitive polyimide precursor. When the content is in the above-defined range, a balance of sensitivity, developing property, and resolution tends to be easily achieved.

Examples of the photopolymerization initiators in the photosensitive composition of the fourth aspect include those exemplified in the photosensitive composition of the first aspect. The content of the photopolymerization initiator is preferably 0.01 parts by mass or more and 40 parts by mass or less relative to 100 parts by mass of the photosensitive polyimide precursor. When the content is in the above-defined range, satisfactory heat resistance and chemical resistance can be provided, coating film forming capability can be improved, and curing failure can be suppressed.

As mentioned above, the photosensitive composition of the fourth aspect contains the hydrogen barrier agent (B). Containing this compound in the photosensitive composition enables a pattern having hydrogen barrier performance to be obtained.

The content of the hydrogen barrier agent (B) is preferably 0.01 mass % or more and 30 mass % or less, more preferably 0.05 mass % or more and 20 mass % or less, and particularly preferably 0.1 mass % or more and 10 mass % or less with respect to the mass of the resin corresponding to the base material component (A) in the photosensitive composition of the fourth aspect. When the content is in the above-defined range, a pattern having hydrogen barrier performance can be obtained and excellent developing property is obtained.

Examples of the organic solvent in the photosensitive composition of the fourth aspect include those exemplified in the photosensitive composition of the first aspect. Among them, solvents including the compound represented by the formula (a04) or polar solvents which completely dissolve the generated polyimide are preferable, and examples of such solvents include N-methyl-2-pyrrolidone, N,N-dimethyl acetamide, N,N-dimethyl formamide, dimethyl sulfoxide, tetramethyl urea, hexamethylphosphoric triamide, γ-butyl lactone, and the like. The content of the organic solvent is preferably an amount such that the solid content concentration of the composition of the fourth aspect is 1 mass % or more and 50 mass % or less, and more preferably 5 mass % or more and 30 mass % or less. The photosensitive composition of the fourth aspect contains various additives mentioned above, if necessary, similar to the photosensitive composition of the first aspect.

(5) Photosensitive Composition of Fifth Aspect

A photosensitive composition of a fifth aspect contains a polyimide precursor, a hydrogen barrier agent (B), and an organic solvent. It is preferable that a photosensitizer is further included.

In the photosensitive composition of fifth aspect, a polyamic acid having a constituent unit represented by the following formula (e-1) can be used as a polyimide precursor.

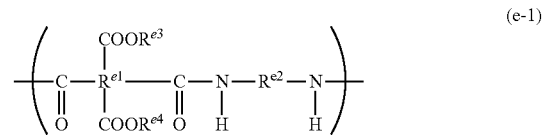

In the formula (e-1), Re1 is a tetravalent organic group, $R^{e2}$ is a divalent organic group, and $R^{e3}$ and $R^{e4}$ are a hydrogen atom or a monovalent organic group.

When $R^{e3}$ and $R^{e4}$ are monovalent organic groups, examples thereof include an alkyl group, an alkenyl group, an alkynyl group, an aryl group, and structures represented by, for example, $C_xH_{2x}OC_yH_{2y+1}$ in which an ether bond is contained in the above groups. As the polyimide precursor, a polyamic acid in which $R^{e3}$ and $R^{e4}$ are hydrogen atoms is suitably used from the viewpoint of alkali developing property.

Note here that the tetravalence of $R^{e1}$ represents only a valence number for bonding with acids, but it may have other further substituents. Similarly, the bivalence of $R^{e2}$ represents only a valence number for bonding with amines, but it may have other further substituents.

The polyamic acid is obtained by reacting a tetracarboxylic dianhydride and a diamine with each other, but from the viewpoint of imparting excellent heat resistance and dimensional stability to the finally obtained polyimide, in the formula (e-1), it is preferable that $R^{e1}$ or $R^{e2}$ is an aromatic group, and it is more preferable that $R^{e1}$ and $R^{e2}$ are aromatic groups. At this time, in $R^{e1}$ of the formula (e-1), the four groups ((—CO—)$_2$(—COOH)$_2$) bonded to the $R^{e1}$ may be bonded to the same aromatic ring, or may be bonded to different aromatic rings. In the same way, in $R^{e2}$ of the formula (e-1), the two groups ((—NH—)$_2$) bonded to the $R^{e2}$ may be bonded to the same aromatic ring, or may be bonded to different aromatic rings.

The polyamic acid represented by the formula (e-1) may consist of a single constituent unit, or may consist of 2 or more constituting units.

As the method for producing a polyimide precursor, conventionally known processes may be applied. Examples of the method include: (1) a process of synthesizing a polyamic acid which is a precursor from a tetracarboxylic dianhydride and a diamine; (2) a process of synthesizing a polyimide precursor by reacting a diamino compound or its derivative with a carboxylic acid of an ester acid or an amic acid monomer, which are synthesized by reacting a primary alcohol, an amino compound, an epoxy compound or the like with a tetracarboxylic dianhydride; and the like.

Examples of a tetracarboxylic dianhydride applicable to the reaction to form a polyimide precursor include aliphatic tetracarboxylic dianhydrides such as ethylene tetracarboxylic dianhydride, butane tetracarboxylic dianhydride, cyclobutane tetracarboxylic dianhydride, methylcyclobutane tetracarboxylic dianhydride, cyclopentane tetracarboxylic dianhydride; aromatic tetracarboxylic dianhydride such as pyromellitic dianhydride, 3,3',4,4'-benzophenone tetracarboxylic dianhydride, 2,2',3,3'-benzophenone tetracarboxylic dianhydride, 2,3',3,4'-benzophenone tetracarboxylic dianhydride, 3,3',4,4'-biphenyl tetracarboxylic dianhydride, 2,2',3,3'-biphenyl tetracarboxylic dianhydride, 2,3',3,4'-biphenyl tetracarboxylic dianhydride, 2,2',6,6'-biphenyl tetracarboxylic dianhydride, 2,2-bis(3,4-dicarboxyphenyl)propane dianhydride, 2,2-bis(2,3-dicarboxyphenyl)propane dianhydride, bis(3,4-dicarboxyphenyl)ether dianhydride, bis(3,4-dicarboxyphenyl)sulfone dianhydride, 1,1-bis(2,3-dicarboxyphenyl)ethane dianhydride, bis(2,3-dicarboxyphenyl)methane dianhydride, bis(3,4-dicarboxyphenyl)methane dianhydride, 2,2-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 1,3-bis[(3,4-dicarboxy)benzoyl]benzene dianhydride, 1,4-bis[(3,4-dicarboxy)benzoyl]benzene dianhydride, 2,2-bis{4-[4-(1,2-dicarboxy)phenoxy]phenyl}propane dianhydride, 2,2-bis{4-[3-(1,2-dicarboxy)phenoxy]phenyl}propane dianhydride, bis{4-[4-(1,2-dicarboxy)phenoxy]phenyl}ketone dianhydride, bis{4-[3-(1,2-dicarboxy)phenoxy]phenyl}ketone dianhydride, 4,4'-bis[4-(1,2-dicarboxy)phenoxy]biphenyl dianhydride, 4,4'-bis[3-(1,2-dicarboxy)phenoxy]biphenyl dianhydride, bis{4-[4-(1,2-dicarboxy)phenoxy]phenyl}ketone dianhydride, bis{4-[3-(1,2-dicarboxy)phenoxy]phenyl}ketone dianhydride, bis{4-[4-(1,2-dicarboxy)phenoxy]phenyl}sulfone dianhydride, bis{4-[3-(1,2-dicarboxy)phenoxy]phenyl}sulfone dianhydride, bis{4-[4-(1,2-dicarboxy)phenoxy]phenyl}sulfide dianhydride, bis{4-[3-(1,2-dicarboxy)phenoxy]phenyl}sulfide dianhydride, 2,2-bis{4-[4-(1,2-dicarboxy)phenoxy]phenyl}-1,1,1,3,3,3-hexafluoropropane dianhydride, 2,2-bis{4-[3-(1,2-dicarboxy)phenoxy]phenyl}-1,1,1,3,3,3-hexafluoropropane dianhydride, 2,3,6,7-naphthalene tetracarboxylic dianhydride, 1,1,1,3,3,3-hexafluoro-2,2-bis(2,3- or 2,4-dicarboxyphenyl)propane dianhydride, 1,4,5,8-naphthalene tetracarboxylic dianhydride, 1,2,5,6-naphthalene tetracarboxylic dianhydride, 1,2,3,4-benzenetetracarboxylic dianhydride, 3,4,9,10-perylene tetracarboxylic dianhydride, 2,3,6,7-anthracene tetracarboxylic anhydride, 1,2,7,8-phenanthrene tetracarboxylic anhydride, pyridine tetracarboxylic dianhydride, sulfonyldipthatlicacid dianhydride, m-terphenyl-3,3',4,4'-tetracarboxylic dianhydride, p-terphenyl-3,3',4,4'-tetracarboxylic dianhydride. These tetracarboxylic dianhydrides can be used alone, or two or more thereof can be used in combination.

Examples of a diamine applicable to the reaction to form a polyimide precursor include aromatic diamines such as p-phenylenediamine, m-phenylenediamine, p-phenylenediamine, 3,3'-diaminodiphenylether, 3,4'-diaminodiphenylether, 4,4'-diaminodiphenylether, 3,3'-diaminodiphenylsulfide, 3,4'-diaminodiphenylsulfide, 4,4'-diaminodiphenylsulfide, 3,3'-diaminodiphenylsulfone, 3,4'-diaminodiphenylsulfone, 4,4'-diaminodiphenylsulfone, 3,3'-diaminobenzophenone, 4,4'-diaminobenzophenone, 3,4'-diaminobenzophenone, 3,3'-diaminodiphenylmethane, 4,4'-diaminodiphenylmethane, 3,4'-diaminodiphenylmethane, 2,2-di(3-aminophenyl)propane, 2,2-di(4-aminophenyl)propane, 2-(3-aminophenyl)-2-(4-aminophenyl)propane, 2,2-di(3-aminophenyl)-1,1,1,3,3,3-hexafluoropropane, 2,2-di(4-aminophenyl)-1,1,1,3,3,3-hexafluoropropane, 2-(3-aminophenyl)-2-(4-aminophenyl)-1,1,1,3,3,3-hexafluoropropane, 1,1-di(3-aminophenyl)-1-phenylethane, 1,1-di(4-aminophenyl)-1-phenylethane, 1-(3-aminophenyl)-1-(4-aminophenyl)-1-phenylethane, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 1,3-bis(3-aminobenzoyl)benzene, 1,3-bis(4-aminobenzoyl)benzene, 1,4-bis(3-aminobenzoyl)benzene, 1,4-bis(4-aminobenzoyl)benzene, 1,3-bis(3-amino-α,α-dimethylbenzyl)benzene, 1,3-bis(4-amino-α,α-dimethylbenzyl)benzene, 1,4-bis(3-amino-α,α-dimethylbenzyl)benzene, 1,4-bis(4-amino-α,α-dimethylbenzyl)benzene, 1,3-bis(3-amino-α,α-ditrifluoromethylbenzyl)benzene, 1,3-bis(4-amino-α,α-ditrifluoromethylbenzyl)benzene, 1,4-bis(3-amino-α,α-ditrifluoromethylbenzyl)benzene, 1,4-bis(4-amino-α,α-ditrifluoromethylbenzyl)benzene, 2,6-bis(3-aminophenoxy)benzonitrile, 2,6-bis(-aminophenoxy)pyridine, 4,4'-bis(3-aminophenoxy)biphenyl, 4,4'-bis(4-aminophenoxy)biphenyl, bis[4-amino(3-phenoxy)phenyl]ketone, bis[4-amino(4-phenoxy)phenyl]ketone, bis[4-amino(3-phenoxy)phenyl]sulfide, bis[4-amino(4-phenoxy)phenyl]sulfide, bis[4-amino(3-phenoxy)phenyl]sulfone, bis[4-amino(4-phenoxy)phenyl]sulfone, bis[4-amino(3-phenoxy)phenyl]ether, bis[4-amino(4-phenoxy)phenyl]ether, 2,2-bis[4-(3-aminophenoxy)phenyl]propane, 2,2-bis[4-(4-aminophenoxy)phenyl]propane, 2,2-bis[4-(3-aminophenoxy)phenyl]-1,1,1,3,3,3-hexafluoropropane, 2,2-bis[4-(4-aminophenoxy)phenyl]-1,1,1,3,3,3-hexafluoropropane, 1,3-bis[4-(3-aminophenoxy)benzoyl]benzene, 1,3-bis[4-(4-aminophenoxy)benzoyl]benzene, 1,4-bis[4-(3-aminophenoxy)benzoyl]benzene, 1,4-bis[4-(4-aminophenoxy)benzoyl]benzene, 1,3-bis[4-(3-aminophenoxy)-α,α-dimethylbenzyl]benzene, 1,3-bis[4-(4-aminophenoxy)-α,α-dimethylbenzyl]benzene, 1,4-bis[4-(3-aminophenoxy)-α,α-dimethylbenzyl]benzene, 1,4-bis[4-(4-aminophenoxy)-α,α-dimethylbenzyl]benzene, 4,4'-bis[4-(4-aminophenoxy)benzoyl]diphenylether, 4,4'-bis[4-(4-amino-α,α-dimethylbenzyl)phenoxy]benzophenone, 4,4'-bis[4-(4-amino-α,α-dimethylbenzyl)phenoxy]diphenylsulfone, 4,4'-bis[4-(4-aminophenoxy)phenoxy]diphenylsulfone, 3,3'-diamino-4,4'-diphenoxybenzophenone, 3,3'-diamino-4,4'-dibiphenoxybenzophenone, 3,3'-diamino-4-phenoxybenzophenone, 3,3'-diamino-4-biphenyloxybenzophenone, 6,6'-bis(3-aminophenoxy)-3,3,3',3'-tetramethyl-1,1'-spirobiindane, 6,6'-bis(4-aminophenoxy)-3,3,3',3'-tetramethyl-1,1'-spirobiindane; aliphatic diamines such as 1,3-bis(3-aminopropyl)tetramethyldisiloxyane, 1,3-bis(4-aminobutyl)tetramethyldisiloxane, α,ω-bis(3-aminopropyl)polydimethylsiloxane, α,ω-bis(3- aminopropyl)polydimethylsiloxane, α,ω-bis(4-aminobutyl) polydimethylsiloxane, bis(aminomethyl)ether, bis(2-aminoethyl)ether, bis(3-aminopropyl)ether, bis[2-(aminomethoxy)ethyl]ether, bis[2-(2-aminoethoxy)ethyl]ether, bis[2-(3-aminopropoxy)ethyl]ether, 1,2-bis(aminomethoxy)ethane, 1,2-bis(2-aminoethoxy)ethane, 1,2-bis[2-(aminomethoxy)ethoxy]ethane, 1,2-bis[2-(2-aminoethoxy) ethoxy]ethane, ethyleneglycol bis(3-aminopropyl)ether, diethyleneglycol bis(3-aminopropyl)ether, triethyleneglycol bis(3-aminopropyl)ether, ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, and 1,12-diaminododecane; and alicyclic diamines such as 1,2-diaminocyclohexane, 1,3-diaminocyclohexane, 1,4-diaminocyclohexane, 1,2-di(2-aminoethyl)cyclohexane, 1,3-di(2-aminoethyl)cyclohexane, 1,4-di(2-aminoethyl)cyclohexane, bis(4-aminocyclohexyl)methane, 2,6-bis(aminomethyl)bicycle[2.2.1]heptane, and 2,5-bis(aminomethyl)bicycle[2.2.1]heptane. Furthermore, diamines in which a part or all of hydrogen atoms on aromatic ring(s) are substituted with a substituent selected from the group consisting of fluoro group, methyl group, methoxy group, trifluoromethyl group and trifluoromethoxy group can be used. These diamines can be used alone, or two or more thereof can be used in combination.

The content of the polyimide precursor is preferably 50 mass % or more and 99 mass % or less, more preferably 70 mass % or more and 95 mass % or less, with respect to the solid content of the photosensitive composition of the fifth aspect. When the content is in the above-defined range, a coating film forming capability can be achieved.

The photosensitive composition of the fifth aspect contains the hydrogen barrier agent (B) as mentioned above. Containing this compound in the photosensitive composition enables a pattern having hydrogen barrier performance to be formed.

The content of the hydrogen barrier agent (B) is preferably 0.01 parts by mass or more and 40 parts by mass or less, and more preferably 0.05 parts by mass or more and 30 parts by mass or less, further preferably 0.1 parts by mass or more and 20 parts by mass or less, and particularly preferably 0.2 parts by mass or more and 10 parts by mass or less, relative to 100 parts by mass of the polyimide precursor. When the content is in the above-defined range, excellent developing property is obtained, and excellent fine patterning property can be obtained.

Organic solvents in the photosensitive composition of the fifth aspect include the organic solvents described as examples in the photosensitive composition of the first aspect. Among them, polar solvents such as propylene glycol monomethyl ether, methyl ethyl ketone, cyclopentanone, cyclohexanone, ethyl acetate, propylene glycol monomethyl ether acetate, N,N-dimethylacetamide, and N-methyl-2-pyrrolidone, γ-butyrolactone, aromatic hydrocarbons such as toluene, and mixtures thereof. The content of the organic solvent is preferably an amount such that the solid content concentration of the photosensitive composition of the fifth aspect is 1 mass % or more and 50 mass % or less, and more preferably 5 mass % or more and 30 mass % or less.

When the photosensitive composition of the fifth aspect is a positive photosensitive composition, it is preferable that the composition further include a photo acid generator as a photosensitizer. Examples of the photo acid generator include a quinone diazide group-containing compound in addition to the compounds described above in the photosensitive composition of the second aspect. Examples of the quinone diazide group-containing compound include an orthoquinone diazide compound, and a diazonaphthoquinone compound, and preferable examples include a complete esterification or partial esterification product of a phenol compound (also referred to as a phenolic hydroxy group-containing compound) and a naphthoquinone diazide sulfonic acid compound; and an orthoquinone diazide compound obtained by condensation-reacting orthoquinone diazide sulfonyl chloride, a hydroxy compound or an amino compound in the presence of a dehydrochloric acid agent (among them, an ester compound obtained by reaction between 1,1-bis(4-hydroxyphenyl)-1-[4-{1-(4-hydroxyphenyl)-1-methyl ethyl}phenyl]ethane, and 1-naphthoquinone-2-diazide-5-sulfonyl chloride is preferable), and the like.

Besides, if necessary, a thermal crosslinking agent, a silicon-containing compound, a non-polymerizable binder polymer, a solvent, an elastomer, a dissolution promoting agent, a dissolution inhibitor, a surface active agent, a leveling agent, a thermal acid generator, and other components, can be contained.

The thermal crosslinking agent is not particularly limited except that it is a compound crosslinked or polymerized in the heat treatment process after development, but preferably a compound having a methylol group, an alkoxy methyl group, an epoxy group or a vinyl ether group in a molecule. For example, compounds having methylol group such as 1,2-benzene dimethanol, 1,3-benzene dimethanol, 1,4-benzene dimethanol, 1,3,5-benzene trimethanol, 4,4'-biphenyl dimethanol, 2,6-pyridine dimethanol, 2,6-bis(hydroxymethyl)-p-cresol, and 4,4'-methylenebis(2,6-dialkoxymethylphenol); compounds having alkoxymethyl group such as 1,4-bis(methoxymethyl)benzene, 1,3-bis(methoxymethyl)benzene, 4,4'-bis(methoxymethyl)biphenyl, 3,4'-bis(methoxymethyl)biphenyl, 3,3'-bis(methoxymethyl)biphenyl, dimethyl 2,6-naphthaledicarboxylate, and 4,4'-methylenebis(2,6-dimethoxymethylphenol); methylolmelamine compounds such as hexamethylolmelamine, and hexabutanolmelamine; alkoxymelamine compounds such as hexamethoxymelamine; alkoxymethylglycoluryl compounds such as tetramethoxymethylglycoluryl; methylol benzoguanamine compounds; methylol urea compounds such as dimethylolethyleneurea; cyano compounds such as dicyanoaniline, dicyanophenol, and cyanophenylsulfonic acid; isocyanato compounds such as 1,4-phenylenediisocyanato, and 3,3'-dimethyldiphenylmethane-4,4'-diisocyanato; epoxy group-containing compounds such as ethyleneglycol diglycidylether, bisphenol A diglycidylether, triglycidyl isocyanurate, bisphenol A type epoxy resin, bisphenol F type epoxy resin, naphthalene type epoxy resin, biphenyl type epoxy resin, and phenolnovolak type epoxy resin; and maleimide compounds such as N,N'-1,3-phenylenedimaleimide, and N,N'-methylenedimaleimide may be exemplified, but not limited thereto. These thermal crosslinking agents can be used alone, or two or more thereof can be used in combination.

As silicon-containing compounds, silicon-containing resin, silicon-containing resin precursor, and silane coupling agent, and the like may be exemplified. Silane coupling agent is preferable, and silane coupling agent including ureido group such as 1-(2-pyridyl)-3-[3-(trimethoxysilyl)propyl]urea, and 1-(3-pyridyl)-3-[3-(trimethoxysilyl)propyl]urea is more preferable.

When the photosensitive composition of the fifth aspect is a negative photosensitive composition, it is preferable that a photobase generator as the photosensitizer is further included. The photobase generator is not particularly limited, and suitable examples thereof include compounds similar to those of the oxime ester compounds mentioned above for the photosensitive composition of the first aspect.

The negative photosensitive composition may contain the other components similar to those defined in the above-mentioned positive photosensitive compositions, if necessary. The proportion of each component other than the hydrogen barrier agent (B) in the photosensitive composition of the fifth aspect is as follows. The content of the polyimide precursor is preferably 50 mass % or more and more preferably 60 mass % or more and 90 mass % or less with respect to the entire solid content of the photosensitive composition. The content of the photosensitizer is preferably 3 parts by mass or more and 50 parts by mass or less, and more preferably 5 parts by mass or more and 30 parts by mass or less, relative to 100 parts by mass of the polyimide precursor from the viewpoint of sensitivity or the like. The content when the thermal crosslinking agent is included is preferably 1 part by mass or more and 50 parts by mass or less, relative to 100 parts by mass of the polyimide precursor. The content when the silane compound is included is preferably 0.1 parts by mass or more and 20 parts by mass or less, and more preferably 1 part by mass or more and 10 parts by mass or less relative to 100 parts by mass of the polyimide precursor. The solid content concentration of the photosensitive composition is preferably 30 mass % or less, more preferably 1 mass % or more and 20 mass % or less, and further preferably 5 mass % or more and 15 mass % or less. The photosensitive composition of the fifth aspect may contain various additives mentioned above as in the photosensitive composition of the first aspect, if necessary.

(6) Photosensitive Composition of Sixth Aspect

A photosensitive composition of a sixth aspect contains an epoxy compound, a hydrogen barrier agent (B), and an organic solvent.

Examples of epoxy compounds in the photosensitive composition of sixth aspect include bisphenol A type epoxy resin derived from bisphenol A and epichlorohydrin, bisphenol F type epoxy resin derived from bisphenol F and epichlorohydrin, bisphenol S type epoxy resin, phenolnovolak type epoxy resin, cresolnovolak type epoxy resin, bisphenol A novolak type epoxy resin, bisphenol F novolak type epoxy resin, alicyclic epoxy resin, diphenylether type epoxy resin, hydroquinone type epoxy resin, naphthalene type epoxy resin, biphenyl type epoxy resin, fluorene type epoxy resin, polyfunctional epoxy resin such as trifunctional epoxy resin and tetrafunctional epoxy resin, glycidylester type epoxy resin, glycidylamine type epoxy resin, hydantoin type epoxy resin, isocyanurate type epoxy resin, and aliphatic chain epoxy resin. These epoxy compounds may be halogenated or hydrogenated. Examples of the commercially available epoxy compound include JER Coat 828, 1001, 801N, 806, 807, 152, 604, 630, 871, YX8000, YX8034, and YX4000 manufactured by Japan Epoxy Resin Co., Epiclon 830, EXA835LV, HP4032D, and HP820 manufactured by DIC Corporation, the EP4100 series, EP4000 series, and EPU series manufactured by ADEKA Corporation, the Celloxide series (2021, 2021P, 2083, 2085, 3000, and the like), the EPOLEAD series, and the EHPE series manufactured by Daicel Corporation, the YD series, YDF series, YDCN series, YDB series, and phenoxy resins (polyhydroxy polyethers synthesized from bisphenols and epichlorohydrin, and having epoxy groups at both terminals; YP series and the like) manufactured by New Nippon Steel Chemical Co., Ltd., the Denacol series manufactured by Nagase Chemtex Corporation, the EPO LIGHT series manufactured by Kyoeisha Chemical Co., Ltd., and the like, without limitation. These epoxy compounds may be used alone or in combination of two or more types thereof.

The content of the epoxy compound is preferably 55 mass % or more and 99 mass % or less and more preferably 70 mass % or more and 95 mass % or less, with respect to the solid content of the photosensitive composition of the sixth aspect. When the content is in the above-defined range, a coating film forming capability can be improved.

The photosensitive composition of the sixth aspect contains the above-mentioned hydrogen barrier agent (B). Since the hydrogen barrier agent (B) is a compound including an imidazole ring, when it is exposed, curing of the epoxy compound is promoted to provide the photosensitive composition with excellent patterning property and hydrogen barrier performance.

The content of the hydrogen barrier agent (B) is preferably 0.01 parts by mass or more and 30 parts by mass or less, more preferably 0.05 parts by mass or more and 20 parts by mass or less, and particularly preferably 0.1 parts by mass or more and 10 parts by mass or less, relative to 100 parts by mass of the epoxy compound. When the content is in the above-defined range, the patterning property and hydrogen barrier performance can be obtained.

Examples of the organic solvents in the photosensitive composition of the sixth aspect include organic solvents described in the photosensitive composition of the first aspect. Among them, polar solvents such as propylene glycol monomethyl ether, methyl ethyl ketone, cyclopentanone, cyclohexanone, ethyl acetate, propylene glycol monomethyl ether acetate, N,N-dimethylacetamide, N-methyl-2-pyrrolidone, and γ-butyrolactone, aromatic hydrocarbons such as toluene, and mixtures thereof, are preferable. The content of the organic solvent is preferably an amount such that the solid content concentration of the photosensitive composition of the sixth aspect becomes preferably 1 mass % or more and 50 mass % or less, and more preferably 5 mass % or more and 30 mass % or less.

The photosensitive composition of the sixth aspect may contain various additives mentioned above as in the photosensitive composition of the first aspect, if necessary.

Note here that in an epoxy-group-containing polycarboxylic acid resin in the sixth aspect mentioned below, all epoxy groups are not necessarily consumed by the reaction between "monocarboxylic acid having an alcoholic hydroxy group" and "polyfunctional acid anhydride", which usually also corresponds to epoxy resin in the photosensitive composition of the sixth aspect from the viewpoint of having a remaining epoxy group. In this point, as the epoxy resin in the photosensitive composition of the sixth aspect, an epoxy-group-containing polycarboxylic acid resin in the photosensitive composition of the sixth aspect may be able to be used. In the present specification, among epoxy resins in the photosensitive composition of the sixth aspect, resin other than an epoxy-group-containing polycarboxylic acid resin in the photosensitive composition of the sixth aspect may be called a non-carboxylic acid modified epoxy resin.

(7) Photosensitive Composition of Seventh Aspect

A photosensitive composition of a seventh aspect is a negative photosensitive composition containing an epoxy-group-containing polycarboxylic acid resin, a photo acid generator, a hydrogen barrier agent (B), and an organic solvent.

As the epoxy group-containing polycarbonate resin in the photosensitive composition of the seventh aspect, for example, it is possible to use a resin obtained, for example, by reacting an epoxy compound having two or more epoxy groups in a molecule with a monocarboxylic acid having one or more alcoholic hydroxy groups in a molecule to obtain a reactant, and further reacting the reactant with a polyfunctional acid anhydride.

Examples of epoxy compounds having two or more epoxy group in one molecule include novolak type epoxy resin, bisphenol type epoxy resin, trisphenolmethane type epoxy resin, tris(2,3-epoxypropyl)isocyanurate, biphenyl diglycidyl ether, alicyclic epoxy resin, copolymer type epoxy resin, and the like.

As the novolak type epoxy resin, an epoxy resin obtainable by reacting a novolak obtainable by reaction of phenols such as phenol, cresol, halogenated phenol, and alkylphenol and formaldehyde in the presence of acid catalyst with epichlorohydrin or methylepichlorohydrin is exemplified. As commercial products, EOCN-102S, EOCN-103S, EOCN-104S, EOCN-1027, EPPN-201, BREN-S (all manufactured by Nippon Kayaku Co., Ltd.); DEN-431, DEN-439 (both manufactured by the Dow Chemical Company); and N-730, N-770, N-865, N-665, N-673, VH-4150 (all manufactured by Dainippon Ink and Chemicals Co.) may be exemplified.

As the bisphenol type epoxy resin, epoxy resins obtainable by reacting bisphenols such as bisphenol A, bisphenol F, bisphenol S, tetrabromobisphenol A, and the like with epichlorohydrin or methylepichlorohydrin, and epoxy resins obtainable by reacting a condensate of glycidyl ether of bisphenol such as bisphenol A and bisphenol F and abovementioned bisphenols with epichlorohydrin or methylepichlorohydrin may be exemplified. As commercial products, Epikote 1004, Epikote 1002, Epikote 4002, and Epikote 4004 (all manufactured by Yuka Shell Co.) may be exemplified.

As the trisphenolmethane type epoxy resin, epoxy resins obtainable by reacting trisphenolmethane or triscresolmethane with epichlorohydrin or methylepichlorohydrin may be exemplified. As commercial products, EPPN-501, and EPPN-502 (both manufactured by Nippon Kayaku Co., Ltd.) may be exemplified.

Examples of the alicyclic epoxy resin include Celloxide 2021 manufactured by Daicel Corporation, Epomic VG-3101 manufactured by Mitsui Chemicals, Inc., E-10315 manufactured by Yuka Shell Epoxy Co., and EPB-13 and EPB-27 manufactured by Nippon Soda Co., Ltd and the like. Furthermore, examples of the copolymer-type epoxy resin include CP-50M and CP-50S manufactured by NOF Corporation, which are copolymers of glycidyl methacrylate and styrene and α-methylstyrene, or copolymers of glycidyl methacrylate and cyclohexyl maleimide, and the like.

Examples of these epoxy resins having 2 or more epoxy group in one molecule include a cresol novolak type epoxy resin, a phenol novolak type epoxy resin, a bisphenol type epoxy resin, a trisphenolmethane type epoxy resin, and the like. Polycondensate of α-hydroxyphenyl-ω-hydropoly(biphenyldimethylene-hydroxyphenylene) and 1-chloro-2,3-epoxypropane and α-2,3-epoxypropoxyphenyl-ω-hydropoly[2-(2,3-epoxypropoxy)benzylidene-2,3-epoxypropxyphenylene] are particularly preferable.

Examples of a monocarboxylic acid having 1 or more alcoholic hydroxy group in one molecule include hydroxy monocarboxylic acids such as a dimethylol propionic acid, a dimethylol acetic acid, a dimethylol lactic acid, a dimethylol valeric acid, a dimethylol caproic acid, and a hydroxy pivalic acid. Among these, a monocarboxylic acid having 1 or more and 5 or less alcoholic hydroxy group in one molecule is preferable.

Example of a polyfunctional acid anhydride include succinic anhydride, maleic anhydride, phthalic anhydride, tetrahydrophthalic anhydride, hexahydrophthalic anhydride, methylendomethylenetetrahydrophthalic anhydride, trimellitic anhydride, and pyromellitic anhydride, and the like.

In the reaction between the above-mentioned epoxy compound and the above-mentioned monocarboxylic acid, the monocarboxylic acid is preferably 0.1 mol or more and 0.7 mol or less and more preferably 0.2 mol or more and 0.5 mol or less relative to 1 equivalent of epoxy group of the epoxy compound. In this reaction, it is preferable to use an organic solvent which does not react with the epoxy compound or the polyfunctional acid anhydride, and which does not have hydroxy groups or carboxy groups. Further, a catalyst (for example, triphenylphosphine, benzyl dimethylamine, trialkyl ammonium chloride, triphenyl stibine, and the like) can be used to promote the reaction. When a catalyst is used, it is preferable to deactivate the catalyst using an organic peroxide or the like particularly after the reaction is finished, because stability and the shelf life are favorable. The amount of the catalyst to be used is preferably 0.1 mass % or more and 10 mass % or less with respect to the reaction mixture, and the reaction temperature is preferably 60° C. or higher and 150° C. or lower. Thus, it is possible to obtain a reactant of the above described epoxy compound and the above described monocarboxylic acid.

In the reaction between this reactant and a polyfunctional acid anhydride, the polyfunctional acid anhydride is preferably reacted in such an amount that the acid value of the finally obtained epoxy group-containing polycarboxylic acid resin is 50 mgKOH/g or more and 150 mgKOH/g or less. The reaction temperature is preferably 60° C. or higher and 150° C. or lower. Thus, an epoxy group-containing polycarboxylic acid resin can be obtained.

These epoxy group-containing polycarboxylic acid resins may be used alone or in combination of two or more types thereof.

The content of the epoxy group-containing polycarboxylic acid resin is preferably 30 mass % or more and 80 mass % or less and more preferably 40 mass % or more and 70 mass % or less, with respect to the solid content of the photosensitive composition of the seventh aspect. When the content is in the above-defined range, a coating film forming capability can be improved.

Examples of the photo acid generators in the photosensitive composition of the seventh aspect include the photo acid generators exemplified for the photosensitive composition of the second aspect. The content of the photo acid generator is preferably 0.5 mass % or more and 30 mass % or less, more preferably 1 mass % or more and 20 mass % or less, with respect to the solid content of the photosensitive composition of the seventh aspect. When the content is in the above-defined range, the curability of the photosensitive composition is improved.

The photosensitive composition of the seventh aspect contains the hydrogen barrier agent (B) as mentioned above. When this compound is contained in a photosensitive composition, it is possible to form a pattern having hydrogen barrier performance.

The content of the hydrogen barrier agent (B) is preferably 0.01 mass % or more and 30 mass % or less, more preferably 0.05 mass % or more and 20 mass % or less, and particularly preferably 0.1 mass % or more and 10 mass % or less, with respect to a mass of the resin corresponding to the base material component (A) of the photosensitive composition of the seventh aspect. When the content is in the above-defined range, it is possible to obtain patterns having hydrogen barrier performance, and excellent developing property is achieved.

The photosensitive composition of the seventh aspect may further contain a sensitizing agent. As the sensitizing agent, for example, an anthracene compound having an alkoxy group at the 9-position and 10-position (9,10-dialkoxy-anthracene derivative) is preferable. Examples of the alkoxy group include an alkoxy group having 1 or more and 4 or less carbon atoms. The 9,10-dialkoxy-anthracene derivative may further have a substituent. Examples of the substituent include a halogen atom, an alkyl group having 1 or more and 4 or less carbon atoms, a sulfonic acid alkyl ester group, a carboxylic acid alkyl ester group, and the like. Examples of the alkyl group in the sulfonic acid alkyl ester group or the carboxylic acid alkyl ester group include an alkyl group having 1 or more and 4 or less carbon atoms. The substitution position of these substituents is preferably the 2-position.

Examples of 9,10-dialkoxy-anthracene derivative include 9,10-dimethoxy-anthracene, 9,10-diethoxy-anthracene, 9,10-dipropoxy-anthracene, 9,10-dimethoxy-2-ethyl-anthracene, 9,10-diethoxy-2-ethyl-anthracene, 9,10-dipropoxy-2-ethyl-anthracene, 9,10-dimethoxy-2-chloro-anthracene, 9,10-dimethoxyanthracene-2-sulfonic acid methyl ester, 9,10-diethoxyanthracene-2-sulfonic acid methyl ester, 9,10-dimethoxyanthracene-2-carboxylic acid methyl ester, and the like.

These compounds are obtained by treating an anthraquinone derivative with a reducing agent such as zinc powder, hydrosulfite, palladium-carbon, and sodium borohydride in an alkali aqueous solution to make a 9,10-dihydroxyanthracene derivative, and then alkoxylating the 9,10-position with a sulfuric acid ester such as dimethyl sulfate, and diethyl sulfate; a toluenesulfonate ester such as methyl toluenesulfonate, ethyl toluenesulfonate, propyl toluenesulfonate, and a monoethylene glycol toluenesulfonate ester; or a benzenesulfonate ester such as methyl benzenesulfonate, ethyl benzenesulfonate, and propyl benzenesulfonate.

These sensitizing agents may be used alone or in combination of two or more types thereof.

The content of the sensitizing agent is preferably 0.1 or more and 6 or less and more preferably 0.2 or more and 4 or less in molar ratio with respect to the above described photo acid generator. When the content is in the above-defined range, the sensitivity and the curability of the photosensitive composition can be improved.

The photosensitive composition of the seventh aspect may further contain a modifying component for adjusting the moisture resistance, heat resistance, adhesiveness, and the like. These modifying components may be ones which are themselves cured by heat, ultraviolet radiation, or the like, or may be ones which react with a residual hydroxy group or a carboxy group or the like of an epoxy group-containing polycarboxylic acid resin by heat, ultraviolet radiation, or the like. Specific examples thereof include an epoxy compound having one or more epoxy groups in a molecule, a melamine derivative (for example, hexamethoxy melamine, hexabutoxylated melamine, condensed hexamethoxy melamine, and the like), bisphenol A-type compounds (for example, tetramethylol bisphenol A and the like), oxazoline compounds, and the like.

Examples of the epoxy compound having one or more epoxy groups in a molecule include bisphenol A-type epoxy resins such as Epikote 1009 and 1031 (both manufactured by Yuka Shell Co.), Epiclon N-3050 and N-7050 (both manufactured by Dainippon Ink and Chemicals Co.), and DER-642U and DER-673MF (both manufactured by the Dow Chemical Company); hydrogenated bisphenol A-type epoxy resins such as ST-2004 and ST-2007 (both manufactured by Tohto Chemical Industry Co., Ltd.); bisphenol F-type epoxy resins such as YDF-2004 and YDF 2007 (both manufactured by Tohto Chemical Industry Co., Ltd.); brominated bisphenol A-type epoxy resins such as SR-BBS and SR-TBA-400 (both manufactured by Sakamoto Yakuhin Kogyo Co., Ltd.), and YDB-600 and YDB-715 (both manufactured by Tohto Chemical Industry Co., Ltd.); novolak-type epoxy resins such as EPPN-201, EOCN-103, EOCN-1020, and BREN (all manufactured by Nippon Kayaku Co., Ltd.); novolak-type epoxy resins of bisphenol A such as Epiclon N-880 manufactured by Dainippon Ink and Chemicals Co.; rubber-modified epoxy resins such as Epiclon TSR-601 manufactured by Dainippon Ink and Chemicals Co. and R-1415-1 manufactured by A.C.R. Co.; bisphenol S-type epoxy resins such as EBPS-200 manufactured by Nippon Kayaku Co., Ltd. and Epiclon EXA-1514 manufactured by Dainippon Ink and Chemicals Co.; diglycidyl terephthalates such as Purenmer DGT manufactured by NOF Corporation; triglycidyl isocyanurates such as TEPIC manufactured by Nissan Chemical Industries Ltd.; bixylenol-type epoxy resins such as YX-4000 manufactured by Yuka Shell Co.; bisphenol-type epoxy resins such as YL-6056 manufactured by Yuka Shell Co.; alicyclic epoxy resins such as Celloxide 2021 manufactured by Daicel Corporation; and the like.

The content of the modifying components is preferably 50 mass % or less and more preferably 30 mass % or less, with respect to the solid content of the photosensitive composition of the seventh aspect.

The photosensitive composition of the seventh aspect, in order to improve the characteristics such as the adhesiveness, hardness and the like, may further contain a well-known filler such as barium sulfate, barium titanate, silica, talc, clay, magnesium carbonate, calcium carbonate, aluminum oxide, and mica. The content of the filler is preferably 60 mass % or less, and more preferably 5 mass % or more and 40 mass % or less with respect to the solid content of the photosensitive composition of the sixth aspect.

The photosensitive composition of the seventh aspect may further contain a coloring agent such as phthalocyanine blue, phthalocyanine green, disazo yellow, crystal violet, titanium oxide, and carbon black; a thickener such as ultrafine powdered silica, and montmorillonite; an anti-foaming agent and/or leveling agent such as a silicone high polymer, and a fluorinated high polymer; an adhesiveness imparting agent such as a silane coupling agent.

Examples of the organic solvent of the photosensitive composition of the seventh aspect include the organic solvents listed as examples in the photosensitive composition of the first aspect. The content of the organic solvent is an amount such that the solid content concentration of the photosensitive composition of the seventh aspect is preferably 1 mass % or more and 50 mass % or less, and preferably 5 mass % or more and 30 mass % or less.

Similar to the photosensitive composition of the first aspect, the photosensitive composition of the seventh aspect may contain various additives as mentioned above, if necessary.

<Method for Preparing Photosensitive Composition>

The photosensitive composition is prepared by mixing each of the above-mentioned components with a stirrer. Note here that the prepared photosensitive composition may be filtered, for example, through a membrane filter so that the composition becomes homogeneous.

<<Method for Producing Hydrogen Barrier Film>>

Use of a hydrogen barrier film forming composition including the hydrogen barrier agent (B) described above allows a hydrogen barrier film including the hydrogen barrier agent (B) to be formed.

When the hydrogen Barrie film forming composition contains resin material such as polyacetal resin, polyamide resin, polycarbonate resin, polyester resin (polybutylene terephthalate, polyethylene terephthalate, polyethylene naphthalate, polyarylate, etc.), FR-AS resin, FR-ABS resin, AS resin, ABS resin, polyphenylene oxide resin, polyphenylene sulfide resin, polysulfone resin, polyether sulfone resin, polyetheretherketone resin, fluorinated resins, polyimide resin, polyamideimide resin, polyamidebismaleimide resin, polyetherimide resin, polybenzoxazole resin, polybenzothiazole resin, polybenzimidazole resin, silicone resin, BT resin, polymethylpentene, ultra high molecular weight polyethylene, FR-polypropylene, (meth)acrylic resin (for example, polymethylmethacrylate), polystyrene as base material component (A), method for forming hydrogen barrier film is the same as aforementioned.

When the hydrogen barrier film forming composition includes a thermosetting material as the base material component (A), the hydrogen barrier film forming composition is formed into a film by a method such as application, and then the formed film is cured by heating the obtained film at temperatures corresponding to types of curable material. Thus, a hydrogen barrier film can be formed.

When the hydrogen barrier film forming composition is the above-mentioned various photosensitive compositions, typically, the hydrogen barrier film is produced by a method including: applying a hydrogen barrier film forming composition on the substrate to form a coating film; and exposing the coating film.

More specifically, firstly, a coating film is formed by a suitable coating method. For example, the photosensitive composition can be applied on the substrate using a contact transfer-type coating applicator such as a roll coater, a reverse coater, and a bar coater, or a non-contact type coating applicator such as a spinner (a rotary coating applicator), and a curtain flow coater, and dried to form the coating film. The drying method is not particularly limited, and, examples of the method include (1) a method of carrying out prebaking for 60 seconds or more and 120 seconds or less on a hot plate at a temperature of 80° C. or higher and 120° C. or lower, and preferably 90° C. or higher and 100° C. or lower; (2) a method of leaving at room temperature for several hours or more and several days or less; or (3) a method of placing in a hot-air heater or infrared ray heater for several tens of minutes or more and several hours or less to remove the solvent, and the like.

Next, the coating film is exposed by irradiation with electromagnetic waves position-selectively. When the photosensitive composition is a negative photosensitive composition hardened by exposure, the exposure may be carried out to an entire surface of the coating film. When the exposure is carried out position-selectively, the electromagnetic waves may be applied via a positive or negative mask, or may be directly applied. An exposure amount differs depending on the photosensitive composition of the composition, but, for example, about 5 mJ/cm$^2$ or more and 500 mJ/cm$^2$ or less is preferable.

When exposure is carried out to the entire surface of the coating film, the exposed coating film can be used as a hydrogen barrier film as it is. When exposure is carried out position-selectively, it is possible to obtain a hydrogen barrier film in which a coating film after exposure is developed with a developing solution and patterned into a desired shape. The developing method is not particularly limited, and, for example, an immersion method, a spray method or the like, can be used. Examples of the developing solution include an organic solution such as monoethanolamine, diethanolamine, and triethanolamine; and an aqueous solution of a sodium hydroxide, potassium hydroxide, sodium carbonate, ammonia, quaternary ammonium salt, or the like.

It is preferable that the patterned hydrogen barrier film after development is subjected to post-baking at about 200° C. or higher and 250° C. or lower.

The hydrogen barrier film formed as mentioned above can be used without limitation for various applications that require shielding of hydrogen gas, and particularly suitably used in the below-mentioned electronic element.

Note here that the hydrogen barrier film can suppress permeation of hydrogen gas having small molecular weight and molecular size, and therefore, it is possible to suppress permeation of gas whose molecular size is larger than that of hydrogen. Examples of such gas include nitrogen gas, oxygen gas, ozone gas, water vapor, carbon monoxide gas, carbon dioxide gas, nitrogen oxide gas, sulfur oxide gas, and the like.

<<Electronic Element>>

A hydrogen barrier film formed using the above-mentioned hydrogen barrier film forming composition is suitably used in electronic elements provided with a passivation film. The passivation film is a film provided for protecting a functional layer such as a semiconductor layer from ions, gas or the like and physical damage or the like.

The electronic element is not particularly limited, and preferable examples of the electronic element include organic electronic elements including an organic conductive layer, an organic semiconductor layer, and an organic light-emitting layer. Suitable specific examples of the electronic element include light-emitting elements such as an LED element and an organic EL element, a semiconductor element, a solar battery element, and a solid-state image sensing device.

The passivation film includes, for example, metal oxide, metal nitride, metal carbide, metal oxynitride, metal oxycarbide, or the like. More specifically, oxide, nitride, carbide, oxynitride, oxycarbide, or the like, including at least one selected from Si, Al, In, Sn, Zn, Ti, Cu, Ce, and Ta, is preferably used. Among these materials, oxide, nitride, or oxynitride of metal selected from Si, Al, In, Sn, Zn, and Ti is preferable, oxide or nitride of Si or Al is more preferable, and silicon nitride (Si nitride) is particularly preferable. These may contain other elements as subsidiary components. For example, silicon nitride may include hydrogen to form hydrogenated silicon nitride, and further include oxygen to form hydrogenated silicon oxynitride. An oxide film or a nitride film of Si may be an oxide film or a nitride film obtained by firing a coating film of a composition containing a silicon-containing polymer such as polysilazane, polysiloxane, polysiloxazane, polysilane, or the like. From the viewpoint of protection performance of the passivation film, the passivation film preferably includes silicon nitride (SiN).

The passivation film described above may include hydrogen gas or a compound such as ammonium or amines capable of generating hydrogen gas depending on raw materials and producing methods. A passivation film including silicon nitride particularly tends to generate hydrogen gas.

On the other hand, the electronic element, like an organic EL element, is often provided with TFT for driving elements. Furthermore, the electronic element is often provided with wiring made of metal such as copper. The function of TFT may be impaired by reductive reaction by contact with hydrogen gas, and the electric characteristics of metal wiring may be changed due to reduction by hydrogen gas.

However, when the electronic element includes a hydrogen barrier film together with a passivation film, hydrogen gas generated from the passivation film is shielded by the hydrogen barrier film, and adverse influences at members that are influenced by hydrogen gas can be suppressed. The hydrogen barrier film is preferably provided between a subject, for example, TFT, to be protected from hydrogen and a generating source of hydrogen. When hydrogen, which is present in an environment outside of an electronic element, may enter the inside of a subject to be protected in the electronic element, a hydrogen barrier agent may be blended with a hard coat layer provided on a surface of the electronic element that is brought into contact with the outside environment to form a hydrogen barrier film. Furthermore, when a subject to be protected, for example, TFT in the electronic element is protected from hydrogen generated from a film such as a passivation film that is a generating source of hydrogen, the hydrogen barrier film is preferably formed between a film as a generating source of hydrogen and the subject to be protected. In this case, for example, a flattened film may be a hydrogen barrier film.

As described above, in an electronic element including a passivation film, when a hydrogen barrier film is provided, members such as TFT and metal wiring, which may be adversely influenced by hydrogen, can be protected, so that an electronic element having high operation reliability can be produced.

EXAMPLES

Hereinafter, the present invention will be described more specifically with reference to Examples, but the scope of the present invention is not limited to these Examples.

Example 1

A processed composition was obtained by dissolving 12 parts by mass of alkali-soluble resin having the following structure, 6 parts by mass of dipentaerythritol hexaacrylate, 1.0 part by mass of photopolymerization initiator having the following structure, 0.04 parts by mass of a surface conditioner (BYK-310, polyester-modified polydimethylsiloxane, manufactured by BYK Chemie Japan) and 2.0 parts by mass of hydrogen barrier agent having the following structure in a mixed solvent.

As the mix solvent, a mix solvent composed of 45 parts by mass of propylene glycol monomethyl ether, 30 parts by mass of diethylene glycol monomethyl ether, and N,N,N',N'-tetramethylurea was used.

A structure of the alkali-soluble resin, a structure of the photopolymerization initiator, and a structure of the hydrogen barrier agent are shown below. As to the alkali-soluble resin, the number of the right lower part of each constituent unit shows a content (mass %) of each constituting unit in the resin.

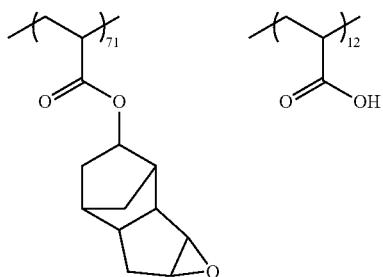

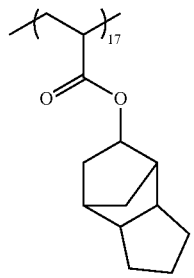

Alkali-soluble Resin

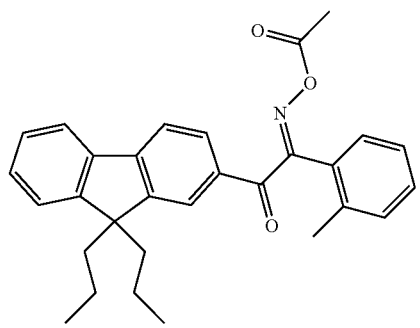

Photopolymerization Initiator

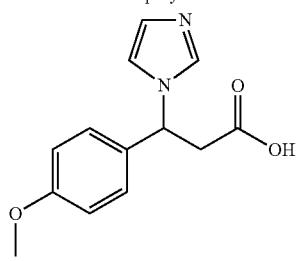

Hydrogen Barrier Agent

The obtained photosensitive composition was applied on a SiN substrate (a laminated body having a SiN layer on a silicon wafer) with a spin coater, followed by prebaking the coating film at 105° C. for 100 seconds. The entire surface of the pre-baked coating film was exposed with an exposure amount of 50 mJ/cm$^2$ (ghi-ray broad band) using an ultraviolet curing device to cure the coating film. The coated film after exposure was post-baked at 230° C. for 20 minutes to obtain a cured film having a film thickness of 2.0 μm.

The SiN substrate having a cured film was heated at the silicon wafer side, and amounts of a component generated from a surface of the cured film having a molecular weight of 1 (hydrogen radical or hydrogen ion), a component having a molecular weight of 2 (hydrogen gas), and a component having a molecular weight of 18 (water vapor) were measured by a thermal deposition spectrometry (TDS) method. Heating at the measurement time of gas generated was carried out with increasing a temperature from 50° C. to 280° C. at a speed of 10° C./min. When the temperature reached 280° C., heating was stopped. Generation amounts (peak strengths) of these gases are shown in Table 1.

Comparative Example 1

In a SiN substrate that does not have a cured film, generation amounts of a component having a molecular weight of 1 (hydrogen radical or hydrogen ion), a component having a molecular weight of 2 (hydrogen gas), and a component having a molecular weight of 18 (water vapor) were measured in the same manner as in Example 1. Generation amounts (peak strengths) of these gases are shown in Table 1. Note here that amount of generated gas is an amount of gas generated from the SiN surface.

Comparative Example 2

A photosensitive composition was obtained in the same manner as in Example 1 except that a hydrogen barrier agent was not used. The resulting photosensitive composition was used to form a cured film on a SiN substrate in the same manner as in Example 1. In a SiN substrate having a cured film, generation amounts of a component having a molecular weight of 1 (hydrogen radical or hydrogen ion), a component having a molecular weight of 2 (hydrogen gas), and a component having a molecular weight of 18 (water vapor) were measured in the same manner as in Example 1. Generation amounts (peak strengths) of these gases are shown in Table 1.

Comparative Example 3

A photosensitive composition was obtained in the same manner as in Example 1 except that a commercially available molecular sieve powder was added and dispersed homogeneously in a photosensitive composition such that the proportion thereof in the solid content became 20 mass %. The resulting photosensitive composition was used to form a cured film on a SiN substrate in the same manner as in Example 1. In a SiN substrate having a cured film, generation amounts of a component having a molecular weight of 1 (hydrogen radical or hydrogen ion), a component having a molecular weight of 2 (hydrogen gas), and a component having a molecular weight of 18 (water vapor) were measured in the same manner as in Example 1. Generation amounts (peak strengths) of these gases are shown in Table 1.

TABLE 1

| | Film formation | Additive in the film | Generation amounts of Gas (peak strength) | | |
|---|---|---|---|---|---|
| | | | Molecular weight of 1 | Molecular weight of 2 | Molecular weight of 18 |
| Ex. 1 | Formed | Hydrogen barrier agent | 3.5E−11 | 6.8E−11 | 3.0E−10 |
| Comp. Ex. 1 | Not formed | — | 1.5E−10 | 8.3E−10 | 1.3E−9 |
| Comp. Ex. 2 | Formed | None | 1.8E−10 | 3.1E−10 | 1.6E−9 |
| Comp. Ex. 3 | Formed | Molecular sieve | 1.6E−10 | 2.9E−10 | 1.6E−9 |

According to a comparison between Example 1 and Comparative Examples 1 and 2, it is shown that when a photosensitive composition including a hydrogen barrier agent having a predetermined structure is used to form a cured film on a SiN substrate, permeation of gas generated from SiN can be effectively achieved by the cured film. On the other hand, according to a comparison between Comparative Example 3 and Comparative Example 1 and 2, it is shown that even when material capable of adsorbing hydrogen gas and water, for example, molecular sieves, is added on a cured film formed using a photosensitive composition, permeation of gas generated from SiN can hardly be suppressed by the cured film.

Examples 2 to 4, Comparative Examples 4 to 5

Example 2

A hydrogen barrier film forming composition was obtained in the same manner as in Example 1 except for using a resin in which the epoxy group-containing constituent unit of the alkali-soluble resin of Example 1 was substituted with a constituent unit derived from glycidyl methacrylate.

Comparative Example 4

A film forming composition for comparison was obtained in the same manner as in Example 2 except that a hydrogen barrier agent having the above-mentioned structure was not used.

Example 3

A hydrogen barrier film forming composition was obtained in the same manner as in Example 1 except for using a resin in which the epoxy group-containing constituent unit of the alkali-soluble resin of Example 1 was substituted with a constituent unit derived from 3,4-epoxy-cyclohexylmethyl methacrylate.

Comparative Example 5

A film forming composition for comparison was obtained in the same manner as in Example 3 except that a hydrogen barrier agent having the above-mentioned structure was not used.

Example 4

A hydrogen barrier film forming composition was obtained in the same manner as in Example 1 except that the addition amount of the hydrogen barrier agent of Example 1 was 0.6 parts by mass.

Each of the obtained compositions was applied on a SiN substrate (a laminated body having a SiN layer on a silicon wafer) to form a coating film, followed by prebaking the coating film at 80° C. for 100 seconds. The entire surface of the pre-baked coating film was exposed with an exposure amount of 50 mJ/cm$^2$ (ghi-ray broad band) using an ultraviolet curing device to cure the coating film. The coating film after exposure was post-baked at 230° C. for 20 minutes to obtain a cured film having a film thickness of 2.0 μm. The obtained cured films are referred to as cured films 2 to 4, and comparative cured films 4 to 5. In the SiN substrate having cured films, generation amounts of gas were compared in the same manner as in Example 1. The cured films 2 to 3 according to Examples suppressed the permeation of gas more effectively than the corresponding comparative cured films 4 to 5. The cured film 4 according to Example suppressed the permeation of gas more effectively than the Comparative Example 2.

Examples 5 to 6, Comparative Examples 6 to 7

Example 5

A hydrogen barrier film forming composition was obtained by mixing 100 parts by mass of a compound represented by the following formula (A-2) as a base material component, 1 part by mass of a curing agent represented by the following formula (a1-2-1), and 10 parts by mass of a hydrogen barrier agent having the above-mentioned structure. (A-2)

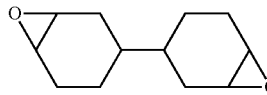

(A-2)

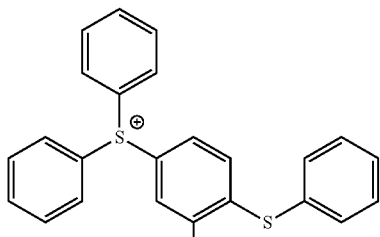

(a1-2-1)

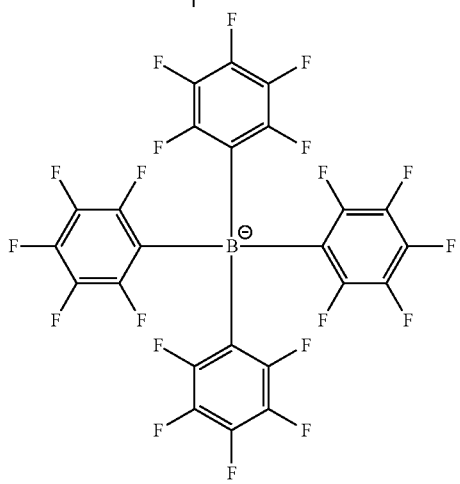

Comparative Example 6

A film forming composition for comparison was obtained in the same manner as in Example 5 except that a hydrogen barrier agent having the above-mentioned structure was not used.

Example 6

A hydrogen barrier film forming composition was obtained in the same manner as in Example 5 except that 100 parts by mass of a compound represented by the following formula (A-3) was used instead of a compound represented by the above-mentioned formula (A-2).

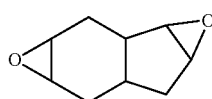

(A-3)

Comparative Example 7

A film forming composition for comparison was obtained in the same manner as in Example 6 except that a hydrogen barrier agent having the above-mentioned structure was not used.

Each of the obtained compositions was applied on a SiN substrate (a laminated body having a SiN layer on a silicon wafer) to form a coating film. Then, an entire surface of the coating film was exposed with an exposure amount of 50 mJ/cm$^2$ (ghi-ray broad band) using an ultraviolet curing device to obtain a cured film having a film thickness of about 2.0 μm. The obtained cured films are referred to as cured films 5 to 6, and comparative cured films 6 to 7. In the SiN substrate having cured films, generation amounts of gas were compared in the same manner as in Example 1. The cured films 5 to 6 according to Examples suppressed the permeation of gas more effectively than the corresponding comparative cured films 6 to 7.

Examples 7 to 8, Comparative Examples 8 to 9

Example 7

A hydrogen barrier film forming composition was obtained by mixing 100 parts by mass of a mixed resin component represented by the following formulae (A-3) and (A-4) (mass ratio of (A-3): (A-4)=70:30) as a base material component, 5 parts by mass of a curing agent (naphthalic acid derivative) represented by the following formula (a1-2-2), and 15 parts by mass of a hydrogen barrier agent having the above-mentioned structure, using 700 parts by mass of propylene glycol monomethyl ether acetate.

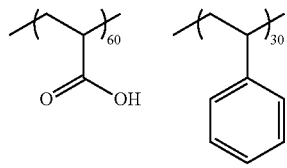

(A-3)

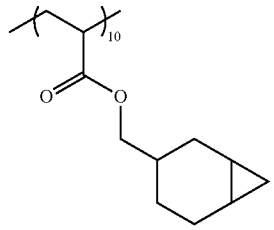

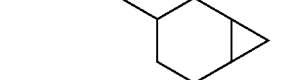

(A-4)

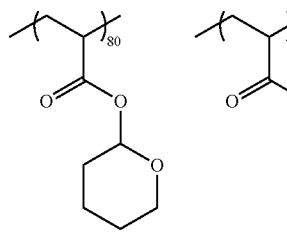

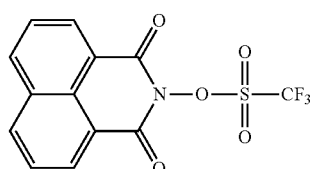

(a1-2-2)

Comparative Example 8

A film forming composition for comparison was obtained in the same manner as in Example 7 except that a hydrogen barrier agent having the above-mentioned structure was not used.

Example 8

The hydrogen barrier film forming composition was obtained in the same manner as in Example 7 except that 100 parts by mass of mixed resin components represented by the following formulae (A-5) and (A-6) (mass ratio of (A-5):(A-6)=70:30) was used as the base material component.

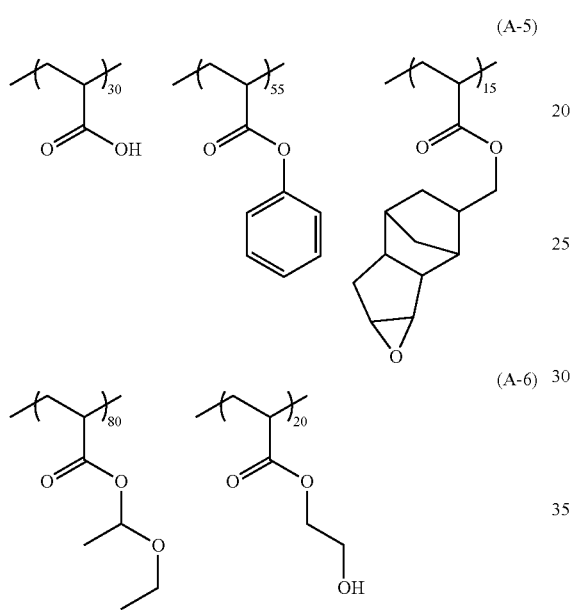

(A-5)

(A-6)

Comparative Example 9

A film forming composition for comparison was obtained in the same manner as in Example 8 except that a hydrogen barrier agent having the above-mentioned structure was not used. Each of the obtained compositions was applied on a SiN substrate (a laminated body having a SiN layer on a silicon wafer) to form a coating film, followed by prebaking the coating film at 80° C. for 120 seconds. The entire surface of the the pre-baked coating film was exposed with an exposure amount of 50 mJ/cm² (ghi-ray broad band) using an ultraviolet curing device to cure the coating film. The coating film after exposure was baked at 100° C. for 20 minutes to obtain a cured film having a film thickness of 2.0 µm. The obtained cured films are referred to as cured films 7 to 8, and comparative cured films 8 to 9. In the SiN substrate having cured films, generation amounts of gas were compared in the same manner as in Example 1. The cured films 7 to 8 according to Examples suppressed the permeation of gas more effectively than the corresponding comparative cured films 8 to 9.

What is claimed is:

1. A hydrogen barrier agent comprising a compound represented by the following formula (0):

[Chem. 1]

(0)

wherein, in the formula (0), $R^2$ represents an optionally substituted aromatic group, $R^{30}$ represents a hydrogen atom or a monovalent substituent having 1 or more and 40 or less carbon atoms;

$R^4$ represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group;

and n is an integer of 0 or more and 3 or less.

2. A hydrogen barrier film forming composition, comprising a base material component (A); and the hydrogen barrier agent (B) according to claim 1.

3. The hydrogen barrier film forming composition according to claim 2, wherein the base material component (A) includes an alkali-soluble resin (A1) and a photopolymerizable compound (A2), and further comprising a photopolymerization initiator (C).

4. A hydrogen barrier film comprising the hydrogen barrier agent (B) according to claim 1.

5. A hydrogen barrier film comprising a cured product of the hydrogen barrier film forming composition according to claim 3.

6. A method for producing a hydrogen barrier film, the method comprising: forming a coating film by applying the hydrogen barrier film forming composition according to claim 3 on a substrate; and exposing the coating film.

7. An electronic element comprising a passivation film; and the hydrogen barrier film according to claim 4.

8. The electronic element according to claim 7, further comprising a thin film transistor (TFT).

* * * * *